United States Patent
Ando et al.

(10) Patent No.: US 10,092,537 B2
(45) Date of Patent: Oct. 9, 2018

(54) USE FOR PAI-1 INHIBITOR

(71) Applicant: RENASCIENCE CO., LTD., Tokyo (JP)

(72) Inventors: Kiyoshi Ando, Kanagawa (JP); Takashi Yahata, Kanagawa (JP); Toshio Miyata, Miyagi (JP)

(73) Assignee: RENASCIENCE CO., LTD., Tokyo (JP)

( * ) Notice: Subject to any disclaimer, the term of this patent is extended or adjusted under 35 U.S.C. 154(b) by 0 days.

(21) Appl. No.: 14/783,447

(22) PCT Filed: Apr. 15, 2014

(86) PCT No.: PCT/JP2014/060760
§ 371 (c)(1),
(2) Date: Jan. 19, 2016

(87) PCT Pub. No.: WO2014/171464
PCT Pub. Date: Oct. 23, 2014

(65) Prior Publication Data
US 2016/0158188 A1 Jun. 9, 2016

(30) Foreign Application Priority Data

Apr. 15, 2013 (JP) ................................. 2013-085313
Dec. 18, 2013 (JP) ................................. 2013-261452

(51) Int. Cl.
A61K 31/4965 (2006.01)
A01N 43/42 (2006.01)
A61K 31/47 (2006.01)
A61K 31/341 (2006.01)
A61K 45/06 (2006.01)
A61K 31/192 (2006.01)
A61K 31/196 (2006.01)
A61K 31/381 (2006.01)
A61K 31/40 (2006.01)
A61K 31/402 (2006.01)
A61K 31/4025 (2006.01)
A61K 31/404 (2006.01)
A61K 31/4418 (2006.01)
A61K 31/445 (2006.01)
A61K 31/4525 (2006.01)
A61K 31/4709 (2006.01)
A61K 31/495 (2006.01)
A61K 31/506 (2006.01)

(52) U.S. Cl.
CPC .......... A61K 31/341 (2013.01); A61K 31/192 (2013.01); A61K 31/196 (2013.01); A61K 31/381 (2013.01); A61K 31/40 (2013.01); A61K 31/402 (2013.01); A61K 31/404 (2013.01); A61K 31/4025 (2013.01); A61K 31/445 (2013.01); A61K 31/4418 (2013.01); A61K 31/4525 (2013.01); A61K 31/47 (2013.01); A61K 31/4709 (2013.01); A61K 31/495 (2013.01); A61K 31/506 (2013.01); A61K 45/06 (2013.01)

(58) Field of Classification Search
None
See application file for complete search history.

(56) References Cited

U.S. PATENT DOCUMENTS

| 5,532,276 A | 7/1996 | Mederski et al. |
| 6,291,478 B1 | 9/2001 | Galey et al. |
| 7,534,894 B2 * | 5/2009 | Commons ............. C07C 233/60 548/253 |
| 2005/0113438 A1 | 5/2005 | Hu et al. |
| 2005/0124667 A1 | 6/2005 | Sartori et al. |
| 2005/0143384 A1 | 6/2005 | Sartori et al. |
| 2008/0019910 A1 | 1/2008 | Romer et al. |
| 2008/0119402 A1 | 5/2008 | Zheng et al. |
| 2009/0124620 A1 | 5/2009 | Miyata et al. |
| 2009/0240052 A1 | 9/2009 | Yokotani et al. |
| 2011/0112140 A1 | 5/2011 | Miyata et al. |
| 2012/0022080 A1 * | 1/2012 | Miyata .................. C07C 233/81 514/255.01 |

FOREIGN PATENT DOCUMENTS

| EP | 0120352 | 10/1984 |
| EP | 0376166 | 7/1990 |
| EP | 1666469 | 6/2006 |
| EP | 2 151 435 | 2/2010 |
| GB | 2 406 856 | 4/2005 |
| JP | 56-7716 | 1/1981 |
| JP | 02-256667 | 10/1990 |
| JP | 07-196656 | 8/1995 |

(Continued)

OTHER PUBLICATIONS

How Imatinib Mesylate works, side effects, interactions, and precautions (Navigating Care, Jan. 15, 2013, https://www.navigatingcare.com/chemotherapy_drugs/gleevec-imatinib-mesylate).*
Johnson et al. (British Journal of Cancer, 200 1, vol. 84, No. 10, pp. 1424-1431) (Year: 2001).*
Sausville et al. (Cancer Res., 2006, vol. 66, No. 7, panes 3351-3354) (Year: 2006).*
Suggitt et al. (Clinical Cancer Research, 2005, vol. 1 1, pp. 971-981) (Year: 2005).*

(Continued)

Primary Examiner — Daniel Michael Podgorski
(74) Attorney, Agent, or Firm — Wenderoth, Lind & Ponack, L.L.P.

(57) ABSTRACT

Provided is a novel use of a plasminogen activator inhibitor-1 inhibitor (PAI-1 inhibitor) that is used as an active ingredient of an agent for controlling a tumor stem cell, an agent for enhancing the antitumor effect of an antitumor agent, an agent for tumor chemotherapy, a stem-cell protecting drug, or a hematopoietic disorder improving agent.

5 Claims, 22 Drawing Sheets

(56) References Cited

FOREIGN PATENT DOCUMENTS

| JP | 2000-503308 | 3/2000 |
|---|---|---|
| JP | 2000-290252 | 10/2000 |
| JP | 2005-275352 | 10/2005 |
| JP | 2007-22943 | 2/2007 |
| JP | 2007-502264 | 2/2007 |
| JP | 2007-506783 | 3/2007 |
| JP | 2008-502699 | 1/2008 |
| WO | 93/11764 | 6/1993 |
| WO | 1997/026244 | 7/1997 |
| WO | 2002098839 | 12/2002 |
| WO | 2003099276 | 12/2003 |
| WO | 2004/018428 | 3/2004 |
| WO | 2004018414 | 4/2004 |
| WO | 2005/016867 | 2/2005 |
| WO | 2005/016870 | 2/2005 |
| WO | 2005/123072 | 12/2005 |
| WO | 2006057845 | 6/2006 |
| WO | 2006062093 | 6/2006 |
| WO | 2006/107719 | 10/2006 |
| WO | 2007002559 | 1/2007 |
| WO | 2007/039112 | 4/2007 |
| WO | 2007/083689 | 7/2007 |
| WO | 2008/070831 | 6/2008 |
| WO | 2008111299 | 9/2008 |
| WO | 2008111300 | 9/2008 |
| WO | 2008124610 | 10/2008 |
| WO | 2009/013915 | 1/2009 |
| WO | 2009/038842 | 3/2009 |
| WO | 2009/065406 | 5/2009 |
| WO | 2009/102468 | 8/2009 |
| WO | 2009/123241 | 10/2009 |
| WO | 2010/086964 | 8/2010 |
| WO | 2010/113022 | 10/2010 |
| WO | 2013/030365 | 3/2013 |

OTHER PUBLICATIONS

Communication pursuant to Article 94(3) EPC dated Aug. 30, 2016 in corresponding European Application No. 13001154.7.
International Search Report dated Jun. 2, 2014 in corresponding International Application No. PCT/JP2014/060760.
Suda, T. et al., "Current State of Leukemia Stem Cell Research and Expectation for Treatment", *Hematology Frontier*, 2010, vol. 20, No. 3, pp. 107-114 (with partial English translation).
Ibrahim, A. et al., "Inhibition of Plasminogen Activator Inhibitor Type-1 Activity Enhances Rapid and Sustainable Hematopoietic Regeneration", *Stem Cells*, 2013, vol. 32, Issue 4, pp. 946-958.
Oda, T. et al., PAI-1 deficiency attenuates the fibrogenic response to ureteral obstruction, Kidney International, 2001, vol. 30, pp. 587-596.
Matsuo, S. et al., Multifunctionality of PAI-1 in fibrogenesis: Evidence from obstructive nephropathy in PAI-1-overexpressing mice, Kidney International, 2005, vol. 67, pp. 2221-2238.
Huang, Y. et al., Noninhibitory PAI-1 enhances plasmin-mediated matrix degradation both in vitro and in experimental nephritis, Kidney International, 2006, vol. 70, pp. 515-522.
Eddy, A. et al., Plasminogen activator inhibitor-1 in chronic kidney disease: Evidence and mechanisms of action, Journal of American Society Nephrology, 2006, vol. 17, pp. 2999-3012.
Roelofs, J. et al., Plasminogen activator inhibitor-1 regulates neutrophil influx during acute pyelonephritis, Kidney International, 2009, vol. 75, pp. 52-59.
Durand, M. et al., Plasminogen activator inhibitor-I and tumour growth, invasion, and metastasis, Thromb Haemost, 2004, vol. 91, pp. 438-449.
Dan, J. et al., Plasminogen activator inhibitor-I in the aqueous humor of patients with and without glaucoma, Arch Ophthalmol, 2005, vol. 123, pp. 220-224.
Basu, A. et al., Plasminogen activator inhibitor-1 (PAI-1) facilitates retinal angiogenesis in a model of oxygen-induced retinopathy, Investigative Ophthalmology & Visual Science, 2009, vol. 50, No. 10, pp. 4974-4981.
Milliat, F. et al., Essential role of plasminogen activator inhibitor type-1 in radiation enteropathy, The American Journal of Pathology, 2008, vol. 172, No. 3, pp. 691-701.
Eren, M. et al., Reactive site-dependent phenotypic alterations in plasminogen activator inhibitor-1 transgenic mice, Journal of Thrombosis and Haemostasis, 2007, vol. 5, pp. 1500-1508.
Devin, J. et al., Transgenic overexpression of plasminogen activator inhibitor-1 promotes the development of polycystic ovarian changes in female mice, Journal of Molecular Endocrinology, 2007, vol. 39, pp. 9-16.
Suzuki, Y. et al., Unique secretory dynamics of tissue plasminogen activator and its modulation by plasminogen activator inhibitor-1 in vascular endothelial cells, Blood, 2009, vol. 113, No. 2, pp. 470-478.
Maemura, K. et al., Circadian rhythms in the CNS and peripheral clock disorders: Role of the biological clock in cardiovascular diseases, Journal of Pharmacological Sciences, 2007, vol. 103, pp. 134-138.
Schoenhard, J. et al., Plasminogen activator inhibitor•1 has a circadian rhythm in blind Individuals, Thromb Haemost, 2007, vol. 98, pp. 479-481.
Egelund, R. et al., A regulatory hydrophobic area in the flexible joint region of plasminogen activator inhibitor-1, defined with fluorescent activity-neutralizing ligands, The Journal of Biological Chemistry, 2001, vol. 276, pp. 13077-13086.
Vaughan, D. et al., PAI-1 antagonists: Predictable indications and unconventional applications, Current Drug Targets, 2007, vol. 8, pp. 962-970.
Crandall, D. et al., Modulation of adipose tissue development by pharmacological inhibition of PAI-1, Arteriosclerosis, Thrombosis, and Vascular Biology, 2006, vol. 26, pp. 2209-2215.
Eitzman, D. et al., Bleomycin-induced pulmonary fibrosis in transgenic mice that either lack or overexpress the murine plasminogen activator inhibitor-1 gene, The Journal of Clinical Investigation, 1996, vol. 97, pp. 232-237.
Hattori, N. et al., Bleomycin-induced pulmonary fibrosis in fibrinogen-null mice, The Journal of Clinical Investigation, 2000, vol. 106, No. 11, pp. 1341-1350.
Kosaka, H. et al., Interferon-gamma is a therapeutic target molecule for prevention of postoperative adhesion formation, Nature Medicine, 2008, vol. 14, No. 4, pp. 437-441.
Jacobsen, J. et al., Enhanced clearance of Aβ in brain by sustaining the plasmin proteolysis cascade, Proceeding of the National Academy of Science, USA, 2008, vol. 105, No. 25, pp. 8754-8759.
International Search Report for PCT/IB2010/00731, dated Jul. 13, 2010.
Aya, N. et al., Tissue-type plasminogen activator and its inhibitor in human glomerulonephritis, Journal of Pathology, 1992, vol. 166, pp. 289-295.
Lassila, M. et al., Plasminogen activator inhibitor-1 production is pathogenetic in experimental murine diabetic renal disease, Diabetologia, 2007, vol. 50, pp. 1315-1326.
Yoshida, Y. et al., Enhanced expression of plasminogen activator inhibitor 1 in patients with nephrotic syndrome, Nephron, 2001, vol. 88, pp. 24-29.
Huang, Y. et al., A mutant, noninhibitory plasminogen activator inhibitor type 1 decreases matrix accumulation in experimental glomerulonephritis, The Journal of Clinical Investigation, 2003, vol. 112, pp. 379-388.
Haraguchi, M. et al., t-PA promotes glomerular plasmin generation and matrix degradation in experimental glomerulonephritis, Kidney International, 2001, vol. 59, pp. 2146-2155.
Ha, H. et al., The role of plasminogen activator inhibitor 1 in renal and cardiovascular diseases, Nephrology, 2009, vol. 5, pp. 203-211.
Matsuo, O. et al., Plasminogen activator in bronchoalveolar fluid, Haemostasis, 1986, vol. 16, pp. 43-50.
Kivirikko, K. et al., Modifications of a specific assay for hydroxyproline in urine, Analytical Biochemistry, 1967, vol. 19, pp. 249-255.
Ashcroft, T. et al., Simple method of estimating severity of pulmonary fibrosis on a numerical scale, Journal of Clinical Pathology, 1988, vol. 41, pp. 467-470.

(56) References Cited

OTHER PUBLICATIONS

Milton, J. et al, Biaryl acids: Novel non-nucleoside inhibitors of HIV reverse transcriptase types 1 and 2, Bioorganic & Medicinal Chemistry Letters, 1998, vol. 8, pp. 2623-2628.
International Search Report for PCT/JP2009/056755, dated Jun. 16, 2009.
International Search Report for PCT/JP2008/054543, dated Jun. 17, 2008.
Database CA [Online], Chemical Abstracts Service, Sheradsky, T. et al., Reaction of carbanions with N-(tosyloxy)phthalimide, Formation of 3,3-disubstituted quinoline-2,4-diones, XP002680341, retrieved from STN, Database accession No. 1987:4834.
Database CA [Online], Chemical Abstracts Service, Ito, K. et al., Preparation of amides as serotonin antagonists, XP002680342, retrieved from STN, Database accession No. 1999:804348.
Supplementary European Search Report dated Aug. 22, 2012, from the European Patent Office in corresponding European Application No. 10758123.3.
Examination Report dated Dec. 11, 2012, from the European Patent Office in corresponding European Patent Application No. 09729173.6.
Partial European Search Report dated May 27, 2013 from the European Patent Office in corresponding European Patent Application No. 13001154.7.
Jones, A. et al., Parallel synthesis and spectroscopic analysis of a collection of heterocycles based on the diazabenz[e]aceanthrylene core structure, Tetrahedron 65 (2009) 563-578.
Border, W.A., et al., t-PA promotes glomerular plasmin generation and matrix degradation in experimental glomerulonephritis, Kidney Int., 59, 2146-2155, 2001.
Lopez-Alvarado, P. et al., Versatile synthesis of malonamic acid derivatives from a beta-ketothioester, Tetrahedron Letters, 2001, vol. 42, No. 27, pp. 4479-4482.
Bezugly, P. et al., Amides of 4-carboxymalonanilic acid with anti-inflammatory and neurotropic activities, Farmacevticnij Zurnal, 1990, No. 4, pp. 37-41.
Petiunin, G. et al., Amides and hydrazides of oxalic acid. XXVI. Synthesis and properties of N-substituted oxamoyl)anthranilic acids, Farmacevticnij Zurnal, 1973, vol. 28, No. 6, pp. 21-24.
CAPLUS 1970 100715.
Silverman, R., "The Organic Chemistry of Drug Design and Drug Action," *Elsevier*, 2004, pp. 29-32.
CAPLUS 2008 564823.
Vippagunta, S. et al., "Crystalline solids", *Adv. Drug Deliv.* Rev. 2001, vol. 48, pp. 3-26.
Supplementary European Search Report for EP Application No. 09729173.6, dated Dec. 20, 2011.
Extended European Search Report dated Nov. 30, 2016 in corresponding European Application No. 14785000.2.
Placencio, V. R. et al., "Small Molecule Inhibitors of Plasminogen Activator Inhibitor-1 Elicit Anti-Tumorigenic and Anti-Angiogenic Activity", PLOS One, 2015, vol. 10, No. 7 pp. 1-18.
Dolzhenko, A.V. et al., "Synthesis and Biological Activity of N-Acyl-5-Bromanthranilic Acids", Pharmaceutical Chemistry Journal, 40(8) pp. 418-420 (2006).
Anderson, M.O. et al., "Parallel Synthesis of Diarylureas and Their Evaluation as Inhibitors of Insulin-Like Growth Factor Receptor", Journal of Combinatorial Chemistry, 8(5) pp. 784-790 (2006).
Hamana et al., "Studies on Tertiary Amine Oxides. XLIII. Reactions of Aromatic N-Oxides with Alkoxyindoles in the Presence of Acylating Agents", Chemical & Pharmaceutical Bulletin, 19(8) pp. 1669-1680 (1971).
Office Action dated Nov. 29, 2017 in related Australian Patent Application No. 2016203847.
Ueda, K. "Biquinolyl. VI. Oxidation of biquinolyl" Yakugaku Zasshi, 57 (99) 817-824 (1937).

* cited by examiner

A

B

C

D

USE FOR PAI-1 INHIBITOR

TECHNICAL FIELD

The present invention relates to a novel use of a plasminogen activator inhibitor-1 inhibitor (PAI-1 inhibitor). More specifically, the present invention relates to a pharmaceutical composition that can be effectively used for tumor stem-cell control, enhancement of the antitumor effect of antitumor agents, tumor chemotherapy, stem-cell protection, and improvement of hematopoietic disorders, based on the stem-cell activation activity of the PAI-1 inhibitor.

BACKGROUND ART

A major complication of cancer chemotherapy, antiviral chemotherapy, or exposure to radiation, including cancer radiotherapy, is damage to bone marrow cells or suppression of their function. Specifically, chemotherapy and exposure to ionizing radiation cause damage to hematopoietic stem cells primarily found in the bone marrow and spleen, or destroy hematopoietic progenitor cells, impairing the production of new blood cells (granulocytes, lymphocytes, erythrocytes, monocytes, platelets, etc.). For example, treatment of cancer patients with cyclophosphamide or 5-fluorouracil can result in leukocytes (lymphocytes and (or) granulocytes) being destroyed, thereby increasing the susceptibility of the patients to infection. Accordingly, some cancer patients die of infection or other consequences of hematopoietic failure after chemotherapy or radiotherapy. Chemotherapy agents can also result in subnormal formation of platelets, which generates a propensity to hemorrhage. Similarly, mustard gas poisoning causes damage to the hematopoietic system, leading to susceptibility to injection. Inhibition of erythrocyte production can result in anemia. When surviving bone marrow stem cells cannot grow and differentiate fast enough to replenish the number of white blood cells, the body cannot resist pathogenic infectious organisms. Various pathological conditions, such as neutropenia, including idiopathic forms, are associated with damage to specific elements of the hematopoietic system.

Therefore, bone marrow transplantation or bone marrow stem-cell transplantation has been used to improve hematopoietic disorders caused by bone-marrow damage or loss of bone-marrow function due to pathological conditions associated with loss of hematopoietic function caused by chemicals, radiation, diseases, or other factors, and to facilitate the recovery of hematopoietic function.

Stem cells undergo self-renewal over the lifetime of an individual while producing cells of all systems, thereby maintaining homeostasis unique to the tissue. The functional loss associated with the stress response and aging of stem cells is directly linked to the malfunction of the entire tissue. Further, breakdown of the mechanism of controlling the self-renewal of stem cells promptly promotes tumorigenic transformation of stem cells, leading to the development of cancer. Therefore, for advancement of medical care using stem cells, it is important to analyze and control the self-renewal mechanism of stem cells.

In particular, hematopoietic stem cells (HSCs) undergo self-renewal cell division while producing differentiated cells, thereby maintaining the homeostasis of the hematopoietic system. However, excessive cell division of HSCs induces the accumulation of intracellular oxidative stress, etc., leading to a reduction in self-renewal capacity, i.e., shortening of the life of stem cells.

This finally increases the possibility of destroying the tissue regeneration mechanism. In particular, in bone marrow transplantation for leukemia, etc., the transplanted HSCs must undergo hematopoietic regeneration associated with active proliferative response. This causes a significant burden. Therefore, in order to establish safer and more effective regenerative medicine techniques, it is important to establish a method that can draw out the maximum tissue regeneration potential of stem cells, while as much as possible minimizing the stress caused by the regeneration response of stem cells, and maintaining stem-cell function for a long period of time.

Further, for radical treatment of tumors, it is necessary to transfer tumor stem cells in the resting phase, which react poorly to antitumor agents, to the mitotic phase, thereby increasing the sensitivity of the cells to antitumor agents.

Plasminogen activator inhibitor-1 (hereinafter, "PAI-1") is a serine protease inhibitor that specifically inhibits tissue plasminogen activator (hereinafter, "tPA") and urokinase-type plasminogen activator (hereinafter, "uPA"). PAI-1 suppresses plasmin production and inhibits fibrin degradation. Based on tertiary structural differences, PAI-1 is present in an active form that shows PA inhibitory activity and in a latent form that shows no PA inhibitory activity. In plasma, PAI-1 is known to be typically present in a concentration of 20 ng/mL, and produced in hepatocytes, megakaryocytes, and lipocytes in addition to vascular endothelial cells, which are the primary PAI-1 producing cells.

PAI-1 is an acute-phase protein and is thought to be one of the factors that cause ischemic organ dysfunctions in sepsis and disseminated intravascular coagulation syndrome (DIC) through accelerated production due to various cytokines and growth factors. Further, genetic polymorphism due to single-base substitutions in the PAI-1 gene promoter is known, and it has been revealed that plasma PAI-1 concentration increases as a result of such genetic polymorphism.

It has been widely studied and reported that PAI-1 is deeply associated with and acts on renal diseases, such as diabetic nephropathy, chronic kidney disease (CKD), nephrotic syndrome, postrenal renal failure, and pyelonephritis (NPL 1 to NPL 5). In addition, PAI-1 is considered to be associated with the formation and development of pathological conditions of various diseases, such as various thromboses, cancer, diabetes, ocular diseases such as glaucoma and retinopathy, polycystic ovary syndrome, radiation injuries, alopecia (baldness), splenohepatomegaly, and arteriosclerosis (NPL 6 to NPL 11). Further, PAI-1 is also considered to be associated with the control of the diurnal rhythm, which is presumably involved in the formation of vascular endothelial cells and the occurrence of events such as cerebral infarction and myocardial infarction (NPL 12 to NPL 14). For this reason, a compound that inhibits PAI-1 activity is useful as a preventive and treatment agent for various diseases such as thrombosis, cancer, diabetes mellitus, diabetic complications, various kidney diseases, ocular diseases such as glaucoma and retinopathy, polycystic ovary syndrome, alopecia, bone-marrow regeneration, splenomegaly due to extramedullary hematopoiesis, amyloidosis, and arteriosclerosis (NPL 15 and NPL 16). In particular, NPL 14 reports that PAI-1 promotes angiogenesis in the retina, and a PAI-1 inhibitor is therefore considered to be useful as an agent for preventing and treating retinopathy and various other diseases that occur in association with angiogenesis. Further, NPL 17 states that a low-molecular-weight PAI-1 inhibitor inhibits differentiation of adipose cells, thereby inhibiting the development of diet-induced obesity. Therefore, a PAI-1 inhibitor is presumably effective for preventing and treating obesity.

Tissue fibril formation occurs in many tissues and organs such as the lungs, heart, blood vessels, liver, and kidneys. A report has disclosed that the progression of pulmonary fibrosis can be suppressed by the administration of a PA or PAI-1 inhibitor to activate the fibrinolysis system (NPL 18). Therefore, a PAI-1 inhibitor is known to be effective for treating tissue fibrosis, in particular pulmonary fibrosis (NPL 16, NPL 19, and NPL 20). It was recently discovered that the decomposition of A (can be promoted by inhibiting PAI-1; this finding suggests that a PAI-1 inhibitor may be usable as a drug for treating Alzheimer's disease (NPL 21).

However, it was not known that a PAI-1 inhibitor acts on stem cells or a microenvironment called "niche" to activate the stem cells.

CITATION LIST

Non-Patent Literature

NPL 1: Takashi Oda et al., PAI-1 deficiency attenuates the fibrogenic response to ureteral obstruction. Kidney International, Vol. 30 (2001), pp. 587-596

NPL 2: Shunya Matsuo et al., Multifunctionality of PAI-1 in fibrogenesis: Evidence from obstructive nephropathy in PAI-1-overexpressing mice. Kidney International, Vol. 67 (2005), pp. 2221-2238

NPL 3: Y Huang et al., Noninhibitory PAI-1 enhances plasmin-mediated matrix degradation both in vitro and in experimental nephritis. Kidney International (2006) 70, 515-522

NPL 4: Allison A. et al., Plasminogen Activator Inhibitor-1 in Chronic Kidney Disease: Evidence and Mechanisms of Action. J Am Soc Nephrol 17: 2999-3012, 2006

NPL 5: Joris J T H Roelofs et al., Plasminogen activator inhibitor-1 regulates neutrophil influx during acute pyelonephritis. Kidney International, Vol. 75 (2009), pp. 52-59

NPL 6: Michelle K. et al., Plasminogen activator inhibitor-1 and tumour growth, invasion, and metastasis. Thromb Haemost 2004; 91: 438-49

NPL 7: Dan J, Belyea D, et al., Plasminogen activator inhibitor-1 in the aqueous humor of patients with and without glaucoma. Arch Ophthalmol. 2005 February; 123(2):220-4.

NPL 8: Anupam Basu et al., Plasminogen Activator Inhibitor-1 (PAI-1) Facilitates Retinal Angiogenesis in a Model of Oxygen-Induced Retinopathy IOVS, October 2009, Vol. 50, No. 10, 4971-4981

NPL 9: Fabien Milliat et al., Essential Role of Plasminogen Activator Inhibitor Type-1 in Radiation Enteropathy. The American Journal of Pathology, Vol. 172, No. 3, March 2008, 691-701

NPL 10: M. EREN et al., Reactive site-dependent phenotypic alterations in plasminogen activator inhibitor-1 transgenic mice. Journal of Thrombosis and Haemostasis, 2007, 5: 1500-1508

NPL 11: Jessica K Devin et al., Transgenic overexpression of plasminogen activator inhibitor-1 promotes the development of polycystic ovarian changes in female mice. Journal of Molecular Endocrinology (2007) 39, 9-16

NPL 12: Yuko Suzuki et al., Unique secretory dynamics of tissue plasminogen activator and its modulation by plasminogen activator inhibitor-1 in vascular endothelial cells. Blood, January 2009, Volume 113, Number 2, 470-478

NPL 13: Koji Maemura et al., Circadian Rhythms in the CNS and Peripheral Clock Disorders: Role of the Biological Clock in Cardiovascular Diseases. J Pharmacol Sci 103, 134-138 (2007)

NPL 14: John A. Schoenhard et al., Plasminogen activator inhibitor-1 has a circadian rhythm in blind individuals. Thromb Haemost 2007; 98: 479-481

NPL 15: Egelund R et al., J. Biol. Chem., 276, 13077-13086, 2001

NPL 16: Douglas E. Vaughan et al., PAI-1 Antagonists: Predictable Indications and Unconventional Applications. Current Drug Targets, 2007, 8, 962-970

NPL 17: David L. Crandall et al., Modulation of Adipose Tissue Development by Pharmacological Inhibition of PAI-1. Arterioscler. Thromb. Vasc. Biol. 2006; 26; 2209-2215

NPL 18: D T Eitzman et al., J. Clin. Invest. 97, 232-237, 1996

NPL 19: Noboru Hattori et al., Bleomycin-induced pulmonary fibrosis in fibrinogen-null mice. J. Clin. Invest. 106:1341-1350 (2000).

NPL 20: Hisashi Kosaka et al., Interferon-γ is a therapeutic target molecule for prevention of postoperative adhesion formation. Nature Medicine, Volume 14, No. 4, April 2008, 437-441

NPL 21: Jacobsen J S et al., Proc Natl Acad Sci USA, 105(25), 8754-9, 2008 Jun. 16

SUMMARY OF INVENTION

Technical Problem

In the normal state, hematopoietic stem cells (HSCs) are supported by a special bone marrow microenvironment called a "niche," which is constructed by non-hematopoietic system cells. The reduction in stem-cell activity caused by division and growth of HSCs is prevented by keeping HSCs in the resting phase. Moreover, HSCs are controlled to supply progenitor cells, as necessary, to regulate the homeostasis of the hematopoietic system.

An object of the present invention is to provide a use of a PAI-1 inhibitor as a stem-cell protecting drug or hematopoietic disorder improving agent, in an effort for establishment of a stem-cell control method based on this niche system, and for application to regenerative medicine. Another object of the present invention is to provide radical treatment of tumors targeting tumor stem cells. Specifically, an object of the present invention is to provide an agent for enhancing the antitumor effect of antitumor agents, and a tumor chemotherapy agent, both of which can increase the sensitivity of tumor stem cells to antitumor agents by transiting the cells in the resting phase to the mitotic phase.

Solution to Problem

It is known that radiation and administration of an antitumor agent as a pretreatment of stem-cell transplantation induces niche damage, such as breakage of the bone marrow microvascular network, and suppresses hematopoietic regenerative response. This is a major factor of hematopoietic disorders. Regarding the niche damage, the present inventors transplanted bone marrow or bone marrow stem cells while administering a PAI-1 inhibitor, and then analyzed the influence of the PAI-1 inhibitor on hematopoietic regeneration. Specifically, the present inventors examined the effect of the PAI-1 inhibitor on the maintenance of stem-cell activity during HSC growth in the transplantation recovery phase and multiple successive transplantations. As a result, the PAI-1 inhibitor had a stem-cell protecting effect, such as facilitation of the amplification of hematopoietic stem cells, and achieved early recovery of hematopoietic system cells reduced due to hematopoietic disorders. This result confirmed that the PAI-1 inhibitor also effectively acts during the hematopoietic recovery in the early stage of HSC transplantation.

Moreover, the present inventors found that the PAI-1 inhibitor has the effect of not only activating normal stem cells to enhance their differentiation potency and self-renewal capacity, but also activating tumor stem cells to transit tumor stem cells in the resting phase to the mitotic phase, and they confirmed that the combined use of the PAI-1 inhibitor with an antitumor agent enables radical treatment of tumors targeting tumor stem cells, specifically suppression of tumor recurrence and metastasis, and improvement of the prognosis of tumor treatment.

The present invention has been completed based on these findings. The present invention characteristically has the following structures.

(i-a-1)

An agent for controlling a tumor stem cell comprising a compound having plasminogen activator inhibitor-1 (PAI-1) inhibitory activity as an active ingredient.

(i-a-2)

An agent for enhancing the antitumor effect of an antitumor agent, comprising the agent for controlling a tumor stem cell according to (i-a-1) as an active ingredient.

(i-a-3)

The agent for enhancing the antitumor effect of an antitumor agent according to (i-a-2), wherein the compound having PAI-1 inhibitory activity is a compound represented by Formula (I) below:

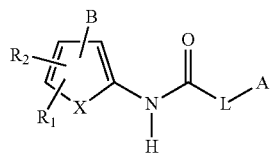

(I)

wherein $R_1$ and $R_2$ are the same or different, and each represents hydrogen, halogen, $C_{1-6}$-alkyl, $C_{3-8}$-cycloalkyl, $C_{3-8}$-cycloalkyl-$C_{1-6}$-alkyl, $C_{3-8}$-cycloalkenyl, $C_{2-6}$-alkynyl, $C_{3-8}$-cycloalkyl-$C_{2-6}$-alkynyl, substituted or unsubstituted aryl, or substituted or unsubstituted 5- to 6-membered ring heteroaryl; $R_1$ and $R_2$ are preferably hydrogen, halogen, $C_{1-6}$-alkyl, aryl optionally having one or two substituents, or 5- to 6-membered ring heteroaryl optionally having one or two substituents, provided that $R_1$ and $R_2$ are not hydrogen at the same time;

X is vinylene (—CH=CH—);

A is a group represented by Formula (I-1) below:

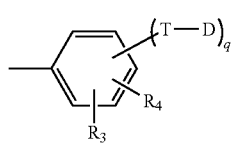

(I-1)

in Formula (I-1), q is an integer of 1;

$R_3$ and $R_4$ are the same or different, and each represents hydrogen, substituted or unsubstituted $C_{1-6}$ alkyl, or $CF_3$;

T is a single bond, substituted or unsubstituted $C_{1-3}$ alkylene, oxygen, —CO—, —O—$C_{1-3}$-alkylene, or $C_{2-6}$ alkynylene;

D is substituted or unsubstituted aryl, benzo-fused heteroaryl, or heteroaryl; substituted or unsubstituted $C_{3-8}$ cycloalkyl or $C_{3-8}$ heterocycloalkyl; substituted or unsubstituted $C_{3-8}$ cycloalkenyl or $C_{3-8}$ heterocycloalkenyl; or adamanthyl; D is preferably aryl, benzo-fused heteroaryl, or heteroaryl, all of which optionally have one or two substituents;

L is a single bond, —[(CH$_2$)$_M$—O—(CH$_2$)$_N$]$_Q$—CONH— (wherein M and N are the same or different, and each represents an integer of 1 to 6, and Q represents 0 or 1), substituted or unsubstituted $C_{1-6}$ alkylene (some carbon atoms in the alkylene optionally form cycloalkyl), substituted or unsubstituted $C_{1-6}$ alkylene-O— (some carbon atoms in the alkylene optionally form cycloalkyl), substituted or unsubstituted $C_{1-6}$ alkylene-NHCO— (in the alkylene-NHCO—, some carbon atoms in the alkylene optionally form cycloalkyl), substituted or unsubstituted $C_{1-6}$ alkylene-NH— (in the alkylene-NH—, some carbon atoms in the alkylene optionally form cycloalkyl), substituted or unsubstituted $C_{2-6}$ alkenylene, substituted or unsubstituted $C_{2-6}$ alkynylene, —CO—, —NH—, 1,4-piperazidinyl, $C_{1-6}$ alkylene-1,4-piperazidinyl, or adamantylene;

B is COOR$_9$ [wherein R$_9$ represents hydrogen or a group converted to hydrogen in vivo, which is selected from the group consisting of $C_{1-6}$-alkyl, aryl, aralkyl, a group represented by —CH(R$_{10}$)—O—CO—R$_{11}$ or —CH(R$_{10}$)—O—CO—OR$_{11}$ (wherein R$_{10}$ is $C_{1-6}$-alkyl or $C_{3-8}$-cycloalkyl, and R$_{11}$ and R$_{12}$ are each $C_{1-6}$-alkyl), and (5-alkyl-2-oxo-1,3-dioxolen-4-yl)methyl represented by Formula (I-2) below:

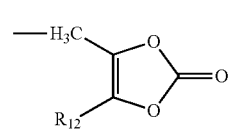

(I-2)

wherein R$_{12}$ is $C_{1-6}$ alkyl]; or a heterocyclic group represented by any of Formulae (I-3) to (I-5) below:

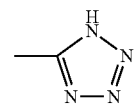

(I-3)

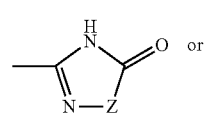

(I-4) or

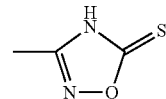

(I-5)

in the heterocyclic group represented by Formula (I-4) above, Z represents sulfur or oxygen.

(i-a-4)

The agent for enhancing the antitumor effect of an antitumor agent according to (i-a-3), wherein the compound is a compound of Formula (I) wherein
B is located at the ortho position of the benzene ring to which imino is bound; and
T is a single bond.

(i-a-5)

The agent for enhancing the antitumor effect of an antitumor agent according to (i-a-3) or (i-a-4), wherein the compound is a compound of Formula (I) wherein
L is a single bond, —CONH— (when Q is 0), or alkyleneoxyalkylene-CONH— (when Q is 1); and
D is substituted or unsubstituted aryl, preferably phenyl; heteroaryl, preferably furyl; or benzo-fused heteroaryl, preferably isoquinolyl or quinolyl, more preferably isoquinolyl.

(i-a-6)

The agent for enhancing the antitumor effect of an antitumor agent according to any one of (i-a-3) to (i-a-5), wherein the heteroaryl is a group other than pyrazolyl.

(i-a-7)

The agent for enhancing the antitumor effect of an antitumor agent according to any one of (i-a-3) to (i-a-6), wherein the compound is a compound of Formula (I) wherein $R_1$ is halogen and is located at the para position of the benzene ring to which imino is bound, and $R_2$ is hydrogen and is located at the meta position of the benzene ring to which imino is bound.

(i-a-8)

The agent for enhancing the antitumor effect of an antitumor agent according to (i-a-3), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]carbonyl}amino)benzoate, and 5-chloro-2-{[(2-{[3-(furan-2-yl)phenyl]amino}-2-oxoethoxy)acetyl]amino}benzoic acid.

(i-a-9)

The agent for enhancing the antitumor effect of an antitumor agent according to any one of (i-a-2) to (i-a-8), which is used in combination with an antitumor agent.

(i-a-10)

The agent for enhancing the antitumor effect of an antitumor agent according to (i-a-9), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

(i-a-11)

The agent for controlling a tumor stem cell according to (i-a-1), wherein the compound having PAI-1 inhibitory activity is a compound represented by Formula (I) below:

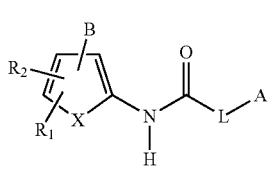

wherein $R_1$, $R_2$, B, L, and A are as defined in (i-a-3).

(i-a-12)

The agent for controlling a tumor stem cell according to (i-a-11), wherein the compound is a compound of Formula (I) wherein
B is located at the ortho position of the benzene ring to which imino is bound; and
T is a single bond.

(i-a-13)

The agent for controlling a tumor stem cell according to (i-a-11) or (i-a-12), wherein the compound is a compound of Formula (I) wherein
L is a single bond, —CONH— (when Q is 0), or alkyleneoxyalkylene-CONH— (when Q is 1); and
D is substituted or unsubstituted aryl, preferably phenyl; heteroaryl, preferably furyl; or benzo-fused heteroaryl, preferably isoquinolyl or quinolyl, more preferably isoquinolyl.

(i-a-14)

The agent for controlling a tumor stem cell according to any one of (i-a-11) to (i-a-13), wherein the heteroaryl is a group other than pyrazolyl.

(i-a-15)

The agent for controlling a tumor stem cell according to any one of (i-a-11) to (i-a-14), wherein the compound is a compound of Formula (I) wherein $R_1$ is halogen and is located at the para position of the benzene ring to which imino is bound, and $R_2$ is hydrogen and is located at the meta position of the benzene ring to which imino is bound.

(i-a-16)

The agent for controlling a tumor stem cell according to (i-a-11), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]carbonyl}amino)benzoate, and 5-chloro-2-{[(2-{[3-(furan-2-yl)phenyl]amino}-2-oxoethoxy)acetyl]amino}benzoic acid.

(i-a-17)

The agent for controlling a tumor stem cell according to any one of (i-a-11) to (i-a-16), which is used in combination with an antitumor agent.

(i-a-18)

The agent for controlling a tumor stem cell according to (i-a-17), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

(i-a-19)

A composition for tumor chemotherapy comprising:
the agent for enhancing the antitumor effect of an antitumor agent according to any one of (i-a-2) to (i-a-8) and an antitumor agent; or
the agent for controlling a tumor stem cell according to (i-a-1) or any one of (i-a-11) to (i-a-16) and an antitumor agent.

(i-a-20)

The composition for tumor chemotherapy according to (i-a-20), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

(i-a-21)
The composition for tumor chemotherapy according to (i-a-19) or (i-a-20), which is an agent for improving the prognosis of tumor treatment.
(i-a-22)
The agent for enhancing the antitumor effect of an antitumor agent according to any one of (i-a-2) to (i-a-10), wherein the antitumor effect is an inhibitory effect on tumor recurrence or metastasis.
(i-a-23)
The agent for enhancing the antitumor effect of an antitumor agent according to any one of (i-a-2) to (i-a-10), which is used to treat a hematopoietic tumor or solid tumor, or to prevent recurrence or metastasis.
(i-a-24)
The agent for enhancing the antitumor effect of an antitumor agent according to any one of (i-a-2) to (i-a-10), which is used to improve the prognosis of treatment of a hematopoietic tumor or solid tumor.
(i-a-25)
The agent for controlling a tumor stem cell according to (i-a-1) or the agent for enhancing the antitumor effect of an antitumor agent according to (i-a-2), wherein the compound having PAI-1 inhibitory activity is a compound represented by any of Formulae (I) to (III) described later, a pharmacologically acceptable salt or ester thereof, or a hydrate thereof.
(i-b-1)
A compound having PAI-1 inhibitory activity for use in the control of a tumor stem cell, enhancement of the antitumor effect of an antitumor agent, or treatment of a tumor by being used in combination with an antitumor agent.
(i-b-2)
The compound according to (i-b-1), wherein the compound having PAI-1 inhibitory activity is a compound represented by Formula (I) below:

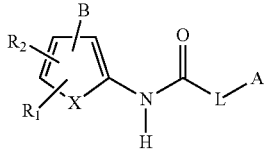

wherein $R_1$, $R_2$, B, L, and A are as defined in Formula (I) of (i-a-3).
(i-b-3)
The compound according to (i-b-2), wherein the compound is a compound of Formula (I) wherein
  B is located at the ortho position of the benzene ring to which imino is bound; and
  T is a single bond.
(i-b-4)
The compound according to (i-b-2) or (i-b-3), wherein the compound is a compound of Formula (I) wherein
  L is a single bond, —CONH—, or alkyleneoxyalkylene-CONH—; and
  D is substituted or unsubstituted aryl, preferably phenyl; heteroaryl, preferably furyl; or benzo-fused heteroaryl, preferably isoquinolyl or quinolyl, more preferably isoquinolyl.
(i-b-5)
The compound according to any one of (i-b-2) to (i-b-4), wherein the heteroaryl is a group other than pyrazolyl.
(i-b-6)
The compound according to any one of (i-b-2) to (i-b-5), wherein the compound is a compound of Formula (I) wherein $R_1$ is halogen and is located at the para position of the benzene ring to which imino is bound, and $R_2$ is hydrogen and is located at the meta position of the benzene ring to which imino is bound.
(i-b-7)
The compound according to (i-b-1), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]carbonyl}amino)benzoate, and 5-chloro-2-{[(2-{[3-(furan-2-yl)phenyl]amino}-2-oxoethoxy)acetyl]amino}benzoic acid.
(i-b-8)
The compound according to any one of (i-b-1) to (i-b-7), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.
(i-b-9)
A composition comprising a compound having PAI-1 inhibitory activity and an antitumor agent, the composition being used for treatment of a tumor.
(i-b-10)
The composition according to (i-b-9), wherein the compound having PAI-1 inhibitory activity is a compound represented by Formula (I) below:

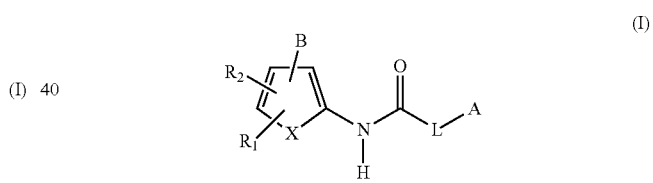

wherein $R_1$, $R_2$, B, L, and A are as defined in Formula (I) of (i-a-3).
(i-b-11)
The composition according to (i-b-10), wherein the compound is a compound of Formula (I) wherein
  B is located at the ortho position of the benzene ring to which imino is bound; and
  T is a single bond.
(i-b-12)
The composition according to (i-b-10) or (i-b-11), wherein the compound is a compound of Formula (I) wherein
  L is a single bond, —CONH—, or alkyleneoxyalkylene-CONH—; and
  D is substituted or unsubstituted aryl, preferably phenyl; heteroaryl, preferably furyl; or benzo-fused heteroaryl, preferably isoquinolyl or quinolyl, more preferably isoquinolyl.
(i-b-13)
The composition according to any one of (i-b-10) to (i-b-12), wherein the heteroaryl is a group other than pyrazolyl.

(i-b-14)

The composition according to any one of (i-b-10) to (i-b-13), wherein the compound is a compound of Formula (I) wherein $R_1$ is halogen and is located at the para position of the benzene ring to which imino is bound, and $R_2$ is hydrogen and is located at the meta position of the benzene ring to which imino is bound.

(i-b-15)

The composition according to (i-b-10), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]carbonyl}amino)benzoate, and 5-chloro-2-{[(2-{[3-(furan-2-yl)phenyl]amino}-2-oxoethoxy)acetyl]amino}benzoic acid.

(i-b-15)

The composition according to (i-b-15) or (i-b-14), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

(i-b-16)

A method for activating a tumor stem cell or method for enhancing the antitumor effect of an antitumor agent, comprising the step of administering a compound having PAI-1 inhibitory activity.

(i-b-17)

The method for activating a tumor stem cell or method for enhancing the antitumor effect of an antitumor agent according to (i-b-16), wherein the compound having PAI-1 inhibitory activity is a compound represented by Formula (I) below:

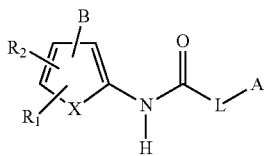

wherein $R_1$, $R_2$, B, L, and A are as defined in Formula (I) of (i-a-3).

(i-b-18)

The method according to (i-b-17), wherein the compound is a compound of Formula (I) wherein
B is located at the ortho position of the benzene ring to which imino is bound; and
T is a single bond.

(i-b-19)

The method according to (i-b-17) or (i-b-18), wherein the compound is a compound of Formula (I) wherein
L is a single bond, —CONH—, or alkyleneoxyalkylene-CONH—; and
D is substituted or unsubstituted aryl, preferably phenyl; heteroaryl, preferably furyl; or benzo-fused heteroaryl, preferably isoquinolyl or quinolyl, more preferably isoquinolyl.

(i-b-20)

The method according to any one of (i-b-17) to (i-b-19), wherein the heteroaryl is a group other than pyrazolyl.

(i-b-21)

The method according to any one of (i-b-17) to (i-b-20), wherein the compound is a compound of Formula (I) wherein $R_1$ is halogen and is located at the para position of the benzene ring to which imino is bound, and $R_2$ is hydrogen and is located at the meta position of the benzene ring to which imino is bound.

(i-b-22)

The method for activating a tumor stem cell or method for enhancing the antitumor effect of an antitumor agent according to (i-b-16), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]carbonyl}amino)benzoate, and 5-chloro-2-{[(2-{[3-(furan-2-yl)phenyl]amino}-2-oxoethoxy)acetyl]amino}benzoic acid.

(i-b-23)

The method for activating a tumor stem cell or method for enhancing the antitumor effect of an antitumor agent according to any one of (i-b-16) to (i-b-22), further comprising the step of administering an antitumor agent.

(i-b-24)

The method for activating a tumor stem cell or method for enhancing the antitumor effect of an antitumor agent according to (i-b-23), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

(i-c-1)

A method for treating a tumor of a patient suffering from a tumor, the method comprising the step of:
administering a compound having PAI-1 inhibitory activity to the patient suffering from a tumor in combination or alternation with an antitumor agent.

(i-c-2)

The method according to (i-c-1), wherein the compound having PAI-1 inhibitory activity is a compound represented by Formula (I) below:

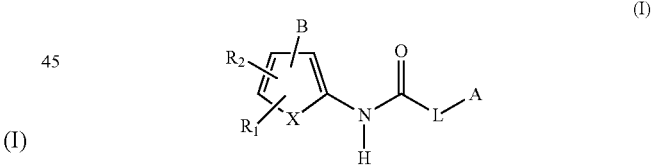

wherein $R_1$, $R_2$, B, L, and A are as defined in Formula (I) of (i-a-3).

(i-c-3)

The method according to (i-c-2), wherein the compound is a compound of Formula (I) wherein
B is located at the ortho position of the benzene ring to which imino is bound; and
T is a single bond.

(i-c-4)

The method according to (i-c-2) or (i-c-3), wherein the compound is a compound of Formula (I) wherein
L is a single bond, —CONH—, or alkyleneoxyalkylene-CONH—; and
D is substituted or unsubstituted aryl, preferably phenyl; heteroaryl, preferably furyl; or benzo-fused heteroaryl, preferably isoquinolyl or quinolyl, more preferably isoquinolyl.

(i-c-5)

The method according to any one of (i-c-2) to (i-c-4), wherein the heteroaryl is a group other than pyrazolyl.

(i-c-6)

The method according to any one of (i-c-2) to (i-c-5), wherein the compound is a compound of Formula (I) wherein $R_1$ is halogen and is located at the para position of the benzene ring to which imino is bound, and $R_2$ is hydrogen and is located at the meta position of the benzene ring to which imino is bound.

(i-c-7)

The method according to (i-c-2), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]carbonyl}amino)benzoate, and 5-chloro-2-{[(2-{[3-(furan-2-yl)phenyl]amino}-2-oxoethoxy)acetyl]amino}benzoic acid.

(i-c-8)

The method according to (i-c-1) or (i-c-7), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

(i-d-1)

Use of a compound having PAI-1 inhibitory activity for preparation of an agent for controlling a tumor stem cell.

(i-d-2)

The use according to (i-d-1), wherein the compound having PAI-1 inhibitory activity is a compound represented by Formula (I) below:

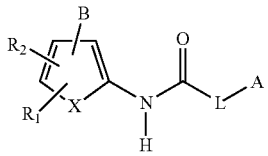

wherein $R_1$, $R_2$, B, L, and A are as defined in Formula (I) of (i-a-3).

(i-d-3)

The use according to (i-d-2), wherein the compound is a compound of Formula (I) wherein B is located at the ortho position of the benzene ring to which imino is bound; and T is a single bond.

(i-d-4)

The use according to (i-d-2) or (i-d-3), wherein the compound is a compound of Formula (I) wherein L is a single bond, —CONH—, or alkyleneoxyalkylene-CONH—; and D is substituted or unsubstituted aryl, preferably phenyl; heteroaryl, preferably furyl; or benzo-fused heteroaryl, preferably isoquinolyl or quinolyl, more preferably isoquinolyl.

(i-d-5)

The use according to any one of (i-d-2) to (i-d-4), wherein the heteroaryl is a group other than pyrazolyl.

(i-d-6)

The use according to any one of (i-d-2) to (i-d-5), wherein the compound is a compound of Formula (I) wherein $R_1$ is halogen and is located at the para position of the benzene ring to which imino is bound, and $R_2$ is hydrogen and is located at the meta position of the benzene ring to which imino is bound.

(i-d-7)

The use according to (i-d-1), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]carbonyl}amino)benzoate, and 5-chloro-2-{[(2-{[3-(furan-2-yl)phenyl]amino}-2-oxoethoxy)acetyl]amino}benzoic acid.

(i-d-8)

Use of a compound having PAI-1 inhibitory activity for preparation of a composition for tumor chemotherapy comprising an antitumor agent.

(i-d-9)

The use according to (i-d-8), wherein the compound having PAI-1 inhibitory activity is a compound represented by Formula (I) below:

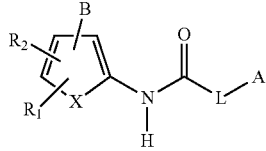

(i-d-10)

The use according to (i-d-9), wherein the compound is a compound of Formula (I) wherein B is located at the ortho position of the benzene ring to which imino is bound; and T is a single bond.

(i-d-11)

The use according to (i-d-9) or (i-d-10), wherein the compound is a compound of Formula (I) wherein L is a single bond, —CONH—, or alkyleneoxyalkylene-CONH—; and D is substituted or unsubstituted aryl, preferably phenyl; heteroaryl, preferably furyl; or benzo-fused heteroaryl, preferably isoquinolyl or quinolyl, more preferably isoquinolyl.

(i-d-12)

The use according to any one of (i-d-9) to (i-d-11), wherein the heteroaryl is a group other than pyrazolyl.

(i-d-13)

The use according to any one of (i-d-9) to (i-d-12), wherein the compound is a compound of Formula (I) wherein $R_1$ is halogen and is located at the para position of the benzene ring to which imino is bound, and $R_2$ is hydrogen and is located at the meta position of the benzene ring to which imino is bound.

(i-d-14)

The use according to (i-d-8), wherein the compound having PAI-1 inhibitory activity is at least one member selected from the group consisting of 5-chloro-2-{[{[3-(furan-3-yl)phenyl]amino}(oxo)acetyl]amino}benzoic acid, 2-[(biphenyl-3-ylcarbonyl)amino]-5-chlorobenzoic acid, sodium 5-chloro-2-({[3-(quinolin-8-yl)phenyl]

carbonyl}amino)benzoate, and 5-chloro-2-{[(2-{[3-(furan-2-yl)phenyl]amino}-2-oxoethoxy)acetyl]amino}benzoic acid.
(i-d-15)

The use according to any one of (i-d-8) to (i-d-14), wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

(ii) Agent for Activating a Stem Cell
(ii-1)

An agent for activating a stem cell comprising a PAI-1 inhibitor as an active ingredient.
(ii-2)

The agent for activating a stem cell according to (ii-1), which is used to activate a stem cell, and enhance the differentiation and/or self-renewal capacity of the stem cell.
(ii-3)

The agent for activating a stem cell according to (ii-1) or (ii-2), wherein the stem cell is a normal cell or a tumor cell.
(ii-4)

The agent for activating a stem cell according to any one of (ii-1) to (ii-3), wherein the stem cell is a hematopoietic stem cell.
(ii-5)

The agent for activating a stem cell according to any one of (ii-1) to (ii-4), which is used as a stem-cell protecting drug or self-renewal capacity enhancer for normal hematopoietic stem cells.
(I-6)

The agent for activating a stem cell according to any one of (ii-1) to (ii-4), which is used to transit a tumor stem cell from the resting phase (G0 phase in the cell cycle) to the mitotic phase (G1 phase to M phase in the cell cycle).
(ii-7)

The agent for activating a stem cell according to any one of (ii-1) to (ii-6), wherein the PAI-1 inhibitor is a compound represented by any of Formulae (I) to (IV) described later, a pharmacologically acceptable salt or ester thereof, or a hydrate thereof.

(iii) Stem-Cell Protecting Drug or Hematopoietic Disorder Improving Agent

A stem-cell protecting drug or hematopoietic disorder improving agent, comprising a PAI-1 inhibitor as an active ingredient.
(iii-2)

The stem-cell protecting drug or hematopoietic disorder improving agent according to (iii-1), wherein the hematopoietic disorder is a secondary hematopoietic disorder caused by radiation or chemotherapy.
(iii-3)

The stem-cell protecting drug or hematopoietic disorder improving agent according to (iii-1) or (iii-2), which is administered to a patient with a hematopoietic disorder or a patient who may develop a hematopoietic disorder, during transplantation of hematopoietic stem cells, hematopoietic progenitor cells, or bone marrow tissue containing at least one of these cells, or in parallel with (before or after) transplantation of these cells or the tissue.
(iii-4)

The stem-cell protecting drug or hematopoietic disorder improving agent according to any one of (iii-1) to (iii-3), wherein the PAI-1 inhibitor is a compound represented by any of Formulae (I) to (III) described later, a pharmacologically acceptable salt or ester thereof, or a hydrate thereof.

Advantageous Effects of Invention

According to the present invention, cancer cells can be more effectively killed by the combined use of an antitumor agent with a plasminogen activator inhibitor-1 inhibitor, compared with conventional antitumor treatment using an antitumor agent. Further, tumor prognosis can be improved.

Moreover, when plasminogen activator inhibitor-1 inhibitor is administered, normal stem cells and tumor stem cells can be stimulated to cause stem cells and tumor stem cells in the resting phase to divide. Furthermore, the divided stem cells can be differentiated into mature cells.

BRIEF DESCRIPTION OF DRAWINGS

FIG. 4A shows a schematic diagram of the experiment procedure of Experimental Example 4 (A), and FIGS. 4B to 4E, and 4G show the track records of the plasminogen level (ng/mL) (B), active tissue-type plasminogen activator (tPA) level (C), cKit ligand level (D), and total level of MMP-9 (matrix metalloprotein-9) (E), all of which were in the plasma collected on days 2, 7, and 21 from bone-marrow transplantation, and white blood cell count (×10E3 cell/μL) in the peripheral blood (G) collected on days 2, 7, and 21 from bone-marrow transplantation (each group: n=6). FIG. 4F shows the track record of the survival rate of mice after bone-marrow transplantation (each group: n=15) (F). In the figures, Com-a indicates compound a.

In FIG. 11A, n=15 for each group. In FIG. 11A, the p value of the log-rank test is 0.0278, and * is $p<0.05$. In FIGS. 11C and 11D, n=6 for each group. In FIGS. 11C and 11D, * and ** indicate the significant difference versus the control group, * is $p<0.05$, and ** is $p<0.001$. # and ## indicate the significant difference versus the tPA-administered group, # is $p<0.05$, and ## is $p<0.001$. FIG. 11B shows the survival curve of the control group, tPA-administered group, and compound a-administered group to which a lethal dose of 5-FU was administered and from which bone marrow was removed. In FIG. 11B, n=15 for each group. In FIG. 11B, the p value of the log-rank test is 0.0190, * indicates $p<0.05$. In every graph, the control group, tPA-administered group, and compound a-administered group are indicated by (-○-), (-|-), and (-■-), respectively.

FIG. 13C shows the proportion of the cells in the $G_0/G_1$ phase, S phase, and $G_2$-M phase by BrdU labeling (C). FIG. 13D shows the frequency of apoptosis cells after bone-marrow transplantation. In the figures, * indicates $p<0.05$. 6 mice were used for each group.

FIG. 14F shows the chimerism of donor-derived bone marrow hematopoietic cells of mice of the control (vehicle) group, tPA-administered group, and PAI-1 inhibitor (compound a)-administered group 12 weeks after the second bone-marrow transplantation. In the figures, *, , and * indicate the significant differences versus the control group. * indicates p<0.05,  indicates p<0.001, and * indicates p<10%[5]. #, ##, ### indicate the significant differences versus the tPA-administered group. # indicates p<0.05, ## indicates p<0.001, and ### indicates p<10%[5]. FIG. 14G shows the FACS analysis of the chimerism (frequency of Ly5.1 positive bone-marrow mononucleic cells) of the control (vehicle) group and PAI-1 inhibitor (compound a)-administered group that were transplanted with bone-marrow mononucleic cells diluted to the limit such that Ly5.1 positive bone-marrow mononucleic cell count was 2×10E3, 6×10E3, 2×10E4, and 6×10E4. FIG. 14H shows the statistical analysis of bone marrow 12 weeks after successive transplantation that was collected from the control (vehicle) group and PAI-1 inhibitor (compound a)-administered group. The number of mice having a frequency of 0.05% or more of Ly5.1 positive cells after successive transplantation was counted. 5 mice were used for each group. In the figures, * indicates the significant differences versus the control group, and * is p<0.05.

FIG. 15A shows the test drug administration protocol followed after CML cell inoculation to chronic myelogenous leukemia model mice. FIG. 15B shows the survival rate of the placebo group (○), imatinib group (▲), and imatinib+compound a (Com-a) group (■). FIG. 15C shows the distribution of 32Dp210-GFP positive cells in bone marrow and spleen obtained by FACSCAN analysis. FIG. 15D shows the frequency of 32Dp210-GFP positive cells in the bone marrow and spleen. The black bar shows the frequency of GFP positive cells in nucleated cells in the bone marrow, and the gray bar shows the frequency of GFP positive cells in nucleated cells in the spleen.

FIG. 16 shows the survival rate of the placebo group (○), imatinib group (▲), and imatinib+compound c (Com-c) group (■).

FIG. 18 shows the survival rate of the placebo group (○), IM group (Δ), IM group+anti-G-CSF group (□), IM+compound c group (▲), and IM+compound c group+anti-G-CSF group (■).

in FIG. 19, "immediately before antitumor agent treatment"), immediately after the administration of a test drug (day 14; in FIG. 19, "immediately after antitumor agent treatment"), and 28 days after the start of administration of a test drug (day 36; in FIG. 19, "after 28 days"). In FIG. 19, "Saline," "Imatinib," and "Imatinib+PAI-1 inhibitor" indicate the placebo group, group administered imatinib alone, and imatinib+compound c group, respectively. The fractions in the lower-right-hand corner of the scattergrams correspond to CML cells.

FIG. 20 shows the survival rate of the placebo group (○), compound a (Com-a) group (▽), imatinib group (▲), and imatinib+compound a group (■).

FIG. 21 shows the survival rate of the placebo group (○), imatinib group (□), imatinib+compound d (Com-d) group (■), and imatinib+compound e (Com-e) group (▲).

FIG. 22 shows the change in tumor volume over time after administration of a test drug in the placebo group (solid line), compound c-non-combined group (dashed line), and compound c (Com-c)-combined group (dotted line).

FIG. 23 shows the change in tumor volume over time after administration of a test drug in the placebo group (solid line), compound c-non-combined group (dashed line), and compound c (Com-c)-combined group (dotted line). The unit of the vertical scale in the graph is $mm^3$ (tumor volume).

FIG. 24 shows the change in tumor volume over time after administration of a test drug in the placebo group (solid line), compound d-non-combined group (dashed line), and compound d (Com-d)-combined group (dotted line). The unit of the vertical scale of the graph is $mm^3$ (tumor volume).

FIG. 25 shows the change in tumor volume over time after administration of a test drug in the placebo group (solid line), group administered compound d (Com-d) alone (dashed line), and compound d (Com-d)-combined group (dotted line). The unit of the vertical scale of the graph is $mm^3$ (tumor volume).

FIG. 26B shows the expression level of PAI-1 protein; the photos above show the evaluation of PAI-1 protein expression observed with a fluorescence microscope, and the lower graph shows quantified fluorescence intensity. FIG. 26C shows the expression level of PAI-1 mRNA.

DESCRIPTION OF EMBODIMENTS

I. PAI-1 Inhibitor

Figure 1:
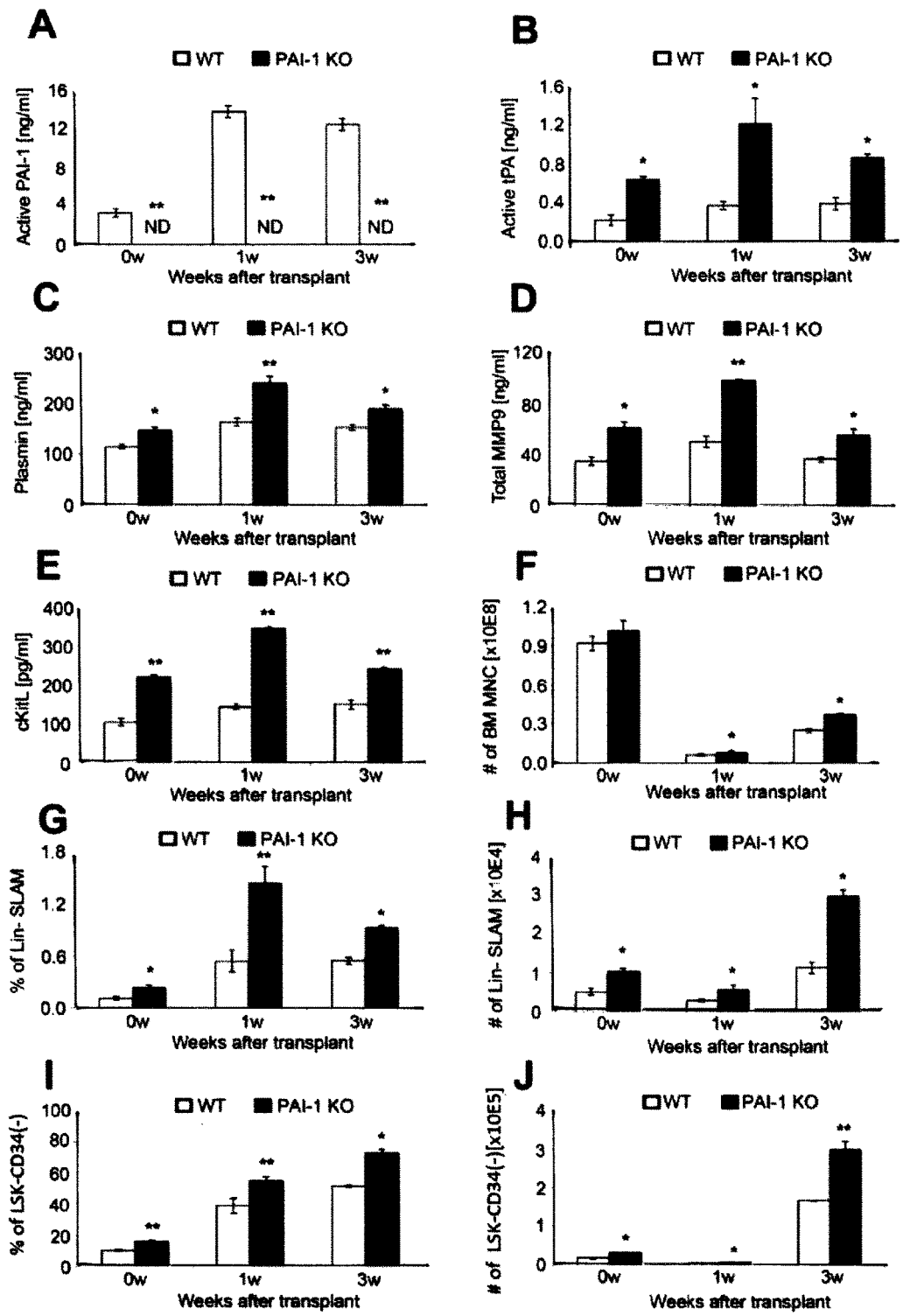
FIGS. 1A to 1J show the active PAI-1 level (A), active tPA (B), plasmin (C), MMP9 (D), cKitL (E), absolute number of bone-marrow mononucleic cells (BM MNC) (F), frequency (%) of donor-derived SLAM (CD150 marker) positive cells (G), absolute number of donor-derived SLAM (CD150 marker) positive cells (H), frequency (%) of LSK-CD34 negative (LSK-CD34(−)) cells (I), and number of LSK-CD34 negative (LSK-CD34(−)) cells (J) in PAI-1-KO mouse recipients that underwent hematopoietic cell transplantation in a hematopoietic regeneration experiment conducted in Experimental Example 1. The black bars indicate PAI-1 KO mouse recipients, and white bars indicate wild-type mouse recipients.

The present invention relates to a novel use of a compound that has an effect of inhibiting plasminogen activator inhibitor-1 (PAI-1) activity, which is collectively referred to as "PAI-1 inhibitor."

The PAI-1 inhibitor targeted by the present invention may be a compound that has an effect of inhibiting PAI-1 activity, and includes not only compounds known as conventionally known PAI-1 inhibitors but also compounds potentially having PAI-1 inhibitory activity.

The PAI-1 inhibitory activity of the compound to be targeted (the target compound) can be evaluated using an in vitro assay system. For example, mentioned as such an in vitro assay system is a method for examining change in PAI-1 activity to t-PA in the presence of the target compound. The change in PAI-1 activity can be examined by setting, as an index, a reaction product produced by the action of t-PA on a substrate. Although there is no limitation, for example, Reference Experiment Examples, described later, show an in vitro assay system for examining change in the PAI-1 activity by setting, as an index, a quantity of p-nitroaniline (reaction product) produced by the action of t-PA on a coloring substrate (S-2288). It can be judged that as the amount of reaction product is less, the t-PA activity is more strongly inhibited, and accordingly the PAI-1 inhibitory activity of the target compound is higher.

The evaluation of PAI-1 inhibitory activity of the target compound can also be carried out by examining the change in formation of a complex of PAI-1 and t-PA (PAI-1/t-PA complex) in the presence of the target compound using, for example, western blotting. In the present invention, it can be judged that as the amount of formation of PAI-1/t-PA complex is smaller (PAI-1/t-PA complex formation inhibition), the PAI-1 inhibitory activity of the target compound is higher.

Specific examples of such a compound having PAI-1 inhibitory activity (PAI-1 inhibitor) include, but are not limited to, (I) the compound represented by Formula (I) in WO2010/113022, which was internationally filed on Mar. 31, 2010 (PCT/IB2010/000731) and internationally published on Oct. 7, 2010; (II) the compound represented by Formula (I) in WO2009/013915, which was internationally filed on Mar. 12, 2008 (PCT/JP2008/054543) and internationally published on Jan. 29, 2009; and (III) the compound represented by Formula (I) in WO2009/123241, which was internationally filed on Mar. 31, 2009 (PCT/JP2009/056755) and internationally published on Oct. 9, 2009.

In the present specification, the compound represented by Formula (I) in the international publication pamphlet (I), a pharmacologically acceptable salt or ester thereof, and a hydrate thereof are collectively called "the compound group 1," and the formula representing them is regarded as Formula (I);

the compound represented by Formula (I) in the international publication pamphlet (II), a pharmacologically acceptable salt or ester thereof, and a hydrate thereof are collectively called "the compound group 2," and the formula representing them is regarded as Formula (II); and the compound represented by Formula (I) in the international publication pamphlet (III), a pharmacologically acceptable salt or ester thereof, and a hydrate thereof are collectively called "the compound group 3," and the formula representing them is regarded as Formula (III).

These compound groups are described below.

(1) Compound Group 1 Targeted by the Present Invention (WO2010/113022)

The compound group 1 targeted by the present invention includes a compound represented by Formula (I) below, a pharmacologically acceptable salt or ester thereof, and a hydrate thereof.

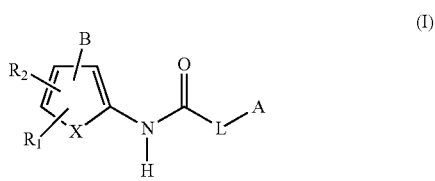

(I)

wherein $R_1$ and $R_2$ are the same or different, and each represents hydrogen, halogen, $C_{1-6}$-alkyl, $C_{3-6}$-cycloalkyl, $C_{3-8}$-cycloalkyl-$C_{1-6}$-alkyl, $C_{3-8}$-cycloalkenyl, $C_{2-6}$-alkynyl, $C_{3-8}$-cycloalkyl-$C_{2-6}$-alkynyl, substituted or unsubstituted aryl, or substituted or unsubstituted 5- to 6-membered ring heteroaryl; $R_1$ and $R_2$ are preferably hydrogen, halogen, $C_{1-6}$-alkyl, aryl optionally having one or two substituents, or 5- to 6-membered ring heteroaryl optionally having one or two substituents, proviso that $R_1$ and $R_2$ are not hydrogen at the same time; more preferably, either $R_1$ or $R_2$ is hydrogen, and the other is halogen, aryl optionally having one substituent, or 5-membered ring heteroaryl; particularly preferably, either $R_1$ or $R_2$ is hydrogen, and the other is halogen.

X represents vinylene (—CH═CH—) or sulfur. Preferably, X is vinylene.

A represents a group represented by any of the following (a) to (f), fluorenyl, or substituted or unsubstituted quinolyl, and is preferably a group represented by (a).

(a) Group Represented by Formula (I-1)

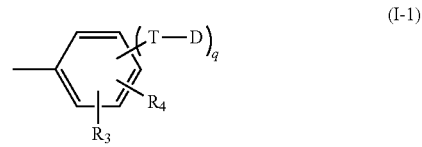

(I-1)

In Formula (I-1), q is an integer 0 or 1, and preferably 0.

$R_3$ and $R_4$ are the same or different, and each represents hydrogen, substituted or unsubstituted $C_{1-6}$ alkyl, or $CF_3$. When q is 0, $R_3$ and $R_4$ are not hydrogen at the same time. When q is 1, preferably $R_3$ and $R_4$ are hydrogen at the same time or either $R_3$ or $R_4$ is hydrogen; in this case, more preferably $R_3$ and $R_4$ are hydrogen at the same time. When both $R_3$ and $R_4$ are groups other than hydrogen, q is preferably 0.

T is a single bond, substituted or unsubstituted $C_{1-3}$ alkylene, oxygen, —CO—, —O—$C_{1-3}$-alkylene, or $C_{2-6}$ alkynylene. T is preferably a single bond.

D is substituted or unsubstituted aryl, benzo-fused heteroaryl, or heteroaryl; substituted or unsubstituted $C_{3-8}$ cycloalkyl or $C_{3-8}$ heterocycloalkyl; substituted or unsubstituted $C_{3-8}$ cycloalkenyl or $C_{3-8}$ heterocycloalkenyl; or adamanthyl. D is preferably aryl, benzo-fused heteroaryl, or heteroaryl, which optionally has one or two substituents.

When L in Formula (I) is substituted or unsubstituted C$_{1-6}$ alkylene-NHCO—, and T in Formula (I-1) is a single bond, D is not an "unsubstituted phenyl."

(b) Group Represented by any of Formulae (I-2)-(I-4)

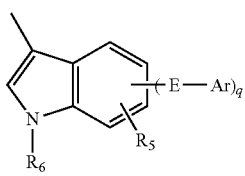
(I-2)

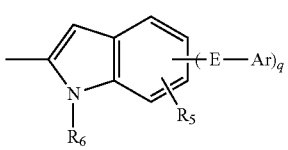
(I-3)

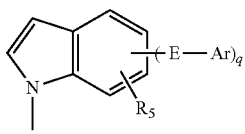
(I-4)

In Formulae (I-2)-(I-4), q is an integer 0 or 1; however, when R$_5$ described later is hydrogen, q is 1.

R$_5$ is hydrogen or halogen. Preferably, when q is 0, R$_5$ is halogen, and when q is 1, R$_5$ is hydrogen.

R$_6$ is hydrogen, C$_{1-6}$ alkyl, or C$_{1-6}$ hydroxyalkyl. Preferably, R$_6$ is hydrogen or C$_{1-6}$ alkyl.

E is a single bond or —O-alkylene. Preferably, E is a single bond.

Ar is substituted or unsubstituted aryl, or substituted or unsubstituted heteroaryl. Preferably, Ar is unsubstituted aryl.

(c) Group Represented by Formula (I-5)

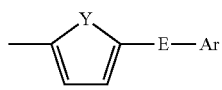
(I-5)

In Formula (I-5), Y is sulfur or oxygen.

E is a single bond or —O-alkylene. Preferably, E is a single bond.

Ar is substituted or unsubstituted aryl, or substituted or unsubstituted heteroaryl. Preferably, Ar is substituted or unsubstituted aryl.

(d) Group Represented by Formula (I-6)

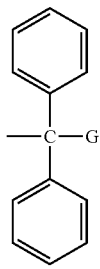
(I-6)

In Formula (I-6), G is hydrogen or C$_{1-6}$ alkyl. Preferably, G is hydrogen.

(e) Group Represented by Formula (I-7)

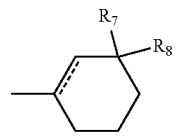
(I-7)

In Formula (I-7), R$_7$ and R$_8$ are hydrogen or alkylene at the same time and bind to each other to form 3- to 8-membered ring cycloalkane. When R$_7$ and R$_8$ are hydrogen at the same time, L described later is substituted or unsubstituted C$_{2-6}$ alkenylene. Preferably, R$_7$ and R$_8$ are hydrogen or alkylene that bind to each other to form cyclohexane.

Further, in Formula (I-7), ----- represents a single or double bond.

Among the groups represented by Formulae (I-1) to (I-7), the groups represented by Formulae (I-1), (I-2), (I-4), (I-5), and (I-7) are preferable, the groups represented by Formulae (I-1), (I-2), and (I-3) are more preferable, and the group represented by Formula (I-1) is particularly preferable.

L is a single bond, —[(CH$_2$)$_M$—O—(CH$_2$)$_N$]$_Q$— CONH— (wherein M and N are the same or different, and each represents an integer of 1 to 6, and Q is 0 or 1) {when Q is 0, L is "—CONH—"; and when Q is 1, L is "alkyleneoxyalkylene-CONH—"}, substituted or unsubstituted C$_{1-6}$ alkylene (some carbon atoms in the alkylene optionally form cycloalkyl), substituted or unsubstituted C$_{1-6}$ alkylene-O— (some carbon atoms in the alkylene optionally form cycloalkyl), substituted or unsubstituted C$_{1-6}$ alkylene-NHCO— (in alkylene-NHCO—, some carbon atoms in the alkylene optionally form cycloalkyl), substituted or unsubstituted C$_{1-6}$ alkylene-NH— (in alkylene-NH—, some carbon atoms in the alkylene optionally form cycloalkyl), substituted or unsubstituted C$_{2-6}$ alkenylene, substituted or unsubstituted C$_{2-6}$ alkynylene, —CO—, —NH—, 1,4-piperazidinyl, C$_{1-6}$ alkylene-1,4-piperazidinyl, adamantylene, or a group represented by (I-8) below:

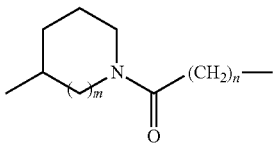
(I-8)

wherein in $(CH_2)_n$, one or more carbons are optionally substituted and may form cycloalkyl with a substituent of the carbon, provided that m is an integer 0 or 1, and n is an integer 0 to 2.

L is preferably a single bond, —CONH—, alkyleneoxyalkylene-CONH—, $C_{1-6}$ alkylene optionally having one or two substituents, $C_{1-6}$ alkylene-O— optionally having one or two substituents, $C_{2-6}$ alkenylene optionally having one or two substituents, $C_{2-6}$ alkynylene optionally having one or two substituents, or a group represented by Formula (I-8) above. L is more preferably a single bond, —CONH—, alkyleneoxyalkylene-CONH—, $C_{1-6}$ alkylene, $C_{1-6}$ alkylene-O—, or a group represented by Formula (IX) above. L is even more preferably a single bond, —CONH—, or alkyleneoxyalkylene-CONH—, and particularly preferably a single bond or —CONH—.

When L is —CONH— or alkyleneoxyalkylene-CONH—, A is a group represented by Formula (I-1), q is 1, T is a single bond, and D is substituted or unsubstituted heteroaryl or aryl, or adamanthyl. In this case, both $R_3$ and $R_4$ are preferably hydrogen. More preferably, A is a group represented by Formula (I-1), wherein q is 1, T is a single bond, D is substituted or unsubstituted heteroaryl, and both $R_3$ and $R_4$ are hydrogen. Here, the compound group 1 is aromatic carboxylic acid whose X is vinylene or a biological equivalent thereof.

When L is 1,4-piperazidinyl or $C_{1-6}$ alkylene-1,4-piperazidinyl, A is a group represented by Formula (I-6). Here, the compound group 1 is aromatic carboxylic acid whose X is vinylene or a biological equivalent thereof.

B is $COOR_9$ or a heterocyclic group represented by any of Formulae (I-10) to (I-12) below.

In the formulae, $R_9$ in $COOR_9$ is, for example, hydrogen; or a group converted to hydrogen in vivo, which is selected from the group consisting of $C_{1-6}$ alkyl, aryl, aralkyl, a group represented by —CH($R_{10}$)—O—COR$_{11}$ or —CH($R_{10}$)—O—CO—OR$_{11}$, and (5-alkyl-2-oxo-1,3-dioxolen-4-yl)methyl represented by Formula (I-9) below:

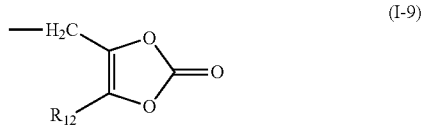

(I-9)

wherein $R_{10}$ is $C_{1-6}$ alkyl or $C_{3-8}$ cycloalkyl. $R_{11}$ and $R_{12}$ each represent $C_{1-6}$ alkyl. $R_9$ in $COOR_9$ is preferably hydrogen or $C_{1-6}$ alkyl, and more preferably hydrogen.

The heterocyclic group B is represented by any of Formulae (I-10) to (I-12) below.

(I-10)

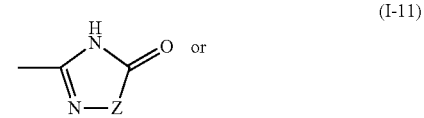

(I-11)

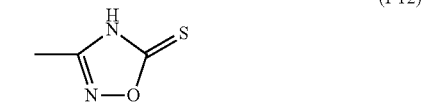

(I-12)

wherein Z is sulfur or oxygen in the heterocyclic group represented by Formula (I-11).

B is preferably carboxy (when $R_9$ in $COOR_9$ is hydrogen), or a heterocyclic group represented by Formula (I-10).

The designation of each group represented by these characters and specific examples thereof are described below.

Examples of the "alkyl" represented by $R_1$, $R_2$, $R_3$, $R_4$, $R_6$, $R_9$, $R_{10}$, $R_{11}$, $R_{12}$, or G in the compound group 1 of the present invention, unless otherwise specified, generally include $C_{1-6}$ linear or branched alkyl groups. Examples of such alkyl groups include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, etc. Preferable groups are $C_{1-4}$ lower alkyl groups such as methyl, ethyl, propyl, isopropyl, butyl and isobutyl; more preferable are methyl and ethyl; and particularly preferable is methyl.

Among these, the "alkyl" represented by $R_3$ or $R_4$ optionally has one or two substituents. Examples of such substituents include halogen, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, and alkoxycarbonyl. Examples of the "alkoxy" or "alkoxy" in "alkoxycarbonyl" include hydroxyl substituted with preferably $C_{1-6}$ and particularly preferably $C_{1-4}$ alkyl. Examples of such alkoxy include methoxy, ethoxy, 1-propoxy, 2-propoxy, 1-buthoxy, 2-buthoxy, 2-methyl-1-propoxy, 2-methyl-2-propoxy, 1-pentyloxy, 2-pentyloxy, 3-pentyloxy, 2-methyl-2-butoxy, 3-methyl-2-butoxy, 1-hexyloxy, 2-hexyloxy, 3-hexyloxy, 2-methyl-1-pentyloxy, 3-methyl-1-pentyloxy, 2-ethyl-1-butoxy, 2,2-dimethyl-1-butoxy, 2,3-dimethyl-1-butoxy, etc. Preferable among these are methoxy, ethoxy, 1-propoxy, and 2-propoxy, with methoxy being more preferable.

The "alkyl" represented by $R_3$ or $R_4$ includes $C_{3-6}$ branched alkyl among the "alkyl" explained above. A preferable example of such branched alkyl is t-butyl.

Examples of "cycloalkyl" represented by $R_1$, $R_2$, or D in the compound group 1 of the present invention or "cycloalkyl ring" of L formed by some carbon atoms in the alkylene include typically $C_{3-8}$, preferably $C_{3-6}$, and more preferably $C_5$ or $C_6$ cyclic alkyl. Examples of such cycloalkyl groups include cyclopropyl, cyclobutyl, cyclopentyl, cyclohexyl, cycloheptyl, cyclooctyl, etc. Among these, the "cycloalkyl" represented by D and "cycloalkyl ring" formed by some carbon atoms of L in the alkylene optionally have one or two substituents at any position. Examples of such substituents include halogen, $C_{1-4}$ alkyl, $C_{1-4}$ halogen-substituted alkyl, $C_{1-4}$ alkoxy, $C_{1-4}$ halogen-substituted alkoxy, hydroxyl, $CF_3$, $CF_3O$, $CHF_2O$, $CF_3CH_2O$, cyano, carboxy, alkoxycarbonyl, etc. Here, the meanings of "alkoxy" and "alkoxy" in "alkoxycarbonyl" are as described above.

Examples of "heterocycloalkyl" represented by D in the compound group 1 of the present invention include 3- to 8-membered ring cycloalkyls having one or more same or different heteroatoms selected from the group consisting of nitrogen, oxygen, and sulfur. Specific examples thereof include oxiranyl (e.g., 2-oxiranyl), azetidinyl (e.g., 2-azetidinyl), oxetanyl (e.g., 2-oxetanyl and 3-oxetanyl), thietanyl (e.g., 2-thietanyl and 3-thietanyl), pyrrolidinyl (e.g., 1-pyrrolidinyl and 2-pyrrolidinyl), tetrahydrofuryl (e.g., tetrahydrofuran-2-yl and tetrahydrofuran-3-yl), thiolanyl (e.g., 2-thiolanyl and 3-thiolanyl), piperidyl (e.g., piperidino, 2-piperidyl, 3-piperidyl, and 4-piperidyl), tetrahydropyranyl (e.g., 2-tetrahydropyranyl, 3-tetrahydropyranyl, and 4-tetrahydropyranyl), thianyl (e.g., 2-thianyl and 3-thianyl), morpholinyl (e.g., morpholino), thiomorpholinyl (e.g., thiomorpholino), 1,1-dioxido-thiomorpholinyl (e.g., 1,1-dioxido-thiomorpholino), piperazinyl (e.g., 1-piperazinyl and 2-piperazinyl), oxazolidinyl (e.g., oxazolidin-2-yl), thiazolidinyl (e.g., thiazolidin-2-yl), imidazolidinyl (e.g., imidazolidin-1-yl and imidazolidin-2-yl), azepanyl (e.g., 1-azepanyl, 2-azepanyl, 3-azepanyl, and 4-azepanyl), oxepanyl (e.g., 2-oxepanyl, 3-oxepanyl, and 4-oxepanyl), thiepanyl (e.g., 2-thiepanyl, 3-thiepanyl, and 4-thiepanyl), oxazepanyl (e.g., 2-oxazepanyl, 3-oxazepanyl, and 4-oxazepanyl), thiazepanyl (e.g., 2-thiazepanyl, 3-thiazepanyl, and 4-thiazepanyl), azocanyl (e.g., 1-azocanyl, 2-azocanyl, 3-azocanyl, and 4-azocanyl), oxocanyl (e.g., 2-oxocanyl, 3-oxocanyl, and 4-oxocanyl), thiocanyl (e.g., 2-thiocanyl, 3-thiocanyl, and 4-thiocanyl), oxazocanyl (e.g., 2-oxazocanyl, 3-oxazocanyl, and 4-oxazocanyl), thiazocanyl (e.g., 2-thiazocanyl, 3-thiazocanyl, and 4-thiazocanyl), and the like.

5- to 6-Membered ring cycloalkyl having nitrogen is preferable, and pyrrolidinyl is more preferable.

As is the case with the cycloalkyl described above, the cycloheteroalkyl may have one or two substituents at any position. Examples of such substituents are the same as those for the cycloalkyl.

In the compound group 1 of the present invention, the "$C_{3-8}$-cycloalkyl-$C_{1-6}$-alkyl groups" represented by $R_1$ or $R_2$ are $C_{1-6}$ alkyls having a typically $C_{3-8}$, preferably $C_{3-6}$, and more preferably $C_5$ or $C_6$ cycloalkyl as a substituent. The number of carbon atoms of the alkyl is preferably 1 to 4, and more preferably 1 or 2. Examples of such cycloalkylalkyl groups include cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, cyclooctylmethyl, cyclooctylethyl, etc.

Examples of the "cycloalkenyl" represented by $R_1$, $R_2$, or D in the compound group 1 of the present invention include cycloalkyl having one or more double bonds. Specific examples thereof are $C_{3-8}$ cyclic alkenyl having 1 or 2 double bonds. The cyclic alkenyls preferably have 3 to 6 carbon atoms, and more preferably 5 or 6 carbon atoms (5- or 6-membered ring). Such cycloalkenyl groups include cyclopropenyl groups (cycloprop-1-en-1-yl, cycloprop-2-en-1-yl, cycloprop-3-en-1-yl, etc.), cyclbutenyl groups (cyclobut-1-en-1-yl, cyclobut-2-en-1-yl, cyclobut-3-en-1-yl, and cyclobut-4-en-1-yl), cyclobutadienyl groups (cyclobuta-1,3-dien-1-yl and cyclobuta-2,4-dien-1-yl), cyclopentenyl groups (cyclopen-1-en-1-yl, cyclopen-2-en-1-yl, cyclopen-3-en-1-yl, cyclopen-4-en-1-yl, and cyclopen-5-en-1-yl), cyclopentadienyl groups (cyclopenta-2,4-dien-1-yl), cyclohexenyl groups (cyclohex-1-en-1-yl, cyclohex-2-en-1-yl, cyclohex-3-en-1-yl, cyclohex-4-en-1-yl, cyclohex-5-en-1-yl, etc.), and cyclohexadienyl groups (cyclohexa-1,3-dien-1-yl, cyclohexa-2,4-dien-1-yl, cyclohexa-3,5-dien-1-yl, etc.), cycloheptenyl groups, cycloheptdienyl groups, cyclooctenyl groups, cyclooctdienyl groups, and the like.

Preferable examples thereof are $C_5$ or $C_6$ cyclic alkenyl groups having one double bond, and more preferably cyclohexenyl groups.

Examples of "heterocycloalkyl" represented by D in the compound group 1 of the present invention include the groups having one or two carbon atoms of the aforementioned cycloalkenyl substituted with same or different heteroatoms selected from the group consisting of nitrogen, oxygen, and sulfur. A preferable example is a $C_5$ or $C_6$ cyclic alkenyl group having one double bond, and a more preferable example is a group in which one of the carbon atoms in a cyclohexenyl group is replaced with an oxygen atom.

The "cycloalkenyl" and "heterocycloalkenyl" represented by D may have one or two substituents at any position. Examples of such substituents include halogen, $C_{1-4}$ alkyl, $C_{1-4}$ halogen-substituted alkyl, $C_{1-4}$ alkoxy, $C_{1-4}$ halogen-substituted alkoxy, hydroxyl, $CF_3$, $CF_3O$, $CHF_2O$, $CF_3CH_2O$, cyano, carboxy, and alkoxycarbonyl. Here, the meanings of "alkoxy" and the "alkoxy" in "alkoxycarbonyl" are as defined above.

Examples of the "alkynyl" represented by $R_1$ or $R_2$ in the compound group 1 of the present invention include $C_{2-6}$ linear or branched alkynyl groups having a triple bond. Specific examples of such alkynyl groups include ethynyl, 2-propynyl, 2-butynyl, 3-butynyl, 1-methyl-2-propynyl, 2-pentynyl, 2-hexynyl, etc. Among these, ethynyl is preferable.

Examples of "$C_{3-8}$-cycloalkyl-$C_{2-6}$-alkynyl" represented by $R_1$ or $R_2$ in the compound group 1 of the present invention include $C_{2-6}$ alkynyl groups having a $C_{3-8}$, preferably $C_{3-6}$, and more preferably $C_5$ or $C_6$ cycloalkyl substituent. The number of carbon atoms in the alkynyl is preferably 2 to 3, and more preferably 2. Such cycloalkylalkynyl groups include cyclopropylethynyl, cyclobutylethynyl, cyclopentylethynyl, cyclohexylethynyl, cycloheptylethynyl, cyclooctylethynyl, and the like.

Preferable examples of the "aryl" represented by $R_1$, $R_2$, D, or Ar in the compound group 1 of the present invention include $C_{6-14}$ aromatic hydrocarbon groups. Examples of such aryl groups include phenyl, naphthyl, anthryl, phenanthryl, acenaphthylenyl, etc. Preferable among these are phenyl and naphthyl, and more preferable is phenyl. These groups may have one or two substituents at any position. However, in the compound group 1, when L is a substituted or unsubstituted alkylene-NHCO—, and, at the same time, A is a group represented by Formula (II) (provided that T is a single bond), the aryl represented by D is aryl other than "unsubstituted phenyl." An example of such aryl is phenyl having one or more substituents.

Examples of the substituents in the aryl represented by $R_1$, $R_2$, D, or Ar include halogen, $C_{1-6}$ alkyl (preferably $C_{1-4}$ alkyl), $C_{1-6}$ cycloalkyl, $C_{1-6}$ alkoxy (preferably $C_{1-4}$ alkoxy), $C_{1-6}$ cycloalkoxy, $C_{1-6}$ halogen-substituted alkoxy, hydroxyl, $CF_3$, $CF_3O$, $CHF_2O$, $CF_3CH_2O$, cyano, carboxy, alkoxycarbonyl, benzoyl, and phenyl.

Here, the meanings of "alkyl" and "cycloalkyl," and "alkoxy" in "alkoxy," "halogen-substituted alkoxy," and "alkoxycarbonyl" are as defined above. Examples of "cycloalkoxy" include $C_{3-8}$, preferably $C_{3-6}$, and more preferably $C_{4-5}$ cyclic alkoxy groups. Such cycloalkoxy groups include cyclopropyloxy, cyclobutyloxy, cyclopentyloxy, cyclohexyloxy, cycloheptyloxy, cyclooctyloxy, etc.

Examples of "heteroaryl" represented by $R_1$, $R_2$, D, or Ar in the compound group 1 of the present invention include 3- to 6-membered ring, preferably 5- to 6-membered ring, aryl groups having one or more same or different heteroatoms selected from the group consisting of nitrogen, oxygen, and sulfur. Specific examples thereof include furyl, pyrrolyl, thienyl, pyrazolyl, imidazolyl, oxazolyl, isoxazolyl, triazolyl, isothiazolyl, oxadiazolyl, thiadiazolyl, triazolyl, tetrazolyl, pyridyl, pyridazinyl, pyrimidinyl, pyrazinyl, and like unsaturated monoheterocyclic groups.

These groups may have one or two substituents at any position. Examples of substituents of the heteroaryl include halogen, $C_{1-6}$ alkyl (preferably $C_{1-4}$ alkyl), $C_{3-8}$ cycloalkyl, $C_{1-6}$ alkoxy (preferably $C_{1-4}$ alkoxy), $C_{3-8}$ cycloalkoxy, $C_{1-6}$ halogen-substituted alkoxy, hydroxyl, $CF_3$, $CF_3O$, $CHF_2O$, $CF_3CH_2O$, cyano, carboxy, alkoxycarbonyl, benzoyl, phenyl, and phosphonooxymethyl. Here, the meanings of "alkyl" and "cycloalkyl," and "alkoxy" in "alkoxy," "cycloalkoxy," "halogen-substituted alkoxy," and "alkoxycarbonyl" are as defined above. Further, the phosphonooxymethyl group is a substituent of "heteroaryl" at the 1-position when the heteroaryl is pyrazolyl or pyrrolyl that is removed in vivo and converts to a pyrazolyl or pyrrolyl group unsubstituted at the 1-position, allowing the pyrazolyl or pyrrolyl group to show PAI-1 inhibition activity. In other words, phosphonooxymethyl is a substituent that serves as a so-called prodrug.

When a substituent of D or Ar is cycloalkyl or cycloalkoxy, the substituent may also have a substituent. Examples of such substituents include halogen, $C_{1-6}$ alkyl, $C_{1-6}$ alkoxy, $C_{1-6}$ halogen-substituted alkoxy, hydroxyl, $CF_3$, $CF_3O$, $CHF_2O$, $CF_3CH_2O$, cyano, carboxy, alkoxycarbonyl, benzoyl, and phenyl.

Examples of the "benzo-fused heteroaryl" represented by D in the compound group 1 of the present invention include groups in which the benzene ring is fused with the above-mentioned heteroaryl. Specific examples thereof include isoquinolyl, quinolyl, indolyl, isoindolyl, benzofuranyl, benzothienyl, benzimidazolyl, benzisoxazolyl, benzothiazolyl, benzisothiazolyl, quinazolinyl, quinoxalinyl, benzoxadiazolyl, benzothiadiazolyl, etc.

The above benzo-fused heteroaryl may have one to three substituents at any position. Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, alkoxycarbonyl having $C_{1-4}$ alkoxy, etc. Here, the meanings of "alkyl," "alkoxy," and "aryl" are as defined above.

Examples of the "alkylene group" and the "alkylene" in "alkylene-O—," "alkylene-NH—," "alkylene-NHCO—," "alkylene-piperazidinyl," and "alkyleneoxyalkylene-CONH—" represented by L in the compound group 1 of the present invention include typically $C_{1-6}$, and preferably $C_{1-4}$ linear or branched alkylene. Examples of such alkylene groups include methylene, ethylene, propylene, trimethylene, 1-ethyl-1,2-ethylene, 1-propyl-1,2-ethylene, 1-isopropyl-1,2-ethylene, 1-butyl-1,2-ethylene, 1,2-dimethyl-1,2-ethylene, tetramethylene, pentamethylene, and hexamethylene. Among these, methylene and ethylene are preferable.

The "alkylene group" and the "alkylene" in "alkylene-O—," "alkylene-NH—," and "alkylene-NHCO—" may be those in which some of the carbon atoms in the alkylene bind to form a $C_{3-8}$ cycloalkyl ring (cycloalkane). Examples of such cycloalkyl rings include cyclopropane, cyclobutane, cyclopentane, cyclohexane, cycloheptane, and cyclooctane.

Examples of "alkenylene" represented by L in the compound group 1 of the present invention include $C_{2-6}$ linear or branched alkenylene having 1 to 3 double bonds. Examples of such alkenylene groups include vinylene, 1-methylvinylene, propenylene, 1-butenylene, 2-butenylene, 1-pentenylene, 2-pentenylene, etc. Preferably, the alkenylene is vinylene.

Examples of the "alkynylene" represented by L and T in the compound group 1 of the present invention include $C_{2-6}$ linear or branched alkynylene groups having one triple bond. Examples of such alkynylene groups include ethynylene, propynylene, 1-methylpropynylene, 1-butynylene, 2-butynylene, 1-methylbutynylene, 2-methylbutynylene, 1-pentynylene, and 2-pentynylene.

The "alkylene," "alkylene-O—," "alkylene-NH—," "alkylene-NHCO—," "alkenylene," and "alkynylene" each may have one or two substituents. Examples of such substituents include halogen, $C_{1-4}$ alkoxy, $C_{1-4}$ halogen-substituted alkoxy, hydroxyl, $CF_3$, $CF_3O$, $CHF_2O$, $CF_3CH_2O$, cyano, carboxy, alkoxycarbonyl, amino, acylamino, benzyloxycarbonylamino (Cbz-NH—), alkoxycarbonylamino (e.g., t-butoxycarbonylamino (tBoc-NH—), methoxycarbonylamino, ethoxycarbonylamino, propoxycarbonylamino, isopropoxycarbonylamino, and butoxypropoxycarbonylamino), acyl, etc. The meaning of the "alkoxy" is as defined above.

Examples of "alkylene" represented by T and E in the compound group 1 of the present invention and "alkylene" represented by T in "—O-alkylene" include typically $C_{1-3}$ linear or branched alkylenes. Such alkylenes include methylene, ethylene, propylene, and trimethylene. Preferably, the alkylene is methylene, ethylene, or trimethylene.

Examples of the "halogen atom" in the compound group 1 of the present invention include fluorine, chlorine, bromine, and iodine. Preferable are chlorine, bromine, and fluorine; chlorine is more preferable.

The quinolyl represented by A in Formula (I) may have one or two substituents at any position. Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, alkoxycarbonyl having $C_{1-4}$ alkoxy, etc. The meanings of "alkyl," "alkoxy," and "aryl" are as defined above. Among these, phenyl is preferable.

Examples of the groups represented by B in Formula (I) include, in addition to carboxyl (COOH), (1) alkoxycarbonyl, aryloxycarbonyl, and aralkyloxycarbonyl, which can be converted to carboxyl when absorbed in vivo; (2) groups that can be easily converted to carboxyl when absorbed in vivo; and (3) groups that have been designated as a group that is biologically equivalent to a carboxyl group. Here, examples of the alkoxycarbonyl, aryloxycarbonyl, and aralkyloxycarbonyl in (1) above include groups that are each represented by $COOR_9$, wherein $R_9$ is $C_{1-6}$ alkyl, aryl (preferably phenyl), or aralkyl (preferably benzyl).

Specific examples of the groups in (2) above include groups represented by $COOR_9$, wherein $R_9$ is a (5-alkyl-2-oxo-1,3-dioxolen-4-yl)methyl group represented by the following formula:

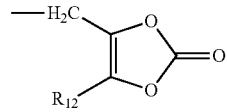

wherein $R_{12}$ is $C_{1-6}$ alkyl;
wherein $R_9$ is a group represented by —$CH(R_{10})$—O—$COR_{11}$ or —$CH(R_{10})$—O—CO—$OR_{11}$, wherein $R_{10}$ is hydrogen or $C_{1-6}$ alkyl, and $R_{11}$ is $C_{1-6}$ alkyl or $C_{3-8}$ cycloalkyl.

Examples of the groups in (3) above include heterocyclic groups such as 1H-tetrazol-5-yl, 4,5-dihydro-5-oxo-4H-1,2,4-oxadiazol-3-yl, 4,5-dihydro-5-oxo-1,2,4-thiadiazol-3-yl, and 4,5-dihydro-5-thioxo-4H-1,2,4-oxadiazol-3-yl represented by the following formulae in order from the left (see, for example, Kohara et al. J. Med. Chem., 1996, 39, 5228-5235).

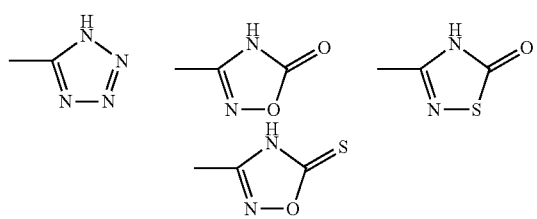
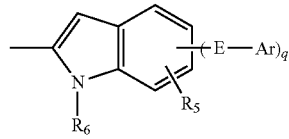
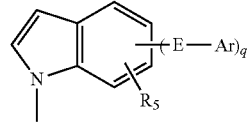

In the present invention, the groups of (1) to (3) mentioned above may each be called a group that is biologically equivalent to a carboxyl group. In this specification, salts of the compound group 1 represented by Formula (I) and the compound group 1 having the above groups (groups that are biologically equivalent to a carboxyl group) may be collectively called a bioisostere of the carboxylic acid.

Specific examples of the "alkoxycarbonyl" represented by B (when B represents —COOR$_9$, wherein R$_9$ is alkyl) in Formula (I) include t-butoxycarbonyl, methoxycarbonyl, ethoxycarbonyl, propoxycarbonyl, isopropoxycarbonyl, butoxycarbonyl, etc.

The compound group 1 targeted by the present invention preferably includes aromatic or heterocyclic carboxylic acids represented by the formula below, and bioisosteres thereof.

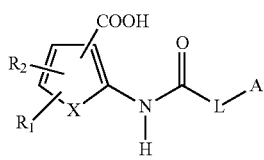

wherein R$_1$, R$_2$, X, L, and A are as defined above.

The compound group (1) of the present invention can be classified into the following categories (I-a) to (I-g) depending on the types of substituent A.

(I-a) Compounds Wherein A is a Group Represented by Formula (I-1)

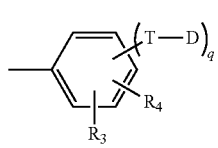

(I-1)

wherein R$_3$, R$_4$, T, D, and q are as defined above.

(I-b) Compounds Wherein A is a Group Represented by any of Formulae (I-2) to (I-4)

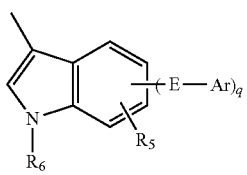

(I-2)

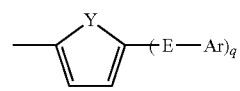

(I-3)

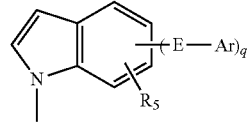

(I-4)

wherein R$_5$, R$_6$, E, Ar, and q are as defined above.

(I-c) Compounds Wherein A is a Group Represented by Formula (I-5)

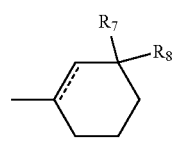

(I-5)

wherein Y, E, Ar, and q are as defined above.

(I-d) Compounds Wherein A is a Group Represented by Formula (I-6)

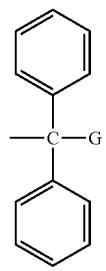

(I-6)

wherein G is as defined above.

(I-e) Compounds Wherein A is a Group Represented by Formula (I-7)

(I-7)

wherein R$_7$ and R$_8$ are as defined above.
(I-f) Compounds Wherein A is Fluorenyl
(I-g) Compounds Wherein A is Substituted or Unsubstituted Quinolyl The compound group 1 of the present invention is explained in detail below for each category of the compounds described above.

(I-a) Compounds Wherein A is a Group Represented by Formula (I-1)

Examples of compounds (I-a) belonging to this category include aromatic or heterocyclic carboxylic acids represented by the formula below, and bioisosteres thereof.

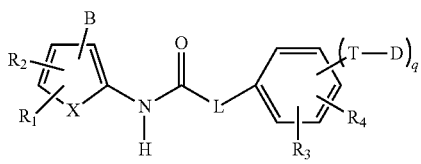

(I-a)

wherein $R_1$ to $R_4$, B, X, L, T, D, and q are as defined above.

The compounds (I-a) can be further classified into (I-a-1) to (I-a-5) described below depending on the types of L.

(I-a-1) Compounds wherein L is a single bond;

(I-a-4) Compounds wherein L is —CONH—, alkyleneoxyalkylene-CONH—, —NH—, —CO—, substituted or unsubstituted $C_{1-6}$-alkylene-NH—, substituted or unsubstituted $C_{1-6}$-alkylene-NHCO—, or a compound represented by Formula (I-8);

(I-a-2) Compounds wherein L is substituted or unsubstituted $C_{1-6}$-alkylene-O—;

(I-a-3) Compounds wherein L is substituted or unsubstituted $C_{1-6}$-alkylene, $C_{1-6}$-alkenylene, or $C_{1-6}$-alkynylene; and (I-a-5) Compounds wherein L is adamantylene.

(I-a-1) Compounds Wherein L is Single Bond

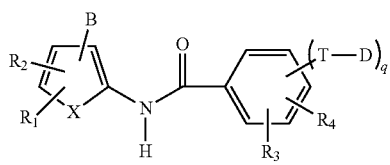

(I-a-1)

wherein $R_1$ to $R_4$, B, X, T, D, and q are as defined above.

Examples of compound (I-a-1) include aromatic carboxylic acids and bioisosteres thereof wherein X in Formula (I-a-1) is vinylene (—CH=CH—), and heterocyclic carboxylic acids and bioisosteres thereof wherein X in Formula (I-a-1) is sulfur.

When X is Vinylene

Aromatic carboxylic acids and bioisosteres thereof wherein X is vinylene are preferable.

In Formula (I-a-1), B, $R_1$, and $R_2$ may be located at any of the ortho, meta, and para positions on the benzene ring to which imino is bound. Preferably B is located at the ortho position, and $R_2$ and $R_1$ are located at the meta and para positions, respectively, on the benzene ring. $R_1$ and $R_2$ are as defined above. Preferably, $R_1$ and $R_2$ are the same or different, and each represents hydrogen, halogen, $C_{3-8}$-cycloalkyl, $C_{3-8}$-cycloalkyl-$C_{1-6}$-alkyl, $C_{3-8}$-cycloalkyl-$C_{2-6}$-alkynyl, $C_{3-8}$-cycloalkenyl, or $C_{2-6}$-alkynyl. More preferably, $R_2$ located at the meta position is hydrogen, and $R_1$ located at the para position is halogen, $C_{3-8}$-cycloalkyl, $C_{3-8}$-cycloalkyl-$C_{2-6}$-alkynyl, $C_{3-8}$-cycloalkenyl, or $C_{2-6}$-alkynyl. Particularly preferably, $R_2$ at the meta position is hydrogen, and $R_1$ at the para position is halogen.

Here, halogen is preferably chlorine or bromine, and more preferably chlorine. The $C_{3-8}$ cycloalkyl is preferably cyclohexyl. The $C_{3-8}$-cycloalkyl-$C_{1-6}$-alkyl is preferably $C_{1-6}$ alkyl having cyclohexyl as a substituent, and more preferably $C_{1-4}$ alkyl having cyclohexyl as a substituent. The $C_{3-8}$-cycloalkyl-$C_{2-6}$-alkynyl is preferably $C_{2-6}$ alkynyl having cyclohexyl as a substituent, and more preferably $C_{2-3}$ alkynyl having cyclohexyl as a substituent. The $C_{3-8}$-cycloalkenyl is preferably a cyclohexenyl, and more preferably cyclohex-1-en-1-yl or cyclohex-6-en-1-yl. The $C_{2-6}$-alkynyl is preferably $C_{2-4}$ alkynyl, and more preferably $C_{2-3}$ alkynyl.

In the formula, q, $R_3$, and $R_4$ are as defined above; however, preferably, when q is 1, $R_3$ and $R_4$ are both hydrogen, and when q is 0, at least one of $R_3$ and $R_4$ is $CF_3$, and more preferably both are $CF_3$. Preferably, q is 1, and both $R_3$ and $R_4$ are hydrogen.

T is as defined above, and is preferably a single bond, oxygen, —O—$C_{1-3}$-alkylene, —CO—, $C_{2-3}$-alkynylene, or substituted or unsubstituted alkylene, and more preferably a single bond.

D is as defined above, and preferable examples thereof include aryl optionally having one or two substituents, heteroaryl optionally having one or two substituents, benzo-fused heteroaryl optionally having one or two substituents, substituted or unsubstituted $C_{3-8}$ cycloalkyl, $C_{3-8}$ heterocycloalkyl optionally having one or two substituents, $C_{3-8}$ cycloalkenyl optionally having one or two substituents, $C_{3-8}$ heterocycloalkenyl optionally having one or two substituents, and adamanthyl. More preferably, D is aryl optionally having one or two substituents, heteroaryl optionally having one or two substituents, or benzo-fused heteroaryl optionally having one or two substituents.

Preferable examples of aryl include phenyl optionally having one substituent and naphthyl, and more preferably phenyl. Examples of the substituents are as described above, and preferable are alkyl and alkoxy.

Preferable examples of the heteroaryl include furyl, pyridyl, and thienyl, which optionally have one substituent. Examples of the substituents are as described above, and preferable are unsubstituted furyl, pyridyl, and thienyl. Specific examples of furyl include furan-2-yl and furan-3-yl; furan-3-yl is preferable. Specific examples of pyridyl include pyridin-2-yl, pyridin-3-yl, and pyridin-4-yl; pyridin-4-yl is preferable. Specific examples of thienyl include thiophen-2-yl and thiophen-3-yl; thiophen-2-yl is preferable.

Preferable examples of benzo-fused heteroaryl include isoquinolyl or quinolyl optionally having one substituent. Examples of the substituents are as described above, and preferable are unsubstituted isoquinolyl and quinolyl. There is no limitation to the binding site of quinolyl and isoquinolyl, and when the substituent is quinolyl, preferable positions are, for example, the 2-position (quinolin-2-yl), 3-position (quinolin-3-yl), 6-position (quinolin-6-yl), and 8-position (quinolin-8-yl); when the substituent is isoquinolyl, for example, the 4-position (isoquinolin-4-yl) and 5-position (isoquinolin-5-yl) are preferable.

Examples of $C_{3-8}$ cycloalkyl preferably include cyclohexyl optionally having one substituent; and examples of $C_{3-8}$ heterocycloalkyl include a 5-membered ring having nitrogen as a heteroatom, and preferably pyrrolidinyl optionally having one substituent. Specific examples of pyrrolidinyl include pyrrolidin-1-yl, pyrrolidin-2-yl, pyrrolidin-3-yl, pyrrolidin-4-yl, pyrrolidin-5-yl, and pyrrolidin-6-yl; pyrrolidin-1-yl is preferable. Examples of the substituents are as described above, and preferable are unsubstituted cycloalkyl and heterocycloalkyl.

Preferable examples of $C_{3-8}$ cycloalkenyl include cyclohexenyl optionally having one substituent. Specific examples of cyclohexenyl include cyclohex-1-en-1-yl, cyclohex-2-en-1-yl, cyclohex-3-en-1-yl, cyclohex-4-en-1-yl, cyclohex-5-en-1-yl, and cyclohex-6-en-1-yl; cyclohex-1-en-1-yl is preferable.

Examples of $C_{3-8}$ heterocycloalkenyl include a 6-membered ring heterocyclohexenyl with oxygen as a heteroatom optionally having one substituent. Examples of such a group include dihydro-2H-pyranyl, and preferably 3,6-dihydro-2H-pyran-4-yl. Examples of the substituents are as described above, and preferable are unsubstituted cycloalkenyl and heterocycloalkenyl.

Preferable examples of adamanthyl include adamanthyl optionally having one substituent, and the adamanthyl is preferably adamantan-1-yl.

Preferable examples of the aromatic carboxylic acid (benzenecarboxylic acid: a compound wherein B is carboxyl) of the present invention of Formula (I-a-1) wherein X is vinylene, or bioisosteres of the carboxylic acid (compounds wherein B is a group that is biologically equivalent to a carboxyl group) include compounds wherein $R_1$ is halogen, all of $R_2$ to $R_4$ are hydrogen, q is 1, T is a single bond, and D is aryl, benzo-fused heteroaryl, or heteroaryl. More preferable are compounds wherein $R_1$ is halogen, all of $R_2$ to $R_4$ are hydrogen, q is 1, T is a single bond, and D is aryl or benzo-fused heteroaryl. The compounds include compounds represented by Examples 4 and 68 (desalted products thereof) among the compounds listed below. Specific examples of the aromatic carboxylic acid (benzene carboxylic acid) of the present invention represented by Formula (I-a-1) and bioisosteres of the carboxylic acid include the following compounds (see Tables 1 and 2):

2-[(biphenyl-3-ylcarbonyl)amino]-5-chlorobenzoic acid (Example 4)
5-chloro-2-({[3-(quinolin-8-yl)phenyl]carbonyl}amino)benzoic acid (desalted product of Example 68)
5-chloro-2-({[3-(furan-3-yl)phenyl]carbonyl}amino)benzoic acid (Example 2)
2-[(biphenyl-2-ylcarbonyl)amino]-5-chlorobenzoic acid (Example 6)
5-chloro-2-({[4-(thiophen-2-yl)phenyl]carbonyl}amino)benzoic acid (Example 7)
5-chloro-2-({[3-(pyridin-4-yl)phenyl]carbonyl}amino)benzoic acid (desalted product of Example 8)
5-chloro-2-({[(4'-methylbiphenyl-3-yl)carbonyl]amino]benzoic acid (Example 32)
5-chloro-2-{[(2'-methoxybiphenyl-3-yl)carbonyl]amino}benzoic acid (Example 33)
5-chloro-2-({[4-(3,6-dihydro-2H-pyran-4-yl)phenyl]carbonyl}amino)benzoic acid (Example 34)
2-({[4-(adamantan-1-yl)phenyl]carbonyl}amino)-5-chlorobenzoic acid (Example 40)
5-chloro-2-{[(4-phenoxyphenyl)carbonyl]amino}benzoic acid (Example 42)
2-({[3,5-bis(trifluoro-methyl)phenyl]carbonyl}amino)-5-chlorobenzoic acid (Example 43)
2-({[4-(adamantan-1-ylmethoxy)phenyl]carbonyl}amino)-5-chlorobenzoic acid (Example 52)
2-({[4-(adamantan-1-ylcarbonyl)phenyl]carbonyl}amino)-5-chlorobenzoic acid (Example 56)
5-chloro-2-{([3-(naphthalen-1-yl)phenyl]carbonyl}amino)benzoic acid (Example 58)
2-({[3-(adamantan-1-yl)phenyl]carbonyl}amino)-5-chlorobenzoic acid (Example 62)
5-chloro-2-({[3-(quinolin-3-yl)phenyl]carbonyl}amino)benzoic acid (desalted product of Example 63)
5-chloro-2-({[3-(isoquinolin-4-yl)phenyl]carbonyl}amino)benzoic acid (desalted product of Example 64)
5-chloro-2-({[3-(quinolin-6-yl)phenyl]carbonyl}amino)benzoic acid (desalted product of Example 65)
5-chloro-2-{([3-(isoquinolin-5-yl)phenyl]carbonyl}amino)benzoic acid (desalted product of Example 66)
5-chloro-2-({[4-(quinolin-8-yl)phenyl]carbonyl}amino)benzoic acid (desalted product of Example 67)
5-chloro-2-{[(4-cyclohexylphenyl)carbonyl]amino}benzoic acid (Example 69)
5-chloro-2-{([3-(cyclohex-1-en-1-yl)phenyl]carbonyl}amino)benzoic acid (Example 79)
5-chloro-2-{[(3-cyclohexylphenyl)carbonyl]amino}benzoic acid (Example 80)
5-(cyclohex-1-en-1-yl)-2-{[(4-cyclohexylphenyl)carbonyl]amino}benzoic acid (Example 81)
5-cyclohexyl-2-{[(4-cyclohexylphenyl)carbonyl]amino}benzoic acid (Example 82)
5-chloro-2-{([4-(pyrrolidin-1-yl)phenyl]carbonyl}amino)benzoic acid hydrochloride (Example 83)
5-chloro-2-({[3-(cyclohexylethynyl)phenyl]carbonyl}amino)benzoic acid (Example 87)
5-chloro-2-({[4-(cyclohexylethynyl)phenyl]carbonyl}amino)benzoic acid (Example 88)
5-(cyclohexylethynyl)-2-{[(4-cyclohexylphenyl)carbonyl]amino}benzoic acid (Example 92)
5-(2-cyclohexylethyl)-2-{[(4-cyclohexylphenyl)carbonyl]amino}benzoic acid (Example 93)
2-{[(4-cyclohexylphenyl)carbonyl]amino}-5-ethynylbenzoic acid (Example 95)
2-{([4-(adamantan-1-ylmethyl)phenyl]carbonyl}amino)-5-chlorobenzoic acid (Example 96)
2-[({4-[adamantan-1-yl(hydroxy)methyl]phenyl}carbonyl)amino]-5-chlorobenzoic acid (Example 97)
5-chloro-2-({[4-(1-methylcyclohexyl)phenyl]carbonyl}amino)benzoic acid (Example 98)
5-chloro-2-({[3-(quinolin-2-ylmethoxy)phenyl]carbonyl}amino)benzoic acid (desalted product of Example 99)
5-chloro-2-{([4-(quinolin-2-ylmethoxy)phenyl]carbonyl}amino)benzoic acid (desalted product of Example 100)
N-[4-chloro-2-(1H-tetrazol-5-yl)phenyl]-3-(quinolin-8-yl)benzamide (Example 102)

When X is Sulfur

When X is sulfur, i.e., the compound represented by Formula (I-a-1) is a heterocyclic carboxylic acid (thiophenecarboxylic acid: a compound wherein B is carboxyl) or a bioisostere thereof (a compound wherein B is a group that is biologically equivalent to a carboxyl group), $R_1$ and $R_2$ are as defined above, preferably are the same or different, and each represents $C_{1-6}$ alkyl or aryl optionally having one or two substituents. The alkyl is preferably $C_{1-4}$ alkyl, and more preferably methyl. A preferable example of aryl is phenyl. Examples of the substituents of aryl are as described above, and unsubstituted phenyl is preferable. Either $R_1$ or $R_2$ (e.g., $R_2$ at the 4-position on the thiophene ring) is preferably aryl, and the other (e.g., $R_1$ at the 5-position on the thiophene ring) is alkyl.

q, $R_3$, and $R_4$ are as defined above, preferably q is 1, and both $R_3$ and $R_4$ are hydrogen.

T is as defined above, and preferably is a single bond.

D is as defined above, and preferably is $C_{3-6}$ cycloalkyl optionally having one or two substituents, or heteroaryl optionally having one or two substituents. A preferable example of cycloalkyl is cyclohexyl. Examples of the heteroaryl include pyridyl, thienyl, and furyl. Among these, furyl is preferable. Specific examples of furyl include furan-2-yl and furan-3-yl, and furan-3-yl is preferable. Examples of substituents are as described above, and cycloalkyl and heteroaryl are preferably groups that do not have a substituent.

In Formula (I-a-1), B, $R_1$, and $R_2$ may be located at any of the 3- to 5-positions on the thiophene ring to which imino is bound. Preferably, B is located at the 3-position on the thiophene ring, and $R_2$ and $R_1$ are located at the 4-position and 5-position, respectively.

Specific examples of the thiophenecarboxylic acid of the present invention represented by Formula (I-a-1) above and bioisosteres thereof include the following compounds (see Tables 1 and 2):

2-({[3-(furan-3-yl)phenyl]carbonyl}amino)-5-methyl-4-phenylthiophene-3-carboxylic acid (Example 5)

2-{[(4-cyclohexylphenyl)carbonyl]amino}-5-methyl-4-phenylthiophene-3-carboxylic acid (Example 74)

(I-a-4) Compounds Wherein L is —CONH—, Alkyleneoxyalkylene-CONH—, —NH—, Substituted or Unsubstituted $C_{1-6}$-Alkylene-NH—, —CO—, Substituted or Unsubstituted $C_{1-6}$-Alkylene-NHCO—, or a Group Represented by Formula (I-8)

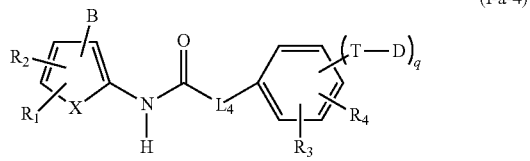

(I-a-4)

wherein $R_1$ to $R_4$, B, X, T, D, and q are as defined above. $L_4$ is —CONH—, alkyleneoxyalkylene-CONH—, —NH—, substituted or unsubstituted $C_{1-6}$-alkylene-NH, —CO—, substituted or unsubstituted $C_{1-6}$-alkylene-NHCO—, or a group represented by Formula (I-8) below.

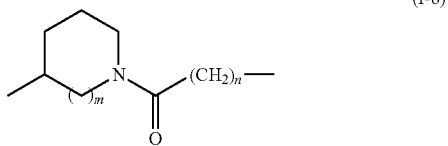

(I-8)

wherein in $(CH_2)_n$, one or more carbons are optionally substituted and may form cycloalkyl, provided that m is an integer 0 or 1, and n is an integer 0 to 2.

In the compound (I-a-4), $L_4$ (represented as "L" in Formula (I)) is preferably —CONH— or alkyleneoxyalkylene-CONH—, and more preferably —CONH—.

Examples of the alkylene represented by "alkyleneoxyalkylene-CONH—," "$C_{1-6}$-alkylene-NH—," and "$C_{1-6}$-alkylene-NHCO—" in $L_4$ include $C_{1-6}$ alkylene, preferably $C_{1-4}$ alkylene, more preferably $C_{1-2}$ alkylene, and particularly preferably $C_1$ alkylene. The alkylene may be linear or branched, and some carbon atoms in the alkylene optionally form a $C_{3-8}$ cycloalkyl ring. Examples of such cycloalkyl rings (cycloalkane) include cyclopropane, cyclobutane, cycloheptane, cyclohexane, cycloheptane, and cyclooctane, and preferably cyclopropane. Linear alkylene is preferable, and specific examples thereof include methylene and ethylene.

The "alkyleneoxyalkylene-CONH—," "$C_{1-6}$-alkylene-NH—," and "$C_{1-6}$-alkylene-NHCO—" may have one or two substituents in alkylene. The substituents are as defined above, and preferably unsubstituted alkylene.

In Formula (I-8), m is 0 or 1. n is an integer 0 to 2, and preferably 0 or 1. When n is an integer 1 or 2, the carbon atom in $(CH_2)_n$ may have one or two substituents. Examples of such substituents include halogen, $C_{1-6}$ alkyl, $C_{1-6}$ alkoxy, $C_{3-8}$ cycloalkyl, and the like. A preferable example of $(CH_2)_n$ is unsubstituted alkylene.

When X is Vinylene

Preferable examples of the compound (I-a-4) include those represented by Formula (I-a-4) wherein X is vinylene (—CH=CH—). In the formula, B, $R_1$, and $R_2$ may be located at any of the ortho, meta, and para positions on the benzene ring to which imino is bound. Preferable compounds are those in which B is located at the ortho position, and $R_2$ and $R_1$ are located at the meta and para positions, respectively, on the benzene ring.

In the compound (I-a-4), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the formula, q, $R_3$, and $R_4$ are as defined above, and preferably q is 1, $R_3$ and $R_4$ are the same or different, and each represents hydrogen or $C_{1-6}$ alkyl. The alkyl is preferably $C_{1-4}$, and more preferably $C_{1-2}$ alkyl. Preferable examples of $R_3$ and $R_4$ are those in which both are hydrogen or one is hydrogen and the other is alkyl. More preferably, $R_3$ and $R_4$ are both hydrogen.

T is as defined above, and preferably is a single bond.

D is as defined above, and preferable examples thereof include heteroaryl optionally having one or two substituents, aryl optionally having one or two substituents, benzo-fused heteroaryl optionally having one or two substituents, and substituted or unsubstituted adamanthyl. More preferably, D is heteroaryl optionally having one or two substituents.

The heteroaryl is as defined above, preferably furyl optionally having one substituent, and more preferably furan-2-yl or furan-3-yl. The substituents are as defined above, and preferably halogen, $C_{1-6}$ alkyl (preferably $C_{1-4}$ alkyl), or $C_{1-6}$ alkoxy (preferably $C_{1-4}$ alkoxy). Preferable examples of heteroaryl include unsubstituted furyl (furan-2-yl or furan-3-yl) and furyl having halogen as a substituent. The halogen is preferably chlorine or fluorine, and more preferably fluorine.

The aryl is as defined above, and preferably phenyl optionally having one substituent. Preferable examples of aryl include unsubstituted phenyl and phenyl having halogen as a substituent. The halogen is preferably chlorine or fluorine, and more preferably fluorine.

The benzo-fused heteroaryl is as defined above, and preferably isoquinolyl or quinolyl optionally having one substituent. Examples of the substituents are as described above, and preferable are unsubstituted isoquinolyl and quinolyl. There is no limitation to the binding site of isoquinolyl and quinolyl, and when the substituent is quinolyl, preferable positions are, for example, the 2-position (quinolin-2-yl), 3-position (quinolin-3-yl), 6-position (quinolin-6-yl), and 8-position (quinolin-8-yl); when the substituent is isoquinolyl, for example, the 4-position (isoquinolin-4-yl) and 5-position (isoquinolin-5-yl) are preferable.

Preferable examples of adamanthyl include adamantan-1-yl. Examples of the substituents of adamanthyl are as described above, and unsubstituted adamanthyl is preferable.

Preferable examples of the aromatic carboxylic acid (benzenecarboxylic acid: a compound wherein B is carboxyl) of the present invention of Formula (I-a-4) wherein X is vinylene, or bioisosteres of the carboxylic acid (compounds wherein B is a group that is biologically equivalent to a carboxyl group) include compounds wherein L is —CONH— or alkyleneoxyalkylene-CONH—, $R_1$ is halogen, all of $R_2$ to $R_4$ are hydrogen, q is 1, T is a single bond, and D is aryl, benzo-fused heteroaryl, or heteroaryl. More preferable are compounds wherein L is —CONH— or alkyleneoxyalkylene-CONH—, $R_1$ is halogen, all of $R_2$ to $R_4$ are hydrogen, q is 1, T is a single bond, and D is heteroaryl. The compounds include compounds represented by Examples 45 (Table 4-4) and 61 (Table 4-6) among the compounds listed below.

Specific examples of the aromatic carboxylic acid (benzene carboxylic acid) of the present invention represented by Formula (I-a-4) and bioisosteres of the carboxylic acid include the following compounds (see Tables 1, 2, 4-4, and 4-6):

5-chloro-2-{[{[3-(furan-3-yl)phenyl]amino}(oxo)acetyl]amino}benzoic acid (Example 45: Table 4-4)

5-chloro-2-{[(2-{[3-(furan-2-yl)phenyl]amino}-2-oxoethoxy)acetyl]amino}benzoic acid (Example 61: Table 4-6)

2-[(biphenyl-4-ylcarbamoyl)amino]-5-chlorobenzoic acid (Example 71: Table 2-2)

5-chloro-2-{[N-(4'-fluoro-4-methylbiphenyl-3-yl)glycyl]amino}benzoic acid (Example 72: Table 2-2)

5-chloro-2-({[5-(furan-3-yl)-1-methyl-1H-indol-3-yl](oxo)acetyl}amino)benzoic acid (Example 14: Table 2-1)

2-[({[4-(adamantan-1-yl)phenyl]amino}(oxo)acetyl)amino]-5-chlorobenzoic acid (desalted product of Example 106: Table 2-3)

5-chloro-2-{[4-({[3-(furan-3-yl)phenyl]carbonyl}amino)butanoyl]amino}benzoic acid (Example 1: Table 1)

5-chloro-2-[(1-{[3-(furan-3-yl)phenyl]acetyl}-L-prolyl)amino]benzoic acid (Example 9: Table 1)

5-chloro-2-[(1-{[3-(furan-3-yl)phenyl]carbonyl}-L-prolyl)amino]benzoic acid (Example 10: Table 1)

5-chloro-2-{[(1-{[3-(furan-3-yl)phenyl]carbonyl}piperidin-3-yl)carbonyl]amino}benzoic acid (desalted product of Example 11: Table 1)

5-chloro-2-{[(1-{[3-(furan-3-yl)phenyl]acetyl}piperidin-3-yl)carbonyl]amino}benzoic acid (Example 12: Table 1)

2-({[1-(biphenyl-3-yl-carbonyl)piperidin-3-yl]carbonyl}amino)-5-chlorobenzoic acid (Example 31: Table 2-1).

When X is Sulfur

When X is sulfur, i.e., the compound represented by Formula (I-a-4) is a heterocyclic carboxylic acid (thiophenecarboxylic acid: a compound wherein B is carboxyl) or a bioisostere thereof (a compound wherein B is a group that is biologically equivalent to a carboxyl group), $R_1$ to $R_4$, $L_4$, T, D, and q are as defined above. The description in section "When X is vinylene" above can be incorporated by reference.

(I-a-2) Compounds Wherein L is Substituted or Unsubstituted $C_{1-6}$-Alkylene-O—

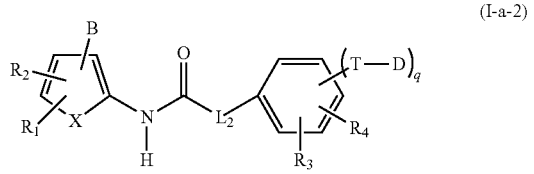

(I-a-2)

wherein $R_1$ to $R_4$, B, X, T, D, and q are as defined above, and $L_2$ is substituted or unsubstituted In the compound (I-a-2), $L_2$ (represented as "L" in Formula (I)) is $C_{1-6}$ alkylene-O—, preferably $C_{1-4}$ alkylene-O—, and more preferably $C_{1-3}$ alkylene-O—. The alkylene may be linear or branched. The alkylene may have 1 or 2 substituents, and is preferably unsubstituted alkylene.

When X is Vinylene

Preferable examples of the compound (I-a-2) include those represented by Formula (I-a-2) wherein X is vinylene (—CH═CH—).

In the formula, B, $R_1$, and $R_2$ may be located at any of the ortho, meta, and para positions on the benzene ring to which imino is bound. Preferably, B is located at the ortho position, and $R_2$ and $R_1$ are located at the meta and para positions, respectively, on the benzene ring.

In the compound (I-a-2), $R_1$ and $R_2$ are as defined above, preferably $R_1$ and $R_2$ are the same or different, and each represents hydrogen, halogen, aryl optionally having one or two substituents, or 5- to 6-membered ring heteroaryl optionally having one or two substituents. More preferably, $R_2$ located at the meta position is hydrogen, and $R_1$ located at the para position is halogen, aryl optionally having one substituent, or 5- to 6-membered ring heteroaryl optionally having one substituent. $R_1$ is preferably halogen.

Here, halogen is preferably chlorine, bromine, or fluorine, and more preferably chlorine.

A preferable example of aryl is phenyl, and a preferable example of 5- to 6-membered ring heteroaryl is aryl having one or two atoms selected from oxygen, sulfur, and nitrogen; the atoms may be the same or different. Preferably, the aryl is 5- to 6-membered ring aryl having one oxygen as a heteroatom. A preferable example thereof is furyl, and specific examples thereof include furan-1-yl, furan-2-yl, furan-3-yl, furan-4-yl, and furan-5-yl. Particularly preferable is furan-3-yl. Examples of the substituents of aryl and heteroaryl are as described above, and preferable are halogen, $C_{1-6}$ (preferably $C_{1-4}$) alkyl, and $C_{1-6}$ (preferably $C_{1-4}$) alkoxy. Among these, $C_{1-4}$ alkyl is preferable, and more preferable are methyl and ethyl.

$R_3$ and $R_4$ are as defined above, and preferably when q is 1, both are hydrogen, and when q is 0, either $R_3$ or $R_4$ is hydrogen and the other is substituted or unsubstituted $C_{1-6}$, or preferably branched alkyl. A preferable example of branched alkyl is tert-butyl.

T is as defined above, and is preferably a single bond.

D is as defined above, and preferable examples thereof include aryl optionally having one or two substituents, heteroaryl optionally having one or two substituents, $C_{3-8}$ cycloalkyl optionally having one or two substituents, $C_{3-8}$ cycloalkenyl optionally having one or two substituents, and adamanthyl. Here, aryl is preferably phenyl; heteroaryl is preferably furyl, and more preferably furan-2-yl or furan-3-yl; cycloalkyl is preferably cyclohexyl; cycloalkenyl is preferably cyclohexenyl, and more preferably cyclohex-1-en-1-yl; and adamanthyl is preferably adamantan-1-yl.

Examples of the substituents are as described above, and preferable are $C_{1-6}$ (preferably $C_{1-4}$) alkyl and $C_{1-6}$ (preferably $C_{1-4}$) alkoxy.

Specific examples of the aromatic carboxylic acid (benzene carboxylic acid) of the present invention represented by the formula above and bioisosteres of the carboxylic acid (I-a-2) include the following compounds (see Tables 1 and 2):

5-chloro-2-({[3-(furan-3-yl)phenoxy]acetyl}amino)benzoic acid (Example 13)

5-bromo-2-({[3-(furan-3-yl)phenoxy]acetyl}amino)benzoic acid (Example 15)

2-{[(3-tert-butylphenoxy)acetyl]amino}-5-chlorobenzoic acid (Example 16)
5-chloro-2-{[(2-cyclohexylphenoxy)acetyl]amino}benzoic acid (Example 17)
2-{[(4-tert-butylphenoxy)acetyl]amino}-5-chlorobenzoic acid (Example 18)
2-{[(biphenyl-4-yloxy)acetyl]amino}-5-chlorobenzoic acid (Example 19)
2-{[(biphenyl-3-yloxy)acetyl]amino}-5-chlorobenzoic acid (Example 20)
2-({[4-(admmntan-1-yl)phenoxy]acetyl}amino)-5-chlorobenzoic acid (Example 21)
4-({[3-(furan-3-yl)phenoxy]acetyl}amino)biphenyl-3-carboxylic acid (Example 22)
5-chloro-2-({[3-(cyclohex-1-en-1-yl)phenoxy]acetyl}amino)benzoic acid (Example 25)
5-chloro-2-{[{3-cyclohexylphenoxy)acetyl]amino}benzoic acid (Example 26)
4-({[3-(furan-3-yl)phenoxy]acetyl}amino)-3'-methylbiphenyl-3-carboxylic acid (Example 27)
4-({[3-(furan-3-yl)phenoxy]acetyl}amino)-3',5'-dimethylbiphenyl-3-carboxylic acid (Example 28)
5-chloro-2-({[4-(furan-3-yl)phenoxy]acetyl}amino)benzoic acid (Example 29)
2-({[3-(adamantan-1-yl)phenoxy]acetyl}amino)-5-chlorobenzoic acid (Example 30)
5-chloro-2-({2-[3-(furan-3-yl)phenoxy]-2-methylpropanoly}amino)benzoic acid (Example 44)
4-{[(biphenyl-3-yloxy)acetyl]amino}biphenyl-3-carboxylic acid (Example 45)
2-{[(biphenyl-4-yloxy)acetyl]amino}-5-(furan-3-yl)benzoic acid (Example 46)
2-({[4-(adamantan-1-yl)phenoxy]acetyl}amino)-5-(furan-3-yl)benzoic acid (Example 47)
5-chloro-2-({[(4'-methylbiphenyl-4-yl)oxy]acetyl}amino)benzoic acid (Example 49)
5-chloro-2-({[(3',5'-dimethylbiphenyl-4-yl)oxy]acetyl}amino)benzoic acid (Example 50)
5-chloro-2-({[3-(furan-2-yl)phenoxy]acetyl}amino)benzoic acid (Example 53)
5-chloro-2-({[4-(furan-2-yl)phenoxy]acetyl}amino)benzoic acid (Example 54)
2-({4-[4-(adamantan-1-yl)phenoxy]butanoyl}amino)-5-chlorobenzoic acid (Example 55)
2-({3-[4-(adamantan-1-yl)phenoxy]propanoly}amino)-5-chlorobenzoic acid (Example 59)
5-chloro-2-({[(2'-methoxybiphenyl-3-yl)oxy]acetyl}amino)benzoic acid (Example 61).

When X is Sulfur

When X is sulfur, i.e., the compound represented by Formula (I-a-2) is a heterocyclic carboxylic acid (thiophenecarboxylic acid: a compound wherein B is carboxyl) or a bioisostere thereof (a compound wherein B is a group that is biologically equivalent to a carboxyl group), $R_1$ to $R_4$, $L_2$, T, D, and q are as defined above. The description in section "When X is vinylene" above can be incorporated by reference.

(I-a-3) Compounds Wherein L is Substituted or Unsubstituted $C_{1-6}$-Alkylene, $C_{2-6}$-Alkenylene, or $C_{2-6}$-Alkynylene

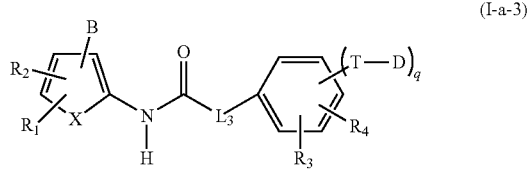

(I-a-3)

wherein $R_1$ to $R_4$, B, X, T, D, and q are as defined above. $L_3$ is substituted or unsubstituted $C_{1-6}$-alkylene, $C_{2-6}$-alkenylene, or $C_{2-6}$-alkynylene.

In the compound (I-a-3), $L_3$ (represented as "L" in Formula (I)) is $C_{1-6}$ alkylene, $C_{2-6}$ alkenylene, or $C_{2-6}$ alkynylene.

The alkylene is preferably $C_{1-4}$ alkylene, and more preferably $C_{1-3}$ alkylene. The alkylene may be linear or branched, and some carbon atoms in the alkylene optionally form a $C_{3-8}$ cycloalkyl ring. Examples of such a cycloalkyl ring (cycloalkane) include cyclopropane, cyclobutane, cycloheptane, cyclohexane, cycloheptane, and cyclooctane. Cyclopropane is preferable.

The alkenylene is preferably $C_{2-3}$ alkenylene, and more preferably vinylene. The alkynylene is preferably $C_{2-3}$ alkynylene, and more preferably $C_2$ alkynylene. These groups optionally have one or two substituents. Such substituents are as defined above, and preferable examples thereof include unsubstituted alkylene, alkenylene, and alkynylene.

When X is Vinylene

Preferable examples of the compound (I-a-3) include those represented by Formula (I-a-3) wherein X is vinylene (—CH═CH—).

In the formula, B, $R_1$, and $R_2$ may be located at any of the ortho, meta, and para positions on the benzene ring to which imino is bound. Preferable compounds include those in which B is located at the ortho position, and $R_2$ and $R_1$ are located at the meta and para position, respectively, on the benzene ring.

In the compound (I-a-3), $R_1$ and $R_2$ are as defined above, are preferably the same or different, and each represents hydrogen or halogen. More preferably, $R_2$ located at the meta position is hydrogen, and $R_1$ located at the para position is halogen. Preferable examples of halogen include chlorine, bromine, and fluorine, and more preferably chlorine.

In the formula, q, $R_3$, and $R_4$ are as defined above. When q is 1, both $R_3$ and $R_4$ are preferably hydrogen. Preferably, q is 1.

T is as defined above, and is preferably a single bond.

D is as defined above, and preferable examples thereof include aryl optionally having one or two substituents, heteroaryl optionally having one or two substituents, benzo-fused heteroaryl optionally having one or two substituents, $C_{3-8}$ cycloalkenyl optionally having one or two substituents, and adamanthyl optionally having one or two substituents.

The aryl is preferably phenyl. Examples of heteroaryl include 5- or 6-membered ring aryl having oxygen or nitrogen as a heteroatom. Preferable are furyl and pyridyl, and more preferable are furan-2-yl, furan-3-yl, and pyridin-3-yl. The benzo-fused heteroaryl is preferably quinolyl or isoquinolyl, and more preferably quinolin-8-yl, quinolin-3-yl, or quinolin-5-yl. The cycloalkenyl is preferably cyclohexenyl, and more preferably is cyclohex-1-en-1-yl. The adamanthyl is preferably adamantan-1-yl. Examples of the substituents are as described above, and preferable are unsubstituted aryl, heteroaryl, benzo-fused heteroaryl, cycloalkenyl, and adamanthyl.

Specific examples of the aromatic carboxylic acid (benzene carboxylic acid) of the present invention represented by the above formula and bioisosteres thereof (I-a-3) include the following compounds (see Tables 1 and 2):
5-chloro-2-({[3-(furan-3-yl)phenyl]acetyl}}amino)benzoic acid (Example 3)
5-chloro-2-[({1-[3-(furan-3-yl)phenyl]cyclopropyl}carbonyl)amino]benzoic acid (Example 35)

5-chloro-2-({3-[3-(furan-3-yl)phenyl]propanoyl}amino)benzoic acid (Example 36)

5-chloro-2-({2-[3-(furan-3-yl)phenyl]-2-methylpropanoly}amino)benzoic acid (Example 37)

2-[(biphenyl-4-ylacetyl)amino]-5-chlorobenzoic acid (Example 70)

2-{[(2E)-3-(biphenyl-4-yl)propa-2-enoyl]amino}-5-chlorobenzoic acid (Example 78)

2-{[(2E)-3-(biphenyl-3-yl)propa-2-enoyl]amino}-5-chlorobenzoic acid (Example 89)

5-chloro-2-({(2E)-3-[3-(cyclohex-1-en-1-yl)phenyl]propa-2-enoyl}amino)benzoic acid (Example 90)

5-chloro-2-({(2E)-3-[3-(quinolin-8-yl)phenyl]propa-2-enoyl}amino)benzoic acid (desalted product of Example 101)

5-chloro-2-({(2E)-3-[3-(pyridin-3-yl)phenyl]propa-2-enoyl}amino)benzoic acid (desalted product of Example 103)

2-({3-[4-(adamantan-1-yl)phenyl]propa-2-ynoyl}amino)-5-chlorobenzoic acid (Example 94).

When X is Sulfur

When X is sulfur, i.e., the compound represented by Formula (I-a-3) is a heterocyclic carboxylic acid (thiophenecarboxylic acid: a compound wherein B is carboxyl) or a bioisostere thereof (a compound wherein B is a group that is biologically equivalent to a carboxyl group), $R_1$ to $R_4$, $L_3$, T, D, and q are as defined above. The description in section "When X is vinylene" above can be incorporated by reference.

(I-a-5) Compounds Wherein L is Adamantyl

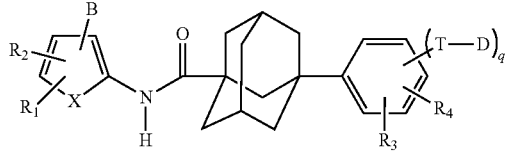

wherein $R_1$ to $R_4$, B, X, T, D, and q are as defined above.

When X is Vinylene

Preferable examples of the compound (I-a-5) include those represented by Formula (I-a-5) wherein X is vinylene (—CH=CH—). In the formula, B, $R_1$, and $R_2$ may be located at any of the ortho, meta, and para positions on the benzene ring to which imino is bound. Preferable compounds are those in which B is located at the ortho position, and $R_2$ and $R_1$ are located at the meta and para positions, respectively, on the benzene ring.

In the compound (I-a-5), $R_1$ and $R_2$ are as defined above, and preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

q, T, D, $R_3$, and $R_4$ are as defined above, preferably q is 0, either $R_3$ or $R_4$ is hydrogen, and the other is $C_{1-6}$ alkyl. The alkyl is preferably $C_{1-4}$, and more preferably $C_{1-2}$ alkyl.

Specific examples of the aromatic carboxylic acid (benzene carboxylic acid) of the present invention represented by the above formula and bioisosteres thereof (Ia-4) include the following compound (see Table 2):

5-chloro-2-({[3-(4-methylphenyl)adamantan-1-yl]carbonyl}amino)benzoic acid (Example 86).

When X is Sulfur

When X is sulfur, i.e., the compound represented by Formula (I-a-5) is a heterocyclic carboxylic acid (thiophenecarboxylic acid: a compound wherein B is carboxyl) or a bioisostere thereof (a compound wherein B is a group that is biologically equivalent to a carboxyl group), $R_1$ to $R_4$, T, D, and q are as defined above. The description in section "When X is vinylene" above can be incorporated by reference.

(I-b) Compounds Wherein A is Represented by Formulae (I-2)-(I-4)

The compounds (Ib) that belong to this category include aromatic or heterocyclic carboxylic acids represented by Formulae (I-b-2) to (I-b-4) below and bioisosteres thereof.

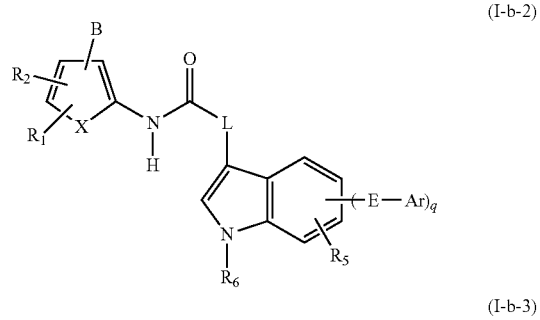

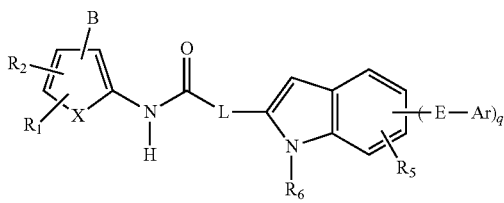

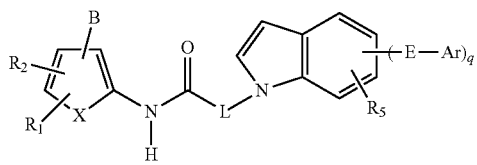

wherein $R_1$, $R_2$, $R_5$, $R_6$, B, X, L, E, Ar, and q are as defined above.

When X is Vinylene

Preferable examples of the compounds (I-b-2) to (I-b-4) (which hereunder may be collectively referred to as "compound (I-b)") include the compounds wherein X in Formulae (I-b-2) to (I-b-4) (which hereunder may be collectively referred to as "Formulae (I-b)") is vinylene (—CH=CH—). In the formula, B, $R_1$, and $R_2$ may be located at any of the ortho, meta, and para positions on the benzene ring to which imino is bound. Preferable compounds are those in which B is located at the ortho position, and $R_2$ and $R_1$ are located at the meta and para positions, respectively, on the benzene ring.

In the compound (I-b), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

q and $R_5$ are as defined above; preferably, when q is 1, $R_5$ is hydrogen, and when q is 0, $R_5$ is halogen. The halogen is preferably chlorine or bromine, and more preferably bromine.

As defined above, $R_6$ is hydrogen, $C_{1-6}$ alkyl, or $C_{1-6}$ hydroxyalkyl. The alkyl is preferably $C_{1-4}$, and more preferably $C_{1-2}$ alkyl, and the alkyl may be either linear or branched. The alkyl in hydroxyalkyl is preferably $C_{1-4}$, more preferably $C_{1-3}$ alkyl, and the alkyl may be either linear or branched.

As defined above, E is a single bond or $C_{1-6}$—O-alkylene. The alkylene in —O-alkylene is preferably $C_{1-4}$, more preferably $C_{1-3}$ alkylene, and the alkylene may be either linear or branched. E is preferably a single bond.

Ar is as defined above, and preferably aryl optionally having one or two substituents, or heteroaryl optionally having two substituents. The aryl is as defined above, and preferably phenyl optionally having one substituent. The substituents are as defined above, and preferably unsubstituted phenyl. The heteroaryl is as defined above, preferably furyl, and more preferably furan-2-yl or furan-3-yl.

In the compound (I-b), L is as defined above. Preferable examples thereof include a single bond, $C_{1-6}$ alkylene optionally having one or two substituents, and —CO—. The alkylene is preferably $C_{1-4}$, more preferably $C_{1-3}$ alkylene, and the alkylene may be either linear or branched. In the case of the compound (I-b-2), L is preferably —CO—; in the case of the compound (I-b-3), L is preferably a single bond; and in the case of the compound (I-b-4), L is preferably $C_{1-6}$ alkylene optionally having one or two substituents.

Specific examples of the aromatic carboxylic acid (benzene carboxylic acid) of the present invention represented by the above formula and bioisosteres thereof (I-b) include the following compounds (see Tables 1 and 2).
Compound (I-b-2)
5-chloro-2-({[5-(furan-3-yl)-1-methyl-1H-indol-3-yl](oxo)acetyl}amino)benzoic acid (Example 14)
2-({[5-(benzyloxy)-1H-indol-3-yl](oxo)acetyl}amino)-5-chlorobenzoic acid (Example 57)
Compound (I-b-3)
2-{[(5-bromo-1-methyl-1H-indol-2-yl)carbonyl]amino}-5-chlorobenzoic acid (Example 23)
5-chloro-2-{[(1-methyl-5-phenyl-1H-indol-2-yl)carbonyl]amino}benzoic acid (Example 48)
5-chloro-2-({[1-(3-hydroxypropyl)-5-phenyl-1H-indol-2-yl]carbonyl}amino)benzoic acid (Example 60)
Compound (I-b-4)
2-{[(5-bromo-1H-indol-1-yl)acetyl]amino}-5-chlorobenzoic acid (Example 24)
5-chloro-2-{[(5-phenyl-1H-indol-1-yl)acetyl]amino}benzoic acid (Example 51)
When X is Sulfur When X is sulfur, i.e., the compound represented by any of Formulae (I-a-2) to (I-b-4) is a heterocyclic carboxylic acid (thiophenecarboxylic acid: a compound wherein B is carboxyl) or a bioisostere thereof (a compound wherein B is a group that is biologically equivalent to a carboxyl group), $R_1$, $R_2$, $R_5$, $R_6$, L, E, Ar, and q are as defined above. The description in section "When X is vinylene" above can be incorporated by reference.

(I-c) Compounds Wherein A is Represented by Formula (I-5)

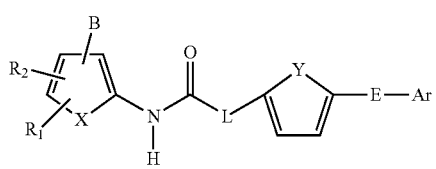

(I-c)

wherein $R_1$, $R_2$, B, X, L, Y, E, and Ar are as defined above.
When X is Vinylene Preferable examples of the compound (I-c) include those represented by Formula (I-c) wherein X is vinylene (—CH=CH—). In the formula, B, $R_1$, and $R_2$ may be located at any of the ortho, meta, and para positions on the benzene ring to which imino is bound. Preferable compounds are those in which B is located at the ortho position, and $R_2$ and $R_1$ are located at the meta and para positions, respectively, on the benzene ring.

In the compound (I-c), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

As defined above, Y is sulfur or oxygen.

E is as defined above, and is preferably a single bond.

Ar is as defined above, and is preferably aryl optionally having one or two substituents, and more preferably phenyl optionally having one substituent. Examples of the substituents are as described above, and halogen is preferable. Preferable examples of halogen include chlorine, bromine, and fluorine, and more preferably fluorine.

In the compound (I-c), L is as defined above, and is preferably a single bond.

Specific examples of the aromatic carboxylic acid (benzene carboxylic acid) of the present invention represented by the above formula and bioisosteres thereof (I-c) include the following compounds (see Table 2):
5-chloro-2-({[5-(4-fluorophenyl)thiophen-2-yl]carbonyl}amino)benzoic acid (Example 104)
5-chloro-2-{[(5-phenylfuran-2-yl)carbonyl]amino}benzoic acid (Example 105)
When X is Sulfur When X is sulfur, i.e., the compound represented by Formula (I-c) is a heterocyclic carboxylic acid (thiophenecarboxylic acid: a compound wherein B is carboxyl) or a bioisostere thereof (a compound wherein B is a group that is biologically equivalent to a carboxyl group), $R_1$, $R_2$, Y, E, and Ar are as defined above. The description in section "When X is vinylene" above can be incorporated by reference.

(I-d) Compounds Wherein A is Represented by Formula (I-6)

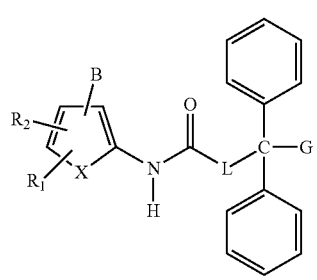

(I-d)

wherein $R_1$, $R_2$, B, X, L, and G are as defined above.
When X is Vinylene

Preferable examples of the compound (I-d) include those represented by Formula (I-d) wherein X is vinylene (—CH=CH—). In the formula, B, $R_1$, and $R_2$ may be located at any of the ortho, meta, and para positions on the benzene ring to which imino is bound. Preferable compounds are those in which B is located at the ortho position, and $R_2$ and $R_1$ are located at the meta and para positions, respectively, on the benzene ring.

In the compound (I-d), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (I-d), L is as defined above, and is preferably a single bond, $C_{1-6}$ alkylene optionally having one or two substituents (some carbon atoms in the alkylene optionally form a cycloalkyl ring), $C_{1-6}$ alkylene-O— optionally having one or two substituents (some carbon atoms in the alkylene optionally form a cycloalkyl ring), $C_{1-6}$ alkylene-NH— optionally having one or two substituents (in "alkylene-NH—," some carbon atoms in the alkylene optionally form a cycloalkyl ring), 1,4-piperazidinyl, or $C_{1-6}$ alkylene-1,4-piperazidinyl. Examples of the "alkylene group" and the "alkylene" in "alkylene-O—," "alkylene-NH—," and "alkylene-1,4-piperazidinyl" include $C_{1-6}$ alkylene, preferably $C_{1-4}$ alkylene, and more preferably $C_{1-2}$ alkylene. The alkylene may be either linear or branched, and some carbon atoms in the alkylene optionally form a $C_{3-6}$ cycloalkyl ring. Examples of such a cycloalkyl ring (cycloalkane) include cyclopropane, cyclobutane, cycloheptane, and cyclohexane; cyclopropane is preferable. These groups may have one or two substituents, but unsubstituted alkylene is preferable.

In the compound (I-d), G is hydrogen or $C_{1-6}$ alkyl, as defined above. The alkyl is preferably $C_{1-4}$, and more preferably $C_{1-2}$ alkyl.

Specific examples of the aromatic carboxylic acid (benzene carboxylic acid) of the present invention represented by the above formula and bioisosteres thereof (I-d) include the following compounds (see Table 2):

5-chloro-2-[(2,2-diphenylpropanoly)amino]benzoic acid (Example 39)
5-chloro-2-[(3,3-diphenylpropanoly)amino]benzoic acid (Example 41)
5-chloro-2-{[N-(diphenylmethyl)glycyl]amino}benzoic acid (Example 73)
5-chloro-2-({[4-(diphenylmethyl)piperazin-1-yl}carbonyl}amino)benzoate hydrochloride (Example 75)
5-chloro-2-{([(diphenylmethoxy)acetyl]amino}benzoic acid (Example 76)
5-chloro-2-({[4-(diphenylmethyl)piperazin-1-yl]acetyl}amino)benzoic acid (Example 77)

When X is Sulfur

When X is sulfur, i.e., the compound represented by Formula (I-d) is a heterocyclic carboxylic acid (thiophenecarboxylic acid: a compound wherein B is carboxyl) or a bioisostere thereof (a compound wherein B is a group that is biologically equivalent to a carboxyl group), $R_1$, $R_2$, and G are as defined above. The description in section "When X is vinylene" above can be incorporated by reference.

(I-e) Compounds Wherein A is Represented by Formula (I-7)

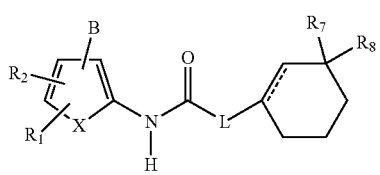

(I-e)

wherein $R_1$, $R_2$, $R_7$, $R_8$, B, X, and L are as defined above.

When X is Vinylene

Preferable examples of the compound (I-e) include those represented by Formula (I-e) wherein X is vinylene (—CH=CH—). In the formula, B, $R_1$, and $R_2$ may be located at any of the ortho, meta, and para positions on the benzene ring to which imino is bound. Preferable compounds are those in which B is located at the ortho position, and $R_2$ and $R_1$ are located at the meta and para positions, respectively, on the benzene ring.

In the compound (I-e), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (I-e), L is as defined above, and preferably a single bond or $C_{2-6}$ alkenylene optionally having one or two substituents. The "alkenylene" is preferably $C_{2-3}$ alkenylene, and more preferably $C_2$ vinylene. The alkenylene may have one or two substituents, and a preferable example of such a substituent is halogen. The halogen is preferably chlorine or fluorine, and more preferably chlorine.

In the compound (I-e), $R_7$ and $R_8$ are as defined above. Both are hydrogen or alkylene at the same time, and bind to each other to form 3- to 8-membered ring cycloalkane. The cycloalkane is preferably 3- to 6-membered ring cycloalkane, and more preferably 6-membered ring cyclohexane.

Further, in Formula (I-e), ═══ represents a single or double bond.

Specific examples of the aromatic carboxylic acid (benzene carboxylic acid) of the present invention represented by the above formula and bioisosteres thereof (I-e) include the following compounds (see Table 2):

5-chloro-2-{[(2E)-3-chloro-3-cyclohexylpropa-2-enoyl]amino}benzoic acid (Example 91)
5-chloro-2-[(spiro[5.5]undec-1-en-2-ylcarbonyl)amino]benzoic acid (Example 84)
5-chloro-2-[(spiro[5.5]undec-1-en-2-ylcarbonyl)amino]benzoic acid (Example 85).

When X is Sulfur

When X is sulfur, i.e., the compound represented by Formula (I-e) is a heterocyclic carboxylic acid (thiophenecarboxylic acid: a compound wherein B is carboxyl) or a bioisostere thereof (a compound wherein B is a group that is biologically equivalent to a carboxyl group), $R_1$ to $R_4$, T, D, and q are as defined above. The description in section "When X is vinylene" above can be incorporated by reference.

(I-f) Compounds Wherein A is Fluorenyl

In the compound (I-f), the position at which the fluorenyl binds to L is not particularly limited, and the fluorenyl may bind to L at any position. Preferably, the fluorenyl binds to L at the 1-position to form the compound represented by the formula below.

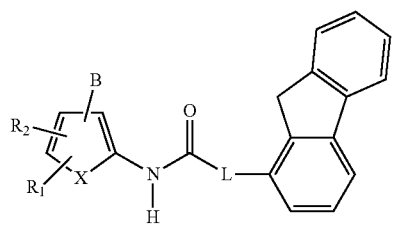

(I-f)

wherein $R_1$, $R_2$, B, X, and L are as defined above.

When X is Vinylene

Preferable examples of the compound (I-f) include those represented by Formula (I-f) wherein X is vinylene (—CH=CH—). In the formula, B, $R_1$, and $R_2$ may be located at any of the ortho, meta, and para positions on the benzene ring to which imino is bound. Preferable compounds are those in which B is located at the ortho position, and $R_2$ and $R_1$ are located at the meta and para positions, respectively, on the benzene ring.

In the compound (I-f), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (I-f), L is as defined above, and preferably a single bond.

Specific examples of the aromatic carboxylic acid (benzene carboxylic acid) of the present invention represented by Formula (I-f) and bioisosteres thereof (I-f) include the following compound (see Table 2):

5-chloro-2-[(9H-fluoren-1-ylcarbonyl)amino]benzoic acid (Example 38).

When X is Sulfur

When X is sulfur, i.e., the compound represented by Formula (I-f) is a heterocyclic carboxylic acid (thiophenecarboxylic acid: a compound wherein B is carboxyl) or a bioisostere thereof (a compound wherein B is a group that is biologically equivalent to a carboxyl group), $R_1$ and $R_2$ are as defined above. The description in section "When X is vinylene" above can be incorporated by reference.

(I-g) Compounds Wherein A is Substituted or Unsubstituted Quinolyl

In the compound (I-g), the position at which the quinolyl binds to L is not particularly limited, and the quinolyl may bind to L at any position. Preferably, quinolyl binds to L at the 4-position to form the compound represented by the formula below.

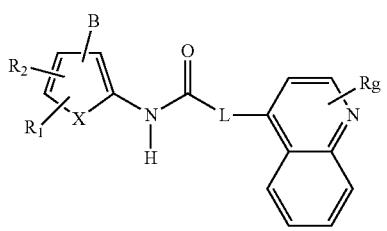

(I-g)

wherein $R_1$, $R_2$, B, X, and L are as defined above. $R_g$ is a substituent.

When X is Vinylene

Preferable examples of the compound (I-g) include those represented by Formula (I-g) wherein X is vinylene (—CH=CH—). In the formula, B, $R_1$, and $R_2$ may be located at any of the ortho, meta, and para positions on the benzene ring to which imino is bound. Preferable compounds include those in which B is located at the ortho position, and $R_2$ and $R_1$ are located at the meta and para positions, respectively, on the benzene ring.

In the compound (I-g), $R_1$ and $R_2$ are as defined above, preferably are the same or different, and each represents hydrogen or halogen. More preferably, $R_2$ located at the meta position is hydrogen, and $R_1$ located at the para position is halogen. The halogen is preferably chlorine, bromine, or fluorine, and more preferably chlorine.

In the compound (I-g), L is as defined above, and preferably a single bond.

In the compound (I-g), quinolyl optionally has a substituent (Rg). Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, and alkoxycarbonyl having $C_{1-4}$ alkoxy. The meanings of "alkyl," "alkoxy," and "aryl" are as defined above. Preferable is aryl optionally having one or two substituents, and more preferable is phenyl optionally having one substituent.

Examples of the substituents of phenyl are as described above, and unsubstituted phenyl is preferable.

Specific examples of the benzene carboxylic acid of the present invention represented by the above formula and bioisosteres thereof (I-g) include the following compound (see Table 2):

5-chloro-2-{[(2-phenylquinolin-4-yl)carbonyl]amino}sodium benzoate (Example 107).

When X is Sulfur

When X is sulfur, i.e., the compound represented by Formula (I-g) is a heterocyclic carboxylic acid (thiophenecarboxylic acid: a compound wherein B is carboxyl) or a bioisostere thereof (a compound wherein B is a group that is biologically equivalent to a carboxyl group), $R_1$, $R_2$, and Rg are as defined above. The description in section "When X is vinylene" above can be incorporated by reference.

The method for producing the compound group 1 represented by Formula (I) is as described in the international publication pamphlet (WO2010/113022), and these compounds can be produced according to this method.

TABLE 1

| Examples | Compounds | Formula M.W. | PAI-1 activity % 50 μM | 20 μM |
|---|---|---|---|---|
| 1 | 5-chloro-2-{[4-({[3-(furan-3-yl)phenyl]carbonyl}amino)butanoyl]amino}benzoic acid | C22H19ClN2O5 426.85 | 48.9 | 95.5 |
| 2 | 5-chloro-2-({[3-(furan-3-yl)phenyl]carbonyl}amino)benzoic acid | C18H12ClNO4 341.75 | 8.7 | 49.0 |
| 3 | 5-chloro-2-({[3-(furan-3-yl)phenyl]acetyl}amino)benzoic acid | C19H14ClNO4 355.77 | 19.6 | 63.7 |
| 4 | 2-[(biphenyl-3-ylcarbonyl)amino]-5-chlorobenzoic acid | C20H14ClNO3 351.78 | 7.6 | 47.7 |
| 5 | 2-({[3-(furan-3-yl)phenyl]carbonyl}amino)-5-methyl-4-phenylthiophene-3-carboxylic acid | C23H17NO4S 403.45 | 6.1 | 14.7 |
| 6 | 2-[(biphenyl-2-ylcarbonyl)amino]-5-chlorobenzoic acid | C20H14ClNO3 351.78 | 22.2 | 51.4 |

TABLE 1-continued

| Examples | Compounds | Formula M.W. | PAI-1 activity % 50 μM | PAI-1 activity % 20 μM |
|---|---|---|---|---|
| 7 | 5-chloro-2-({[4-(thiophen-2-yl)phenyl]carbonyl}amino)benzoic acid | C18H12ClNO3S 357.81 | 7.4 | 54.2 |
| 9 | 5-chloro-2-[(1-{[3-(furan-3-yl)phenyl]acetyl}-L-prolyl)amino]benzoic acid | C24H21ClN2O5 452.89 | 53.2 | 98.1 |
| 10 | 5-chloro-2-[(-{[3-(furan-3-yl)phenyl]carbonyl}-L-prolyl)amino]benzoic acid | C23H19ClN2O5 438.86 | 38.3 | 73.0 |
| 11 | sodium 5-chloro-2-{[(1-{[3-(furan-3-yl)phenyl]carbonyl}piperidin-3-yl)carbonyl]amino}benzoate | C24H20ClN2NaO5 474.87 | 26.1 | 68.2 |
| 12 | 5-chloro-2-{[(1-{[3-(furan-3-yl)phenyl]acetyl}piperidin-3-yl)carbonyl]amino}benzoic acid | C25H23ClN2O5 466.91 | 15.7 | 57.7 |
| 13 | 5-chloro-2-({[3-(furan-3-yl)phenoxy]acetyl}amino)benzoic acid | C19H14ClNO5 371.77 | 8.2 | 39.9 |
| 14 | 5-chloro-2-({[5-(furan-3-yl)-1-methyl-1H-indol-3-yl](oxo)acetyl}amino)benzoic acid | C22H15ClN2O5 422.82 | 12.9 | 22.1 |
| Known compound (1) | 2-{[(4-tert-butylphenyl)carbonyl]amino}-5-chlorobenzoic acid | C18H18ClNO3 331.79 | 11.0 | 44.0 |
| Known compound (2) | 2-[(biphenyl-4-ylcarbonyl)amino]-5-chlorobenzoic acid | C20H14ClNO3 351.78 | 8.0 | 41.8 |

TABLE 2

| Examples | Compounds | Formula M.W. | PAI-1 activity % 10 μM | PAI-1 activity % 2.5 μM |
|---|---|---|---|---|
| 2 | 5-chloro-2-({[3-(furan-3-yl)phenyl]carbonyl}amino)benzoic acid | C18H12ClNO4 341.75 | 12.7 | 100.6 |
| 4 | 2-[(biphenyl-3-ylcarbonyl)amino]-5-chlorobenzoic acid | C20H14ClNO3 351.78 | 0.6 | 62.1 |
| 5 | 2-({[3-(furan-3-yl)phenyl]carbonyl}amino)-5-methyl-4-phenylthiophene-3-carboxylic acid | C23H17NO4S 403.45 | 0.3 | 46.4 |
| 7 | 5-chloro-2-({[4-(thiophen-2-yl)phenyl]carbonyl}amino)benzoic acid | C18H12ClNO3S 357.81 | 0.4 | 99.8 |
| 8 | sodium 5-chloro-2-({[3-(pyridin-4-yl)phenyl]carbonyl}amino)benzoate | C19H12ClN2NaO3 374.75 | 28.5 | 100.3 |
| 13 | 5-chloro-2-({[3-(furan-3-yl)phenoxy]acetyl}amino)benzoic acid | C19H14ClNO5 371.77 | 4.9 | 92.7 |
| 14 | 5-chloro-2-({[5-(furan-3-yl)-1-methyl-1H-indol-3-yl](oxo)acetyl}amino)benzoic acid | C22H15ClN2O5 422.82 | 4.3 | 87.4 |
| 15 | 5-bromo-2-({[3-(furan-3-yl)phenoxy]acetyl}amino)benzoic acid | C19H14BrNO5 416.22 | 3.0 | 87.3 |
| 16 | 2-{[(3-tert-butylphenoxy)acetyl]amino}-5-chlorobenzoic acid | C19H20ClNO4 361.82 | 21.9 | 77.4 |
| 17 | 5-chloro-2-{[(2-cyclohexylphenoxy)acetyl]amino}benzoic acid | C21H22ClNO4 387.86 | 0.8 | 52.8 |
| 18 | 2-{[(4-tert-butylphenoxy)acetyl]amino}-5-chlorobenzoic acid | C19H20ClNO4 361.82 | 16.1 | 81.4 |
| 19 | 2-{[(biphenyl-4-yloxy)acetyl]amino}-5-chlorobenzoic acid | C21H16ClNO4 381.81 | 2.5 | 72.4 |
| 20 | 2-{[(biphenyl-3-yloxy)acetyl]amino}-5-chlorobenzoic acid | C21H16ClNO4 381.81 | 1.9 | 55.7 |
| 21 | 2-({[4-(adamantan-1-yl)phenoxy]acetyl}amino)-5-chlorobenzoic acid | C25H26ClNO4 439.93 | 0.3 | 10.0 |
| 22 | 4-({[3-(furan-3-yl)phenoxy]acetyl}amino)biphenyl-3-carboxylic acid | C25H19NO5 413.42 | 0.4 | 29.9 |
| 23 | 2-{[(5-bromo-1-methyl-1H-indol-2-yl)carbonyl]amino}-5-chlorobenzoic acid | C17H12BrClN2O3 407.65 | 1.8 | 97.3 |
| 24 | 2-{[(5-bromo-1H-indol-1-yl)acetyl]amino}-5-chlorobenzoic acid | C17H12BrClN2O3 407.65 | 19.1 | 101.5 |
| 25 | 5-chloro-2-({[3-(cyclohex-1-en-1-yl)phenoxy]acetyl}amino)benzoic acid | C21H20ClNO4 385.84 | 0.0 | 85.8 |
| 26 | 5-chloro-2-{[(3-cyclohexylphenoxy)acetyl]amino}benzoic acid | C21H22ClNO4 387.86 | 0.6 | 98.0 |
| 27 | 4-({[3-(furan-3-yl)phenoxy]acetyl}amino)-3'-methylbiphenyl-3-carboxylic acid | C26H21NO5 427.45 | 0.7 | 69.1 |
| 28 | 4-({[3-(furan-3-yl)phenoxy]acetyl}amino)-3',5'-dimethylbiphenyl-3-carboxylic acid | C27H23NO5 441.48 | 0.5 | 33.6 |
| 29 | 5-chloro-2-({[4-(furan-3-yl)phenoxy]acetyl}amino)benzoic acid | C19H14ClNO5 371.77 | 24.3 | 93.2 |
| 30 | 2-({[3-(adamantan-1-yl)phenoxy]acetyl}amino)-5-chlorobenzoic acid | C25H26ClNO4 439.93 | 1.3 | 19.3 |

TABLE 2-continued

| | | | | |
|---|---|---|---|---|
| 31 | 2-({[1-(biphenyl-3-ylcarbonyl)piperidin-3-yl]carbonyl}amino)-5-chlorobenzoic acid | C26H23ClN2O4 462.92 | 20.2 | 88.0 |
| 32 | 5-chloro-2-{[(4'-methylbiphenyl-3-yl)carbonyl]amino}benzoic acid | C21H16ClNO3 365.81 | 1.7 | 94.4 |
| 33 | 5-chloro-2-{[(2'-methoxybiphenyl-3-yl)carbonyl]amino}benzoic acid | C21H16ClNO4 381.81 | 21.6 | 92.8 |
| 34 | 5-chloro-2-({[4-(3,6-dihydro-2H-pyran-4-yl)phenyl]carbonyl}amino)benzoic acid | C19H16ClNO4 357.79 | 45.1 | 97.1 |
| 35 | 5-chloro-2-[({1-[3-(furan-3-yl)phenyl]cyclopropyl}carbonyl)amino]benzoic acid | C21H16ClNO4 381.81 | 15.6 | 98.8 |
| 36 | 5-chloro-2-({3-[3-(furan-3-yl)phenyl]propanoyl}amino)benzoic acid | C20H16ClNO4 369.80 | 3.7 | 95.7 |
| 37 | 5-chloro-2-({2-[3-(furan-3-yl)phenyl]-2-methylpropanoyl}amino)benzoic acid | C21H18ClNO4 383.82 | 5.9 | 53.1 |
| 38 | 5-chloro-2-[(9H-fluoren-1-ylcarbonyl)amino]benzoic acid | C21H14ClNO3 363.79 | 2.5 | 94.8 |
| 39 | 5-chloro-2-(2,2-diphenylpropanoyl)amino]benzoic acid | C22H18ClNO3 379.84 | 22.1 | 88.6 |
| 40 | 2-({[4-(adamantan-1-yl)phenyl]carbonyl}amino)-5-chlorobenzoic acid | C24H24ClNO3 409.91 | 1.7 | 19.3 |
| 41 | 5-chloro-2-[(3,3-diphenylpropanoyl)amino]benzoic acid | C22H18ClNO3 379.84 | 12.9 | 72.4 |
| 42 | 5-chloro-2-{[(4-phenoxyphenyl)carbonyl]amino}benzoic acid | C20H14ClNO4 367.78 | 3.8 | 98.6 |
| 43 | 2-({[3,5-bis(trifluoro-methyl)phenyl]carbonyl}amino)-5-chlorobenzoic acid | C16H8ClF6NO3 411.68 | 14.1 | 98.4 |
| 44 | 5-chloro-2-({2-[3-(furan-3-yl)phenoxy]-2-methylpropanoyl}amino) benzoic acid | C21H18ClNO5 399.82 | 20.4 | 97.8 |
| 45 | 4-{[biphenyl-3-yloxy)acetyl]amino}biphenyl-3-carboxylic acid | C27H21NO4 423.46 | 0.9 | 76.9 |
| 46 | 2-{[biphenyl-4-yloxy)acetyl]amino}-5-(furan-3-yl)benzoic acid | C25H19NO5 413.42 | 0.4 | 69.9 |
| 47 | 2-({[4-(adamantan-1-yl)phenoxy]acetyl}amino)-5-(furan-3-yl)benzoic acid | C29H29NO5 471.54 | 0.6 | 9.7 |
| 48 | 5-chloro-2-{[(1-methyl-5-phenyl-1H-indol-2-yl)carbonyl]amino}benzoic acid | C23H17ClN2O3 404.85 | 1.7 | 2.5 |
| 49 | 5-chloro-2-({[(4'-methylbiphenyl-4-yl)oxy]acetyl}amino)benzoic acid | C22H18ClNO4 395.84 | 1.1 | 82.1 |
| 50 | 5-chloro-2-({[(3',5'-dimethylbiphenyl-4-yl)oxy]acetyl}amino)benzoic acid | C23H20ClNO4 409.86 | 0.1 | 58.9 |
| 51 | 5-chloro-2-{[(5-phenyl-1H-indol-1-yl)acetyl]amino}benzoic acid | C23H17ClN2O3 404.85 | 1.7 | 37.8 |
| 52 | 2-({[4-(adamantan-1-ylmethoxy)phenyl]carbonyl}amino)-5-chlorobenzoic acid | C25H26ClNO4 439.93 | 5.1 | 7.2 |
| 53 | 5-chloro-2-({[3-(furan-2-yl)phenoxy]acetyl}amino)benzoic acid | C19H14ClNO5 371.77 | 21.6 | 95.3 |
| 54 | 5-chloro-2-({[4-(furan-2-yl)phenoxy]acetyl}amino)benzoic acid | C19H14ClNO5 371.77 | 15.5 | 94.4 |
| 55 | 2-({4-[4-(adamantan-1-yl)phenoxy]butanoyl}amino)-5-chlorobenzoic acid | C27H30ClNO4 467.98 | 1.1 | 29.8 |
| 56 | 2-({[4-(adamantan-1-ylcarbonyl)phenyl]carbonyl}amino)-5-chlorobenzoic acid | C25H24ClNO4 437.92 | 0.7 | 75.8 |
| 57 | 2-({[5-(benzyloxy)-1H-indol-3-yl](oxo)acetyl}amino)-5-chlorobenzoic acid | C24H17ClN2O5 448.85 | 0.2 | 38.6 |
| 58 | 5-chloro-2-({[3-(naphthalen-1-yl)phenyl]carbonyl}amino)benzoic acid | C24H16ClNO3 401.84 | 0.0 | 0.0 |
| 59 | 2-({3-[4-(adamantan-1-yl)phenoxy]propanoyl}amino)-5-chlorobenzoic acid | C26H28ClNO4 453.96 | 1.4 | 56.3 |
| 60 | 5-chloro-2-({[1-(3-hydroxypropyl)-5-phenyl-1H-indol-2-yl]carbonyl}amino)benzoic acid | C25H21ClN2O4 448.90 | 0.9 | 25.0 |
| 61 | 5-chloro-2-({[(2'-methoxybiphenyl-3-yl)oxy]acetyl}amino)benzoic acid | C22H18ClNO5 411.84 | 38.9 | 92.4 |
| 62 | 2-({[3-(adamantan-1-yl)phenyl]carbonyl}amino)-5-chlorobenzoic acid | C24H24ClNO3 409.91 | 0.6 | 29.1 |
| 63 | sodium 5-chloro-2-({[3-(quinolin-3-yl)phenyl]carbonyl}amino)benzoate | C23H14ClN2NaO3 424.81 | 0.3 | 21.3 |
| 64 | sodium 5-chloro-2-({[3-(isoquinolin-4-yl)phenyl]carbonyl}amino)benzoate | C23H14ClN2NaO3 424.81 | 0.7 | 74.3 |
| 65 | sodium 5-chloro-2-({[3-(quinolin-6-yl)phenyl]carbonyl}amino)benzoate | C23H14ClN2NaO3 424.81 | 0.4 | 71.7 |
| 66 | sodium 5-chloro-2-({[3-(isoquinolin-5-yl)phenyl]carbonyl}amino)benzoate | C23H14ClN2NaO3 424.81 | 0.1 | 22.6 |
| 67 | sodium 5-chloro-2-({[4-(quinolin-8-yl)phenyl]carbonyl}amino)benzoate | C23H14ClN2NaO3 424.81 | 0.6 | 90.4 |
| 68 | sodium 5-chloro-2-({[3-(quinolin-8-yl)phenyl]carbonyl}amino)benzoate | C23H14ClN2NaO3 424.81 | 2.1 | 2.4 |
| 69 | 5-chloro-2-{[(4-cyclohexylphenyl)carbonyl]amino}benzoic acid | C20H20ClNO3 357.83 | 0.6 | 44.7 |
| 70 | 2-[(biphenyl-4-ylacetyl)amino]-5-chlorobenzoic acid | C21H16ClNO3 365.81 | 4.4 | 94.6 |

TABLE 2-continued

| | | | | |
|---|---|---|---|---|
| 71 | 2-[(biphenyl-4-ylcarbamoyl)amino]-5-chlorobenzoic acid | C20H15ClN2O3 366.80 | 2.1 | 39.6 |
| 72 | 5-chloro-2-{[N-(4'-fluoro-4-methylbiphenyl-3-yl)glycyl]amino}benzoic acid | C22H18ClFN2O3 412.84 | 3.6 | 31.1 |
| 73 | 5-chloro-2-{[N-(diphenylmethyl)glycyl]amino}benzoic acid | C22H19ClN2O3 394.85 | 31.2 | 82.2 |
| 74 | 2-{[(4-cyclohexylphenyl)carbonyl]amino}-5-methyl-4-phenylthiophene-3-carboxylic acid | C25H25NO3S 419.54 | 0.2 | 8.6 |
| 75 | 5-chloro-2-({[4-(diphenylmethyl)piperazin-1-yl]carbonyl}amino)benzoic acid hydrochloride | C25H25Cl2N3O3 486.39 | 4.7 | 86.4 |
| 76 | 5-chloro-2-{[(diphenylmethoxy)acetyl]amino}benzoic acid | C22H18ClNO4 395.84 | 30.6 | 92.9 |
| 77 | 5-chloro-2-({[4-(diphenylmethyl)piperazin-1-yl]acetyl}amino)benzoic acid | C26H26ClN3O3 463.96 | 19.3 | 89.6 |
| 78 | 2-{[(2E)-3-(biphenyl-4-yl)prop-2-enoyl]amino}-5-chlorobenzoic acid | C22H16ClNO3 377.82 | 0.3 | 25.3 |
| 79 | 5-chloro-2-({[3-(cyclohex-1-en-1-yl)phenyl]carbonyl}amino)benzoic acid | C20H18ClNO3 355.81 | 1.6 | 44.5 |
| 80 | 5-chloro-2-{[(3-cyclohexylphenyl)carbonyl]amino}benzoic acid | C20H20ClNO3 357.83 | 0.0 | 45.5 |
| 81 | 5-(cyclohex-1-en-1-yl)-2-{[(4-cyclohexylphenyl)carbonyl]amino}benzoic acid | C26H29NO3 403.51 | 0.0 | 1.0 |
| 82 | 5-cyclohexyl-2-{[(4-cyclohexylphenyl)carbonyl]amino}benzoic acid | C26H31NO3 405.53 | 1.4 | 1.7 |
| 83 | 5-chloro-2-({[4-(pyrrolidin-1-yl)phenyl]carbonyl}amino)benzoic acid hydrochloride | C18H18Cl2N2O3 381.25 | 26.6 | 99.1 |
| 84 | 5-chloro-2-[(spiro[5.5]undec-1-en-2-ylcarbonyl)amino]benzoic acid | C19H22ClNO3 347.84 | 5.5 | 97.0 |
| 85 | 5-chloro-2-[(spiro[5.5]undec-2-ylcarbonyl)amino]benzoic acid | C19H24ClNO3 349.85 | 11.0 | 97.5 |
| 86 | 5-chloro-2-({[3-(4-methylphenyl)adamantan-1-yl]carbonyl}amino)benzoic acid | C25H26ClNO3 423.93 | 1.4 | 63.5 |
| 87 | 5-chloro-2-({[3-(cyclohexylethynyl)phenyl]carbonyl}amino)benzoic acid | C22H20ClNO3 381.85 | 1.2 | 20.5 |
| 88 | 5-chloro-2-({[4-(cyclohexylethynyl)phenyl]carbonyl}amino)benzoic acid | C22H20ClNO3 381.85 | 0.8 | 35.5 |
| 89 | 2-{[(2E)-3-(biphenyl-3-yl)prop-2-enoyl]amino}-5-chlorobenzoic acid | C22H16ClNO3 377.82 | 0.1 | 60.7 |
| 90 | 5-chloro-2-({(2E)-3-[3-(cyclohex-1-en-1-yl)phenyl]prop-2-enoyl}amino) benzoic acid | C22H20ClNO3 381.85 | 0.1 | 65.3 |
| 91 | 5-chloro-2-{[(2E)-3-chloro-3-cyclohexylprop-2-enoyl]amino}benzoic acid | C16H17Cl2NO3 342.22 | 16.7 | 96.9 |
| 92 | 5-(cyclohexylethynyl)-2-{[(4-cyclohexylphenyl)carbonyl]amino}benzoic acid | C28H31NO3 429.55 | 0.4 | 0.0 |
| 93 | 5-(2-cyclohexylethyl)-2-{[(4-cyclohexylphenyl)carbonyl]amino}benzoic acid | C28H35NO3 433.58 | 0.0 | 0.0 |
| 94 | 2-({3-[4-(adamantan-1-yl)phenyl]prop-2-ynoyl}amino)-5-chlorobenzoic acid | C26H24ClNO3 433.93 | 7.4 | 3.5 |
| 95 | 2-{[(4-cyclohexylphenyl)carbonyl]amino}-5-ethynylbenzoic acid | C22H21NO3 347.41 | 0.3 | 80.5 |
| 96 | 2-({[4-(adamantan-1-ylmethyl)phenyl]carbonyl}amino)-5-chlorobenzoic acid | C25H26ClNO3 423.93 | 5.0 | 23.9 |
| 97 | 2-[({4-[adamantan-1-yl(hydroxy)methyl]phenyl}carbonyl)amino]-5-chlorobenzoic acid | C25H26ClNO4 439.93 | 0.7 | 89.9 |
| 98 | 5-chloro-2-({[4-(1-methylcyclohexyl)phenyl]carbonyl}amino)benzoic acid | C21H22ClNO3 371.86 | 0.1 | 41.5 |
| 99 | sodium 5-chloro-2-({[3-(quinolin-2-ylmethoxy)phenyl]carbonyl}amino)benzoate | C24H16ClN2NaO4 454.84 | 0.3 | 87.8 |
| 100 | sodium 5-chloro-2-({[4-(quinolin-2-ylmethoxy)phenyl]carbonyl}amino)benzoate | C24H16ClN2NaO4 454.84 | 0.7 | 92.1 |
| 101 | sodium 5-chloro-2-({(2E)-3-[3-(quinolin-8-yl)phenyl]prop-2-enoyl}amino)benzoate | C25H16ClN2NaO3 450.85 | 0.2 | 24.7 |
| 102 | N-[4-chloro-2-(1H-tetrazol-5-yl)phenyl]-3-(quinolin-8-yl)benzamide | C23H15ClN6O 426.86 | 1.5 | 91.3 |
| 103 | sodium 5-chloro-2-({(2E)-3-[3-(pyridin-3-yl)phenyl]prop-2-enoyl}amino)benzoate | C21H14ClN2NaO3 400.79 | 34.2 | 92.3 |
| 104 | 5-chloro-2-({[5-(4-fluorophenyl)thiophen-2-yl]carbonyl}amino)benzoic acid | C18H11ClFNO3S 375.80 | 0.9 | 84.8 |
| 105 | 5-chloro-2-{[(5-phenylfuran-2-yl)carbonyl]amino}benzoic acid | C18H12ClNO4 341.75 | 23.5 | 89.9 |
| 106 | sodium 2-[({[4-(adamantan-1-yl)phenyl]amino}(oxo)acetyl)amino]-5-chlorobenzoate | C25H24ClN2NaO4 474.91 | 26.3 | 88.4 |
| 107 | sodium 5-chloro-2-{[(2-phenylquinolin-4-yl)carbonyl]amino}benzoate | C23H14ClN2NaO3 424.81 | 6.7 | 100.0 |

TABLE 2-continued

| Examples | Compounds | Formula M.W. | | PAI-1 activity % |
|---|---|---|---|---|
| Known compound (1) | 2-{[(4-tert-butylphenyl)carbonyl]amino}-5-chlorobenzoic acid | C18H18ClNO3 | 331.79 | 12.7 | 100.5 |
| Known compound (2) | 2-[(biphenyl-4-ylcarbonyl)amino]-5-chlorobenzoic acid | C20H14ClNO3 | 351.78 | 0.2 | 70.7 |
| Known compound (3) | 5-chloro-2-{[(4-cyclohexylphenoxy)acetyl]amino} benzoic acid | C21H22ClNO4 | 387.86 | 0.3 | 36.3 |
| Known compound (4) | 5-chloro-2-{[(4-(phenylcarbonyl)phenyl]carbonyl}amino} benzoic acid | C21H14ClNO4 | 379.79 | 8.1 | 79.6 |
| Known compound (5) | 5-chloro-2-[(5,6,7,8-tetrahydronaphthalene-2-ylcarbonyl)amino] benzoic acid | C18H16ClNO3 | 329.78 | 18.8 | 98.5 |
| Known compound (6) | 5-chloro-2-[(diphenylacetyl)amino] benzoic acid | C21H16ClNO3 | 365.81 | 37.4 | 85.0 |
| Salt of Known compound (7) | 5-chloro-2-({[4-(1H-pyrrol-1-yl)phenyl]carbonyl}amino)benzoic acid hydrochloride | C18H14Cl2N2O3 | 377.22 | 3.7 | 100.1 |

(2) Compound Group 2 (WO2009/013915) of the Present Invention

The compound group 2 targeted by the present invention includes an aromatic or heterocyclic carboxylic acid represented by Formula (II) below (wherein B is carboxyl), an ester thereof (wherein B is alkoxycarbonyl), and a bioisostere of the carboxylic acid (wherein B is a group that is biologically equivalent to a carboxyl group):

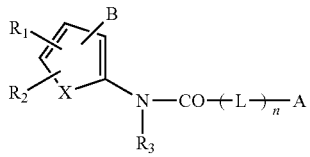
(II)

wherein $R_1$ and $R_2$ are the same or different, and each represents hydrogen, halogen, alkyl, cycloalkyl, cycloalkylalkyl, alkenyl, cycloalkenyl, alkynyl, hydroxyl, alkoxy, cycloalkoxy, alkenyloxy, cycloalkenyloxy, aryloxy, aralkyl, aralkyloxy, heterocyclic group, heterocyclic-alkyl, heterocyclic-alkyloxy; aryl optionally having a substituent; amino or carbamoyl, each of which is optionally substituted with one or two substituents; cyano, carboxy, or alkoxycarbonyl; and $R_1$ and $R_2$ are optionally adjoined with each other to form a ring; preferably one of $R_1$ and $R_2$ is hydrogen, and the other is halogen.

$R_3$ is hydrogen; or substituted or unsubstituted alkyl, alkenyl, alkynyl, cycloalkyl, aryl, or aralkyl. $R_3$ is preferably hydrogen.

X is —C($R_5$)═C($R_6$)—, sulfur, oxygen, —N($R_4$)—, —C($R_7$)═N—, or —N═C($R_8$)—. In these groups, $R_4$ represents hydrogen, or substituted or unsubstituted alkyl. $R_5$, $R_6$, $R_7$, and $R_8$ are each hydrogen, halogen, substituted or unsubstituted alkyl or alkoxy; $R_5$, $R_6$, $R_7$ and $R_8$ are preferably hydrogen. That is, —C($R_5$)═C($R_6$)— is preferably vinylene (—CH═CH—). X is preferably vinylene (—CH═CH—) or sulfur, and more preferably vinylene.

B is carboxyl or a group that is biologically equivalent to a carboxyl group. Specifically, B is alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl. B is preferably carboxyl.

L is substituted or unsubstituted alkyleneoxyalkylene, alkylene (some carbon atoms in the alkylene optionally form a cycloalkyl ring), alkenylene, alkynylene, cycloalkylene, alkylenethioalkylene, alkylene-SO-alkylene, or alkylene-SO$_2$-alkylene; or alkylene-N($R_9$)-alkylene. $R_9$ is hydrogen or substituted or unsubstituted alkyl.

n is an integer of 0 or 1, and preferably 1.

A is a group represented by the following formula:

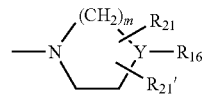

[in the above formula, m is an integer of 1 to 4;

Y is nitrogen, CH—, C($R_{16}'$)—, C(OH)—, or CH—O—;

$R_{16}$ and $R_{16}'$ are the same or different, and each represents substituted or unsubstituted aralkyl (including diphenylalkyl), hydrogen, or substituted or unsubstituted alkyl, cycloalkyl, alkenyl, cycloalkenyl, alkynyl, bicycloalkyl, bicycloalkenyl, adamanthyl, aryl, or fluorenyl;

$R_{21}$ and $R_{21}'$ are the same or different, and each represents hydrogen, substituted or unsubstituted alkyl, or phenyl], a group represented by the following formula:

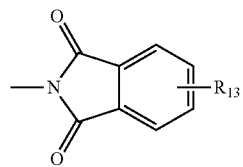

[wherein $R_{13}$ is hydrogen, halogen, alkyl, or alkoxy], —N($R_{11}$)—COR$_{12}$, —N($R_{11}$)—SO$_2$—R$_{12}$, or —N($R_{11}$)—CONH—R$_{12}$.

Among these groups, $R_{10}$, $R_{11}$, and $R_{12}$ are each represent the following group:

$R_{11}$ is hydrogen or alkyl;

$R_{12}$ is substituted or unsubstituted alkyl, cycloalkyl, aryl, or aralkyl (including diphenylalkyl); and $R_{10}$ is $N(R_{14})(R_{15})$, wherein $R_{14}$ and $R_{15}$ are the same or different, and each represents hydrogen; substituted or unsubstituted alkyl, alkenyl, cycloalkenyl, alkynyl, bicycloalkyl, bicycloalkenyl, adamanthyl, aryl, heterocyclic group, aralkyl (including diphenylalkyl), or heterocyclicalkyl.

The designation of each group represented by these characters and specific examples thereof are described below.

Examples of the "alkyl" represented by $R_1$, $R_2$, $R_3$, $R_4$, $R_5$, $R_6$, $R_7$, $R_8$, $R_9$, $R_{11}$, $R_{12}$, $R_{13}$, $R_{14}$, $R_{15}$, $R_{16}$, $R_{16}'$, $R_{21}$, or $R_{21}'$, particularly $R_1$, $R_2$, $R_9$, $R_{14}$, $R_{21}$, or $R_{21}'$, in the compound group 2 of the present invention include typically $C_{1-12}$, preferably $C_{1-10}$, more preferably $C_{1-8}$, further preferably $C_{1-6}$, and particularly preferably $C_{1-4}$ linear or branched lower alkyl groups. Examples of such alkyl groups include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, heptyl, 1-methylpentyl, 2-methylpentyl, n-heptyl, isoheptyl, secheptyl, tert-heptyl, n-octyl, tert-octyl, 2-methylhexyl, 2-ethylhexyl, etc. Preferable groups are methyl, ethyl, propyl, isopropyl, butyl and isobutyl; more preferable are methyl and ethyl; and particularly preferable is methyl. Among these, the "alkyl" represented by $R_3$, $R_4$, $R_5$, $R_6$, $R_7$, $R_8$, $R_9$, $R_{12}$, $R_{14}$, $R_{15}$, $R_{16}$, $R_{16}'$, $R_{21}$, or $R_{21}'$, particularly the "alkyl" represented by $R_9$, $R_{14}$, $R_{21}$, or $R_{21}'$, optionally has a substituent. Examples of such substituents include halogen, $C_{1-6}$ lower alkoxy, halogen-substituted $C_{1-6}$ lower alkoxy, hydroxyl, $CF_3$, $CF_3O$, $CHF_2O$, $CF_3CH_2O$, cyano, carboxy, alkoxycarbonyl, etc.

Examples of the "cycloalkyl" represented by $R_1$, $R_2$, $R_3$, $R_{12}$, $R_{16}$, or $R_{16}'$ in the compound group 2 of the present invention include typically $C_{3-7}$, and preferably $C_5$ or $C_6$ cyclic alkyl groups. Examples of such cycloalkyl groups include cyclopropyl, cyclobutyl, cyclopentyl, cyclohexyl, cycloheptyl, etc. Among these, the "cycloalkyl" represented by $R_3$, $R_{12}$, $R_{16}$, or $R_{16}'$ optionally has one or plural substituents at any position. Examples of such substituents include halogen, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl.

Examples of the "cycloalkylalkyl" represented by $R_1$ or $R_2$ in the compound group 2 of the present invention include typically $C_{3-7}$, and preferably $C_5$ or $C_6$ cyclic alkyl groups, having $C_{1-6}$ lower alkyl as a substituent. Examples of such cycloalkylalkyl groups include cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, etc.

Examples of the "alkoxy" represented by $R_1$, $R_2$, $R_5$, $R_6$, $R_7$, $R_8$, or $R_{13}$, particularly $R_1$ or $R_2$, in the compound group 2 of the present invention include hydroxyl groups substituted with the above-mentioned $C_{1-12}$, preferably $C_{1-10}$, more preferably $C_{1-8}$, further preferably $C_{1-6}$, and particularly preferably $C_{1-4}$ alkyl groups. Examples of such alkoxy groups include methoxy, ethoxy, 1-propoxy, 2-propoxy, 1-buthoxy, 2-buthoxy, 2-methyl-1-propoxy, 2-methyl-2-propoxy, 1-pentyloxy, 2-pentyloxy, 3-pentyloxy, 2-methyl-2-butoxy, 3-methyl-2-butoxy, 1-hexyloxy, 2-hexyloxy, 3-hexyloxy, 2-methyl-1-pentyloxy, 3-methyl-1-pentyloxy, 2-ethyl-1-butoxy, 2,2-dimethyl-1-butoxy, 2,3-dimethyl-1-butoxy, etc. Preferable among these are methoxy, ethoxy, 1-propoxy, and 2-propoxy, with methoxy being more preferable. Of these, the "alkoxy" represented by $R_5$, $R_6$, $R_7$, or $R_8$ optionally has a substituent. Examples of such substituents include halogen, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, alkoxycarbonyl, etc.

Examples of the "cycloalkoxy" represented by $R_1$ or $R_2$ in the compound group 2 of the present invention include $C_{2-8}$, preferably $C_{4-5}$ cyclic alkoxy groups. Such cycloalkoxy groups include cyclopropyloxy, cyclobutyloxy, cyclopentyloxy, cyclohexyloxy, cycloheptyloxy, etc.

Examples of the "alkenyl" represented by $R_1$, $R_2$, $R_3$, $R_{14}$, $R_{15}$, $R_{16}$, or $R_{16}'$ in the compound group 2 of the present invention include $C_{2-6}$ linear or branched alkenyl groups having 1 to 3 double bonds. Examples of such alkenyl groups include vinyl, 1-propenyl, 1-methyl-1-propenyl, 2-methyl-1-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl. Of these, the "alkenyl" represented by $R_3$, $R_{14}$, $R_{15}$, $R_{16}$, or $R_{16}'$ optionally has a substituent. Examples of such substituents include halogen, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl.

Examples of the "alkenyloxy" represented by $R_1$ or $R_2$ in the compound group 2 of the present invention include hydroxyl groups substituted with the above-mentioned $C_{2-6}$ linear or branched alkenyl groups having 1 to 3 double bonds. Specific examples of such alkenyloxy groups include vinyloxy, 1-propenyloxy, 1-methyl-1-propenyloxy, 2-methyl-1-propenyloxy, 2-propenyloxy, 2-butenyloxy, 1-butenyloxy, 3-butenyloxy, 2-pentenyloxy, 1-pentenyloxy, 3-pentenyloxy, 4-pentenyloxy, 1,3-butadienyloxy, 1,3-pentadienyloxy, 2-penten-4-yloxy, 2-hexenyloxy, 1-hexenyloxy, 5-hexenyloxy, 3-hexenyloxy, 4-hexenyloxy, 3,3-dimethyl-1-propenyloxy, 2-ethyl-1-propenyloxy, 1,3,5-hexatrienyloxy, 1,3-hexadienyloxy, and 1,4-hexadienyloxy.

Examples of the "cycloalkenyl" represented by $R_1$, $R_2$, $R_{14}$, $R_{15}$, $R_{16}$, or $R_{16}'$ in the compound group 2 of the present invention include $C_{2-6}$ cyclic alkenyl groups having 1 to 3 double bonds. Of these, the "cycloalkenyl" represented by $R_{14}$, $R_{15}$, $R_{16}$, or $R_{16}'$ optionally has one or more substituents at suitable positions.

Examples of such substituents include halogen, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl.

Examples of the "cycloalkenyloxy" represented by $R_1$ or $R_2$ in the compound group 2 of the present invention include $C_{2-6}$ cyclic alkenyloxy groups having 1 to 3 double bonds.

Examples of the "alkynyl" represented by $R_1$, $R_2$, $R_3$, $R_{14}$, $R_{15}$, $R_{16}$, or $R_{16}'$ in the compound group 2 of the present invention include $C_{2-6}$ linear or branched alkynyl groups having a triple bond. Specific examples of such alkynyl groups include ethynyl, 2-propynyl, 2-butynyl, 3-butynyl, 1-methyl-2-propynyl, 2-pentynyl, 2-hexynyl, etc. In particular, the "alkynyl" represented by $R_3$, $R_{14}$, $R_{15}$, or $R_{16}$ optionally has a substituent. Examples of such substituents include halogen, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl.

Preferable examples of the "aryl" represented by $R_1$, $R_2$, $R_3$, $R_{14}$, $R_{15}$, $R_{16}$, or $R_{16}'$, particularly $R_1$, $R_2$, $R_{12}$, $R_{14}$, $R_{15}$, $R_{16}$, or $R_{16}'$, in the compound group 2 of the present invention include $C_{6-14}$ aromatic hydrocarbon groups. Examples of such aryl groups include phenyl, naphthyl, anthryl, phenanthryl, acenaphthylenyl, etc. Preferred among these are phenyl and naphthyl, and more preferred is phenyl. These groups, particularly the "aryl" represented by $R_1$, $R_2$, $R_{12}$, $R_{14}$, $R_{15}$, $R_{16}$, or $R_{16}'$, optionally have a substituent.

Examples of substituents of the aryl represented by $R_1$ or $R_2$ include halogen, $C_{1-6}$ alkyl (preferably $C_{1-4}$ alkyl), halogen-substituted lower alkyl, $C_{1-6}$ alkoxy (preferably $C_{1-4}$ alkoxy), halogen-substituted lower alkoxy, hydroxyl, $CF_3$, $CF_3O$, $CHF_2O$, $CF_3CH_2O$, cyano, carboxy, alkoxycarbonyl, and amino optionally having one or two substituents. Examples of the substituent substituted for the hydrogen atom of the amino group include $C_{1-6}$ alkyl, preferably $C_{1-2}$ alkyl. In the amino group, the alkyl groups substituted for two hydrogen atoms of the amino group optionally form a ring via oxygen or nitrogen. Examples of such groups include morpholino and (substituted) piperazino. Preferable examples include halogen, $C_{1-4}$ alkoxy, cyano, and amino optionally having one or two substituents (particularly amino in which $C_{1-2}$ alkyl groups substituted for two hydrogen atoms of the amino form a ring via oxygen).

Examples of substituents of the aryl represented by $R_{12}$, $R_{14}$, $R_{15}$, $R_{16}$, or $R_{16}'$ include halogen, $C_{1-6}$ alkyl (preferably $C_{1-4}$ alkyl), halogen-substituted lower alkyl, $C_{1-6}$ alkoxy (preferably $C_{1-4}$ alkoxy), halogen-substituted lower alkoxy, hydroxyl, $CF_3$, $CF_3O$, $CHF_2O$, $CF_3CH_2O$, cyano, carboxy, alkoxycarbonyl, benzoyl, and phenyl; preferably halogen, $C_{1-4}$ alkyl, carboxy, $CF_3$, benzoyl, and phenyl. The phenyl of the aryl represented by $R_{15}$ does not have a substituent.

Examples of the "aryloxy" represented by $R_1$ or $R_2$ in the compound group 2 of the present invention include hydroxyl groups substituted with $C_{6-14}$ aromatic hydrocarbon groups. Examples of such aryloxy groups include phenyloxy, naphthyloxy, anthryloxy, phenanthryloxy, acenaphthylenyloxy, etc.

Examples of the "aralkyl" represented by $R_1$, $R_2$, $R_3$, $R_{12}$, $R_{14}$, $R_{15}$, $R_{16}$, or $R_{16}'$, particularly $R_1$, $R_2$, $R_{14}$, $R_{15}$, $R_{16}$, or $R_{16}'$, in the compound group 2 of the present invention include the abovementioned alkyl groups substituted with one or more aryl groups such as phenyl or naphthyl. These aralkyl groups include benzyl (phenylmethyl); monophenylalkyl, such as 1-phenylethyl, 2-phenylethyl, 3-phenylpropyl, and 4-phenylbutyl; diphenylalkyl, such as diphenylmethyl and diphenylethyl; and mononaphthyl alkyl, such as 1-naphthylmethyl, 1-naphthylethyl, 2-naphthylmethyl, and 2-naphthylethyl. Among them, the "aralkyl" represented by $R_{16}$ is preferably diphenylalkyl, more preferably diphenylmethyl. The "aralkyl" represented by $R_3$, $R_{12}$, $R_{14}$, $R_{15}$, $R_{16}$, or $R_{16}'$, particularly the "aralkyl" represented by $R_{14}$, $R_{15}$, $R_{16}$, or $R_{16}'$, optionally has a substituent. Examples of substituents include halogen, $C_{1-6}$ lower alkyl, halogen-substituted lower alkyl, $C_{1-6}$ lower alkoxy, halogen-substituted lower alkoxy, hydroxyl, $CF_3$, $CF_3O$, $CHF_2O$, $CF_3CH_2O$, cyano, carboxy, and alkoxycarbonyl. Examples of aralkyl having such a substituent include α-hydroxybenzyl, fluorobenzyl, trifluoromethylbenzyl, 1-hydroxy-3-phenylpropyl, 1-hydroxy-1-phenylethyl, bis(4-fluorophenyl)methyl, etc.

Examples of the "aralkyloxy" represented by $R_1$ or $R_2$ in the compound group 2 of the present invention include the abovementioned aralkyl-substituted hydroxyl. The aralkyloxy is preferably benzyloxy.

Examples of the "halogen" represented by $R_1$, $R_2$, $R_5$, $R_6$, $R_7$, $R_8$, or $R_{13}$ in the compound group 2 of the present invention include fluorine, chlorine, bromine, and iodine. Preferable are fluorine and chlorine, and more preferable is chlorine.

Examples of the "alkylene" in the "alkylene," "cycloalkylene," "alkyleneoxyalkylene," "alkylenethioalkylene," "alkylene-SO-alkylene," "alkylene-$SO_2$-alkylene," and "alkylene-N($R_9$)-alkylene" represented by L in Formula (II) generally include $C_{1-2}$, preferably $C_{1-10}$, more preferably $C_{1-8}$, even more preferably $C_{1-6}$, particularly preferably $C_{1-4}$, linear or branched alkylene; even more preferably $C_{1-2}$ alkylene. Examples of the alkylene include methylene, ethylene, propylene, trimethylene, 1-ethyl-1,2-ethylene, 1-propyl-1,2-ethylene, 1-isopropyl-1,2-ethylene, 1-butyl-1,2-ethylene, 1,2-dimethyl-1,2-ethylene, tetramethylene, pentamethylene, hexamethylene, heptamethylene, and octamethylene. More particularly preferable is methylene or ethylene.

The alkylene include one in which some carbon atoms in the alkylene are bound to form a cycloalkane ring, as shown in Example 93. Examples of the cycloalkane ring include cyclopropane, cyclobutane, cyclopentane, and cyclohexane.

Preferable examples of the "cycloalkylene" include cyclopropylene, cyclobutylene, cyclopentylene, cyclohexylene, cyclooctylene, etc.; preferable examples of the "alkyleneoxyalkylene" include methyleneoxymethylene, ethyleneoxymethylene, methyleneoxyethylene, ethyleneoxyethylene, etc.; preferable examples of the "alkylenethioalkylene" include methylenethiomethylene, ethylenethiomethylene, methylenethioethylene, and ethylenethioethylene; preferable examples of the "alkylene-SO-alkylene" include methylene-SO-methylene, ethylene-SO-methylene, methylene-SO-ethylene, and ethylene-SO-ethylene; and preferable examples of the "alkylene-$SO_2$-alkylene" include methylene-$SO_2$-methylene, ethylene-$SO_2$-methylene, methylene-$SO_2$-ethylene, and ethylene-$SO_2$-ethylene. Examples of the "alkylene-N($R_9$)-alkylene" include lower alkylene-lower alkylamino-lower alkylene. Examples of the lower alkylene used herein include $C_{1-6}$ alkylene, and preferable examples thereof include methylene, ethylene, propylene, and trimethylene; examples of the lower alkylamino include $C_{1-6}$ alkylamino, and preferable examples thereof include methylamino, ethylamino, propylamino, isopropylamino, and butylamino. Preferred are methylene-methylamino-methylene, ethylene-methylamino-methylene, methylene-methylamino-ethylene, and ethylene-methylamino-ethylene.

Examples of the "alkenylene" represented by L in Formula (II) include $C_{2-6}$ linear or branched alkenylene groups having 1 to 3 double bonds. Examples of such alkenylene groups include vinylene, 1-methylvinylene, propenylene, 1-butenylene, 2-butenylene, 1-pentenylene, 2-pentenylene, etc.

Examples of the "alkynylene" represented by L in Formula (II) include $C_{2-6}$ linear or branched alkynylene groups having one triple bond. Examples of such alkynylene groups include ethynylene, propynylene, 1-methylpropynylene, 1-butynylene, 2-butynylene, 1-methylbutynylene, 2-methylbutynylene, 1-pentynylene, and 2-pentynylene.

The above-mentioned "alkylene," "cycloalkylene," "alkyleneoxyalkylene," "alkylenethioalkylene," "alkylene-SO-alkylene," "alkylene-$SO_2$-alkylene," "alkylene-N($R_9$)- alkylene," "alkenylene" and "alkynylene" may have a substitute. Examples of such substituents include halogen, $C_{1-4}$ lower alkyl, halogenated lower alkyl, $C_{1-4}$ lower alkoxy, halogenated lower alkoxy, hydroxyl, $CF_3$, $CF_3O$, $CHF_2O$, $CF_3CH_2O$, cyano, carboxy, alkoxycarbonyl having $C_{1-4}$ alkoxy, amino, acylamino, benzyloxycarbonylamino (Cbz-NH—), alkoxycarbonylamino (e.g., t-butoxycarbonylamino (tBoc-NH—), methoxycarbonylamino, ethoxycarbonylamino, propoxycarbonylamino, isopropoxycarbonylamino, butoxypropoxycarbonylamino), acyl, etc.

Examples of the "heterocyclic group" represented by $R_1$, $R_2$, $R_{14}$, or $R_{15}$ in the compound group 2 of the present invention include saturated and unsaturated 4- to 10-membered heterocyclic groups containing 1 to 3 identical or different heteroatoms selected from the group consisting of nitrogen, oxygen and sulfur. Specific examples thereof include unsaturated heterocyclic groups, such as pyrrolyl, furyl, thiophenyl, thienyl, pyrazolyl, imidazolyl, oxazolyl, isoxazolyl, triazolyl, isothiazolyl, oxadiazolyl, thiadiazolyl, triazolyl, tetrazolyl, pyranyl, pyridyl, pyridazinyl, pyrimidinyl, pyrazinyl, azepinyl, azocinyl, etc.; groups in which the above-mentioned unsaturated heterocyclic groups are partially or completely reduced, such as azetidinyl, pyrrolidinyl, pyrrolinyl, imidazolidinyl, imidazolinyl, pyrazolidinyl, pyrazolinyl, piperidyl, piperazinyl, morpholinyl, thiomorpholinyl, perhydroazepinyl, perhydroazocinyl, 1,4,5,6-tetrahydropyrimidinyl, 1,2,3,6-tetrahydropyridyl, etc.; and groups in which the above-mentioned unsaturated heterocyclic rings are condensed with each other, or groups in which a benzene ring is condensed with the above-mentioned unsaturated heterocyclic ring, such as indolyl, indolinyl, benzofuranyl, benzothienyl, benzimidazolyl, benzisooxazolyl, benzisoxazolyl, benzothiazolyl, benzisothiazolyl, benzthiophenyl, quinolyl, isoquinolyl, quinazolinyl, quinoxalinyl, benzoxadiazolyl, benzothiadiazolyl, pyrrolopyrrolyl, pyrrolooxazolyl, pyrrolothiazolyl, pyrrolopyridyl, furopyrrolyl, furopyridyl, thienopyrrolyl, thienopyridyl, imidazopyrrolyl, imidazoimidazolyl, imidazooxazolyl, imidazothiazolyl, imidazoisothiazolyl, imidazopyridyl, imidazopyridazinyl, imidazopyrimidinyl, imidazopyrazinyl, oxazooxazolyl, oxazoisoxazolyl, oxazothiazolyl, oxazoisothiazolyl, oxazopyridyl, thiazoloooxazolyl, thiazoloisoxazolyl, thiazolothiazolyl, thiazoloisothiazolyl, thiazolopyridyl, etc. Preferable examples include azetidinyl, pyrrolidinyl, piperidinyl, morpholinyl, piperazinyl, homopiperazinyl, tetrahydrofuryl, tetrahydrothienyl, tetrahydropyranyl, pyrrolyl, furyl, thienyl, oxazolyl, isoxazolyl, thiazolyl, isothiazolyl, pyrazolyl, pyridyl, pyrimidinyl, indolyl, isoindolyl, benzofuranyl, benzoxazolyl, benzothiazolyl, benzothiophenyl, quinolyl, and benzisoxazolyl.

These heterocyclic rings may have 1 to 3 substituents at suitable positions. Examples of such substituents include halogen, $C_{1-4}$ lower alkyl, halogenated lower alkyl, $C_{1-4}$ lower alkoxy, halogenated lower alkoxy, hydroxyl, $CF_3$, $CF_3O$, $CHF_2O$, $CF_3CH_2O$, aryl (preferably phenyl), halogenated aryl, cyano, carboxy, alkoxycarbonyl, etc.

Preferable examples of the heterocyclic ring in $R_1$ and $R_2$ include pyrazolyl (e.g., pyrazol-4-yl), pyridyl (e.g., pyridin-3-yl, pyridin-4-yl), 2-methylpyrazolyl, quinolyl(quinolin-3-yl), thiazolyl (e.g., thiazol-5-yl), 2,4-dimethylthiazolyl (e.g., 2,4-dimethylthiazol-5-yl), and benzothiophenyl (e.g., benzothiophen-2-yl). Preferable examples of the heterocyclic ring in $R_{14}$ and $R_{15}$ include thiophenyl (preferably thienyl); and thiophenyl (preferably thienyl) substituted with $C_{1-4}$ alkyl, carboxy, alkoxycarbonyl (e.g., t-butoxycarbonyl), or aryl (preferably phenyl).

Examples of the "heterocyclic-alkyl" represented by $R_1$, $R_2$, $R_{14}$, or $R_{15}$ in the compound group 2 of the present invention include groups in which the hydrogen atom of the above heterocyclic ring is replaced by alkyl. Examples of the "heterocyclic-alkoxy" represented by $R_1$ or $R_2$ include groups in which the hydrogen atom of the above heterocyclic ring is replaced by alkoxy. Examples of the "alkyl" and "alkoxy" as used herein include those mentioned above.

Examples of the "alkoxycarbonyl" represented by $R_1$, $R_2$, or B in Formula (I) include t-butoxycarbonyl, methoxycarbonyl, ethoxycarbonyl, propoxycarbonyl, isopropoxycarbonyl, butoxycarbonyl, etc.

Specific examples of the "fluorenyl" represented by $R_{16}$ or $R_{16}'$ in Formula (I) include 9H-fluoren-9-yl shown in Example 36.

Examples of the "bicycloalkyl" represented by $R_{14}$, $R_{15}$, $R_{16}$, or $R_{16}'$ in the compound group 2 of the present invention generally include $C_{5-30}$ substituted or unsubstituted bicycloalkyl, i.e., a monovalent group in which one hydrogen atom is removed from $C_{5-30}$ bicycloalkane. Examples thereof include bicyclo[1,2,2]heptan-2-yl, bicyclo[2,2,2]octan-3-yl, etc. Examples of the "bicycloalkenyl" represented by $R_{14}$, $R_{15}$, $R_{16}$, or $R_{16}'$ generally include $C_{3-30}$ substituted or unsubstituted bicycloalkenyl, i.e., a monovalent group in which one hydrogen atom is removed from $C_{3-30}$ bicycloalkene having one double bond. Examples thereof include bicyclo[2,2,1]hept-2-en-1-yl, bicyclo[2,2,2]oct-2-en-4-yl, etc.

Aromatic or heterocyclic carboxylic acids (when the substituent B is carboxyl; hereinafter the same) or bioisosteres of the carboxylic acids (when the substituent B is a group that is biologically equivalent to a carboxyl group; hereinafter the same) (II) targeted by the present invention preferably include thiophene-3-carboxylic acid represented by Formula (II-1) below or bioisosteres of the carboxylic acid, and benzenecarboxylic acid represented by Formula (II-2) below or bioisosteres of the carboxylic acid.

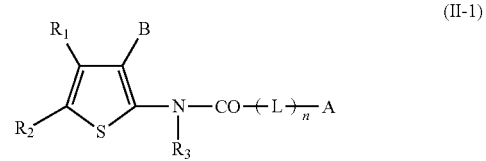

(II-1)

wherein $R_1$, $R_2$, $R_3$, L, B, n, and A are as defined above.

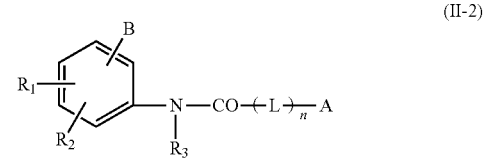

(II-2)

wherein $R_1$, $R_2$, $R_3$, L, B, n, and A are as defined above.

The thiophene-3-carboxylic acid or bioisosteres of the carboxylic acid (II-1) mentioned herein refers to a compound having a structure in which the hydrogen atom located at the 3-position of thiophene is replaced by carboxy represented by the substituent B or a group that is biologically equivalent to a carboxyl group. Further, the benzenecarboxylic acid or bioisostere of the carboxylic acid (II-2) refers to a compound having a structure in which one hydrogen atom of benzene (hydrogen located at the ortho, meta, or para position) is replaced by carboxy represented by the substituent B or a group that is biologically equivalent to a carboxyl group. Preferable is benzenecarboxylic acid or bioisosteres thereof (II-2).

(2-1) Thiophene-3-Carboxylic Acid or Bioisosteres of the Carboxylic Acid (II-1)

Preferable examples of the thiophene-3-carboxylic acid or bioisosteres of the carboxylic acid (II-1) include the following compounds:

(II-1-1) thiophene-3-carboxylic acid represented by Formula (II-1) above, wherein $R_3$ is hydrogen, n is 1, and L is substituted or unsubstituted alkylene; an ester thereof; or a bioisostere of the carboxylic acid; and (II-1-2) thiophene-3-carboxylic acid represented by Formula (II-1) above, wherein $R_3$ is hydrogen, n is 1, and L is substituted or unsubstituted alkyleneoxyalkylene; an ester thereof;

or a bioisostere of the carboxylic acid.

(i) Thiophene-3-Carboxylic Acid or Bioisosteres of the Carboxylic Acid (II-1-1)

A preferable example of the thiophene-3-carboxylic acid or bioisosteres of the carboxylic acid (II-1-1) is a compound represented by the following formula wherein L is butylene.

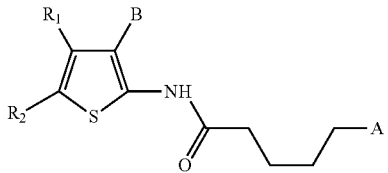

wherein B is carboxyl, or a group that is biologically equivalent to a carboxyl group selected from alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl.

In the compound (II-1-1) (preferably a compound represented by the above formula), the groups represented by $R_1$ and $R_2$ are as defined above; preferably $R_1$ and $R_2$ are the same or different, and each represents hydrogen, lower alkyl, substituted or unsubstituted aryl, or substituted or unsubstituted heterocyclic ring. The lower alkyl is preferably $C_{1-4}$ alkyl, more preferably methyl or ethyl; the aryl is preferably phenyl; and the heterocyclic ring is preferably pyridyl, more preferably pyridin-3-yl or pyridin-4-yl. $R_1$ and $R_2$ are preferably the same or different, and each represents hydrogen or phenyl.

A is also as defined above, and is preferably —$COR_4$, —$N(R_{11})$—$COR_{12}$, or a group represented by the following formula:

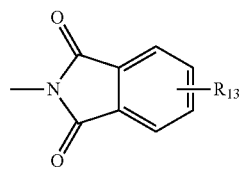

wherein $R_{13}$ is as defined above.

wherein $R_{10}$ in —$COR_4$ is as defined above, and is preferably —$N(R_{14})(R_{15})$ or a group represented by the following formula:

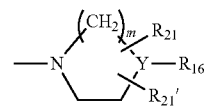

wherein $R_{14}$ to $R_{16}$, m, $R_{21}$, and $R_{21}'$ are as defined above.

The group represented by the above formula is preferably a group wherein m is 2; Y is CH or nitrogen; $R_{16}$ is substituted or unsubstituted alkyl, aryl (preferably phenyl), or aralkyl; and $R_{21}$ and $R_{21}'$ are hydrogen or substituted or unsubstituted alkyl. The aryl is preferably phenyl; the aralkyl is preferably diphenylalkyl, more preferably diphenylmethyl; and the alkyl is preferably methyl. Examples of the substituents of the alkyl, aryl, or aralkyl include halogen, alkyl, alkoxy, hydroxyl, carboxy or salts thereof, and alkoxycarbonyl; preferably halogen.

—$N(R_{14})(R_{15})$ is preferably a group having hydrogen as $R_{14}$, and unsubstituted or substituted aryl (preferably phenyl) as $R_{15}$. Examples of substituents include halogen, $CF_3$, benzoyl, alkyl, alkoxy, hydroxyl, carboxy, alkoxycarbonyl, unsubstituted phenyl, and salts thereof; preferably halogen.

—$N(R_{11})$—$COR_{12}$ is preferably a group having hydrogen as $R_{11}$, and substituted or unsubstituted aryl (preferably phenyl) as $R_{12}$. Examples of substituents include halogen, alkyl, alkoxy, hydroxyl, carboxy, alkoxycarbonyl, and salts thereof; preferably carboxy.

Moreover, the group represented by the following formula:

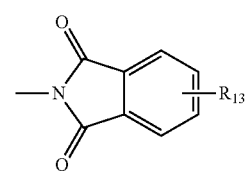

is preferably a group having hydrogen as $R_{13}$.

Specific examples the thiophene-3-carboxylic acid represented by the above formula or bioisosteres of the carboxylic acid (II-1-1) include compounds represented by the following formulae (see Table 3):

2-(6-oxo-6-(4-phenylpiperidin-1-yl)hexanamido)-4-phenylthiophene-3-carboxylic acid (Example 5)

2-(6-(4-chlorophenylamino)-6-oxohexanamido)-4-phenylthiophene-3-carboxylic acid (Example 6)

2-(5-(1,3-dioxoisoindolin-2-yl)pentanamide)-4-phenylthiophene-3-carboxylic acid (Example 16)

2-(5-(2-carboxybenzamido)pentanamide)-4-phenylthiophene-3-carboxylic acid (deesterified product of Example 17).

(ii) Thiophene-3-Carboxylic Acid or Bioisosteres of the Carboxylic Acid (II-1-2)

Preferable examples of the thiophene-3-carboxylic acid or bioisosteres of the carboxylic acid (II-1-2) include compounds represented by the following formula, wherein L is methyleneoxymethylene:

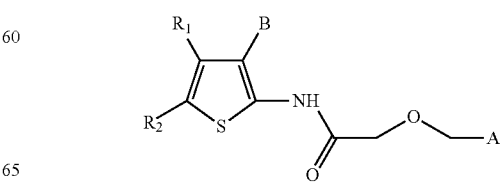

wherein B is carboxyl or a group that is biologically equivalent to a carboxyl group selected from alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl.

In the compound (II-1-2) (preferably a compound represented by the above formula), the groups represented by $R_1$ and $R_2$ are as defined above; preferably $R_1$ and $R_2$ are the same or different, and each represents hydrogen, alkyl, substituted or unsubstituted aryl, or substituted or unsubstituted heterocyclic ring. The alkyl is preferably $C_{1-4}$ alkyl, and more preferably methyl or ethyl; the aryl is preferably phenyl; the heterocyclic ring is preferably pyridyl, more preferably pyridin-3-yl or pyridine-4-yl, or thiazolyl, more preferably thiazol-5-yl. Examples of substituents of the aryl and heterocyclic ring include halogen, alkyl, alkoxy, hydroxyl, carboxy, alkoxycarbonyl, and salts thereof; preferably alkyl.

A is also as defined above, but is preferably a group represented by —$COR_{10}$.

$R_{10}$ in —$COR_{10}$ is as defined above, and preferably —$N(R_{14})(R_{15})$ or a group represented by the following formula:

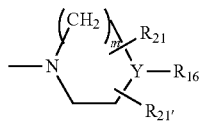

wherein $R_{14}$ to $R_{16}$, m, $R_{21}$, and $R_{21}'$ are as defined above.

The group represented by the above formula is preferably a group wherein m is 2; Y is nitrogen; $R_{16}$ is substituted or unsubstituted aryl or aralkyl; and $R_{21}$ and $R_{21}'$ are hydrogen or substituted or unsubstituted alkyl. The aryl is preferably phenyl, and the aralkyl is preferably diphenylalkyl, more preferably diphenylmethyl. Examples of substituents include halogen, alkyl, alkoxy, hydroxyl, carboxy, alkoxycarbonyl, and salts thereof.

—$N(R_{14})(R_{15})$ is preferably a group having hydrogen as $R_{14}$, and unsubstituted or substituted thienyl or aralkyl as $R_{15}$. Examples of substituents include halogen, alkyl, alkoxy, aryl (preferably phenyl), hydroxyl, carboxy, alkoxycarbonyl, and salts thereof.

Specific examples the thiophene-3-carboxylic acid represented by the above formula or bioisosteres of the carboxylic acid (II-1-2) include compounds represented by the following formulae (see Table 2):

2,2'-(oxybis((1-oxo-2,1-ethanediyl)imino)bis(5-methyl-4-phenylthiophene-3-carboxylic acid) (Example 7)

2,2'-(oxybis((1-oxo-2,1-ethanediyl)imino))bis(5-phenylthiophene-3-carboxylic acid) (Example 8)

2,2'-(oxybis((1-oxo-2,1-ethanediyl)imino))bis-(4-phenylthiophene-3-carboxylic acid) (Example 9)

2-(2-(2-(3-(tert-butoxycarbonyl)-5-methyl-4-phenylthiophen-2-ylamino)-2-oxoethoxy)acetamido)-5-methyl-4-phenylthiophene-3-carboxylic acid (Example 10)

2-(2-(2-(4-benzhydrylpiperazin-1-yl)-2-oxoethoxy)acetamido)-5-methyl-4-(pyridin-4-yl)thiophene-3-carboxylic acid (Example 13)

2-(2-(2-(4-benzhydrylpiperazin-1-yl)-2-oxoethoxy)acetamido)-5-methyl-4-(pyridin-3-yl)thiophene-3-carboxylic acid (Example 14)

2-(2-(2-(4-benzhydrylpiperazin-1-yl)-2-oxoethoxy)acetamido)-5-methyl-4-phenylthiophene-3-carboxylic acid (desalted product of Example 15)

2-(2-(2-(4-benzhydrylpiperazin-1-yl)-2-oxoethoxy)acetamido)-5-(2,4-dimethylthiazol-5-yl)benzoic acid (desalted product of Example 81)

2-(2-(2-(benzhydrylamino)-2-oxoethoxy)acetamido)-5-methyl-4-phenylthiophene-3-carboxylic acid (Example 82)

2-(2-(4-benzhydrylpiperazin-1-yl)-2-oxoethoxy)-N-(5-methyl-4-phenyl-3-(1H-tetrazol-5-yl)thiophen-2-yl)acetamide (Example 90).

(2-2) Benzenecarboxylic Acid or Bioisosteres of the Carboxylic Acid (II-2)

Preferable examples of the benzenecarboxylic acid or bioisosteres of the carboxylic acid (II-2) include the following:

(II-2-2) benzenecarboxylic acid represented by Formula (II-2), wherein $R_3$ is hydrogen, n is 1, and L is substituted or unsubstituted alkyleneoxyalkylene; or bioisosteres of the carboxylic acid;

(II-2-1) benzenecarboxylic acid represented by Formula (II-2), wherein $R_3$ is hydrogen, n is 1, and L is substituted or unsubstituted alkylene (some carbon atoms in the alkylene optionally form cycloalkyl); or bioisosteres of the carboxylic acid;

(II-2-3) benzenecarboxylic acid represented by Formula (II-2), wherein $R_3$ is hydrogen, n is 1, and L is substituted or unsubstituted alkylene-$N(R_9)$-alkylene; or bioisosteres of the carboxylic acid;

(II-2-4) benzenecarboxylic acid represented by Formula (II-2), wherein $R_3$ is hydrogen, n is 1, and L is substituted or unsubstituted alkylenethioalkylene, alkylene-SO-alkylene, or alkylene-$SO_2$-alkylene; or bioisosteres of the carboxylic acid;

(II-2-5) benzenecarboxylic acid represented by Formula (II-2), wherein $R_3$ is hydrogen, n is 1, and L is substituted or unsubstituted cycloalkylene; or bioisosteres of the carboxylic acid; and (II-2-6) benzenecarboxylic acid represented by Formula (II-2), wherein $R_3$ is hydrogen, and n is 0; or bioisosteres of the carboxylic acid.

(i) Benzenecarboxylic Acid or Bioisosteres of the Carboxylic Acid (II-2-1)

Preferable examples of the benzenecarboxylic acid or bioisosteres of the carboxylic acid (II-2-1) include compounds represented by the following formulae:

(II-2-1-1) wherein L is butylene;
(II-2-1-2) wherein L is substituted propylene; and
(II-2-1-3) wherein L is alkylene, wherein some carbon atoms in the alkylene optionally form a cycloalkane ring.

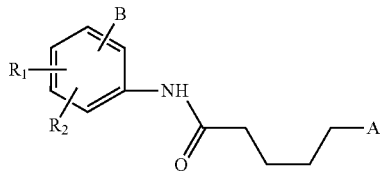

(II-2-1-1)

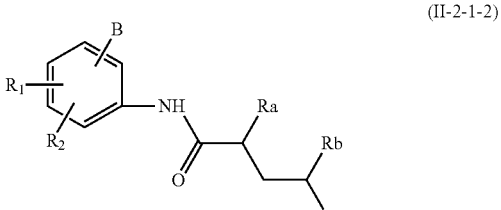

(II-2-1-2)

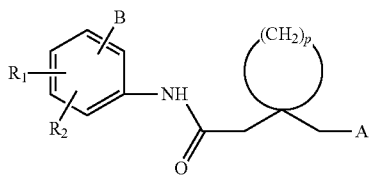

(II-2-1-3)

wherein B is carboxyl or a group that is biologically equivalent to a carboxyl group selected from alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl. $R_1$, $R_2$, and A are as defined above. Ra and Rb are the same or different, and each represents hydrogen or a substituent. p is an integer of 2 to 5.

B, $R_1$, and $R_2$ may be located at any of the ortho, meta, and para positions of the benzene ring to which imino is bound. Preferably, in any of the compounds (II-2-1-1) to (II-2-1-3), B is located at the ortho position, and $R_1$ and $R_2$ are located respectively at the meta and para positions of the benzene ring.

$R_1$ and $R_2$ are as defined above; preferably $R_1$ and $R_2$ are the same or different, and each represents hydrogen, halogen, alkyl, substituted or unsubstituted aryl, or substituted or unsubstituted heterocyclic ring. The halogen is preferably chlorine or fluorine, and more preferably chlorine. The alkyl is preferably $C_{1-4}$ alkyl, and more preferably methyl or ethyl. The aryl is preferably phenyl. The heterocyclic ring is preferably pyridyl, more preferably pyridin-3-yl or pyridin-4-yl. Preferably, $R_2$ located at the meta position is hydrogen, and $R_1$ located at the para position is halogen, preferably chlorine.

A is also as defined above, and is preferably a group represented by —$COR_{10}$, —$N(R_{11})$—$COR_{12}$, or —$N(R_{11})$—$SO_2$—$R_{12}$.

$R_{10}$ in —$COR_{10}$ is as defined above, and preferably a group represented by the following formula or —$N(R_{14})(R_{15})$:

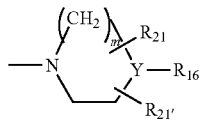

wherein $R_{14}$ to $R_{16}$, m, $R_{21}$, and $R_{21}'$ are as defined above.

The group represented by the above formula is preferably a group wherein m is 2; Y is nitrogen; $R_{16}$ is substituted or unsubstituted aryl or aralkyl; and $R_{21}$ and $R_{21}'$ are hydrogen or substituted or unsubstituted alkyl, preferably hydrogen. The aryl is preferably phenyl, and the aralkyl is preferably diphenylalkyl, more preferably diphenylmethyl. Examples of substituents include halogen, alkyl, alkoxy, hydroxyl, carboxy or salts thereof, and alkoxycarbonyl; preferably halogen.

—$N(R_{14})(R_{15})$ is preferably a group having hydrogen or alkyl as $R_{14}$, and substituted or unsubstituted thienyl or aryl (preferably phenyl) as $R_{15}$. Examples of substituents of the aryl include halogen, $CF_3$, benzoyl, alkyl, alkoxy, hydroxyl, carboxy, alkoxycarbonyl, unsubstituted phenyl, and salts thereof; preferably halogen. Examples of substituents of the thienyl include aryl, halogen, alkyl, alkoxy, hydroxyl, carboxy, alkoxycarbonyl, and salts thereof; preferably unsubstituted aryl (particularly phenyl), carboxy, alkoxycarbonyl, alkyl (particularly isopropyl), and salts thereof.

—$N(R_{11})$—$CONH$—$R_{12}$ and —$N(R_{11})$—$SO_2$—$R_{12}$ are preferably groups wherein $R_{11}$ is hydrogen, and $R_{12}$ is substituted or unsubstituted aryl, preferably phenyl. Examples of substituents include halogen, alkyl, alkoxy, hydroxyl, carboxy or salts thereof, and alkoxycarbonyl; preferably halogen.

In the benzenecarboxylic acid or bioisosteres of the carboxylic acid (II-2-1-1), A is preferably —$COR_{10}$, —$N(R_{11})$—$CONH$—$R_{12}$, or —$N(R_{11})$—$SO_2$—$R_{12}$. —$COR_{10}$ is as defined above, and is preferably a group having —$N(R_{14})(R_{15})$ as $R_{10}$. $R_{14}$ is preferably hydrogen. $R_{15}$ is preferably substituted or unsubstituted aryl, more preferably phenyl; or substituted or unsubstituted heterocyclic ring, more preferably thienyl. Examples of substituents are as defined above.

In the benzenecarboxylic acid or bioisostere of the carboxylic acid (II-2-1-2), A is preferably —$COR_{10}$, more preferably —$COR_{10}$ wherein $R_{10}$ is —$N(R_{14})(R_{15})$ or a group represented by the following formula:

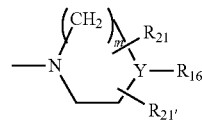

wherein m, Y, $R_{16}$, $R_{21}$, and $R_{21}'$ are as defined above; preferably m is 2; Y is nitrogen; $R_{16}$ is substituted or unsubstituted aryl, preferably phenyl, or substituted or unsubstituted aralkyl, preferably diphenylalkyl, more preferably diphenylalkyl; $R_{21}$ and $R_{21}'$ are hydrogen. The substituent is preferably halogen.

—$N(R_{14})(R_{15})$ is preferably a group having hydrogen or alkyl as $R_{14}$, and substituted or unsubstituted aryl, preferably phenyl, as $R_{15}$. Examples of substituents of the aryl include halogen, $CF_3$, benzoyl, alkyl, alkoxy, hydroxyl, carboxy, alkoxycarbonyl, unsubstituted phenyl, and salts thereof; preferably halogen.

In the benzenecarboxylic acid or bioisosteres of the carboxylic acid (II-2-1-2), the substituents Ra and Rb of the propylene are the same or different, and each represents hydrogen, amino, or amino protected by a protecting group. As the protecting group, well-known amino-protecting groups can be widely used. Examples thereof include benzyloxycarbonyl (Cbz), tert-butoxycarbonyl (tBoc), fluorenylmethoxycarbonyl (Fmoc), alkoxycarbonyl (e.g., methoxycarbonyl, ethoxycarbonyl, propoxycarbonyl, isopropoxycarbonyl, and butoxycarbonyl), and acyl.

In the benzenecarboxylic acid or bioisosteres of the carboxylic acid (II-2-1-3), A is preferably —$COR_{10}$, more preferably —$COR_{10}$ wherein $R_{10}$ is a group represented by the following formula:

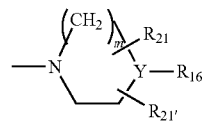

wherein m, Y, $R_{16}$, $R_{21}$, and $R_{21}'$ are as defined above; preferably m is 2; Y is nitrogen; $R_{16}$ is substituted or unsubstituted aryl, preferably phenyl, or substituted or unsubstituted aralkyl, preferably diphenylalkyl, more preferably diphenylalkyl; $R_{21}$ and $R_{21}'$ are hydrogen. The substituent is preferably halogen.

Examples of the cycloalkyl ring in the benzenecarboxylic acid or bioisosteres of the carboxylic acid (II-2-1-3) include a cyclopropane ring [p is 2 in Formula (II-2-1-3)], a cyclobutane ring [p is 3 in Formula (II-2-1-3)], a cyclopentane ring [p is 4 in Formula (II-2-1-3)], and a cyclohexane ring [p is 5 in Formula (II-2-1-3)]. A cyclohexane ring is preferable.

B, $R_1$, and $R_2$ may be located at any of the ortho, meta, and para positions of the benzene ring. Preferably, B, $R_2$, and $R_1$ are located at the ortho, meta, and para positions of benzene ring, respectively; $R_2$ is hydrogen; and $R_1$ is halogen.

Specific examples the benzenecarboxylic acid represented by the above formula or bioisosteres of the carboxylic acid (II-2-1) include compounds represented by the following formulae (see Table 3):

(II-2-1-1) Benzenecarboxylic Acid or Bioisosteres of the Carboxylic Acid
2-(6-(3-(tert-butoxycarbonyl)-4-phenylthiophen-2-ylamino)-6-oxohexanamido)benzoic acid (desalted product of Example 1)
2-(6-(3-(tert-butoxycarbonyl)-4-phenylthiophen-2-ylamino)-6-oxohexanamido)-5-chlorobenzoic acid (desalted product of Example 2)
2-(6-oxo-6-(4-phenylthiophen-2-ylamino)hexanamido)benzoic acid (Example 3)
2-(6-(2-carboxy-4-chlorophenylamino)-6-oxohexanamido)-4-phenylthiophene-3-carboxylic acid (Example 4)
2-(6-(3-(tert-butoxycarbonyl)-4-isopropylthiophen-2-ylamino)-6-oxohexanamido)benzoic acid (desalted product of Example 11)
2-(6-(4-isopropylthiophen-2-ylamino)-6-oxohexanamido) benzoic acid (Example 12)
5-chloro-2-(6-(4-chlorophenylamino)-6-oxohexanamido) benzoic acid (Example 27)
5-chloro-2-(5-(3-(4-chlorophenylureido)pentanamide)benzoic acid (Example 60)
5-chloro-2-(5-(4-chlorophenylsulfonamide)pentanamide) benzoic acid (Example 61).

(II-2-1-2) Benzenecarboxylic Acid or Bioisosteres of the Carboxylic Acid
2-(2-(benzyloxycarbonylamino)-5-(4-chlorophenylamino)-5-oxopentanamido)-5-chlorobenzoic acid (Example 18)
2-(2-(benzyloxycarbonylamino)-5-((4-chlorophenyl) (methyl)amino)-5-oxopentanamido)-5-chlorobenzoic acid (Example 19)
2-(2-(benzyloxycarbonylamino)-5-oxo-5-(4-phenylpiperazin-1-yl)pentanamido)-5-chlorobenzoic acid (Example 20)
2-(5-(4-benzhydrylpiperazin-1-yl)-2-(benzyloxycarbonylamino)-5-oxopentanamido)-5-chlorobenzoic acid (desalted product of Example 21)
2-(5-(4-benzhydrylpiperazin-1-yl)-4-(benzyloxycarbonylamino)-5-oxopentanamido)-5-chlorobenzoic acid (Example 22)
2-(5-(4-benzhydrylpiperazin-1-yl)-2-(tert-butoxycarbonylamino)-5-oxopentanamido)-5-chlorobenzoic acid (Example 23)
2-(2-amino-5-(4-benzhydrylpiperazin-1-yl)-5-oxopentanamido)-5-chlorobenzoic acid (Example 24)
2-(5-(4-benzhydrylpiperazin-1-yl)-5-oxopentanamido)-5-chlorobenzoic acid (Example 80).

(II-2-1-3) Benzenecarboxylic Acid or Bioisosteres of the Carboxylic Acid
2-(2-(1-(2-(4-benzhydrylpiperazin-1-yl)-2-oxoethyl)cyclohexyl)acetamido)-5-chlorobenzoic acid (desalted product of Example 93).

(ii) Benzenecarboxylic Acid or Bioisosteres of the Carboxylic Acid (II-2-2)

Preferable examples of the benzenecarboxylic acid or bioisosteres of the carboxylic acid (II-2-2) include compounds represented by Formula (II-2) below, wherein $R_3$ is hydrogen, and L is methyleneoxymethylene.

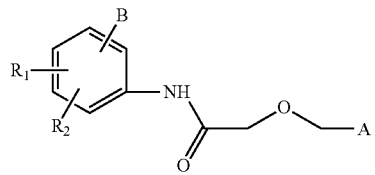

wherein B is carboxyl or a group that is biologically equivalent to a carboxyl group selected from alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl. $R_1$, $R_2$, and A are as defined above.

B, $R_1$, and $R_2$ may be located at any of the ortho, meta, and para positions of the benzene ring to which imino is bound. Although there is no limitation, B is preferably located at the ortho position, and $R_1$ and $R_2$ are preferably located at the meta and para positions, respectively, of the benzene ring. More preferably, $R_2$ is hydrogen, and $R_1$ is halogen, particularly chlorine.

The compound (II-2-2) (preferably a compound represented by the above formula) is preferably a compound having —$COR_{10}$ as A. The following compounds are more preferable. Among them, the compound specified by (II-2-2-2) is preferable.

(II-2-2-1) Compound wherein $R_{10}$ in $COR_{10}$ is $N(R_{14})(R_{15})$; and (II-2-2-2) Compound wherein $R_{10}$ in $COR_{10}$ is a group represented by the following formula:

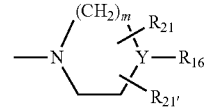

wherein Y, $R_{16}$, m, $R_{21}$, and $R_{21}'$ are as defined above.

—$N(R_{14})(R_{15})$ is preferably a group having hydrogen or aryl (preferably phenyl) as $R_{14}$, and substituted or unsubstituted aryl, aralkyl, thienyl, or adamanthyl as $R_{15}$. The aryl is preferably phenyl, and the aralkyl is preferably diphenylalkyl (more preferably diphenylmethyl) or mononaphthylalkyl (more preferably mononaphthylmethyl). Examples of substituents of the aryl or aralkyl include halogen, $CF_3$, benzoyl, alkyl, alkoxy, hydroxyl, carboxy, alkoxycarbonyl, unsubstituted phenyl, and salts thereof. Examples of substituents of the aryl include halogen, benzoyl, carboxy, alkoxycarbonyl, unsubstituted phenyl, and salts thereof. More preferred examples of substituents of the aralkyl include halogen, $CF_3$, carboxyl, alkoxycarbonyl, and salts thereof. Examples of substituents of the thienyl include halogen, phenyl, alkyl, alkoxy, hydroxyl, carboxy, alkoxycarbonyl, and salts thereof; preferably halogen, alkyl, phenyl carboxyl, alkoxycarbonyl, and salts thereof.

In the above formula, Y, m, $R_{16}$, $R_{21}$, and $R_{21}'$ are as defined above.

Preferable compounds are as follows:

(a) a compound wherein m is 2; Y is nitrogen; $R_{16}$ is substituted or unsubstituted aralkyl, preferably diphenylmethyl; substituted or unsubstituted aryl, preferably phenyl; or substituted or unsubstituted fluorenyl, preferably fluoren-9-yl; $R_{21}$ and $R_{21}'$ are the same or different, and each represents hydrogen; or alkyl, preferably $C_{1-4}$ alkyl, more preferably methyl. Examples of substituents include halogen, alkyl, alkoxy, hydroxyl, carboxy, alkoxycarbonyl, and salts thereof; preferably halogen. More preferable examples include compounds wherein m is 2, Y is nitrogen, $R_{16}$ is substituted or unsubstituted aralkyl, preferably diphenylmethyl; and $R_{21}$ and $R_{21}'$ are both hydrogen.

(b) a compound wherein m is 2; Y is CH—O—; $R_{16}$ is substituted or unsubstituted aralkyl, preferably diphenylmethyl; and $R_{21}$ and $R_{21}'$ are both hydrogen. Examples of substituents include halogen, alkyl, alkoxy, hydroxyl, carboxy, and alkoxycarbonyl, and salts thereof; preferably halogen.

(c) a compound wherein m is 2; Y is $C(R_{16}')$—; $R_{16}$ is substituted or unsubstituted aryl, preferably phenyl; and $R_{16}'$ is substituted or unsubstituted aryl, preferably phenyl. Examples of substituents include halogen, alkyl, alkoxy, hydroxyl, carboxy, alkoxycarbonyl, and salts thereof; preferably halogen.

In the compound of (II-2-2-1), $R_1$ and $R_2$ are as defined above; preferably $R_1$ and $R_2$ are the same or different, and each represents hydrogen, halogen, substituted or unsubstituted aryl, or substituted or unsubstituted heterocyclic ring. Preferably, $R_2$ located at the meta position is hydrogen, and $R_1$ located at the para position is halogen, particularly chlorine.

The aryl is preferably phenyl; and the heterocyclic ring is preferably pyridyl, more preferably pyridin-3-yl or pyridin-4-yl. Examples of substituents include halogen, alkyl, alkoxy, cyano, alkyl-substituted amino, and morpholino; preferably morpholin-4-yl.

In the compound of (II-2-2-2), $R_1$ and $R_2$ are as defined above; preferably $R_1$ and $R_2$ are the same or different, and each represents hydrogen, halogen, substituted or unsubstituted alkyl, substituted or unsubstituted alkoxy, substituted or unsubstituted aryl, or substituted or unsubstituted heterocyclic ring. The alkyl is preferably $C_{1-4}$ alkyl, more preferably methyl or isobutyl. The alkoxy is preferably $C_{1-4}$ alkyl, more preferably methoxy or isobutoxy. The aryl is preferably phenyl. The heterocyclic ring is preferably pyridyl, more preferably pyridin-3-yl or pyridin-4-yl; pyrazolyl, preferably pyrazol-4-yl; quinolyl, preferably quinolin-3-yl; or benzothiophenyl, preferably benzothiophen-2-yl. Examples of substituents include halogen, alkyl, alkoxy, cyano, alkyl-substituted amino, aryl (preferably phenyl), and morpholino (preferably morpholin-4-yl). Preferably, $R_2$ located at the meta position is hydrogen, and $R_1$ located at the para position is halogen, particularly chlorine.

Specific examples the benzenecarboxylic acid represented by the above formula or bioisosteres of the carboxylic acid (II-2-2-1) or (II-2-2-2) include compounds represented by the following formulae (see Table 3):

(II-2-2-1) Carboxylic Acid or Bioisosteres of the Carboxylic Acid 2-(2-(2-(4-chloro-2-(methoxycarbonyl)phenylamino)-2-oxoethoxy)acetamido)-5-methyl-4-phenylthiophene-3-carboxylic acid (Example 33)

2-(2-(2-(3-(tert-butoxycarbonyl-5-methyl-4-phenylthiophen-2-ylamino)-2-oxoethoxy)acetamido)-5-chlorobenzoic acid (Example 38)

2-(2-(2-(adamantylamino)-2-oxoethoxy)acetamido)-5-chlorobenzoic acid (Example 35)

2-(2-(2-(benzhydrylamino)-2-oxoethoxy)acetamido)-5-chlorobenzoic acid (Example 37)

2-(2-(2-benzhydrylamino)-2-oxoethoxy)acetamido-5-(pyridin-4-yl)benzoic acid (Example 52)

4-(2-(2-(benzhydrylamino)-2-oxoethoxy)acetamido)-4'-fluorobiphenyl-3-carboxylic acid (Example 66)

5-chloro-2-(2-(2-oxo-2-(4-phenylbutylamino)ethoxy)acetamido)benzoic acid (Example 70)

2-(2-(2-(bis(4-fluorophenyl)methylamino)-2-oxoethoxy)acetamido)-5-chlorobenzoic acid (Example 71)

2-(2-(2-(bis(4-(trifluoromethyl)benzyl)amino)-2-oxoethoxy)acetamido)-5-chlorobenzoic acid (Example 72)

2-(2-(2-(bis(4-fluorobenzyl)amino)-2-oxoethoxy)acetamido)-5-chlorobenzoic acid (desalted product of Example 73)

5-chloro-2-(2-(2-(2,2-diphenylethylamino)-2-oxoethoxy)acetamido)benzoic acid (Example 84)

5-chloro-2-(2-(2-(1-(naphthalen-1-yl)ethylamino)-2-oxoethoxy)acetamido)benzoic acid (Example 68)

5-chloro-2-(2-(2-(4-chlorophenylamino)-2-oxoethoxy)acetamido)benzoic acid (Example 39)

4-(2-(2-(4-chlorophenylamino)-2-oxoethoxy)acetamido)biphenyl-3-carboxylic acid (Example 58)

2,2'-(oxybis(1-oxo-2,1-ethanediyl)imino))bis(5-phenylbenzene-1-carboxylic acid) (Example 59)

2-(2-(2-(3,5-bis(trifluoromethyl)phenylamino)-2-oxoethoxy)acetamido)-5-chlorobenzoic acid (Example 74)

5-chloro-2-(2-(2-(diphenylamino)-2-oxoethoxy)acetamido)benzoic acid (Example 83)

2-(2-(2-(2-benzoyl-4-chlorophenylamino)-2-oxoethoxy)acetamido)-5-chlorobenzoic acid (Example 40)

(II-2-2-2) Carboxylic Acid or Bioisosteres of the Carboxylic Acid 2-(2-(2-(4-benzhydrylpiperazin-1-yl)-2-oxoethoxy)acetamido)-5-chlorobenzoic acid (desalted product of Example 30)

2-(2-(2-(4-benzhydrylpiperazin-1-yl)-2-oxoethoxy)acetamido)-5-methoxybenzoic acid (Example 28)

5-chloro-2-(2-(4-(4-chlorophenyl)piperazin-1-yl)-2-oxoethoxy)acetamido)benzoic acid (desalted product of Example 29)

2-(2-(2-(4-(bis(4-fluorophenyl)methyl)piperazin-1-yl)-2-oxoethoxy)acetamido)-5-chlorobenzoic acid (Example 34)

2-(2-(2-(4-(9H-fluoren-9-yl)piperazin-1-yl)-2-oxoethoxy)acetamido)-5-chlorobenzoic acid (Example 36)

2-(2-(2-(4-benzhydrylpiperazin-1-yl)-2-oxoethoxy)acetamido)-5-fluorobenzoic acid (Example 41)

3-(2-(2-(4-benzhydrylpiperazin-1-yl)-2-oxoethoxy)acetamido)benzoic acid (Example 42)

4-(2-(2-(4-benzhydrylpiperazin-1-yl)-2-oxoethoxy)acetamido)-3-chlorobenzoic acid (Example 43)

4-(2-(2-(4-benzhydrylpiperazin-1-yl)-2-oxoethoxy)acetamido)-4'-fluorobiphenyl-3-carboxylic acid (desalted product of Example 44)

4-(2-(2-(4-benzhydrylpiperazin-1-yl)-2-oxoethoxy)acetamido)-2',4'-difluorobiphenyl-3-carboxylic acid (desalted product of Example 45)

4-(2-(2-(4-benzhydrylpiperazin-1-yl)-2-oxoethoxy)acetamido)-4'-cyano-biphenyl-3-carboxylic acid (desalted product of Example 46)

4-(2-(2-(4-benzhydrylpiperazin-1-yl)-2-oxoethoxy)acetamido)-4'-(dimethylamino)biphenyl-3-carboxylic acid (desalted product of Example 47)
4-(2-(2-(4-benzhydrylpiperazin-1-yl)-2-oxoethoxy)acetamido)-4'-methoxybiphenyl-3-carboxylic acid (desalted product of Example 48)
4-(2-(2-(4-benzhydrylpiperazin-1-yl)-2-oxoethoxy)acetamido)-4'-morpholinobiphenyl-3-carboxylic acid (desalted product of Example 49)
2-(2-(2-(4-benzhydrylpiperazin-1-yl)-2-oxoethoxy)acetamido)-5-(pyridin-4-yl)benzoic acid (desalted product of Example 50)
2-(2-(2-(4-benzhydrylpiperazin-1-yl)-2-oxoethoxy)acetamido)-5-bromobenzoic acid (desalted product of Example 51)
2-(2-(2-(4-benzhydrylpiperazin-1-yl)-2-oxoethoxy)acetamido)-5-(pyridin-3-yl)benzoic acid (Example 53)
2-(2-(2-(4-benzhydrylpiperazin-1-yl)-2-oxoethoxy)acetamido)-5-(pyridin-4-yl)benzoic acid (Example 54)
2-(2-(2-(4-benzhydrylpiperazin-1-yl)-2-oxoethoxy)acetamido)-5-(1-methyl-1H-pyrazol-4-yl)benzoic acid (Example 55)
2-(2-(2-(4-benzhydrylpiperazin-1-yl)-2-oxoethoxy)acetamido)-5-benzyl benzoate (desalted product of Example 56)
4-(2-(2-(4-benzhydrylpiperazin-1-yl)-2-oxoethoxy)acetamido)biphenyl-3-carboxylic acid (desalted product of Example 57)
2-(2-(2-(4-benzhydrylpiperazin-1-yl)-2-oxoethoxy)acetamido)-5-isobutylbenzoic acid (desalted product of Example 62)
2-(2-(2-(4-benzhydrylpiperazin-1-yl)-2-oxoethoxy)acetamido)-5-(1H-pyrazol-4-yl)benzoic acid (desalted product of Example 63)
2-(2-(2-(4-benzhydrylpiperazin-1-yl)-2-oxoethoxy)acetamido)-5-(quinolin-3-yl)benzoic acid (Example 64)
2-(2-(2-(4-benzhydrylpiperazin-1-yl)-2-oxoethoxy)acetamido)-5-(benzo[b]thiophen-2-yl)benzoic acid (Example 65)
2-(2-(2-(4-benzhydrylpiperazin-1-yl)-2-oxoethoxy)acetamido)-4-chlorobenzoic acid (desalted product of Example 75)
2-(2-(2-(4-benzhydrylpiperazin-1-yl)-2-oxoethoxy)acetamido)-4-bromobenzoic acid (desalted product of Example 76)
2-(2-(2-(4-benzhydrylpiperazin-1-yl)-2-oxoethoxy)acetamido)-4-(pyridin-4-yl)benzoic acid (Example 77)
3-(2-(2-(4-benzhydrylpiperazin-1-yl)-2-oxoethoxy)acetamido)-4'-fluorobiphenyl-4-carboxylic acid (Example 78)
2-(2-(2-((3S*,5R*)-4-benzhydryl-3,5-dimethylpiperazin-1-yl)-2-oxoethoxy)acetamido)-5-chlorobenzoic acid (Example 85)
2-(2-(2-(4-benzhydrylpiperazin-1-yl)-2-oxoethoxy)acetamido)-5-(benzyloxy)benzoic acid (desalted product of Example 86)
2-(2-(2-(4-benzhydrylpiperazin-1-yl)-2-oxoethoxy)acetamido)-5-isobutoxybenzoic acid (desalted product of Example 87)
2-(2-(4-benzhydrylpiperazin-1-yl)-2-oxoethoxy)-N-(4-chloro-2-(1H-tetrazol-5-yl)phenyl)acetamide (Example 88)
2-(2-(4-benzhydrylpiperazin-1-yl)-2-oxoethoxy)-N-(4-chloro-2-(5-oxo-4,5-dihydro-1,2,4-oxadiazol-3-yl)phenyl)acetamide (Example 89)
2-(2-(2-(4-benzhydryloxy)piperidin-1-yl)-2-oxoethoxy)acetamido-5-chlorobenzoic acid (desalted product of Example 31)
5-chloro-2-(2-(2-(4,4-diphenylpiperidin-1-yl)-2-oxoethoxy)acetamido)benzoic acid (desalted product of Example 32).

(iii) Benzenecarboxylic Acid or Bioisosteres of the Carboxylic Acid (II-2-3)

Preferable examples of the benzenecarboxylic acid or bioisosteres of the carboxylic acid (II-2-3) include compounds represented by Formula (II-2) below, wherein $R_3$ is hydrogen, and L is methylene-N($R_9$)-methylene:

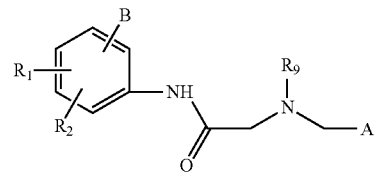

wherein B is carboxyl or a group that is biologically equivalent to a carboxyl group selected from alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl. $R_1$, $R_2$, $R_9$, and A are as defined above.

B, $R_1$, and $R_2$ may be located at any of the ortho, meta, and para positions of the benzene ring to which imino is bound. Although there is no limitation, B is preferably located at the ortho position, and $R_1$ and $R_2$ are preferably located at the meta and para positions, respectively, of the benzene ring.

$R_1$ and $R_2$ are as defined above; preferably $R_1$ and $R_2$ are the same or different, and each represents hydrogen, halogen, alkyl, substituted or unsubstituted aryl, or substituted or unsubstituted heterocyclic ring. The alkyl is preferably $C_{1-4}$ alkyl, more preferably methyl or ethyl. The aryl is preferably phenyl. The heterocyclic ring is preferably pyridyl, more preferably pyridin-3-yl or pyridin-4-yl; or pyrazolyl, preferably pyrazol-4-yl. Examples of substituents include halogen, alkyl, alkoxy, cyano, alkyl-substituted amino, aryl (preferably phenyl), and morpholino (preferably morpholin-4-yl). $R_1$ and $R_2$ are preferably hydrogen and halogen. More preferably, $R_2$ located at the meta position is hydrogen, and $R_1$ located at the para position is halogen, particularly chlorine.

A is as defined above, and preferably a group represented by —$COR_{10}$. $R_{10}$ in the —$COR_{10}$ is more preferably a group represented by the following formula or —N($R_{14}$)($R_{15}$).

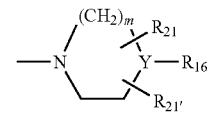

wherein Y, $R_{16}$, m, $R_{21}$, and $R_{21}'$ are as defined above.

—N($R_{14}$)($R_{15}$) is preferably a group having hydrogen as $R_{14}$, and unsubstituted or substituted aryl or aralkyl as $R_{15}$. The aryl is preferably phenyl, and the aralkyl is preferably diphenylalkyl (preferably diphenylmethyl). Examples of substituents of the aryl or aralkyl include halogen, $CF_3$, benzoyl, alkyl, alkoxy, hydroxyl, carboxy, alkoxycarbonyl, unsubstituted phenyl, and salts thereof.

In the above formula, Y, m, $R_{16}$, $R_{21}$, and $R_{21}'$ are as defined above; preferably, m is 2; Y is nitrogen, $R_{16}$ is substituted or unsubstituted aryl, preferably phenyl; or substituted or unsubstituted aralkyl, preferably diphenylmethyl; $R_{21}$ and $R_{21}'$ are the same or different, and each represents hydrogen. Examples of substituents include halogen, alkyl, alkoxy, hydroxyl, carboxy, alkoxycarbonyl, and salts thereof; preferably halogen.

$R_9$ is hydrogen or substituted or unsubstituted alkyl, preferably alkyl, particularly methyl.

Specific examples the benzenecarboxylic acid represented by the above formula or bioisosteres of the carboxylic acid (II-2-3) include compounds represented by the following formulae (see Table 3):

5-chloro-2-(2-(2-(4-chlorophenylamino)-2-oxoethyl) (methyl)(amino)acetamido)benzoic acid (Example 25)

2-(2-(2-(4-benzhydrylpiperazin-1-yl)-2-oxoethyl)(methyl) (amino)acetamido)-5-chlorobenzoic acid (Example 26)

2-(2-(2-(benzhydrylamino)-2-oxoethyl)(methyl)(amino)acetamido)-5-chlorobenzoic acid (Example 91).

(iv) Benzenecarboxylic Acid or Bioisosteres of the Carboxylic Acid (II-2-4)

Preferable examples of the benzenecarboxylic acid or bioisosteres of the carboxylic acid (II-2-4) include compounds represented by Formula (II-2) below, wherein $R_3$ is hydrogen, and L is methylenethiomethylene, methylene-SO-methylene, or methylene-$SO_2$— methylene.

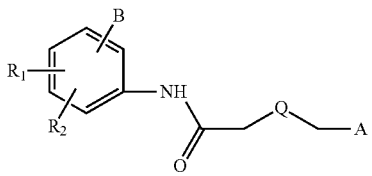

wherein Q is sulfur, sulfinyl, or sulfonyl; B is carboxyl or a group that is biologically equivalent to a carboxyl group selected from alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl. $R_1$, $R_2$, and A are as defined above.

B, $R_1$, and $R_2$ may be located at any of the ortho, meta, and para positions of the benzene ring to which imino is bound. Although there is no limitation, B is preferably located at the ortho position, and $R_1$ and $R_2$ are preferably located at the meta and para positions, respectively, of the benzene ring.

$R_1$ and $R_2$ are as defined above; preferably $R_1$ and $R_2$ are the same or different, and each represents hydrogen, halogen, alkyl, substituted or unsubstituted aryl, or substituted or unsubstituted heterocyclic ring. The alkyl is preferably $C_{1-4}$ alkyl, more preferably methyl or ethyl. The aryl is preferably phenyl. The heterocyclic ring is preferably pyridyl, more preferably pyridin-3-yl or pyridin-4-yl; or pyrazolyl, preferably pyrazol-4-yl. Examples of substituents include halogen, alkyl, alkoxy, cyano, alkyl-substituted amino, phenyl, and morpholino; preferably morpholin-4-yl. $R_1$ and $R_2$ are preferably hydrogen and halogen.

A is as defined above, and preferably a group represented by —$COR_{10}$. $R_{10}$ in —$COR_{10}$ is more preferably —$N(R_{14})(R_{15})$ or a group represented by the following formula:

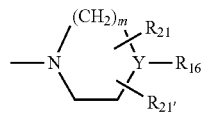

wherein Y, $R_{16}$, m, $R_{21}$, and $R_{21}'$ are as defined above.

—$N(R_{14})(R_{15})$ is preferably a group having hydrogen as $R_{14}$, and substituted or unsubstituted aryl or aralkyl as $R_{15}$. The aryl is preferably phenyl, and the aralkyl is preferably diphenylalkyl (preferably diphenylmethyl). Examples of substituents of the aryl or aralkyl include halogen, $CF_3$, benzoyl, alkyl, alkoxy, hydroxyl, carboxy, alkoxycarbonyl, unsubstituted phenyl, and salts thereof.

In the above formula, Y, m, $R_{16}$, $R_{21}$, and $R_{21}'$ are as defined above. Preferably, m is 2; Y is N; $R_{16}$ is substituted or unsubstituted aryl, preferably phenyl; or substituted or unsubstituted aralkyl, preferably diphenylmethyl; $R_{21}$ and $R_{21}'$ are the same or different, and each represents hydrogen. Examples of substituents include halogen, alkyl, alkoxy, hydroxyl, carboxy, alkoxycarbonyl, and salts thereof; preferably halogen.

Specific examples the benzenecarboxylic acid represented by the above formula, esters thereof, or bioisosteres of the carboxylic acid (II-2-4) include a compound represented by the following formula (see Table 3):

2-(2-(2-(4-benzhydrylpiperazine-1-yl)-2-oxoethylthio)acetamido)-5-chlorobenzoic acid (Example 92).

(v) Benzenecarboxylic Acid or Bioisostere of the Carboxylic Acid (II-2-5)

Preferable examples of the benzenecarboxylic acid or bioisosteres of the carboxylic acid (II-2-5) include compounds represented by Formula (II-2) below, wherein $R_3$ is hydrogen, and L is substituted or unsubstituted cycloalkylene.

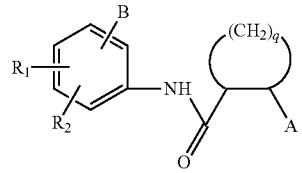

wherein B is carboxyl, alkoxycarbonyl, or a group that is biologically equivalent to a carboxyl group selected from 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl. $R_1$, $R_2$, and A are as defined above. q is an integer of 1 to 4.

B, $R_1$, and $R_2$ may be located at any of the ortho, meta, and para positions of the benzene ring to which imino is bound. Although there is no limitation, B is preferably located at the ortho position, and $R_1$ and $R_2$ are preferably located at the meta and para positions, respectively, of the benzene ring.

$R_1$ and $R_2$ are as defined above; preferably $R_1$ and $R_2$ are the same or different, and each represents hydrogen, halogen, alkyl, substituted or unsubstituted aryl, or substituted or unsubstituted heterocyclic ring. The alkyl is preferably $C_{1-4}$ alkyl, more preferably methyl or ethyl; the aryl is preferably phenyl; the heterocyclic ring is preferably pyridyl, more preferably pyridin-3-yl or pyridin-4-yl; or pyrazolyl, preferably pyrazol-4-yl. Examples of substituents include halogen, alkyl, alkoxy, cyano, alkyl-substituted amino, aryl (preferably phenyl), or morpholino (preferably morpholin-4-yl). $R_1$ and $R_2$ are each preferably hydrogen and halogen.

A is as defined above, and preferably a group represented by —$COR_{10}$. $R_{10}$ in —$COR_{10}$ is preferably a group represented by the following formula or —$N(R_{14})(R_{15})$.

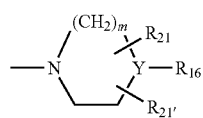

wherein Y, $R_{16}$, m, $R_{21}$, and $R_{21}'$ are as defined above.

—$N(R_{14})(R_{15})$ is preferably a group wherein $R_{14}$ is hydrogen, and $R_{15}$ is substituted or unsubstituted aryl or aralkyl. The aryl is preferably phenyl, and the aralkyl is preferably diphenylalkyl (more preferably diphenylmethyl). Examples of substituents of the aryl or aralkyl include halogen, $CF_3$, benzoyl, alkyl, alkoxy, hydroxyl, carboxy, alkoxycarbonyl, unsubstituted phenyl, and salts thereof.

In the above formula, Y, m, $R_{16}$, $R_{21}$, and $R_{21}'$ are as defined above. Preferably, m is 2; Y is nitrogen; $R_{16}$ is substituted or unsubstituted aryl, preferably phenyl, or substituted or unsubstituted aralkyl, preferably diphenylmethyl; and $R_{21}$ and $R_{21}'$ are the same or different, and each is hydrogen. Examples of substituents include halogen, alkyl, alkoxy, hydroxy, carboxy, alkoxycarbonyl, and salts thereof. Preferable is halogen.

Examples of substituents of the cycloalkylene include $C_{1-6}$, preferably $C_{1-4}$, lower alkyl.

Specific examples the benzenecarboxylic acid represented by the above formula or bioisosteres of the carboxylic acid (II-2-5) include compounds represented by the following formulae (see Table 3):

2-((1S*,2S*)-2-(4-benzhydrylpiperazine-1-carbonyl)cyclohexanecarboxamide)-5-chlorobenzoic acid (desalted product of Example 94)

2-((1S*,2R*)-2-(4-benzhydrylpiperazine-1-carbonyl)cyclohexanecarboxamide)-5-chlorobenzoic acid (desalted product of Example 95).

(vi) Benzenecarboxylic Acid or Bioisosteres of the Carboxylic Acid (II-2-6)

Preferable examples of the benzenecarboxylic acid or bioisosteres of the carboxylic acid (II-2-6) include compounds represented by Formula (II-2) below, wherein $R_3$ is hydrogen, and n is 0.

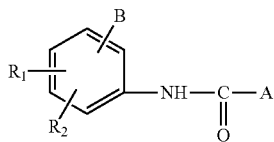

wherein B is carboxyl or a group that is biologically equivalent to a carboxyl group selected from alkoxycarbonyl, 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl. $R_1$, $R_2$, and A are as defined above.

B, $R_1$, and $R_2$ may be located at any of the ortho, meta, and para positions of the benzene ring to which imino is bound. Although there is no limitation, B is preferably located at the ortho position, and $R_1$ and $R_2$ are preferably located at the meta and para positions, respectively, of the benzene ring.

$R_1$ and $R_2$ are as defined above; preferably $R_1$ and $R_2$ are the same or different, and each represents hydrogen, halogen, alkyl, substituted or unsubstituted aryl, or substituted or unsubstituted heterocyclic ring. The alkyl is preferably $C_{1-4}$ alkyl, more preferably methyl or ethyl. The aryl is preferably phenyl. The heterocyclic ring is preferably pyridyl, more preferably pyridin-3-yl or pyridin-4-yl; or pyrazolyl, preferably pyrazol-4-yl. Examples of substituents include halogen, alkyl, alkoxy, cyano, alkyl-substituted amino, aryl (preferably phenyl), and morpholino (preferably morpholin-4-yl). $R_1$ and $R_2$ are each preferably hydrogen and halogen.

A is as defined above, and preferably a group represented by —$COR_{10}$. $R_{10}$ in —$COR_{10}$, is more preferably —$N(R_{14})(R_{15})$ or a group represented by the following formula.

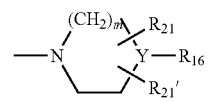

wherein Y, $R_{16}$, m, $R_{21}$, and $R_{21}'$ are as defined above.

—$N(R_{14})(R_{15})$ is preferably a group having hydrogen as $R_{14}$, and substituted or unsubstituted aryl or aralkyl as $R_{15}$. The aryl is preferably phenyl, and the aralkyl is preferably diphenylalkyl (more preferably diphenylmethyl). Examples of substituents of the aryl or aralkyl include halogen, $CF_3$, benzoyl, alkyl, alkoxy, hydroxyl, carboxy, alkoxycarbonyl, unsubstituted phenyl, and salts thereof.

In the above formula, Y, m, $R_{16}$, $R_{21}$, and $R_{21}'$ are as defined above. Preferably, m is 2; Y is nitrogen; $R_{16}$ is substituted or unsubstituted aryl, preferably phenyl; or substituted or unsubstituted aralkyl, preferably diphenylmethyl; $R_{21}$ and $R_{21}'$ are the same or different, and each represents hydrogen. Examples of substituents include halogen, alkyl, alkoxy, hydroxyl, carboxy, alkoxycarbonyl, and salts thereof; preferably halogen.

Specific examples the benzenecarboxylic acid represented by the above formula or bioisosteres of the carboxylic acid (II-2-6) include a compound represented by the following formula (see Table 3):

2-(2-(benzhydrylamino)-2-oxoacetamido)-5-chlorobenzoic acid (Example 79).

TABLE 3

| Ex of cpd 2 | Chemical name | Formula M.W. | PAI-1 activity % 100 μM | 50 μM | 20 μM |
|---|---|---|---|---|---|
| 1 | 2-(6-(3(tert-butoxycarbonyl)-4-phenylthiophen-2-ylamino)-6-oxohexanamido)benzoic acid sodium salt | C28H29N2NaO6S 544.60 | 12.1 | 97.8 | — |
| 2 | 2-(6-(3(tert-butoxycarbonyl)-4-phenylthiophen-2-ylamino)-6-oxohexanamido)-5-chlorobenzoic acid sodium salt | C28H28ClN2NaO6S 579.04 | 12.5 | 42.5 | — |
| 3 | 2-(6-oxo-6-(4-phenylthiophen-2-ylamino)hexanamido)benzoic acid | C23H22N2O4S 422.5 | 41.4 | 99.9 | — |
| 4 | 2-(6-(2-carboxy-4-chlorophenylamino)-6-oxohexanamido)-4-phenylthiophene-3-carboxylic acid | C24H21ClN2O6S 500.96 | 35.7 | 99.8 | — |
| 5 | 2-(6-oxo-6-(4-phenylpiperidin-1-yl)hexanamido)-4-phenylthiophene-3-carboxylic acid | C28H30N2O4S 490.61 | 12.0 | 97.7 | — |

TABLE 3-continued

| | | | | | |
|---|---|---|---|---|---|
| 6 | 2-(6-(4-chlorophenylamino)-6-oxohexanamido)-4-phenylthiophene-3-carboxylic acid | C23H21ClN2O4S 456.94 | 10.8 | 67.5 | — |
| 7 | 2,2'-(oxybis((1-oxo-2,1-ethanediyl)imino)bis(5-methyl-4-phenylthiophene-3-carboxylic acid) | C28H24N2O7S2 564.63 | 7.9 | 15.5 | — |
| 8 | 2,2'-(oxybis((1-oxo-2,1-ethanediyl)imino))bis(5-phenylthiophene-3-carboxylic acid) | C26H20N2O7S2 536.58 | 9.3 | 12.9 | — |
| 9 | 2,2'-(oxybis((1-oxo-2,1-ethanediyl)imino))bis-(4-phenylthiophene-3-carboxylic acid) | C26H20N2O7S2 536.58 | 19.8 | 94.2 | — |
| 10 | 2-(2-(2-(3-(tert-butoxycarbonyl)-5-methyl-4-phenylthiophen-2-ylamino)-2-oxoethoxy)acetamido)-5-meth-yl-4-phenylthiophene-3-carboxylic acid | C32H32N2O7S2 620.74 | — | 12.7 | 34.8 |
| 11 | 2-(6-(3-(tert-butoxycarbonyl)-4-isopropylthiophen-2-ylamino)-6-oxohexanamido)benzoic acid sodium salt | C25H31N2NaO6S 510.58 | 20.7 | 99.3 | — |
| 12 | 2-(6(4-isopropylthiophen-2-ylamino)-6-oxohexanamido)benzoic acid | C20H24N2O4S 388.48 | 24.5 | 69.6 | — |
| 13 | 2-(2-(2-(4-benzhydrylpiperazin-1-yl)-2-oxoethoxy)acetamido)-5-methyl-4-(pyridin-4-yl)thiophene-3-carboxylic acid | C32H32N4O5S 584.69 | — | 12.7 | 89.7 |
| 14 | 2-(2-(2-(4-benzhydrylpiperazin-1-yl)-2-oxoethoxy)acetamido)-5-methyl-4-(pyridin-3-yl)thiophene-3-carboxylic acid | C32H32N4O5S 584.69 | — | 20.5 | 92.3 |
| 15 | 2-(2-(2-(4-benzhydrylpiperazin-1-yl)-2-oxoethoxy)acetamido)-5-methyl-4-phenylthiophene-3-carboxylic acid sodium | C33H32N3NaO5S 605.68 | — | 5.8 | 35.6 |
| 16 | 2-(5-(1,3-dioxoisoindolin-2-yl)pentanamide)-4-phenylthiophene-3-carboxylic acid | C24H20N2O5S 448.49 | 32.8 | 100.0 | — |
| 17 | 2-(5-(3-(tert-butoxycarbonyl)-4-phenylthiophen-2-ylamino)-5-oxopentylcarbamoyl)benzoic acid | C28H30N2O6S 522.61 | 38.2 | 98.9 | — |
| 18 | 2-(2-(benzyloxycarbonylamino)-5-(4-chlorophenylamino)-5-oxopentanamido)-5-chlorobenzoic acid | C26H23Cl2N3O6 544.38 | 12.3 | 47.7 | — |
| 19 | 2-(2-(benzyloxycarbonylamino)-5-((4-chlorophenyl)(methyl)amino-5-oxopentanamido)-5-chlorobenzoic acid | C27H25Cl2N3O6 568.41 | 14.6 | 73.6 | — |
| 20 | 2-(2-(benzyloxycarbonylamino)-5-oxo-5-(4-phenlpiperazin-1-yl)pentanamido)-5-chlorobenzoic acid | C30H31ClN4O6 579.04 | 14.2 | 45.4 | — |
| 21 | 2-(5-(4-benzhydrylpiperazin-1-yl)-2-(benzyloxycarbonylamino)-5-oxopentanamido)-5-chlorobenzoic acid sodium salt | C37H36ClN4NaO6 691.15 | 7.1 | 17.9 | — |
| 22 | 2-(5-(4-benzhydrylpiperazin-1-yl)-4-(benzyloxycarbonyl amino)-5-oxopentanamido)-5-chlorobenzoic acid | C37H37ClN4O6 669.17 | — | 13.5 | 88.3 |
| 23 | 2-(5-(4-benzhydrylpiperazin-1-yl)-2-(tert-butoxycarbonyl amino)-5-oxopentanamido)-5-chlorobenzoic acid | C34H39ClN4O6 635.15 | — | 7.0 | 89.6 |
| 24 | 2-(2-amino-5-(4-benzhydrylpiperazin-1-yl)-5-oxopentanamido)-5-chlorobenzoic acid | C29H31ClN4O4 535.03 | — | 74.3 | 97.7 |
| 25 | 5-chloro-2-(2-((2-(4-chlorophenylamino)-2-oxoethyl)(methyl)amino)acetamido)benzoic acid | C16H17Cl2N3O4 410.25 | 48.2 | 100.0 | — |
| 26 | 2-(((2-(4-benzhydrypiperazin-1-yl)-2-oxoethyl)(methyl)amino)acetamido)-5-chlorobenzoic acid | C29H31ClN4O4 535.03 | 14.9 | 99.9 | — |
| 27 | 5-chloro-2-(6-(4-chlorophenylamino)-6-oxohexanamido)benzoic acid | C19H18Cl2N2O4 409.26 | 37.7 | 99.9 | — |
| 28 | 2-(2-(2-(4-benzhydrylpiperazin-1-yl)-2-oxoethoxy)acetamido)-5-methoxybenzoic acid | C29H31N3O6 517.57 | — | 86.7 | 99.1 |
| 29 | 5-chloro-2-(2-(4-(4-chlorophenyl)piperazin-1-yl)-2-oxoethoxy)acetamido)benzoic acid sodium salt | C21H20Cl2N3NaO5 488.30 | — | 60.5 | 91.4 |
| 30 | 2-(2-(2-(4-benzhydrylpiperazin-1-yl)-2-oxoethoxy)acetamido)-5-chlorobenzoic acid sodium salt | C28H27ClN3NaO5 543.97 | 10.9 | 37.4 | — |
| 31 | 2-(2-(2-(4-benzhydryloxy)piperidin-1-yl)-2-oxoethoxy)acetamido-5-chlorobenzoic acid sodium salt | C29H28ClN2NaO6 558.99 | — | 9.8 | 90.0 |
| 32 | 5-chloro-2-(2-(2-(4,4-diphenypiperidin-1-yl)-2-oxoethoxy)acetamido)benzoic acid sodium salt | C28H26ClN2NaO5 628.96 | — | 7.6 | 81.0 |
| 33 | 2-(2-(2-(4-chloro-2-(methoxycarbonyl)phenylamino)-2-oxoethoxy)acetamido)-5-methyl-4-phenylthiophene-3-carboxylic acid | C24H21ClN2O7S 516.96 | — | 5.0 | 59.0 |
| 34 | 2-(2-(2-(4-(bis(4-fluorophenyl)methyl)piperazin-1-yl)-2-oxoethoxy)acetamido)-5-chlorobenzoic acid | C28H26ClF2N3O5 557.97 | — | 15.5 | 98.8 |
| 35 | 2-(2-(2-(adamantylamino)-2-oxoethoxy)acetamido)-5-chlorobenzoic acid | C21H25ClN2O5 420.89 | — | 49.6 | 89.0 |
| 36 | 2-(2-(2-(4-(9H-fluoren-9-yl)piperazin-1-yl)-2-oxoethoxy)acetamido)-5-chlorobenzoic acid | C28H26ClN3O5 519.98 | — | 26.8 | 86.1 |
| 37 | 2-(2-(benzhydrylamino)-2-oxoethoxy)acetamido)-5-chlorobenzoic acid | C24H21ClN2O5 452.89 | — | 47.5 | 98.4 |
| 38 | 2-(2-(2-(3-(tert-butoxycarbonyl-5-methyl-4-phenylthiophen-2-ylamino)-2-oxoethoxy)acetamido)-5-chlorobenzoic acid | C27H27ClN2O7S 559.03 | — | 14.7 | 79.2 |
| 39 | 5-chloro-2-(2-(2-(4-chlorophenylamino)-2-oxoethoxy)acetamido)benzoic acid | C17H14ClN2O5 397.21 | 36.1 | 100.0 | — |
| 40 | 2-(2-(2-benzoyl-4-chlorophenylamino)-2-oxoethoxy)acetamido)-5-chlorobenzoic acid | C24H18Cl2N2O6 501.32 | 13.0 | 98.7 | — |
| 41 | 2-(2-(4-benzhydrylpiperazin-1-yl)-2-oxoethoxy)acetamido)-5-fluorobenzoic acid | C28H28 FN3O5 505.54 | — | 50.4 | 92.3 |
| 42 | 3(2-(2-(4-benzhydrylpiperazin-1-yl)-2-oxoethoxy)acetamido)benzoic acid | C28H29N3O5 487.55 | — | 88.2 | 98.7 |

TABLE 3-continued

| | | Formula M.W. | PAI-1 activity % 50 μM | PAI-1 activity % 20 μM |
|---|---|---|---|---|
| 43 | 4-(2-(2-(4-benzhydrylpiperazin-1-yl)-2-oxoethoxy)acetamido)-3-chlorobenzoic acid | C28H28ClN3O5 521.99 | — | 70.9 | 97.4 |
| 44 | 4(2-(2-(4-benzhydrylpiperazin-1-yl)-2-oxoethoxy)acetamido)-4'-fluorobiphenyl-3-carboxylic acid sodium salt | C34H31FN3NaO5 603.62 | — | 7.5 | 82.9 |
| 45 | 4-(2-(2-(4-benzhydrylpiperazin-1-yl)-2-oxoethoxy)acetamido)-2',4'-difluorobiphen-3-carboxylic acid sodium salt | C34H30F2N3NaO5 621.61 | — | 7.7 | 79.6 |
| 46 | 4-(2-(2-(4-benzhydrylpiperazin-1-yl)-2-oxoethoxy)acetamido)-4'-cyano-biphenyl-3-carboxylic acid sodium salt | C35H31N4NaO5 610.63 | — | 8.4 | 85.4 |
| 47 | 4-(2-(2-(4-benzhydrylpiperazin-1-yl)-2-oxoethoxy)acetamido)-4'-(dimethylamino)biphenyl-3-carboxylic acid sodium salt | C36H37N4NaO5 628.69 | — | 6.4 | 28.9 |
| 48 | 4-(2-(2-(4-benzhydrylpiperazin-1-yl)-2-oxoethoxy)acetamido)-4'-methoxybiphenyl-3-carboxylic acid sodium salt | C35H34N3NaO6 615.65 | — | 12.2 | 96.5 |
| 49 | 4-(2-(2-(4-benzhydrylpiperazin-1-yl)-2-oxoethoxy)acetamido)-4'-morpholinobiphenyl-3-carboxylic acid sodium salt | C38H39N4NaO6 670.73 | — | 12.7 | 97.3 |
| 50 | 2-(2-(2-(4-benzhydrylpiperazin-1-yl)-2-oxoethoxy)acetamido)-5-(pyridin-4-yl)benzoic acid sodium salt | C33H31N4NaO5 686.61 | — | 17.8 | 98.5 |
| 51 | 2-(2-(2-(4-benzhydrylpiperazin-1-yl)-2-oxoethoxy)acetamido)-5-bromobenzoic acid sodium salt | C28H27N3NaO5 588.42 | 10.1 | 23.0 | — |
| 52 | 2-(2-(2-benzhydrylamino)-2-oxoethoxy)acetamido-5-(pyridin-4-yl)benzoic acid | C29H25N3O5 495.53 | — | 0.9 | 34.0 |
| 53 | 2-(2-(2-(4-benzhydrylpiperazin-1-yl)-2-oxoethoxy)acetamido)-5-(pyridin-3-yl)benzoic acid | C33H32N4O5 564.63 | — | 11.8 | 86.1 |
| 54 | 2-(2-(2-(4-benzhydrylpiperazin-1-yl)-2-oxoethoxy)acetamido)-5-(pyridin-4-yl)benzoic acid | C33H32N4O5 564.63 | — | 5.0 | 42.8 |
| 55 | 2-(2-(2-(4-benzhydrylpiperazin-1-yl)-2-oxoethoxy)acetamido)-5-(1-methyl-1H-pyrazol-4-yl)benzoic acid | C32H33N5O5 567.64 | — | 12.3 | 49.5 |
| 56 | 2-(2-(2-(4-benzhydrylpiperazin-1-yl)-2-oxoethoxy)acetamido)-5-benzyl benzoate sodium salt | C35H34N3NaO5 599.65 | — | 9.5 | 98.9 |
| 57 | 4-(2-(2-(4-benzhydrylpiperazin-1-yl)-2-oxoethoxy)acetamido)biphenyl-3-carboxylic acid sodium salt | C34H32N3NaO5 585.62 | — | 16.8 | 83.8 |
| 58 | 4-(2-(2-(4-chlorophenylamino)-2-oxoethoxy)acetamido)biphenyl-3-carboxylic acid | C23H19ClN2O5 438.86 | — | 19.7 | 92.0 |
| 59 | 2,2'-(oxybis((1-oxo-2,1-ethanediyl)imino))bis(5-phenylbenzene-1-carboxylic acid) | C30H24N2O7 524.52 | 5.5 | 9.9 | — |
| 60 | 5-chloro-2-(5-(3-(4chlorophenyl)ureido) pentanamide)benzoic acid | C19H19Cl2N3O4 424.28 | 20.7 | 98.9 | — |
| 61 | 5-chloro-2-(5-(4-chlorophenylsulfonamide) pentanamide)benzoic acid | C18H18Cl2N2O5S 445.32 | 66.0 | 99.9 | — |

| Ex of cpd 2 | Chemical name | Formula M.W. | PAI-1 activity % 50 μM | PAI-1 activity % 20 μM |
|---|---|---|---|---|
| 62 | 2-(2-(2-(4-benzhydrylpiperazin-1-yl)-2-oxoethoxy)acetamido)-5-isobutylbenzoic acid sodium salt | C32H36NaO5 565.64 | 9.4 | 91.6 |
| 63 | 2-(2-(2-(4-benzhydrylpiperazin-1-yl)-2-oxoethoxy)acetamido)-5-(1H-pyrazol-4-yl)benzoic acid sodium salt | C31H30N5NaO5 575.59 | 21.4 | 78.2 |
| 64 | 2-(2-(2-(4-benzhydrylpiperazin-1-yl)-2-oxoethoxy)acetamido)-5-(quinolin-3-yl)benzoic acid | C37H24N4O5 614.69 | 7.5 | 62.7 |
| 65 | 2-(2-(2-(4-benzhydrylpiperazin-1-yl)-2-oxoethoxy)acetamido)-5-(benzo[b]thiophen-2-yl)benzoic acid | C36H33N3O5S 619.73 | 10.8 | 76.9 |
| 66 | 4-(2-(2-(benzhydrylamino)-2-oxoethoxy)acetamido)-4'-fluorobiphenyl-3-carboxylic acid | C30H25FN2O5 512.53 | 13.1 | 97.7 |
| 67 | 5-chloro-2-(2-(2-(2,6-diisopropylphenylamino)-2-oxoethoxy)acetamido benzoic acid | C23H27ClN2O5 446.92 | 75.0 | 99.8 |
| 68 | 5-chloro-2-(2-(2-(1-(naphthalen-1-yl)ethylamino)-2-oxoethoxy)acetamido)benzoic acid | C23H21ClN2O5 440.88 | 66.3 | 99.8 |
| 69 | 5-chloro-2-(2-(2-(5-isopropyl-2-methylphenylamino)-2-oxoethoxy) acetamido)benzoic acid | C21H23ClN2O5 418.87 | 52.8 | 99.3 |
| 70 | 5-chloro-2-(2-(2-oxo-2-(4-phenylbutylamino)ethoxy)acetamido)benzoic acid | C21H23ClN2O5 418.87 | 50.4 | 88.3 |
| 71 | 2-(2-(2-(bis(4-fluorophenyl)methylamino)-2-oxoethoxy)acetamido)-5-chlorobenzoic acid | C24H19ClF2N2O5 488.87 | 30.3 | 83.7 |
| 72 | 2-(2-(2-(bis(4-(trifluoromethyl)benzyl)amino)-2-oxoethoxy)acetamido)-5-chlorobenzoic acid | C27H21ClF6N2O5 602.91 | 5.0 | 66.0 |
| 73 | 2-(2-(2-(bis(4-fluorobenzyl)amino)-2-oxoethoxy)acetamido)-5-chlorobenzoic acid sodium salt | C25H20ClF2N2NaO5 524.88 | 12.4 | 71.1 |
| 74 | 2-(2-(3,5-bis(trifluoromethyl)phenylamino)-2-oxoethoxy)acetamido)-5-chlorobenzoic acid | C19H13ClF6N2O5 498.76 | 17.5 | 75.6 |
| 75 | 2-(2-(2-(4-benzhydrylpiperazin-1-yl)-2-oxoethoxy)acetamido)-4-chlorobenzoic acid sodium salt | C28H27ClN3NaO5 543.97 | 13.3 | 91.3 |
| 76 | 2-(2-(2-(4-benzhydrylpiperazin-1-yl)-2-oxoethoxy)acetamido)-4-bromobenzoic acid sodium salt | C28H27BrN3NaO5 588.42 | 10.2 | 79.8 |
| 77 | 2-(2-(2-(4-benzhydrylpiperazin-1-yl)-2-oxoethoxy)acetamido)-4-(pyridin-4-yl)benzoic acid | C33H32N4O5 584.63 | 9.6 | 48.6 |
| 78 | 3-(2-(2-(4-benzhydrylpiperazin-1-yl)-2-oxoethoxy)acetamido)-4'-fluorobiphenyl-4-carboxylic acid | C34H32FN3O5 581.63 | 13.5 | 91.0 |

TABLE 3-continued

| | | | | |
|---|---|---|---|---|
| 79 | 2-(2-(benzhydrylamino)-2-oxoacetamido)-5-chlorobenzoic acid | C22H17ClN2O4 408.83 | 27.2 | 83.4 |
| 80 | 2-(5-(4-benzhydrylpiperazin-1-yl)-5-oxopentanamido)-5-chlorobenzoic acid | C29H30ClN3O4 520.02 | 16.4 | 85.1 |
| 81 | 2-(2-(2-(4-benzhydrylpiperazin-1-yl)-2-oxoethoxy)acetamido)-5-(2,4-dimethylthiazol-5-yl)benzoic acid sodium salt | C33H33N4NaO5S 620.69 | 14.5 | 99.8 |
| 82 | 2-(2-(2-(benzhydrylamino)-2-oxoethoxy)acetamido)-5-methyl-4-phenylthiophene-3-carboxylic acid | C29H26N2O5S 514.59 | 11.1 | 89.3 |
| 83 | 5-chloro-2-(2-(2-(diphenylamino)-2-oxoethoxy)acetamido)benzoic acid sodium salt | C23H18ClN2NaO5 460.84 | 77.8 | 99.8 |
| 84 | 5-chloro-2-(2-(2-(2,2-diphenylethylamino)-2-oxoethoxy)acetamido)benzoic acid | C25H23ClN2O5 486.91 | 32.2 | 96.1 |
| 85 | 2-(2-(2-((3S,5R)-4-benzhydryl-3,5-dimethylpiperazin-1-yl)-2-oxoethoxy)acetamido)-5-chlorobenzoic acid hydrochloride | C30H33Cl2N3O5 586.51 | 7.2 | 42.7 |
| 86 | 2-(2-(2-(4-benzhydrylpiperazin-1-yl)-2-oxoethoxy)acetamido)-5-(benzyloxy)benzoic acid sodium salt | C35H34N2NaO6 615.65 | 9.7 | 99.3 |
| 87 | 2-(2-(2-(4-benzhydrylpiperazin-1-yl)-2-oxoethoxy)acetamido)-5-isobutoxybenzoic acid sodium salt | C32H36N3NaO6 581.63 | 12.2 | 99.3 |
| 88 | 2-(2-(4-benzhydrylpiperazin-1-yl)-2-oxoethoxy)-N-(4-chloro-2-(1H-tetrazol-5-yl)phenyl)acetamide | C28H28ClN7O3 546.02 | 15.1 | 71.6 |
| 89 | 2-(2-(4-benzhydrylpiperazin-1-yl)-2-oxoethoxy)-N-(4-chloro-2-(5-oxo-4,5-dihydro-1,2,4-oxadiazol-3-yl)phenyl)acetamide | C29H28ClN5O5 562.02 | 9.4 | 78.3 |
| 90 | 2-(2-(4-benzhydrylpiperazin-1-yl)-2-oxoethoxy)-N-(5-methyl-4-phenyl-3-(1H-tetrazol-5-yl)thiophen-2-yl)acetamide | C33H33N7O3S 607.73 | 7.0 | 63.1 |
| 91 | 2-(2-((2-(benzhydrylamino)-2-oxoethyl)(methyl)amino)acetamido)-5-chlorobenzoic acid hydrochloride | C25H25Cl2N3O4 502.39 | 42.5 | 98.4 |
| 92 | 2-(2-(2-(4-benzhydrylpiperazine-1-yl)-2-oxoethylthio)acetamido)-5-chlorobenzoic acid hydrochloride | C28H29ClN3O4S 574.52 | 15.9 | 71.2 |
| 93 | 2-(2-(1-(2-(4-benzhydrylpiperazin-1-yl)-2-oxoethyl)cyclohexyl)acetamido)-5-chlorobenzoic acid hydrochloride | C34H39Cl2N3O4 624.60 | 6.5 | 35.1 |
| 94 | 2-((1S,2S)-2-(4-benzhydrylpiperazine-1-carbonyl)cyclohexanecarboxamide)-5-chlorobenzoic acid hydrochloride | C32H35Cl2N3O4 596.54 | 5.7 | 26.7 |
| 95 | 2-((1S,2R)-2-(4-benzhydrylpiperazine-1-carbonyl)cyclohexanecarboxamide)-5-chlorobenzoic acid hydrochloride | C32H35Cl2N3O4 595.54 | 17.7 | 53.7 |

Note)
—: not measured (3) Compound Group 3 of the Present Invention (WO2009/123241)

The compound group 3 targeted by the present invention includes compounds represented by Formula (III) below:

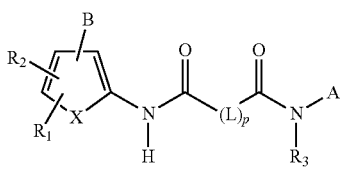

(III)

wherein $R_1$ and $R_2$ are the same or different, and each represents hydrogen, halogen, alkyl, cycloalkyl, cycloalkylalkyl, alkenyl, cycloalkenyl, alkynyl, hydroxyl, alkoxy, cycloalkoxy, alkenyloxy, cycloalkenyloxy, aryloxy, aralkyl, aralkyloxy, heterocyclic-alkyl, heterocyclic-alkyloxy; aryl optionally having one or two substituents; 5- to 6-membered ring heteroaryl optionally having one or two substituents, or benzo-fused heteroaryl optionally having one or two substituents; amino or carbamoyl, each of which is optionally substituted with one or two substituents; or cyano, carboxy, or alkoxycarbonyl; and $R_1$ and $R_2$ are optionally adjoined with each other to form a ring; $R_1$ and $R_2$ are preferably hydrogen, halogen, or aryl (in particular phenyl) optionally having one or two substituents; more preferably one of $R_1$ and $R_2$ is hydrogen, and the other is halogen.

$R_3$ is hydrogen, alkyl, cycloalkyl, or aryl optionally having one or two substituents. $R_3$ is preferably hydrogen, $C_{3-6}$ cycloalkyl, $C_{1-6}$ alkyl, or aryl (in particular phenyl), and more preferably hydrogen.

X is —C($R_5$)=C($R_6$)—, sulfur, oxygen, —N($R_4$)—, —C($R_7$)=N—, or —N=C($R_8$)—, wherein $R_4$ represents hydrogen, or alkyl optionally having one or two substituents. $R_5$, $R_6$, $R_7$ and $R_8$ are the same or different, and each represents hydrogen, halogen, alkyl optionally having one or two substituents, or alkoxy. $R_5$, $R_6$, $R_7$ and $R_8$ are more preferably hydrogen. X is preferably —C($R_5$)=C($R_6$)— or sulfur, more preferably —C($R_5$)=C($R_6$)—, and particularly preferably a vinylene group (—CH=CH—) in which $R_5$ and $R_6$ are both hydrogen.

L is alkyleneoxyalkylene, alkylene (some carbon atoms in the alkylene optionally form a cycloalkyl ring), alkenylene, alkynylene, cycloalkylene, alkylenethioalkylene, alkylene-SO-alkylene, or alkylene-SO$_2$-alkylene, each of which optionally has one or two substituents; or alkylene-N($R_9$)-alkylene, wherein $R_9$ represents hydrogen, or alkyl optionally having one or two substituents. L is preferably alkyleneoxyalkylene, alkylene, alkylenethioalkylene, alkylene-SO-alkylene, or alkylene-SO$_2$-alkylene, each of which optionally has one or two substituents; and more preferably alkyleneoxyalkylene.

p represents an integer of 0 or 1. p is preferably 1 when L is alkyleneoxyalkylene, alkylenethioalkylene, alkylene-SO-alkylene, or alkylene-SO$_2$-alkylene group, each of which optionally has a substituent; or alkylene-N($R_9$)-alkylene; particularly when L is alkyleneoxyalkylene.

A is a group represented by any of the following Formulae (c), (a), and (b). A is preferably a group represented by Formula (c).

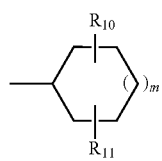

In Formula (a), $R_{10}$ and $R_{11}$ are the same or different, and each represents hydrogen or alkyl, and m represents an integer of 0 to 10. Of these, groups represented by Formula (a), wherein $R_{10}$ and $R_{11}$ are both hydrogen, and m is 1 to 10, are preferable.

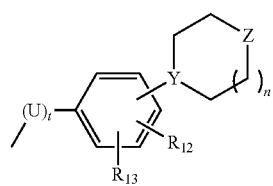

In Formula (b), each symbol represents the following groups.

$R_{12}$ and $R_{13}$ are the same or different, and each represents hydrogen; halogen; or alkyl optionally having one or two substituents, cycloalkyl optionally having one or two substituents, or alkoxy optionally having one or two substituents. $R_{12}$ and $R_{13}$ are preferably hydrogen.

Y represents CH or nitrogen, preferably CH.
Z represents $CH_2$, oxygen, or N-alkyl, preferably $CH_2$.
n represents an integer of 0 to 3, preferably 1.
U represents alkylene.
t represents an integer of 0 or 1.

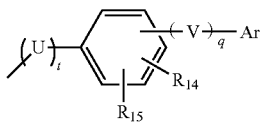

In Formula (c), each symbol represents the following groups.

$R_{14}$ and $R_{15}$ are the same or different, and each represents hydrogen; halogen; or alkyl optionally having one or two substituents, cycloalkyl optionally having one or two substituents, or alkoxy optionally having one or two substituents. $R_{14}$ and $R_{15}$ are preferably hydrogen, halogen, or alkyl optionally having one or two substituents, and more preferably hydrogen.

V represents alkylene, alkyleneoxyalkylene, oxyalkylene, alkyleneoxy, or oxygen. V is preferably alkylene, oxyalkylene, or oxygen.

q represents an integer of 0 or 1. q is preferably 0.
U represents alkylene.
t represents an integer of 0 or 1.
Ar represents 5- to 6-membered ring heteroaryl optionally having one or two substituents, aryl having one or two substituents (the one or two substituents optionally form a ring with a part of carbon atoms in the aryl group), or benzo-fused heteroaryl optionally having one to three substituents. Ar is preferably heteroaryl optionally having one or two substituents or phenyl having one or two substituents, and more preferably heteroaryl optionally having one or two substituents. Examples of heteroatoms include at least one member selected from the group consisting of nitrogen, oxygen, and sulfur. Preferable examples of the heteroaryl groups include furyl (e.g., furan-2-yl, furan-3-yl).

Preferable examples of substituents of Ar include halogen, alkyl, alkoxy, and phosphonooxymethyl. When Ar is aryl having an alkyl or alkoxy group as a substituent, the substituent may form a ring with a part of carbon atoms of the aryl group.

In Formula (III), B represents $COOR_{16}$, or a 1H-tetrazol-5-yl group, a 4,5-dihydro-5-oxo-4H-1,2,4-oxadiazol-3-yl group, a 4,5-dihydro-5-thioxo-4H-1,2,4-oxadiazol-3-yl group, or a 4,5-dihydro-5-oxo-1,2,4-thiadiazol-3-yl group represented by the following formulae (sequentially from the left).

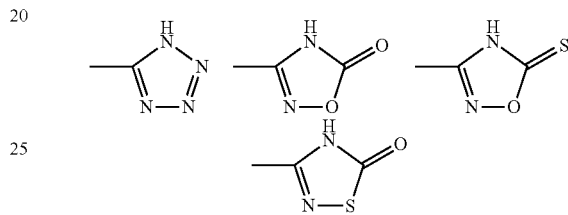

$R_{16}$ in $COOR_{16}$ represents hydrogen; alkyl, aryl or aralkyl; a (5-alkyl-2-oxo-1,3-dioxolen-4-yl)methyl group represented by the following formula:

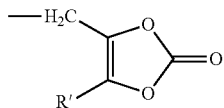

wherein R' represents alkyl;
or a group represented by $CH(R_{17})$—O—$COR_{18}$ or —CH$(R_{17})$—O—CO—$OR_{18}$, wherein $R_{17}$ is hydrogen or alkyl, and $R_{18}$ is alkyl or cycloalkyl. B is preferably carboxy (when $R_{16}$ in $COOR_{16}$ is hydrogen), alkoxycarbonyl (when $R_{16}$ in $COOR_{16}$ is alkyl), aralkyloxycarbonyl (when $R_{16}$ in $COOR_{16}$ is benzyl), (5-alkyl-2-oxo-1,3-dioxolen-4-yl)methyl, or a group represented by —CH($R_{17}$)—O—$COR_{18}$ or —CH($R_{17}$)—O—CO—$OR_{18}$, wherein $R_{17}$ and $R_{18}$ are as defined above.

The designation of each group represented by these characters and specific examples thereof are described below.

Examples of the "alkyl" represented by $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, or R', and the "alkyl" represented by Z as "N-alkyl" in the compound group 3 of the present invention include typically $C_{1-12}$, preferably $C_{1-10}$, more preferably $C_{1-8}$, further preferably $C_{1-6}$, and particularly preferably $C_{1-4}$ linear or branched alkyl groups. Examples of such alkyl groups include methyl, ethyl, propyl, isopropyl, butyl, isobutyl, s-butyl, t-butyl, pentyl, 1-methylbutyl, 2-methylbutyl, 3-methylbutyl, 1,1-dimethylpropyl, 1,2-dimethylpropyl, 2,2-dimethylpropyl, 1-ethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2- trimethylpropyl, heptyl, 1-methylpentyl, 2-methylpentyl, n-heptyl, isoheptyl, sec-heptyl, tert-heptyl, n-octyl, tert-octyl, 2-methylhexyl, 2-ethylhexyl, etc. Preferable groups are $C_{1-4}$ lower alkyl groups such as methyl, ethyl, propyl, isopropyl, butyl, and isobutyl; more preferable are methyl and ethyl; and particularly preferable is methyl.

Among these, the "alkyl" represented by $R_4$, $R_5$, $R_6$, $R_7$, $R_8$, $R_9$, $R_{12}$, $R_{13}$, $R_{14}$, or $R_{15}$ optionally has one or two substituents. Examples of such substituents include halogen, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, alkoxycarbonyl having $C_{1-6}$ alkoxy, etc.

Examples of the "cycloalkyl" represented by $R_1$, $R_2$, $R_3$, $R_{12}$, $R_{13}$, $R_{14}$, $R_{15}$, or $R_{18}$ in the compound group 3 of the present invention include typically $C_{3-7}$, and preferably $C_5$ or $C_6$ cyclic alkyl groups. Examples of such cycloalkyl groups include cyclopropyl, cyclobutyl, cyclopentyl, cyclohexyl, cycloheptyl, etc. Among these, the "cycloalkyl" represented by $R_{12}$, $R_{13}$, $R_{14}$, or $R_{15}$ optionally has one or two substituents at any position. Examples of such substituents include halogen, $C_{1-6}$ alkyl, halogen-substituted $C_{1-6}$ alkyl, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, and alkoxycarbonyl having $C_{1-6}$ alkoxy. Preferred are unsubstituted cycloalkyl groups.

Examples of the "cycloalkylalkyl" represented by $R_1$ or $R_2$ in the compound group 3 of the present invention include typically $C_{3-7}$, and preferably $C_5$ or $C_6$ cyclic alkyl (cycloalkyl) groups having a $C_{1-6}$ alkyl substituent. Examples of such cycloalkylalkyl groups include cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl, cycloheptylethyl, etc.

Examples of the "alkoxy" represented by $R_1$, $R_2$, $R_5$, $R_6$, $R_7$, $R_8$, $R_{12}$, $R_{13}$, $R_{14}$, or $R_{15}$ in the compound group 3 of the present invention include hydroxyl groups substituted with the above-mentioned $C_{1-12}$, preferably $C_{1-10}$, more preferably $C_{1-8}$, further preferably $C_{1-6}$, and particularly preferably $C_{1-4}$ alkyl groups. Examples of such alkoxy groups include methoxy, ethoxy, 1-propoxy, 2-propoxy, 1-buthoxy, 2-buthoxy, 2-methyl-1-propoxy, 2-methyl-2-propoxy, 1-pentyloxy, 2-pentyloxy, 3-pentyloxy, 2-methyl-2-butoxy, 3-methyl-2-butoxy, 1-hexyloxy, 2-hexyloxy, 3-hexyloxy, 2-methyl-1-pentyloxy, 3-methyl-1-pentyloxy, 2-ethyl-1-butoxy, 2,2-dimethyl-1-butoxy, 2,3-dimethyl-1-butoxy, etc. Preferable among these are methoxy, ethoxy, 1-propoxy, and 2-propoxy, with methoxy being more preferable. Of these, the "alkoxy" represented by $R_{12}$, $R_{13}$, $R_{14}$, or $R_{15}$ optionally has one or two substituents. Examples of such substituents include halogen, $C_{1-6}$ alkyl, halogen-substituted $C_{1-6}$ alkyl, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, alkoxycarbonyl having $C_{1-6}$ alkoxy, etc.

Examples of the "cycloalkoxy" represented by $R_1$ or $R_2$ in the compound group 3 of the present invention include $C_{2-8}$, preferably $C_{4-5}$ cyclic alkoxy groups. Such cycloalkoxy groups include cyclopropyloxy, cyclobutyloxy, cyclopentyloxy, cyclohexyloxy, cycloheptyloxy, etc.

Examples of the "alkenyl" represented by $R_1$ or $R_2$ in the compound group 3 of the present invention include $C_{2-6}$ linear or branched alkenyl groups having 1 to 3 double bonds. Examples of such alkenyl groups include vinyl, 1-propenyl, 1-methyl-1-propenyl, 2-methyl-1-propenyl, 2-propenyl, 2-butenyl, 1-butenyl, 3-butenyl, 2-pentenyl, 1-pentenyl, 3-pentenyl, 4-pentenyl, 1,3-butadienyl, 1,3-pentadienyl, 2-penten-4-ynyl, 2-hexenyl, 1-hexenyl, 5-hexenyl, 3-hexenyl, 4-hexenyl, 3,3-dimethyl-1-propenyl, 2-ethyl-1-propenyl, 1,3,5-hexatrienyl, 1,3-hexadienyl, and 1,4-hexadienyl.

Examples of the "alkenyloxy" represented by $R_1$ or $R_2$ in the compound group 3 of the present invention include hydroxyl groups substituted with the above-mentioned $C_{2-6}$ linear or branched alkenyl groups having 1 to 3 double bonds. Specific examples of such alkenyloxy groups include vinyloxy, 1-propenyloxy, 1-methyl-1-propenyloxy, 2-methyl-1-propenyloxy, 2-propenyloxy, 2-butenyloxy, 1-butenyloxy, 3-butenyloxy, 2-pentenyloxy, 1-pentenyloxy, 3-pentenyloxy, 4-pentenyloxy, 1,3-butadienyloxy, 1,3-pentadienyloxy, 2-penten-4-yloxy, 2-hexenyloxy, 1-hexenyloxy, 5-hexenyloxy, 3-hexenyloxy, 4-hexenyloxy, 3,3-dimethyl-1-propenyloxy, 2-ethyl-1-propenyloxy, 1,3,5-hexatrienyloxy, 1,3-hexadienyloxy, and 1,4-hexadienyloxy.

Examples of the "cycloalkenyl" represented by $R_1$ or $R_2$ in the compound group 3 of the present invention include $C_{2-6}$ cyclic alkenyl groups having 1 to 3 double bonds.

Examples of the "cycloalkenyloxy" represented by $R_1$ or $R_2$ in the compound group 3 of the present invention include $C_{2-6}$ cyclic alkenyloxy groups having 1 to 3 double bonds.

Examples of the "alkynyl" represented by $R_1$ or $R_2$ in the compound group 3 of the present invention include $C_{2-6}$ linear or branched alkynyl groups having a triple bond. Specific examples of such alkynyl groups include ethynyl, 2-propynyl, 2-butynyl, 3-butynyl, 1-methyl-2-propynyl, 2-pentynyl, 2-hexynyl, etc.

Preferable examples of the "aryl" represented by $R_1$, $R_2$, $R_3$, $R_{16}$, or Ar in the compound group 3 of the present invention include $C_{6-14}$ aromatic hydrocarbon groups. Examples of such aryl groups include phenyl, naphthyl, anthryl, phenanthryl, acenaphthylenyl, etc. Preferred among these are phenyl and naphthyl, and more preferred is phenyl.

Of these, the "aryl" represented by $R_1$, $R_2$, or $R_3$ optionally has one or two substituents at any position, preferably meta or para position. Further, the "aryl" represented by Ar has one or two substituents at any position. Examples of substituents as used herein include halogen, acetylamino, $C_{1-6}$ alkylamino, hydroxyl, $C_{1-6}$ alkyl (preferably $C_{1-4}$ alkyl), $C_{1-6}$ cycloalkyl, $C_{1-6}$ alkoxy (preferably $C_{1-4}$ alkoxy), and $C_{1-6}$ cycloalkoxy. The substituents of the "aryl" represented by $R_1$, $R_2$, or $R_3$ are preferably halogen or $C_{1-6}$ alkyl, and particularly preferably halogen. The substituents of the "aryl" represented by Ar are preferably halogen, $C_{1-6}$ alkyl, $C_{1-6}$ alkoxy, or acetylamino. When the "aryl" represented by Ar, which is preferably phenyl, has two adjacent substituents, the adjacent substituents may together form a ring. Examples of such "aryl" include (methylenedioxy)phenyl, (ethylenedioxy)phenyl, dihydrobenzofuranyl, dihydroisobenzofuranyl, chromanyl, chromenyl, isochromanyl, isochromenyl, indanyl, indenyl, tetrahydronaphthyl, dihydronaphthyl, indolinyl, etc.

The substituents of the aryl groups, in particular cycloalkyl and cycloalkoxy, may further have a substituent. Examples of such substituents include halogen, $C_{1-6}$ alkyl, $C_{1-6}$ alkoxy, halogen-substituted $C_{1-6}$ alkoxy, hydroxyl, $CF_3$, $CF_3O$, $CHF_2O$, $CF_3CH_2O$, cyano, carboxy, alkoxycarbonyl having $C_{1-6}$ alkoxy, benzoyl, phenyl, etc.

Examples of the "heteroaryl" represented by $R_1$, $R_2$ or Ar in the compound group 3 of the present invention include 5- to 6-membered ring aryl groups having one or more identical or different heteroatoms selected from the group consisting of nitrogen, oxygen and sulfur. Specific examples thereof include pyrrolyl, furyl, thienyl, pyrazolyl, imidazolyl, oxazolyl, isoxazolyl, triazolyl, isothiazolyl, oxadiazolyl, thiadiazolyl, triazolyl, tetrazolyl, pyridyl, pyridazinyl, pyrimidinyl, imidazolyl, pyrazinyl, and like unsaturated heterocyclic groups.

Preferable examples of the heteroaryl groups represented by $R_1$ or $R_2$ include pyrazolyl (e.g., pyrazol-4-yl), pyridyl (e.g., pyridin-3-yl, pyridin-4-yl), 2-methylpyrazolyl, quinolyl (quinolin-3-yl), and thiazolyl (e.g., thiazol-5-yl).

Preferable examples of the heteroaryl groups represented by Ar include furyl (e.g., furan-2-yl, furan-3-yl), pyrrolyl (e.g., pyrrol-1-yl, pyrrol-3-yl), oxazolyl (e.g., oxazol-5-yl), isoxazolyl (e.g., isoxazol-5-yl, isoxazol-4-yl), thienyl (e.g., thiophen-3-yl, thiophen-2-yl), pyrazolyl (e.g., pyrazol-4-yl), and pyridyl (e.g., pyridin-2-yl, pyridin-3-yl, pyridin-4-yl).

These groups may have one or two substituents at any position. Examples of substituents of the heteroaryl groups represented by Ar include halogen, $C_{1-6}$ alkyl (preferably $C_{1-4}$ alkyl), $C_{1-6}$ cycloalkyl, $C_{1-6}$ alkoxy (preferably $C_{1-4}$ alkoxy), $C_{1-6}$ cycloalkoxy, and phosphonooxymethyl. A phosphonooxymethyl group is a substituent of "heteroaryl" at the 1-position when the heteroaryl represented by Ar is pyrazolyl or pyrrolyl; the phosphonooxymethyl substituent is removed in vivo, which converts the phosphonooxymethyl-substituted pyrazolyl or pyrrolyl group to a pyrazolyl or pyrrolyl group unsubstituted at the 1-position, allowing the pyrazolyl or pyrrolyl group to show PAI-1 inhibition activity. In other words, phosphonooxymethyl is a substituent that serves as a so-called prodrug.

When a substituent of Ar is cycloalkyl or cycloalkoxy, they may also have a substituent. Examples of such substituents include halogen, $C_{1-6}$ alkyl, $C_{1-6}$ alkoxy, halogen-substituted alkoxy having $C_{1-6}$ alkoxy, hydroxyl, $CF_3$, $CF_3O$, $CHF_2O$, $CF_3CH_2O$, cyano, carboxy, alkoxycarbonyl, benzoyl, and phenyl.

Examples of the "benzo-fused heteroaryl" represented by $R_1$, $R_2$, or Ar in the compound group 3 of the present invention include groups in which the benzene ring is fused with the above-mentioned heteroaryl. Specific examples thereof include indolyl, isoindolyl, benzofuranyl, benzothienyl, benzimidazolyl, benzisoxazolyl, benzothiazolyl, benzisothiazolyl, quinolyl, isoquinolyl, quinazolinyl, quinoxalinyl, benzoxadiazolyl, benzothiadiazolyl, etc. Preferable examples of the "benzo-fused heteroaryl" represented by Ar include quinolyl (e.g., quinolin-8-yl) and benzofuranyl (benzofuran-2-yl).

The above benzo-fused heteroaryl may have one to three substituents at any position. Examples of such substituents include halogen, $C_{1-4}$ alkyl, $C_{1-4}$ halogenated alkyl, $C_{1-4}$ alkoxy, $C_{1-4}$ halogenated alkoxy, hydroxyl, $CF_3$, $CF_3O$, $CHF_2O$, $CF_3CH_2O$, aryl (preferably phenyl), halogenated aryl, cyano, carboxy, alkoxycarbonyl having $C_{1-4}$ alkoxy, etc.

Examples of the "aryloxy" represented by $R_1$ or $R_2$ in the compound group 3 of the present invention include hydroxyl groups substituted with $C_{6-14}$ aromatic hydrocarbon groups. Examples of such aryloxy groups include phenyloxy, naphthyloxy, anthryloxy, phenanthryloxy, acenaphthylenyloxy, etc.

Examples of the "aralkyl" represented by $R_1$, $R_2$, or $R_{16}$ in the compound group 3 of the present invention include aralkyl groups substituted with one or more aryl groups mentioned above such as phenyl, naphthyl, etc. Examples of these aralkyl groups include benzyl (phenylmethyl); monophenylalkyl groups such as 1-phenylethyl, 2-phenylethyl, 3-phenylpropyl, 4-phenylbutyl, etc.; diphenylalkyl groups such as diphenylmethyl, diphenylethyl, etc.; and mononaphthyl alkyl groups such as 1-naphthyl methyl, 1-naphthyl ethyl, 2-naphtyl methyl, 2-naphthyl ethyl, etc. Among these, benzyl is preferable.

Examples of the "aralkyloxy" represented by $R_1$ or $R_2$ in the compound group 3 of the present invention include hydroxyl groups substituted with the above-mentioned aralkyl groups. Preferred among these is benzyloxy.

Examples of the "heterocyclic-alkyl" represented by $R_1$ or $R_2$ in the compound group 3 of the present invention include groups formed by bonding a bonding hand of the heterocyclic group mentioned below to either of the bonding hands of an alkylene group. Examples of the "heterocyclic-alkoxy" represented by $R_1$ or $R_2$ include groups formed by bonding a bonding hand of the heterocyclic group mentioned below to a bonding hand of the alkylene group of an alkyleneoxy group. Examples of the "alkyl" and "alkoxy" as used herein include those mentioned earlier. Examples of the heterocyclic rings include saturated and unsaturated 4- to 10-membered ring heterocyclic groups containing 1 to 3 identical or different heteroatoms selected from the group consisting of nitrogen, oxygen, and sulfur. Specific examples thereof include unsaturated heterocyclic groups, such as pyrrolyl, furyl, thienyl, pyrazolyl, imidazolyl, oxazolyl, isoxazolyl, triazolyl, isothiazolyl, oxadiazolyl, thiadiazolyl, triazolyl, tetrazolyl, pyranyl, pyridyl, pyridazinyl, pyrimidinyl, pyrazinyl, azepinyl, azocinyl, etc.; groups in which the above-mentioned unsaturated heterocyclic groups are partially or completely reduced, such as azetidinyl, pyrrolidinyl, pyrrolinyl, imidazolidinyl, imidazolinyl, pyrazolidinyl, pyrazolinyl, piperidyl, piperazinyl, morpholinyl, thiomorpholinyl, perhydroazepinyl, perhydroazocinyl, 1,4,5,6-tetrahydropyrimidinyl, 1,2,3,6-tetrahydropyridyl, etc.; and groups in which the above-mentioned unsaturated heterocyclic rings are condensed with each other, or groups in which a benzene ring is condensed with the above-mentioned unsaturated heterocyclic ring, such as indolyl, isoindolyl, indolinyl, benzofuranyl, benzothienyl, benzimidazolyl, benzisoxazolyl, benzothiazolyl, benzisothiazolyl, benzthiophenyl, quinolyl, isoquinolyl, quinazolinyl, quinoxalinyl, benzoxadiazolyl, benzothiadiazolyl, pyrrolopyrrolyl, pyrrolooxazolyl, pyrrolothiazolyl, pyrrolopyridyl, furopyrrolyl, furopyridyl, thienopyrrolyl, thienopyridyl, imidazopyrrolyl, imidazoimidazolyl, imidazooxazolyl, imidazothiazolyl, imidazoisothiazolyl, imidazopyridyl, imidazopyridazinyl, imidazopyrimidinyl, imidazopyrazinyl, oxazooxazolyl, oxazoisoxazolyl, oxazothiazolyl, oxazoisothiazolyl, oxazopyridyl, thiazolooxazolyl, thiazoloisoxazolyl, thiazolothiazolyl, thiazoloisothiazolyl, thiazolopyridyl, etc. Preferable examples of heterocyclic groups include azetidinyl, pyrrolidinyl, piperidinyl, morpholinyl, piperazinyl, homopiperazinyl, tetrahydrofuryl, tetrahydrothienyl, tetrahydropyranyl, pyrrolyl, furyl, thienyl, oxazolyl, isoxazolyl, thiazolyl, isothiazolyl, pyrazolyl, pyridyl, pyrimidinyl, indolyl, isoindolyl, benzofuranyl, benzoxazolyl, benzothiazolyl, benzothiophenyl, and quinolyl.

Examples of the "halogen atom" in the compound group 3 of the present invention include fluorine, chlorine, bromine, and iodine. Preferred are fluorine and chlorine, and more preferred is chlorine.

Examples of the "alkylene" represented by L, U, or V in Formula (I) includes typically $C_{1-12}$, preferably $C_{1-10}$, more preferably $C_{1-8}$, further preferably $C_{1-6}$, and particularly preferably $C_{1-4}$ linear or branched alkylene groups. Examples of such alkylene groups include methylene, ethylene, propylene, trimethylene, 1-ethyl-1,2-ethylene, 1-propyl-1,2-ethylene, 1-isopropyl-1,2-ethylene, 1-butyl-1,2-ethylene, 1,2-dimethyl-1,2-ethylene, tetramethylene, pentamethylene, hexamethylene, heptamethylene, and octamethylene. Examples of the "alkylene" in the "cycloalkylene," "alkyleneoxyalkylene," "alkylenethioalkylene," "alkylene-SO-alkylene," "alkylene-SO$_2$-alkylene," and "alkylene-N(R$_9$)-alkylene" represented by L include the same as exemplified above; and examples of the "alkylene" in the "alkyleneoxyalkylene," "oxyalkylene," and "alkyleneoxy" represented by V also include the same as exemplified above.

Specific examples of the "alkylene" represented by L include methylene, ethylene, propylene (trimethylene), tetramethylene, pentamethylene, and hexamethylene, with trimethylene and tetramethylene being preferable. These alkylene groups may be those in which some of the carbon atoms in the alkylene combine to form a cycloalkane ring. Examples of such cycloalkane rings include cyclopropane, cyclobutane, cyclopentane, and cyclohexane.

Specific examples of the "alkylene" represented by U or V include methylene, ethylene, propylene (trimethylene), tetramethylene, pentamethylene, and hexamethylene. Among these, preferable as an alkylene group represented by U is methylene, and preferable as alkylene groups represented by V are methylene, ethylene, and trimethylene.

The "alkylene" in the "alkyleneoxyalkylene," "oxyalkylene," or "alkyleneoxy" represented by V is preferably methylene or ethylene.

Preferable examples of the "cycloalkylene" include cyclopropylene, cyclobutylene, cyclopentylene, cyclohexylene, cyclooctylene, etc.; preferable examples of the "alkyleneoxyalkylene" include methyleneoxymethylene, ethyleneoxymethylene, methyleneoxyethylene, ethyleneoxyethylene, etc.; preferable examples of the "alkylenethioalkylene" include methylenethiomethylene, ethylenethiomethylene, methylenethioethylene, and ethylenethioethylene; preferable examples of the "alkylene-SO-alkylene" include methylene-SO-methylene, ethylene-SO-methylene, methylene-SO-ethylene, and ethylene-SO-ethylene; and preferable examples of the "alkylene-SO$_2$-alkylene" include methylene-SO$_2$-methylene, ethylene-SO$_2$-methylene, methylene-SO$_2$-ethylene, and ethylene-SO$_2$-ethylene. Examples of the "alkylene-N(R$_9$)-alkylene group" include lower alkylene-lower alkylamino-lower alkylene. Examples of the lower alkylene used herein include C$_{1-6}$ alkylene, and preferable examples thereof include methylene, ethylene, propylene, and trimethylene; examples of the lower alkylamino include C$_{1-6}$ alkylamino, and preferable examples thereof include methylamino, ethylamino, propylamino, isopropylamino, and butylamino. Preferred are methylene-methylamino-methylene, ethylene-methylamino-methylene, methylene-methylamino-ethylene, and ethylene-methylamino-ethylene.

Examples of the "alkenylene" represented by L in Formula (III) include C$_{2-6}$ linear or branched alkenylene groups having 1 to 3 double bonds. Examples of such alkenylene groups include vinylene, 1-methylvinylene, propenylene, 1-butenylene, 2-butenylene, 1-pentenylene, 2-pentenylene, etc.

Examples of the "alkynylene" represented by L in Formula (III) include C$_{2-6}$ linear or branched alkynylene groups having one triple bond. Examples of such alkynylene groups include ethynylene, propynylene, 1-methylpropynylene, 1-butynylene, 2-butynylene, 1-methylbutynylene, 2-methylbutynylene, 1-pentynylene, and 2-pentynylene.

The above-mentioned "alkylene," "cycloalkylene," "alkyleneoxyalkylene," "alkylenethioalkylene," "alkylene-SO-alkylene," "alkylene-SO$_2$-alkylene," "alkylene-N(R$_9$)-alkylene," "alkenylene," and "alkynylene" may have one or two substitutes. Examples of such substituents include halogen, C$_{1-4}$ lower alkyl, C$_{1-4}$ halogenated alkyl, C$_{1-4}$ alkoxy, C$_{1-4}$ halogenated alkoxy, hydroxyl, CF$_3$, CF$_3$O, CHF$_2$O, CF$_3$CH$_2$O, cyano, carboxy, alkoxycarbonyl having C$_{1-4}$ alkoxy, amino, acylamino, benzyloxycarbonylamino (Cbz-NH—), alkoxycarbonylamino (e.g., t-butoxycarbonylamino (tBoc-NH—), methoxycarbonylamino, ethoxycarbonylamino, propoxycarbonylamino, isopropoxycarbonylamino, butoxypropoxycarbonylamino), acyl, etc.

Examples of the groups represented by B in Formula (III) include, in addition to carboxyl (COOH), (1) alkoxycarbonyl, aryloxycarbonyl, and aralkyloxycarbonyl, which can be converted to a carboxyl group when absorbed in vivo; (2) groups that can be easily converted to a carboxyl group when absorbed in vivo; and (3) groups that have been designated as a group that is biologically equivalent to a carboxyl group. Here, examples of the alkoxycarbonyl, aryloxycarbonyl and aralkyloxycarbonyl in (1) above include groups that are each represented by COOR$_{16}$, wherein R$_{16}$ is respectively C$_{1-6}$ alkyl, aryl (preferably phenyl) or aralkyl (preferably benzyl).

Specific examples of the groups in (2) above include groups represented by COOR$_{16}$, wherein R$_{16}$ is a (5-alkyl-2-oxo-1,3-dioxolen-4-yl)methyl group represented by the following formula:

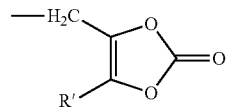

wherein R' is alkyl;
or a group represented by —CH(R$_{17}$)—O—COR$_{18}$ or —CH(R$_{17}$)—O—OR$_{18}$, wherein R$_{17}$ is hydrogen or C$_{1-6}$ alkyl, and R$_{18}$ is C$_{1-6}$ alkyl or cycloalkyl.

Examples of the groups in (3) above include heterocyclic groups, such as 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, and 4,5-dihydro-5-oxo-1,2,4-thiadiazol-3-yl, represented by the following formulae in order from the left (see, for example, Kohara et al. J. Med. Chem., 1996, 39, 5228-5235).

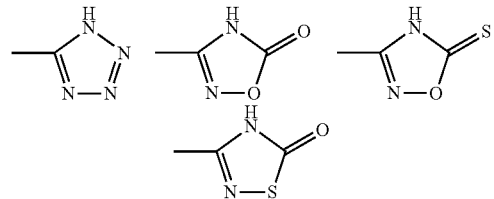

In the present invention, the groups of (1) to (3) mentioned above may each be called "a group that is biologically equivalent to a carboxyl group," and a compound (I) having the above group may be called a bioisostere of the carboxylic acid.

Specific examples of the "alkoxycarbonyl" represented by R$_1$, R$_2$, or B (when B represents —COOR$_{16}$, wherein R$_{16}$ is alkyl) in Formula (III) include t-butoxycarbonyl, methoxycarbonyl, ethoxycarbonyl, propoxycarbonyl, isopropoxycarbonyl, butoxycarbonyl, etc.

The compound (I) targeted by the present invention preferably includes benzene carboxylic acids represented by Formula (III-1) below, wherein X in Formula (I) is vinylene, and bioisosteres thereof:

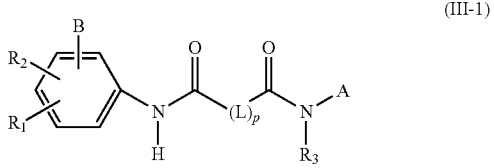

(III-1)

wherein $R_1$, $R_2$, $R_3$, L, B, A, and p are as defined above.

The benzene carboxylic acids and bioisosteres thereof (III-1) herein refer to compounds having a structure in which a single hydrogen atom (at the ortho, meta, or para position) of the benzene is substituted with a carboxyl group represented by substituent B, or with a group that is biologically equivalent to a carboxyl group (e.g., a group that is converted in vivo to a carboxyl group; or 1H-tetrazol-5-yl, 4,5-dihydro-5-oxo-4H-1,2,4-oxadiazol-3-yl, 4,5-dihydro-5-thioxo-4H-1,2,4-oxadiazol-3-yl, or 4,5-dihydro-5-oxo-1,2,4-thiadiazol-3-yl).

(3-1) Benzene Carboxylic Acid or Bioisostere of the Carboxylic Acid (III-1)

The above-mentioned benzene carboxylic acids or bioisosteres of the carboxylic acids (III-1) preferably include the following compounds.

(III-1-3) Benzene carboxylic acids represented by Formula (III-1), wherein A is a group represented by Formula (c), or bioisosteres of the benzene carboxylic acids.

(III-1-1) Benzene carboxylic acids represented by Formula (III-1), wherein A is a group represented by Formula (a), or bioisosteres of the benzene carboxylic acids.

(III-1-2) Benzene carboxylic acids represented by Formula (III-1), wherein A is a group represented by Formula (b), or bioisosteres of the benzene carboxylic acids.

(III-1-1) Benzene Carboxylic Acid or Bioisostere of the Benzene Carboxylic Acid

Preferable examples of benzene carboxylic acids or bioisosteres of the benzene carboxylic acids (III-1-1) include compounds represented by the following formula.

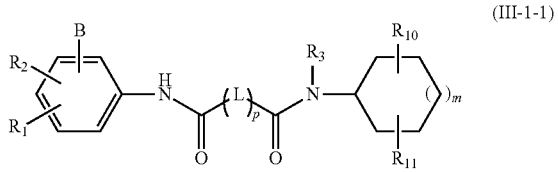

(III-1-1)

In the above formula, B represents a carboxyl group or a group that is biologically equivalent to a carboxyl group. Of these, a carboxyl group is preferable. B, $R_1$ and $R_2$ may be located at any of the ortho, meta, and para positions of the benzene ring to which imino is bound. It is preferable, but not required, that B be located at the ortho position, and $R_2$ and $R_1$ be respectively located at the meta and para positions, within the benzene ring.

$R_1$ and $R_2$ are as defined above, and are preferably the same or different, and each represents hydrogen, halogen, alkyl, unsubstituted aryl, or aryl substituted with one or two substituents. The halogen is preferably chlorine or fluorine, and more preferably chlorine. The alkyl is preferably $C_{1-4}$ alkyl, and more preferably methyl or ethyl. Preferable examples of aryl include phenyl, and preferable examples of the substituents thereof include the above-mentioned halogen. $R_1$ and $R_2$ are preferably the same or different, and each represents hydrogen or halogen; and more preferably, either of them (e.g., $R_2$) is hydrogen, and the other (e.g., $R_1$) is halogen.

$R_3$ is as defined above, and is preferably hydrogen, $C_{3-8}$ (preferably $C_6$) cycloalkyl, unsubstituted aryl (preferably phenyl), or aryl (preferably phenyl) having one or two substituents.

$R_{10}$ and $R_{11}$ are as defined above, and are preferably hydrogen.

m is an integer of 1 to 10, preferably 1 to 9, and more preferably 1 to 7.

L is as defined above, and is preferably, for example, alkylene, alkyleneoxyalkylene, or alkylenethioalkylene. Among these, L is more preferably alkyleneoxyalkylene or alkylenethioalkylene. Preferable examples of alkylene include methylene.

p is as defined above, and is preferably an integer of 1.

Specific examples of the benzene carboxylic acids represented by the above formula, or bioisosteres of the benzene carboxylic acid (III-1-1), of the present invention, include the following compounds (see Table 4):

5-chloro-2-({[2-(dicyclohexylamino)-2-oxoethoxy]acetyl}amino)benzoic acid (desalted product of Example 9)

5-chloro-2-({[2-(cyclododecylamino)-2-oxoethoxy]acetyl}amino)benzoic acid (Example 11)

5-chloro-2-[({2-[cyclohexyl(phenyl)amino]-2-oxoethoxy}acetyl)amino]benzoic acid (desalted product of Example 15)

5-chloro-2-[({[2-(cyclododecylamino)-2-oxoethyl]sulfanyl}acetyl)amino]benzoic acid (Example 28)

(II-1-2) Benzene Carboxylic Acid or Bioisostere of the Benzene Carboxylic Acid

Preferable examples of the benzene carboxylic acids or bioisosteres of the benzene carboxylic acids (III-1-2) include compounds represented by the following formula.

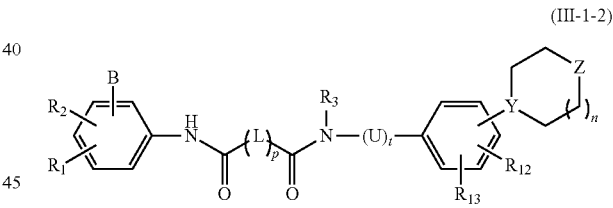

(III-1-2)

In the above formula, B represents a carboxyl group or a group that is biologically equivalent to a carboxyl group. Of these, a carboxyl group is preferable. B, $R_1$ and $R_2$ may be located at any of the ortho, meta, and para positions of the benzene ring to which imino is bound. It is preferable, but not required, that B be located at the ortho position, and $R_2$ and $R_1$ be respectively located at the meta and para positions, within the benzene ring.

$R_1$ and $R_2$ are as defined above, and are preferably the same or different, and each represents hydrogen, halogen, alkyl, unsubstituted aryl, or aryl substituted with one or two substituents. The halogen is preferably chlorine or fluorine, and more preferably chlorine. The alkyl is preferably $C_{1-4}$ alkyl, and more preferably methyl or ethyl. Preferable examples of aryl include phenyl, and preferable examples of the substituents thereof include the above-mentioned halogen. $R_1$ and $R_2$ are preferably the same or different, and each represents hydrogen or halogen; and more preferably, either of them (e.g., $R_2$) is hydrogen, and the other (e.g., $R_1$) is halogen.

$R_3$, $R_{12}$ and $R_{13}$ are as defined above, and are preferably hydrogen.

Y and Z are as defined above. Y is preferably CH, and Z is preferably $CH_2$.

n is an integer of 0 to 3, preferably 1.

L is as defined above, and is preferably, for example, alkylene, alkyleneoxyalkylene, or alkylenethioalkylene. Among these, L is more preferably alkyleneoxyalkylene or alkylenethioalkylene. Preferable examples of alkylene include methylene.

p is as defined above, and is preferably an integer of 1.

U and t are as defined above. t is preferably 0.

Specific examples of the benzene carboxylic acids represented by the formula above, or bioisosteres of the benzene carboxylic acid (III-1-2), of the present invention, include the following compounds (see Table 4):

5-chloro-2-[({2-[(4-cyclohexylphenyl)amino]-2-oxoethoxy}acetyl)amino]benzoic acid (desalted product of Example 10)

5-chloro-2-[({2-[(3-cyclohexylphenyl)amino]-2-oxoethoxy}acetyl)amino]benzoic acid (Example 26)

5-chloro-2-{[({2-[(4-cyclohexylphenyl)amino]-2-oxoethyl}sulfanyl)acetyl]amino}benzoic acid (Example 27)

(III-1-3) Benzene Carboxylic Acid or Bioisostere of the Benzene Carboxylic Acid

Preferable examples of the benzene carboxylic acids or bioisosteres of the benzene carboxylic acids (III-1-3) include compounds represented by the following formula.

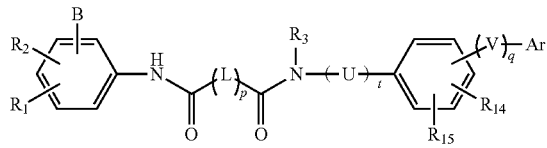

(III-1-3)

In the above formula, B represents a carboxyl group or a group that is biologically equivalent to a carboxyl group. Of these, a carboxyl group is preferable. Preferable examples of groups that are biologically equivalent to a carboxyl group include groups represented by —$CH(R_{17})$—O—$COR_{18}$ or —$CH(R_{17})$—O—CO—$OR_{18}$, wherein $R_{17}$ is hydrogen or alkyl, and $R_{18}$ is alkyl or cycloalkyl; and (5-alkyl-2-oxo-1,3-dioxolen-4-yl)methyl. B, $R_1$ and $R_2$ may be located at any of the ortho, meta, and para positions of the benzene ring to which imino is bound. It is preferable, but not required, that B be located at the ortho position, and $R_2$ and $R_1$ be respectively located at the meta and para positions, within the above benzene ring.

$R_1$ and $R_2$ are as defined above, and are preferably the same or different, and each represents hydrogen, halogen, alkyl, unsubstituted aryl, or aryl substituted with one or two substituents. The halogen is preferably chlorine or fluorine, and more preferably chlorine. The alkyl is preferably $C_{1-4}$ alkyl, and more preferably methyl or ethyl. Preferable examples of aryl include phenyl, and preferable examples of the substituents thereof include the above-mentioned halogen. $R_1$ and $R_2$ are preferably the same or different, and each represents hydrogen, halogen, or aryl substituted with one or two substituents; and more preferably, either of them (e.g., $R_2$) is hydrogen, and the other (e.g., $R_1$) is halogen, unsubstituted phenyl, or phenyl having one halogen as a substituent. More preferably, $R_2$ located at the meta position is hydrogen, and $R_1$ located at the meta position is halogen, particularly chlorine.

$R_3$ is as defined above, and is preferably hydrogen or $C_{1-6}$ alkyl. $R_3$ is more preferably hydrogen.

U and t are as defined above. When t is 1, U is preferably $C_1$ alkylene (methylene). Preferably, t is 0.

$R_{14}$ and $R_{15}$ are as defined above, and are preferably the same or different, and each represents hydrogen, $C_{1-6}$ alkyl, or halogen. $R_{14}$ and $R_{15}$ may be located at any of the ortho, meta, and para positions of the benzene ring. It is preferable, but not required, that $R_{15}$ be located at the ortho position, and $R_{14}$ at the para position, within the above benzene ring. More preferably, when either $R_{14}$ or $R_{15}$ is $C_{1-6}$ alkyl or halogen, the other one is hydrogen. Particularly preferably, $R_{14}$ and $R_{15}$ are both hydrogen.

V and q are as defined above, and when q is 1, V is preferably $C_1$ alkylene (methylene), oxyalkylene (oxymethylene), or oxygen. Preferably, q is 0.

Ar is as defined above, and is preferably 5- to 6-membered ring heteroaryl having one or two substituents; aryl having one or two substituents; or benzo-fused heteroaryl having one or two substituents or unsubstituted benzo-fused heteroaryl. The aryl is preferably phenyl.

Specific examples of heteroaryl groups include furyl (e.g., furan-3-yl, furan-2-yl), pyridyl (e.g., pyridin-4-yl, pyridin-3-yl, pyridin-2-yl), pyrrolyl (e.g., pyrrol-1-yl), thienyl (e.g., thiophen-3-yl, thiophen-2-yl), pyrazolyl (e.g., pyrazol-4-yl), isoxazolyl (e.g., isoxazol-3-yl, isoxazol-4-yl, isoxazol-5-yl), and oxazolyl (e.g., oxazol-5-yl). Preferred is furyl (e.g., furan-3-yl, furan-2-yl).

Specific examples of benzo-fused heteroaryl include quinolyl (e.g., quinolin-8-yl), which is a fused group of a 6-membered ring heteroaryl having nitrogen and a benzene ring; and benzofuranyl, which is a fused group of a 5-membered ring heteroaryl (e.g., benzofuran-2-yl) having oxygen and a benzene ring.

The substituents of the aryl, heteroaryl and benzo-fused heteroaryl are also as defined above, and are preferably $C_{1-4}$ alkyl, $C_{1-4}$ alkoxy, halogen, acetylamino, or phosphonooxymethyl. When Ar is phenyl, the substituent thereof may form a ring with some carbon atoms of the phenyl, and may form a benzo-fused heterocyclic ring with Ar. Examples of such benzo-fused heterocyclic rings include 1,3-benzodioxolyl (1,3-benzodioxol-5-yl), which is a fused product in which a 5-membered ring cycloalkyl having two oxygens is fused with a benzene ring.

Ar may be located at any of the ortho, meta, and para positions of the benzene ring. Preferred is the meta position.

p is as defined above, and is an integer of 0 or 1.

L is as defined above, and when p is 1, L is preferably alkyleneoxyalkylene, alkylene, alkylenethioalkylene, alkylene-SO-alkylene, or alkylene-$SO_2$-alkylene. Preferable examples of the alkylene as used herein include $C_{1-3}$ alkylene (methylene, ethylene or trimethylene). Preferable examples of the alkylene in "alkyleneoxyalkylene," "alkylenethioalkylene," "alkylene-SO-alkylene," and "alkylene-$SO_2$-alkylene" include methylene. Preferred is alkyleneoxyalkylene, and more preferred is methyleneoxymethylene.

Examples of the benzene carboxylic acids (compounds wherein B is carboxyl) of the present invention represented by Formula (III-1-3) above, or bioisosteres of the benzene carboxylic acids (compounds wherein B is a group that is biologically equivalent to a carboxyl group) preferably include compounds wherein $R_1$ is halogen, all of $R_2$, $R_3$, $R_{14}$, and $R_{15}$ are hydrogen, t and q are both 0, and Ar is heteroaryl, aryl, or benzo-fused heteroaryl, which optionally have a substituent. Preferable are compounds wherein Ar is heteroaryl optionally having a substituent. The compounds include compounds wherein p is 0, and compounds wherein p is 1, and L is alkyleneoxyalkylene, preferably methyleneoxymethylene. The compounds wherein Ar is heteroaryl optionally having a substituent, and p is 0 include compounds represented by Example 45 (Table 4-4) among the compounds listed below. The compounds wherein Ar is heteroaryl optionally having a substituent, p is 1, and L is alkyleneoxyalkylene include compounds represented by Example 61 (Table 4-6) among the compounds listed below.

Specific examples of the benzene carboxylic acids of the present invention represented by Formula (II-1-3) above, or bioisosteres of the benzene carboxylic acids include the following compounds (see Table 4).

Compounds of Formula (III-1-3), Wherein Ar is Aryl Having a Substituent 5-chloro-2-[({2-[(4'-fluorobiphenyl-2-yl)amino]-2-oxoethoxy}acetyl)amino]benzoic acid (Example 3)

5-chloro-2-[({2-[(4'-fluoro-4-methylbiphenyl-3-yl)amino]-2-oxoethoxy}acetyl)amino]benzoic acid (Example 5)

5-chloro-2-[({2-oxo-2-[(3',4,5'-trimethylbiphenyl-3-yl)amino]ethoxy}acetyl)amino]benzoic acid (Example 6)

5-chloro-2-[({2-[(4'-fluorobiphenyl-4-yl)amino]-2-oxoethoxy}acetyl)amino]benzoic acid (desalted product of Example 7)

5-chloro-2-[({2-[(4'-fluorobiphenyl-3-yl)amino]-2-oxoethoxy}acetyl)amino]benzoic acid (desalted product of Example 8)

5-chloro-2-{[({2-[(4'-fluorobiphenyl-3-yl)amino]-2-oxoethyl}sulfanyl)acetyl]amino}benzoic acid (desalted product of Example 12)

5-chloro-2-{[({2-[(4'-fluorobiphenyl-3-yl)amino]-2-oxoethyl}sulfinyl)acetyl]amino}benzoic acid (Example 13)

5-chloro-2-{[({2-[(4'-fluorobiphenyl-3-yl)amino]-2-oxoethyl}sulfonyl)acetyl]amino}benzoic acid (Example 14)

5-chloro-2-({[(4'-fluoro-4-methylbiphenyl-3-yl)amino](oxo)acetyl}amino)benzoic acid (desalted product of Example 20)

5-chloro-2-[({2-[(4'-fluoro-4-methylbiphenyl-3-yl)(2-methylpropyl)amino]-2-oxoethoxy}acetyl)amino]benzoic acid (desalted product of Example 22)

4'-fluoro-4-[({2-[(4'-fluoro-4-methylbiphenyl-3-yl)amino]-2-oxoethoxy}acetyl)amino]biphenyl-3-carboxylic acid (desalted product of Example 23)

5-chloro-2-{[({2-oxo-2-[(3',4,5'-trimethylbiphenyl-3-yl)amino]ethyl}sulfanyl)acetyl]amino}benzoic acid (Example 24)

5-chloro-2-[({2-[ethyl(4'-fluoro-4-methylbiphenyl-3-yl)amino]-2-oxoethoxy}acetyl)amino]benzoic acid (Example 29)

5-chloro-2-{[({2-[ethyl(4'-fluoro-4-methylbiphenyl-3-yl)amino]-2-oxoethyl}sulfanyl)acetyl]amino}benzoic acid (Example 30)

5-chloro-2-({5-[ethyl(4'-fluoro-4-methylbiphenyl-3-yl)amino]-5-oxopentanoyl}amino)benzoic acid (Example 31)

5-chloro-2-[({2-[(2'-methoxy-4-methylbiphenyl-3-yl)amino]-2-oxoethoxy}acetyl)amino]benzoic acid (Example 38)

5-chloro-2-[({2-[(3'-methoxy-4-methylbiphenyl-3-yl)amino]-2-oxoethoxy}acetyl)amino]benzoic acid (Example 39)

5-chloro-2-[({2-[(4'-methoxy-4-methylbiphenyl-3-yl)amino]-2-oxoethoxy}acetyl)amino]benzoic acid (Example 40)

2-{[(2-{[5-(1,3-benzodioxol-5-yl)-2-methylphenyl]amino}-2-oxoethoxy)acetyl]amino}-5-chlorobenzoic acid (Example 41)

2-{[(2-{[3'-(acetylamino)-4-methylbiphenyl-3-yl]amino}-2-oxoethoxy)acetyl]amino}-5-chlorobenzoic acid (Example 43)

2-{[(2-{[4'-(acetylamino)-4-methylbiphenyl-3-yl]amino}-2-oxoethoxy)acetyl]amino}-5-chlorobenzoic acid (Example 44)

5-chloro-2-[({2-oxo-2-[(2-phenoxyphenyl)amino]ethoxy}acetyl)amino]benzoic acid (Example 56)

5-chloro-2-{[({2-oxo-2-[(2-phenoxyphenyl)amino]ethyl}sulfanyl)acetyl]amino}benzoic acid (Example 57).

Compounds of Formula (III-1-3), Wherein Ar is Heteroaryl Optionally Having a Substituent 5-chloro-2-{[{[3-(furan-3-yl)phenyl]amino}(oxo)acetyl]amino}benzoic acid (Example 45)

5-chloro-2-{[(2-{[3-(furan-2-yl)phenyl]amino}-2-oxoethoxy)acetyl]amino}benzoic acid (Example 61)

5-chloro-2-{[(2-oxo-2-{[4-(pyridin-4-yl)phenyl]amino}ethoxy)acetyl]amino}benzoic acid (Example 1)

5-chloro-2-{[(2-oxo-2-{[3-(pyridin-4-yl)phenyl]amino}ethoxy)acetyl]amino}benzoic acid (Example 2)

5-chloro-2-{[(2-oxo-2-{[2-(pyridin-4-yl)phenyl]amino}ethoxy)acetyl]amino}benzoic acid (desalted product of Example 4)

5-chloro-2-{[(2-oxo-2-{[3-(pyridin-4-yl)phenyl]amino}ethoxy)acetyl]amino}benzoic acid [(2,2-dimethylpropanoyl)oxy]methyl ester (Example 16)

5-chloro-2-{[(2-oxo-2-{[3-(pyridin-4-yl)phenyl]amino}ethoxy)acetyl]amino}benzoic acid 1-{[(cyclohexyloxy)carbonyl]oxy}ethyl ester (Example 17)

5-chloro-2-{[(2-oxo-2-{[3-(pyridin-4-yl)phenyl]amino}ethoxy)acetyl]amino}benzoic acid (5-methyl-2-oxo-1,3-dioxol-4-yl)methyl ester (Example 18)

5-chloro-2-{[(2-oxo-2-{[3-(pyridin-3-yl)phenyl]amino}ethoxy)acetyl]amino}benzoic acid (desalted product of Example 19)

5-chloro-2-{[(2-oxo-2-{[3-(pyridin-2-yl)phenyl]amino}ethoxy)acetyl]amino}benzoic acid (desalted product of Example 21)

5-chloro-2-({[(2-oxo-2-{[3-(pyridin-4-yl)phenyl]amino}ethyl)sulfanyl]acetyl}amino)benzoic acid (Example 25)

5-chloro-2-{[(2-{[5-(furan-3-yl)-2-methylphenyl]amino}-2-oxoethoxy)acetyl]amino}benzoic acid (Example 32)

5-chloro-2-({[(2-{[5-(furan-3-yl)-2-methylphenyl]amino}-2-oxoethyl)sulfanyl]acetyl}amino)benzoic acid (Example 33)

5-chloro-2-[(5-{[5-(furan-3-yl)-2-methylphenyl]amino}-5-oxopentanoyl)amino]benzoic acid (Example 34)

5-chloro-2-{[(2-{ethyl[5-(furan-3-yl)-2-methylphenyl]amino}-2-oxoethoxy)acetyl]amino}benzoic acid (Example 35)

5-chloro-2-({[(2-{ethyl[5-(furan-3-yl)-2-methylphenyl]amino}-2-oxoethyl)sulfanyl]acetyl}amino)benzoic acid (Example 36)

5-chloro-2-[(5-{ethyl[5-(furan-3-yl)-2-methylphenyl]amino}-5-oxopentanoyl)amino]benzoic acid (Example 37)

5-chloro-2-({[(2-{[3-(furan-3-yl)phenyl]amino}-2-oxoethyl)sulfanyl]acetyl}amino)benzoic acid (Example 46)

5-chloro-2-{[(2-{[3-(2,6-dimethoxypyridin-3-yl)phenyl]amino}-2-oxoethoxy)acetyl]amino}benzoic acid (Example 47)

5-chloro-2-{[(2-oxo-2-{[3-(1H-pyrrol-1-yl)phenyl]amino}ethoxy)acetyl]amino}benzoic acid (desalted product of Example 48)

5-chloro-2-{[(2-{[2-fluoro-5-(furan-3-yl)phenyl]amino}-2-oxoethoxy)acetyl]amino}benzoic acid (Example 49)

5-chloro-2-{[(2-{[4-fluoro-3-(furan-3-yl)phenyl]amino}-2-oxoethoxy)acetyl]amino}benzoic acid (Example 50)

5-chloro-2-[(3-{[3-(furan-3-yl)phenyl]amino}-3-oxopropanoyl)amino]benzoic acid (Example 52)

5-chloro-2-{[{[3-(furan-3-yl)benzyl]amino}(oxo)acetyl]amino}benzoic acid (Example 53)

5-chloro-2-{[(2-{[3-(furan-2-ylmethyl)phenyl]amino}-2-oxoethoxy)acetyl]amino}benzoic acid (Example 54)

5-chloro-2-{[(2-{[3-(furan-3-ylmethyl)phenyl]amino}-2-oxoethoxy)acetyl]amino}benzoic acid (Example 55)

5-chloro-2-{[(2-{[3-(furan-3-yl)phenyl]amino}-2-oxoethoxy)acetyl]amino}benzoic acid (Example 58)

5-chloro-2-{[(2-oxo-2-{[3-(thiophen-3-yl)phenyl]amino}ethoxy)acetyl]amino}benzoic acid (Example 59)

5-chloro-2-{[(2-{[3-(1-methyl-1H-pyrazol-4-yl)phenyl]amino}-2-oxoethoxy)acetyl]amino}benzoic acid (Example 60)

5-chloro-2-{[(2-{[3-(3,5-dimethylisoxazol-4-yl)phenyl]amino}-2-oxoethoxy)acetyl]amino}benzoic acid (desalted product of Example 62)

5-chloro-2-{[(2-oxo-2-{[3-(thiophen-2-yl)phenyl]amino}ethoxy)acetyl]amino}benzoic acid (Example 63)

5-chloro-2-{[(2-{[4-(furan-3-yl)phenyl]amino}-2-oxoethoxy)acetyl]amino}benzoic acid (Example 64)

5-chloro-2-{[(2-{[3-(furan-2-ylmethoxy)phenyl]amino}-2-oxoethoxy)acetyl]amino}benzoic acid (Example 65)

5-chloro-2-{[(2-{[3-(furan-3-yl)benzyl]amino}-2-oxoethoxy)acetyl]amino}benzoic acid (Example 66)

5-chloro-2-{[(2-{[3-(furan-2-yl)benzyl]amino}-2-oxoethoxy)acetyl]amino}benzoic acid (Example 67)

5-chloro-2-{[(2-oxo-2-{[3-(1H-pyrazol-4-yl)phenyl]amino}ethoxy)acetyl]amino}benzoic acid (Example 68)

5-chloro-2-[({2-oxo-2-[(3-{1-[(phosphonateoxy)methyl]-1H-pyrazol-4-yl}phenyl)amino]ethoxy}acetyl)amino]benzoic acid (desalted product of Example 69)

5-chloro-2-{[(2-{[3-(1,3-oxazol-5-yl)phenyl]amino}-2-oxoethoxy)acetyl]amino}benzoic acid (Example 70)

5-chloro-2-{[(2-{[3-(isoxazol-5-yl)phenyl]amino}-2-oxoethoxy)acetyl]amino}benzoic acid (Example 71)

5-chloro-2-{[(2-oxo-2-{[3-(thiophen-3-yl)benzyl]amino}ethoxy)acetyl]amino}benzoic acid (Example 72)

5-chloro-2-{[(2-oxo-2-{[3-(thiophen-2-yl)benzyl]amino}ethoxy)acetyl]amino}benzoic acid (Example 73)

5-chloro-2-{[{[3-(furan-2-yl)benzyl]amino}(oxo)acetyl]amino}benzoic acid (Example 74)

5-chloro-2-{[(2-{[3-(5-chlorothiophen-2-yl)benzyl]amino}-2-oxoethoxy)acetyl]amino}benzoic acid (Example 75)

5-chloro-2-{[(2-{[3-(5-methylthiophen-2-yl)benzyl]amino}-2-oxoethoxy)acetyl]amino}benzoic acid (Example 76)

5-chloro-2-{[(2-{[3-(furan-3-yl)phenyl]amino}-2-oxoethoxy)acetyl]amino}benzoic acid (desalted product of Example 77)

5-chloro-2-{[(2-{[3-(furan-3-yl)phenyl]amino}-2-oxoethoxy)acetyl]amino}benzoic acid (desalted product of Example 78)

5-chloro-2-{[(2-{[3-(isoxazol-3-yl)phenyl]amino}-2-oxoethoxy)acetyl]amino}benzoic acid (Example 79)

5-chloro-2-{[(2-{[3-(5-methylfuran-3-yl)phenyl]amino}-2-oxoethoxy)acetyl]amino}benzoic acid (Example 80)

Compounds of Formula (III-1-3), Wherein Ar is Benzo-Fused Heteroaryl Optionally Having a Substituent 5-chloro-2-{[(2-{[2-methyl-5-(quinolin-8-yl)phenyl]amino}-2-oxoethoxy)acetyl]amino}benzoic acid (desalted product of Example 42)

2-{[(2-{[3-(1-benzofuran-2-yl)phenyl]amino}-2-oxoethoxy)acetyl]amino}-5-chlorobenzoic acid (Example 51).

The compounds of Examples 16 to 18 mentioned above are all converted in vivo to the compound of Example 2, and the compound of Example 69 is converted in vivo to the compound of Example 68. Specifically, these compounds show PAI-1 activity as the compound of Example 2 or 68 when metabolized in vivo, and are thus so-called prodrugs of the compounds of Example 2 or 68.

TABLE 4

| Example of Cpd. 3 | Chemical name | Formula M.W. | PAI-1 activity % 50 μM | 20 μM |
|---|---|---|---|---|
| 1 | 5-Chloro-2-([(2-oxo-2-([4-(pyridin-4-yl)phenyl]amino)ethoxy)acetyl]amino)benzoic acid | C22H18ClN3O5 439.85 | 0.6 | 28.7 |
| 2 | 5-Chloro-2-([(2-oxo-2-([3-pyridin-4-yl)pheny]amino)ethoxy)acetyl]amino)benzoic acid | C22H18ClN3O5 439.85 | 12.8 | 14.6 |
| 3 | 5-Chloro-2-[((2-[4'-fluorobiphenyl-2-yl)amino)-2-oxoethoxy)acetyl)amino]benzoic acid | C23H18ClFN2O5 456.85 | 39.6 | 82.4 |
| 4 | 5-Chloro-2-([(2-oxo-2-((pyridin-4-yl)phenyl]amino)ethoxy)acetyl]amino)benzoic acid hydrochloride | C22H19Cl2N3O5 476.31 | 24.3 | 65.1 |
| 5 | 5-Chloro-2-[(2-[(4'-fluoro-4-methylbiphenyl-3-yl)amino)-2-oxoethoxy)acetyl)amino]benzoic acid | C24H20ClFN2O5 470.88 | 8.1 | 48.5 |
| 6 | 5-Chloro-2-[((2-oxo-2-[3',4',5'-trimethylbiphenyl-3-yl)amino]ethoxy]acetyl)amino]benzoic acid | C26H25ClN2O5 480.94 | 13.6 | 96.6 |
| 7 | 5-Chloro-[((2-[(4'-fluorobiphenyl-4-yl)amino]-2-oxoethoxy)acetyl)amino]benzoic acid sodium salt | C23H17ClFN2NaO5 478.83 | 15.6 | 92.2 |
| 8 | 5-Chloro-2-[((2-[4'-fluorobiphenyl-3-yl)amino]-2-oxoethoxy)acetyl)amino]benzoic acid sodium salt | C23H17ClF2NaO5 478.83 | 12.4 | 95.6 |
| 9 | 5-Chloro-2-(([2-(dicyclohexylamino)-2-oxoethoxy]acetyl)amino)benzoic acid sodium salt | C23H30ClN2NaO5 472.94 | 19.6 | 79.3 |
| 10 | 5-Chloro-2-[((2-[(4-cyclohexylphenyl)amino]-2-oxoethoxy)acetyl)amino]benzoic acid | C23H24ClN2NaO5 466.89 | 31.9 | 93.2 |
| 11 | 5-Chloro-2-(([2-(cyclodelamino)-2-oxoethoxy]acetyl)amino)benzoic acid | C23H33ClN2O5 452.97 | 11.5 | 64.7 |
| 12 | 5-Chloro-2-([((2-((4'-fluorobiphenyl-3-yl)amino]-2-oxoethyl)sulfanyl]acetyl)amino)benzoic acid sodium salt | C23H17ClFN2NaO4S 494.90 | 29.2 | 92.7 |

TABLE 4-continued

| Example of Cpd. 3 | Chemical name | Formula M.W. | PAI-1 activity % 50 μM | 20 μM |
|---|---|---|---|---|
| 13 | 5-Chloro-2-([((2-[(4'-fluorobiphenyl-3-yl)amino]-2-oxoethyl)sulfinyl)acetyl]amino)benzoic acid | C23H18ClFN2O5S 488.92 | 27.8 | 95.1 |
| 14 | 5-Chloro-2-([((2-[4'-fluorobiphenyl-3-yl-amino]-2-oxoethyl)sulfinyl]amino)benzoic acid | C23H18ClFN2O6S 504.92 | 30.9 | 99.7 |
| 15 | 5-Chloro-2-[((2-[cyclohexyl(phenyl)amino]-2-oxoethoxy)acetyl]amino]benzoic acid sodium salt | C23H24ClN2NaO5 466.89 | 16.8 | 55.9 |
| 16 | 5-Chloro-2-([(2-oxo-2-([3-(pyridin-4-yl)phenyl]amino)ethoxy)acetyl]amino)benzoic acid [(2,2-dimethylpropanyl)oxy]methyl ester | C28H28ClN3O7 553.99 | 99.1 | 99.2 |
| 17 | 5-Chloro-2-([(2-oxo-2-([3-pyridin-4-yl)phenyl]amino)ethoxy)acetyl]amino)benzoic acid 1-([cyclohexy]carbonyl)oxy)ethylester | C31H32ClN3O8 610.05 | 99.3 | 99.8 |
| 18 | 5-Chloro-2-([(2-oxo-2-([3-pyridin-4-yl)phenyl]amino)ethoxy)acetyl]amino benzoic acid (5-methyl-2-oxo-1,3 dioxol-4-yl)methyl ester | C27H22ClN3O8 551.93 | 94.0 | 97.7 |
| 19 | 5-Chloro-2-([(2-oxo-2-([3-pyridin-3-yl)phenyl]amino)ethoxy)acetyl]amino benzoic acid sodium salt | C22H27ClN3NaO5 461.83 | 22.0 | 74.2 |
| 20 | 5-Chloro-2-(([(4'-fluoro-4-methylbiphenyl-3-yl)amino](oxo)acetyl)amino)benzoic acid sodium salt | C22H15ClFN2NaO4 448.81 | 27.2 | 31.1 |
| 21 | 5-Chloro-2-(((2-oxo-2-((3-pyridin-2-yl)phenyl)amino)ethoxy)acetyl)amino)benzoic acid sodium salt | C22H17ClN3NaO5 461.83 | 41.3 | 76.7 |
| 22 | 5-Chloro-2-[((2-[(4'-fluoro-4-methylbiphenyl-3-yl) (2-methylpropyl)amino]-2-exoethoxy)acetyl)amino] benzoic acid | C28H28ClFN2O5 526.98 | 6.7 | 42.6 |
| 23 | 4'-Fluoro-4-[((2-[(4'-fluoro-4-methylbiphenyl-3-yl)amino]-2-oxoethoxy)acetyl]amino]biphenyl-3-carboxylic acid sodium salt | C30H23F2N2NaO5 552.50 | 7.6 | 96.8 |
| 24 | 5-Chloro-2-([(2-oxo-2-[(3',4',5'-trimethylbiphenyl-3-yl)amino]ethyl)sulfanyl]acetyl]amino)benzoic acid | C26H25ClN2O4S 497.01 | 17.0 | 66.0 |
| 25 | 5-Chloro-2-((([(2-oxo-2-([3-(pyridin-4-yl)phenyl]amino)ethyl]sulfanyl]acetyl]amino)benzoic acid | C23H18ClN3O4S 455.91 | 18.4 | 16.4 |
| 26 | 5-Chloro-2-[((2-[(3-cyclohexylphenyl)amino]-2-oxoethoxy)acetyl]amino]benzoic acid | C23H25ClN2O5 444.91 | 6.4 | 34.9 |
| 27 | 5-Chloro-2-([((2-[(4-cyclohexylphenyl)amino]-2-oxoethyl)sulfanyl)acetyl]benzoic acid | C23H25ClN2O4S 460.97 | 24.5 | 72.5 |
| 28 | 5-Chloro-2-[(((2-(cyclododecylamino-2-oxoethyl]sulfanyl)acetyl]amino)benzoic acid | C23H33ClN2O4S 469.04 | 10.3 | 51.6 |
| 29 | 5-Chloro-2-[((2-[ethyl(4'-fluoro-4-methylbiphenyl-3-yl)amino]-2-oxoethoxy)acetyl]amino)benzoic acid | C26H24ClFN2O5 498.93 | 8.0 | 58.5 |
| 30 | 5-Chloro-2-([((2-[ethyl(4'-fluoro-4-methylbiphenyl-3-yl)amino]-2-oxoethyl)sulfanyl]acetyl]amino)benzoic acid | C26H24ClFN2O4S 515.00 | 13.2 | 55.0 |
| 31 | 5-Chloro-2-((5-[ethyl(4'-fluoro-4-methylbiphenyl-3-yl)amino]-5-oxopentanoyl)amino)benzoic acid | C27H26ClFN2O4 496.96 | 12.5 | 75.4 |
| 32 | 5-Chloro-2-([(2-((5-(furan-3-yl)-2-methylphenyl]amino)-2-oxoethoxy)acetyl]amino)benzoic acid | C22H19ClN2O6 442.85 | 17.2 | 63.6 |
| 33 | 5-Chloro-2-(((2-([5-(furan-3-yl)-2-methylphenyl]amino)-2-oxoethyl]sulfanyl]acetyl)amino)benzoic acid | C22H19ClN2O5S 458.91 | 13.5 | 43.8 |
| 34 | 5-Chloro-2-[(5-([5-(furan-3-yl)-2-methylphenyl]amino)-5-oxopentanoyl]amino]benzoic acid | C23H21ClN2O5 440.88 | 23.6 | 74.0 |
| 35 | 5-Chloro-2-([(2-(ethyl[5-(furan-3-yl)-2-methylphenyl]amino)-2-oxoethyl)acetyl]amino)benzoic acid | C24H23ClN2NaO6 470.90 | 30.5 | 72.2 |
| 36 | 5-Chloro-2-(((2-(ethyl[5-(furan-3-yl)-2-methylphenyl]amino-2-oxoethyl]sulfanyl)acetyl)amino}benzoic acid | C24H23ClN2O5S 486.97 | 37.3 | 78.2 |
| 37 | 5-Chloro-2-[(5-(ethyl[5-(furan-3-yl)-2-methylphenyl]amino-5-oxopentanoyl)amino]benzoic acid | C25H25ClN2O5 468.93 | 37.7 | 78.9 |
| 38 | 5-Chloro-2-(((2-[2'-methoxy-4-methylphenyl-3-yl]amino-2-oxoethoxy)acetyl)amino)benzoic acid | C25H23ClN2NaO6 482.91 | 11.3 | 73.7 |
| 39 | 5-Chloro-2-((([(2-[3'-methoxy-4-methylphenyl-3-yl]amino-2-oxoethoxy)acetyl]amino)benzoic acid | C25H23ClN2O6 482.91 | 6.9 | 64.3 |
| 40 | 5-Chloro-2-((([(2-[4'-methoxy-4-methylphenyl-3-yl]amino-2-oxoethoxy)acetyl]amino)benzoic acid | C25H23ClN2O6 482.91 | 11.2 | 61.5 |
| 41 | 2-([[(2-([5-(1,3-Benzodioxol-5-yl)-2-methylphenyl]amino)-2-oxoethoxy)acetyl)amino)-5-chlorobenzoic acid | C25H21ClN2O7 496.90 | 9.5 | 87.5 |
| 42 | 5-Chloro-2-([(2-([2-methyl-5-(quinolin-8-yl)phenyl]amino)-2-oxoethoxy)acetyl]amino)benzoic acid hydrochloride | C27H23Cl2N3O5 540.39 | 7.2 | 54.2 |
| 43 | 2-([[(2-([3'-(Acetylamino)-4-methylbiphenyl-3-yl]amino)-2-oxoethoxy)acetyl]amino)-5-chlorobenzoic acid | C26H24ClN3O6 509.94 | 31.6 | 88.9 |
| 44 | 2-([[(2-([4'-(Acetylamino)-4-methylbiphenyl-3-yl]amino)-2-oxoethoxy)acetyl]amino)-5-chlorobenzoic acid | C26H24ClN3O6 509.94 | 6.7 | 41.4 |
| 45 | 5-Chloro-2-([([3-(furan-3-yl)phenyl]amino)(oxo)acetyl]amino)benzoic acid | C19H13ClN2O5 384.77 | 8.4 | 47.8 |
| 46 | 5-Chloro-2-(((2-[3-(furan-3-yl)phenyl)amino)-2-oxoethyl)sulfanyl]acetyl]amino)benzoic acid | C21H17ClNO5S 444.89 | 47.3 | 83.9 |
| 47 | 5-Chloro-2-([(2-([3-(2,6-dimethoxypyridin-3-yl)phenyl]amino)-2-oxoethoxy)acetyl]amino)benzoic acid | C24H22ClN3O7 449.90 | 11.0 | 76.5 |
| 48 | 5-Chloro-2-([(2-oxo-2-([3-(1H-pyrrol-1-yl)phenyl]amino)ethoxy)acetyl]amino)benzoic acid sodium salt | C21H17ClN3NaO5 499.82 | 14.5 | 64.0 |

TABLE 4-continued

| Example of Cpd. 3 | Chemical name | Formula M.W. | PAI-1 activity % 50 μM | 20 μM |
|---|---|---|---|---|
| 49 | 5-Chloro-2-([(2-([2-(fluoro-5-(furan-3-yl)phenyl]amino)-2-oxoethoxy)acetyl]amino)benzoic acid | C21H16ClFN2O6 446.81 | 15.9 | 61.7 |
| 50 | 5-Chloro-2-([(2-([4-fluoro-3-(furan-3-yl)phenyl]amino)-2-oxoethoxy)acetyl]amino)benzoic acid | C21H16ClFN2O6 446.81 | 9.4 | 60.8 |
| 51 | 2-([(2-([3-(1-Benzofuran-2-yl)phenyl]amino)-2-oxoethoxy)acetyl]amino)-5-chlorobenzoic acid | C25H19ClN2O6 478.88 | 5.7 | 44.9 |
| 52 | 5-Chloro-2-[(3-([13-(furan-3-yl)phenyl]amino)-3-oxopropanoyl)amino]benzoic acid | C20H15ClN2O5 398.80 | 25.4 | 72.3 |
| 53 | 5-Chloro-2-([([3-(furan-3-yl)benzyl]amino)(oxo)acetyl]amino)benzoic acid | C20H15ClN2O5 398.80 | 8.6 | 46.9 |
| 54 | 5-Chloro-2-([{2-([3-(furan-2-ylmethyl)phenyl]amino)-2-oxoethoxy)acetyl]amino)benzoic acid | C22H19ClN2O6 442.85 | 21.4 | 72.0 |
| 55 | 5-Chloro-2-([(2-([3-(furan-3-ylmethyl)phenyl]amino)-2-oxoehtoxy)acetyl]amino)benzoic acid | C22H19ClN2O6 442.85 | 13.6 | 60.2 |
| 56 | 5-Chloro-2-[((2-oxo-2-[(2-phenoxyphenyl)amino]ethoxy)acetyl)amino]benzoic acid | C23H19ClN2O6 454.86 | 31.5 | 74.7 |
| 57 | 5-Chloro-2-([(((2-oxo-2-[(2-phenoxyphenyl)amino]ethyl]sulfanyl)acetyl]amino)benzoic acid | C23H19ClN2O5S 470.93 | 26.9 | 64.6 |
| 58 | 5-Chloro-2-([(2-([3-(furan-3-yl)phenyl]amino)-2-oxoehtoxy)acetyl]amino)benzoic acid | C21H17ClN2O6 428.82 | 6.4 | 16.2 |
| 59 | 5-Chloro-2-([(2-oxo-2-([3-(thiophene-3-yl)phenyl]amino)ethoxy)acetyl]amino)benzoic acid | C21H17ClN2O5S 444.89 | 10.2 | 63.8 |
| 60 | 5-Chloro-2-([(2-([3-(1-methyl-1H-pyrazol-4-yl)phenyl]amino)-2-oxoethoxy)acetyl]amino)benzoic acid | C21H19ClN4O5 442.85 | 19.6 | 96.1 |
| 61 | 5-Chloro-2-([(2-([3-(furan-2-yl)phenyl]amino)-2-oxoethoxy)acetyl]amino)benzoic acid | C21H17ClN2O6 428.82 | 13.7 | 69.9 |
| 62 | 5-Chloro-2-([(2-([3-(3,5-dimethylisoxazol-4-yl)phenyl]amino)-2-oxoethoxy)acetyl]amino)benzoic acid sodium salt | C22H19ClN3NaO6 479.85 | 35.8 | 75.8 |
| 63 | 5-Chloro-2-([{(2-oxo-2-([3-(thiophen-2-yl)pheny]amino)ethoxy)acetyl]amino)benzoic acid | C21H17ClNO5S 444.89 | 10.6 | 64.3 |
| 64 | 5-Chloro-2-{[(2-([4-(furan-3-yl)phenyl]amino)-2-oxoethoxy)acetyl]amino)benzoic acid | C21H17ClN2O6 428.82 | 19.2 | 71.6 |
| 65 | 5-Chloro-2-([(2-([3-[furan-2-ylmethoxy)phenyl]amino)-2-oxoethoxy)acetyl]amino)benzoic acid | C22H19ClN2O7 458.85 | 25.4 | 86.0 |
| 66 | 5-Chloro-2-([(2-([3-[furan-3-yl)benzyl]amino)-2-oxoethoxy)acetyl]amino)benzoic acid | C22H19ClN2O6 442.85 | 17.7 | 59.2 |
| 67 | 5-Chloro-2-([(2-([3-(furan-2-yl)benzyl]amino)-2-oxoethoxy)acetyl]amino)benzoic acid | C22H19ClN2O6 442.85 | 8.1 | 57.6 |
| 68 | 5-Chloro-2-([(2-oxo-2-[3-(1H-pyrazol-4-yl)phenyl]amino)othoxy)acetyl]amino)benzoic acid | C20H17ClN4O5 428.83 | 9.4 | 20.7 |
| 69 | 5-Chloro-2-[((2-oxo-2-[3-(1-[phosphonatoxy)methyl]1H-pyrazol-4-yl)phenyl)amino]ethoxy)acetyl)amino)benzoic acid trisodium salt | C21H17ClN4Na3O9P 604.78 | 98.6 | 99.4 |
| 70 | 5-Chloro-2-([(2-([3-(1,3-oxazol-5-yl)phenyl]amino)-2-oxoethoxy)acetyl]amino)benzoic acid | C20H16ClN3O6 429.81 | 63.3 | 94.2 |
| 71 | 5-chloro-2-([(2-([3-(isoxazol-5-yl)phenyl]amino)-2-oxoethoxy)acetyl]amino)benzoic acid | C20H16ClN3O6 429.81 | 36.6 | 77.9 |
| 72 | 5-Chloro-2-([(-2-oxo-2-([3-(triophene-3-yl)benzyl]amino)ethoxy)acetyl]amino)benzoic acid | C22H19ClN2O5S 458.91 | 19.9 | 72.1 |
| 73 | 5-Chloro-2-([( 2-oxo-2-([3-(thiophen-2-yl)benzyl]amino)ethoxy)acetyl]amino)benzoic acid | C22H19ClN2O5S 458.91 | 18.5 | 67.6 |
| 74 | 5-Chloro-2-([([3-(furan-2-yl)benzyl]amino)(oxo)acetyl]amino)benzoic acid | C20H15ClN2O5 398.80 | 12.3 | 38.9 |
| 75 | 5-Chloro-2-([(2-([3-(5-chlorothiophen-2-yl)benzyl]amino-2-oxoethoxy)acetyl]amino)benzoic acid | C22H18Cl2N2O5S 493.36 | 7.4 | 46.1 |
| 76 | 5-Chloro-2-([(2-([3-(5-methyl thiophen-2-yl)benzyl]amino-2-oxoethoxy)acetyl]amino)benzoic acid | C23H21ClN2O5S 472.94 | 12.1 | 67.9 |
| 77 | 5-Chloro-2-([(2-([3-(furan-3-yl)phenyl]amino)-2-oxoethoxy)acethyl]amino)benzoic acid N-methyl-D-glucamine salt | C28H34ClN3O11 624.04 | 16.3 | 63.5 |

Each of the compound groups 1 to 4 targeted by the present invention may be in free, salt, or ester form.

Examples of salts as used herein typically include pharmaceutically acceptable salts, e.g., a salt formed with an inorganic base or organic base, a salt formed with a basic amino acid, and other salts. Examples of inorganic bases include alkali metals such as sodium, potassium, etc.; alkaline earth metals such as calcium, magnesium, etc.; and aluminium, ammonium, etc. Examples of organic bases include primary amines such as ethanolamine, tromethamine, ethylenediamine, etc.; secondary amines such as diethylamine, diethanolamine, meglumine, dicyclohexylamine, N,N'-dibenzylethylenediamine, etc.; and tertiary amines such as trimethylamine, triethylamine, pyridine, picoline, triethanolamine, etc. Examples of basic amino acids include arginine, lysine, ornithine, histidine, etc. Further, the compound of the present invention may form a salt with an inorganic acid or organic acid. Examples of inorganic acids include hydrochloric acid, hydrobromic acid, sulfuric acid, phosphoric acid, etc. Examples of organic acids include formic acid, acetic acid, trifluoroacetic acid, maleic acid, tartaric acid, fumaric acid, citric acid, lactic acid, methanesulfonic acid, benzenesulfonic acid, toluenesulfonic acid, etc.

Examples of esters as used herein typically include pharmaceutically acceptable esters, such as alkoxycarbonyl, aryloxycarbonyl, and aralkyloxycarbonyl, which can be converted to carboxyl when absorbed in vivo. In particular, specific examples of the "alkoxycarbonyl" represented by B in Formulae (1) to (3) include t-butoxycarbonyl, methoxycarbonyl, ethoxycarbonyl, propoxycarbonyl, isopropoxycarbonyl, butoxycarbonyl, etc.

Further, when the carboxylic acid represented by Formula (I), (II), (III), or (IV), a bioisostere of the carboxylic acid, or a salt or ester thereof forms a solvate (e.g., hydrate, alcohol), such a solvate is also encompassed in the present invention. Furthermore, the present invention encompasses all of the compounds (e.g., so-called prodrugs) that are converted, when metabolized in vivo, to a carboxylic acid represented by any of Formulae (I) to (IV), a bioisostere thereof, or a pharmaceutically acceptable salt or ester thereof.

The "agent for activating a stem cell," "agent for enhancing the antitumor effect of an antitumor agent," "tumor chemotherapy agent," and "hematopoietic disorder improving agent" described below all comprise the PAI-1 inhibitor mentioned herein as an active ingredient. Therefore, the description in section I is incorporated by reference in the following sections II, III, and IV.

II. Agent for Activating a Stem Cell and Agent for Controlling a Tumor Stem Cell The agent for activating a stem cell ("stem-cell activating agent") and the agent for controlling a tumor stem cell (tumor stem-cell controlling agent) according to the present invention comprise a compound having PAI-1 inhibitory activity as an active ingredient.

Compounds having PAI-1 inhibitory activity can activate stem cells of normal cells (normal stem cells) to thereby enhance differentiation capability of the normal stem cells, and to increase the self-renewal capacity for producing normal stem cells that have ability equivalent to their own ability. In this sense, when normal stem cells are targeted, the stem-cell activating agent of the present invention, which comprises a compound having PAI-1 inhibitory activity as an active ingredient can be used as an "agent for promoting the differentiation of stem cells" or/and an "agent for enhancing the self-renewal capacity of stem cells."

Since the stem-cell activating agent of the present invention particularly induces the differentiation of normal hematopoietic stem cells and promotes the amplification (growth) of the stem cells themselves, it can be effectively used to accelerate hematopoietic regeneration. In particular, the bone marrow environment after radiation is severe, and dead hematopoietic cells must be reproduced from one cell. This causes significant stress. In such an environment, even the stem cells have self-renewal capacity, the activity of self-renewaling is considered to be reduced. Compounds having PAI-1 inhibitory activity not only can promote the growth of stem cells and accelerate hematopoietic regeneration, as described above, but also induce the amplification of stem cells in such an environment and maintain the homeostasis of the hematopoietic system over a long period of time. In this sense, it can be said that the stem-cell activating agent of the present invention has the effect of protecting normal stem cells, particularly normal hematopoietic stem cells, from regeneration stress. Therefore, when normal stem cells, particularly hematopoietic stem cells, are targeted, the stem-cell activating agent of the present invention, which comprises a compound having PAI-1 inhibitory activity as an active ingredient, can be used as a stem-cell protecting drug or a hematopoietic disorder improving agent. This will be described in more detail in section V.

Moreover, compounds having PAI-1 inhibitory activity can activate (or control) stem cells of tumor cells (tumor stem cells) to thereby transit the stem cells in the resting phase (G0 phase in the cell cycle) in, for example, a microenvironment called a "niche," to the mitotic phase (from G1 phase to M phase in the cell cycle), and proliferate cells in the DNA replication phase (S phase). In this sense, when tumor stem cells are targeted, the stem-cell activating agent of the present invention, which comprises a compound having PAI-1 inhibitory activity as an active ingredient, can be used as a "tumor stem-cell controlling agent" to transit tumor stem cells in the resting phase to the mitotic phase.

Accordingly, when tumor stem cells (hematopoietic tumor, solid tumor) are targeted, the "tumor stem-cell controlling agent" of the present invention, which comprises a compound having PAI-1 inhibitory activity as an active ingredient, can be used as an "agent for enhancing the antitumor effect of an antitumor agent" that is used in combination with an antitumor agent, or as a "tumor chemotherapy agent" in combination with an antitumor agent. This will be described in more detail in sections III and IV.

The "stem cells" targeted by the present invention are cells having self-renewal capacity and multipotency, regardless of whether they are normal cells or cancer cells (tumor cells). Examples thereof include embryonic stem cells (ES cells), induced pluripotent stem cells (iPS cells), tissue stem cells such as hematopoietic stem cells, tumor stem cells such as leukemia stem cells and tumor stem cells, progenitor cells with proliferative capacity derived from these cells, and the like.

Multipotency is the ability to differentiate into one or more types of cells of the same cell lineage or different cell lineages.

Preferred examples of stem cells for both normal cells and tumor cells include hematopoietic stem cells.

In the case of mice, examples of hematopoietic stem cells include cells having $CD34^-$ or $CD34^+$ as a cell surface marker, and cells having $Lin^{neg/Low}$, $c\text{-}Kit^{high}$, Sca $1^+$ (hereinafter "LSK"), or the like, and cells having $Lin^{neg}$ and $CD150^+$, CD244, and CD48 (hereinafter "SLAM"). These cells can differentiate into any of lymphocytic cells, granulocytic cells, monocytic cells, erythrocytic cells, and megakaryocytic cells.

In the case of humans, examples of hematopoietic tumor stem cells include cells having $CD34^+$ or AC133 as a cell surface marker.

Examples of tumor stem cells include cells having CD44, CD90, AC133, EpCAMESA, ABCB5, or the like as a surface marker.

The stem-cell activating agent and tumor stem-cell controlling agent of the present invention can be used in a method for activating stem cells or a method for controlling tumor stem cells, the methods transiting stem cells or tumor stem cells in the resting phase to the mitotic phase.

The dosages of the stem-cell activating agent and tumor stem-cell controlling agent of the present invention can be determined according to the dosage of an agent for enhancing the antitumor effect of antitumor agents described below.

III. Agent for Enhancing the Antitumor Effect of Antitumor Agents

The agent for enhancing the antitumor effect of antitumor agents ("antitumor effect enhancing agent") according to the present invention comprises a compound having PAI-1 inhibitory activity, mentioned above, as an active ingredient.

As shown in Experiment Examples provided later, the compound having PAI-1 inhibitory activity acts on tumor stem cells and stimulates tumor stem cells in the G0 phase to thereby transit (control) the cells to the G1 phase. Accordingly, the compound having PAI-1 inhibitory activity can transit tumor stem cells in the resting phase, which generally react poorly to antitumor agents, to the mitotic phase, thereby increasing the sensitivity of the cells to antitumor agents. Therefore, the antitumor effect enhancing agent of the present invention is used in combination with an antitumor agent. When used in combination with an antitumor agent, the antitumor effect enhancing agent of the present invention characteristically exhibits the effect of enhancing the antitumor effect of the antitumor agent.

Examples of the "antitumor effect of antitumor agents" generally include tumor cell killing activity, tumor cell growth inhibitory activity, tumor cell infiltration or metastasis inhibitory activity, and tumor recurrence inhibitory activity.

When the antitumor effect enhancing agent of the present invention is used in combination with an antitumor agent, the effect (tumor stem-cell activation activity) of a compound having PAI-1 inhibitory activity, described later, makes it possible to enhance the tumor cell killing activity and/or tumor cell growth inhibitory activity of the antitumor agent, prevent the infiltration or metastasis of tumor cells, suppress tumor recurrence after treatment (including chemotherapy, ablative operation, and radiotherapy), and provide a good or improved prognosis, depending on the antitumor effect of the antitumor agent used in combination.

The tumors targeted by the present invention include both non-epithelial malignant tumors and epithelial malignant tumors. Specific examples thereof include respiratory malignant tumors generated in the trachea, bronchi, lung, or the like; gastrointestinal tract malignant tumors generated in the epipharynx, esophagus, stomach, duodenum, jejunum, ileum, cecum, appendix, ascending colon, transverse colon, sigmoid colon, rectum, anal area, or the like; liver cancer; pancreatic cancer; urinary malignant tumors generated in the bladder, ureter, or kidney; female genital malignant tumors generated in the ovary, oviduct, uterus, or the like; breast cancer; prostatic cancer; skin cancer; malignant tumors in the endocrine system, such as hypothalamus, pituitary gland, thyroid, parathyroid, or adrenal gland; central nervous system malignant tumors; malignant tumors generated in the bone-soft tissue; and like solid tumors; as well as hematopoietic system tumors, such as myelodysplastic syndrome, acute lymphocytic leukemia, acute myelogenous leukemia, chronic lymphocytic leukemia, chronic myelogenous leukemia, acute myelomonocytic leukemia, chronic myelomonocytic leukemia, acute monocytic leukemia, chronic monocytic leukemia, acute promyelocytic leukemia, acute megakaryocytic leukemia, erythroleukemia, eosinophilic leukemia, chronic eosinophilic leukemia, chronic neutrophilic leukemia, adult T-cell leukemia, hairy cell leukemia, plasma cell leukemia, multiple myeloma, and malignant lymphoma; lymph malignant tumors; and like hematopoietic organ tumors. Preferable examples are hematopoietic organ tumors, ovarian cancer, breast cancer, stomach cancer, large bowel cancer originating from the ascending colon, transverse colon, sigmoid colon, or rectum, etc. Most preferable examples of hematopoietic organ tumors include chronic myelogenous leukemia, chronic eosinophilic leukemia, and acute lymphocytic leukemia. Most preferable examples of solid tumors include ovarian cancer, breast cancer, and stomach cancer.

When the tumors targeted by the present invention are expressed in different classification, examples thereof include human epidermal growth factor receptor (EGFR)-expressed tumor, human epidermal growth factor receptor 2 (HER2)-overexpressed tumor, CD20-positive tumor, CD33-positive tumor, CD52-positive tumor, vascular endothelial growth factor (VEGF)-positive tumor, Philadelphia chromosome-positive tumor, CD117-positive tumor, etc. More preferable examples of non-epithelial malignant tumors include Philadelphia chromosome-positive tumor and CD117 (c-kit)-positive tumor, and more preferable examples of epithelial malignant tumors include EGFR-expressed tumor and HER2-overexpressed tumor. The most preferable example of non-epithelial malignant tumors is Philadelphia chromosome-positive tumor, and the most preferable example of epithelial malignant tumors is HER2-overexpressed tumor.

Further, other examples of tumors include tumors in which the PAI-1 expression level of tumor stem cells is equal to or higher than the PAI-1 expression level of chronic myelogenous leukemia (CML) tumor stem cells in Examples, described later. The phrase "equal to or higher than" refers to a state in which, for example, when the PAI-1 expression level of CML tumor stem cells is taken as 100%, 50 to 80% or higher, preferably 100 to 120% or higher, more preferably 150% or higher, and most preferably 200% or higher, of expression is observed.

Examples of the antitumor agent whose antitumor effect can be enhanced by the antitumor effect enhancing agent of the present invention include those generally used as anticancer agents. The antitumor agent can be suitably selected from alkylating agents, antimetabolites, antitumor antibiotics, microtubule inhibitors, hormones or hormone-like drugs, platinum-based drugs, topoisomerase inhibitors, cytokines, antibody drugs, radioimmunotherapy drugs, molecular targeted drugs, non-specific immunostimulants, and other antitumor agents, depending on the target tumor.

Although there is no limitation, examples of alkylating agents include cyclophosphamide, ifosfamide, busulfan, melphalan, bendamustine hydrochloride, nimustine hydrochloride, ranimustine, dacarbazine, procarbazine hydrochloride, temozolomide, etc.; examples of antimetabolites include methotrexate, pemetrexed sodium, fluorouracil, doxifluridine, capecitabine, tegafur, cytarabine, cytarabine ocfosfate hydrate, enocitabine, gemcitabine hydrochloride, mercaptopurine hydrate, fludarabine phosphate, nelarabine, pentostatin, cladribine, calcium levofolinate, calcium folinate, hydroxycarbamide, L-asparaginase, azacytidine, etc.; examples of antitumor antibiotics include doxorubicin hydrochloride, daunorubicin hydrochloride, pirarubicin, epirubicin hydrochloride, idarubicin hydrochloride, aclarubicin hydrochloride, amrubicin hydrochloride, mitoxantrone hydrochloride, mitomycin-C, actinomycin-D, bleomycin, peplomycin sulfate, zinostatin stimalamer, etc.; examples of microtubule inhibitors include vincristine sulfate, vinblastine sulfate, vindesine sulfate, vinorelbine tartrate, paclitaxel, docetaxel hydrate, eribulin mesilate, etc.; examples of hormones or hormone-like drugs (hormonal agents) include anastrozole, exemestane, letrozole, tamoxifen citrate, toremifene citrate, fulvestrant, flutamide, bicalutamide, methylhydroxyprogesterone acetate, estramustine phosphate sodium hydrate, goserelin acetate, leuprorelin acetate, etc.; examples of platinum-based drugs include cisplatin, miriplatin hydrate, carboplatin, nedaplatin, oxaliplatin, etc.; examples of topoisomerase inhibitors include topoisomerase I inhibitors such as irinotecan hydrochloride hydrate and nogitecan hydrochloride, and topoisomerase II inhibitors such as etoposide and sobuzoxane; examples of cytokines include interferon gamma-1a, teceleukin, celmoleukin, etc.; examples of antibody drugs include trastuzumab, rituximab, gemtuzumab ozogamicin, bevacizumab, cetuximab, panitumumab, alemtuzumab, etc.; examples of radioimmunotherapy drugs include ibritumomab, tiuxetan combination drugs, etc.; examples of molecular targeted drugs include gefitinib, imatinib mesilate, bortezomib, erlotinib hydrochloride, sorafenib tosilate, sunitinib malate, thalidomide, nilotinib hydrochloride hydrate, dasatinib hydrate, lapatinib tosilate hydrate, everolimus, lenalidomide hydrate, dexamethasone, temsirolimus, vorinostat, tretinoin, tamibarotene, etc.; and examples of non-specific immunostimulants include OK-432, dried BCG, trametes versicolor-polysaccharide preparation, lentinan, ubenimex, etc. In addition, aceglatone, porfimer sodium, talaporfin sodium, ethanol, arsenic trioxide, and the like can also be used. Although there is no limitation, antimetabolites are preferably used in terms of effects, and molecular targeted drugs and antibody drugs are preferably used in terms of less side effects.

When hematopoietic organ tumors are targeted, the molecular targeted drug is preferably imatinib mesilate, nilotinib hydrochloride hydrate, or dasatinib hydrate. When solid tumors are targeted, the molecular targeted drug is preferably gefitinib, erlotinib hydrochloride, or lapatinib tosilate hydrate, and particularly preferably imatinib mesilate.

The antibody drug is preferably trastuzumab or panitumumab, and particularly preferably trastuzumab.

The embodiment of the combined use (combination) of the antitumor effect enhancing agent of the present invention with an antitumor agent is not particularly limited, as long as the effects of the present invention are obtained. For example, the antitumor effect enhancing agent may be administered simultaneously with the administration of an antitumor agent, or the antitumor effect enhancing agent may be administered before or after the administration of an antitumor agent. In this case, the antitumor effect enhancing agent and an antitumor agent may be administered alternately. Further, after the administration of an antitumor agent, the antitumor effect enhancing agent may be administered together in the middle of the administration of the antitumor agent, depending on the degree of shrinkage of tumor tissue, etc. Conversely, after the administration of the antitumor effect enhancing agent, an antitumor agent may be administered together in the middle of the administration of the antitumor effect enhancing agent.

Moreover, the antitumor effect enhancing agent of the present invention may be administered in a single dose, multiple doses, or intermittent doses, as long as it is used in combination with an antitumor agent. For example, when the antitumor effect enhancing agent of the present invention is administered before the administration of an antitumor agent, the antitumor effect enhancing agent can be daily administered once a day, starting from 7 days before the start of the administration of the antitumor agent to the day of the start of administration, or starting from 3 days before the start of the administration of the antitumor agent to the day of the start of administration.

The antitumor effect enhancing agent of the present invention is provided in various forms (dosage forms) of pharmaceutical compositions depending on the administration route (administration method) thereof, and is administered to a target tumor patient in combination with an antitumor agent. The tumor patient may be at the stage of before, during, or after antitumor treatment, such as chemotherapy, radiotherapy, and/or ablative operation (surgical treatment).

The administration route (administration method) of the antitumor effect enhancing agent is not particularly limited. Examples thereof include oral administration, and parenteral administration such as intravenous administration, intramuscular administration, subcutaneous administration, transmucosal administration, transdermal administration, and intrarectal administration. Preferable are oral administration and intravenous administration, and more preferable is oral administration. The form of the pharmaceutical composition depending on each administration route (administration method) and the method for producing the same will be described in the following section VI.

The dosage of the antitumor effect enhancing agent of the present invention can vary depending on the type and location of tumor to be treated, the stage (progression) of the tumor, the pathological conditions, age, sex, and body weight of the patient, the type of antitumor agent to be used in combination, etc., and can be suitably determined depending on these factors.

When the antitumor effect enhancing agent of the present invention is orally administered to a human, the dosage thereof in terms of the amount of the compound having PAI-1 inhibitory activity, which is an active ingredient, can be suitably determined within the range of 0.01 to 300 mg/kg/day, preferably 0.03 to 30 mg/kg/day, and more preferably 0.1 to 10 mg/kg/day.

The dosage of an antitumor agent to be combined in this case is not limited, but can be suitably determined within the range of 1 to 5,000 mg/kg/day, 1 to 5,000 mg/kg/time, 1 to 5,000 mg/m$^2$/time, or 100,000 to 5 million JRU/time. The dosage of the antitumor agent can be suitably determined within the range of 0.2 to 5 times larger than the recommended dosage of the agent. The dosage is more preferably 0.5 to 2 times larger than the recommended dosage of the agent.

As for the dose frequency, administration can be continued for 1 to 8 days, and drug holidays of 5 days to 9 weeks can be provided.

When the antitumor effect enhancing agent of the present invention is an intravenously administered agent, it can be administered in an amount of 0.03 to 300 mg/kg per day so that the effective blood level of the compound having PAI-1 inhibitory activity is 0.2 to 50 µg/mL, and preferably 0.5 to 20 µg/mL. The dosage of an antitumor agent to be combined in this case is not limited, but can be suitably determined within the range of 10 to 100%, preferably 10 to 95%, of the general dosage.

When the antitumor effect enhancing agent and an antitumor agent are used in combination, the antitumor agent can be administered according to the general administration method and dosage of the agent.

IV. Tumor Chemotherapy Agent and Composition for Tumor Treatment

The tumor chemotherapy agent and composition for tumor treatment according to the present invention comprise a compound having PAI-1 inhibitory activity, mentioned above, in combination with an antitumor agent.

Examples of the antitumor agent to be combined with the compound having PAI-1 inhibitory activity include, as described in section III, alkylating agents, antimetabolites, antitumor antibiotics, microtubule inhibitors, hormones or hormone-like drugs, platinum-based drugs, topoisomerase inhibitors, cytokines, antibody drugs, radioimmunotherapy drugs, molecular targeted drugs, non-specific immunostimulants, and other antitumor agents. The antitumor agent can be suitably selected from these, depending on the target tumor. Preferable are antimetabolites, molecular targeted drugs, etc. The details are as described in section III and are incorporated herein by reference.

The tumors targeted by the tumor chemotherapy agent of the present invention include both non-epithelial malignant tumors and epithelial malignant tumors. As described in section III, specific examples thereof include respiratory malignant tumors, gastrointestinal tract malignant tumors, liver cancer, pancreatic cancer, urinary system malignant tumors, female genital malignant tumors, breast cancer, prostatic cancer, skin cancer, endocrine system malignant tumors, malignant central nervous system tumors, malignant tumors generated in the bone soft tissue, and like solid tumors, as well as hematopoietic organ tumors. The details are as described in section III and are incorporated herein by reference.

As described above, the compound having PAI-1 inhibitory activity acts on tumor stem cells and stimulates tumor stem cells in the G0 phase to thereby transit the cells to the mitotic phase. Accordingly, the compound can transit tumor stem cells in the resting phase, which generally react poorly to antitumor agents, to the mitotic phase, thereby increasing the sensitivity of the cells to antitumor agents. Therefore, when the compound having PAI-1 inhibitory activity is used in combination with an antitumor agent, tumor stem cells that can differentiate into tumor cells can be eradicated. As a result, tumor recurrence and/or metastasis can be suppressed. That is, the tumor chemotherapy agent of the present invention, which comprises a compound having PAI-1 inhibitory activity in combination with an antitumor agent, allows radical treatment of tumors that was conventionally difficult even by using antitumor agents singly or in combination. It is also possible to suppress tumor recurrence and/or metastasis, and provide a good or improved prognosis of antitumor treatment (chemotherapy, radiotherapy, and surgical treatment such as ablative operation).

The "prognosis of antitumor treatment" mentioned herein can be evaluated according to, for example, the tumor recurrence rate, metastasis rate, five-year survival rate, or ten-year survival rate of the tumor patient after antitumor treatment.

The tumor chemotherapy agent of the present invention includes an embodiment in which an antitumor agent and a compound having PAI-1 inhibitory activity are administered simultaneously or separately.

In an embodiment in which an antitumor agent and a compound having PAI-1 inhibitory activity are administered simultaneously, for example, an antitumor agent and a compound having PAI-1 inhibitory activity are formulated into a single pharmaceutical composition (combination drug). Specifically, the pharmaceutical composition is a combination drug in a desired dosage form containing the above-mentioned antitumor agent and compound having PAI-1 inhibitory activity, and optionally containing a pharmacologically acceptable carrier or additive. The compound having PAI-1 inhibitory activity is preferably at least one member selected from the compound group consisting of compound 1, compound 2, and compound 3 described in section I. The carrier or additive used herein may be one that does not impair the effects of the tumor chemotherapy agent of the present invention. The details thereof will be described in the following section VI. The form of the combination drug can be suitably determined depending on the administration route (dosage form) thereof. The administration route (administration method) is not particularly limited. Examples thereof include oral administration, and parenteral administration such as intravenous administration, intramuscular administration, subcutaneous administration, transmucosal administration, transdermal administration, and intrarectal administration. Preferable are oral administration and intravenous administration, and more preferable is oral administration. The form of the combination drug depending on each administration route (administration method) and the method for producing the same will be described in the following "VI. Pharmaceutical composition" section.

In another embodiment in which an antitumor agent and a compound having PAI-1 inhibitory activity are simultaneously administered, for example, an antitumor agent and a compound having PAI-1 inhibitory activity in different packaging forms are mixed immediately before application to a tumor patient. Specific examples thereof include a tumor chemotherapy agent that is used such that a compound having PAI-1 inhibitory activity is added and mixed with an antitumor agent in the form of a liquid (e.g., infusion or oral liquid) immediately before administration to a tumor patient (before use).

In this case, the combination ratio of the antitumor agent and the compound having PAI-1 inhibitory activity is not limited, as long as the effects of the present invention are obtained. The ratio can be suitably determined depending on the type and location of tumor to be treated, the stage (severity and progression) of the tumor, the pathological conditions, age, sex, and body weight of the patient, the type of antitumor agent to be used in combination, etc.

Specifically, for example, when the tumor chemotherapy agent is an orally administered agent, the dosage thereof in terms of the amount of the compound having PAI-1 inhibitory activity, which is an active ingredient, can be suitably determined within the range of 0.01 to 300 mg/kg/day, preferably 0.03 to 30 mg/kg/day, and more preferably 0.1 to 10 mg/kg/day.

The dosage of an antitumor agent to be combined can also be suitably determined within the range of 0.1 to 5,000 mg/kg/day, 0 to 5,000 mg/kg/time, 0.1 to 5,000 mg/kg/time, 0.1 to 5,000 mg/m$^2$/time, or 100,000 to 5 million JRU/time. The dosage of the antitumor agent can be suitably determined within the range of 0.2 to 5 times larger than the recommended dosage of the agent. The dosage is more preferably 0.5 to 2 times larger than the recommended dosage of the agent.

As for the dose frequency, administration can be continued for 1 to 8 days, and drug holidays of 5 days to 9 weeks can be provided.

When the tumor chemotherapy agent of the present invention is an intravenously administered agent, it can be administered in an amount of 0.03 to 300 mg/kg per day so that the effective blood level of the compound having PAI-1 inhibitory activity is 0.2 to 50 μg/mL, and preferably 0.5 to 20 μg/mL. The dosage of the antitumor agent can also be suitably determined within the range of 10 to 100%, preferably 10 to 95%, of the general dosage.

Furthermore, when the tumor chemotherapy agent of the present invention is administered, a compound having PAI-1 inhibitory activity can be singly administered after antitumor treatment at the above dosage, thereby preventing recurrence of the tumor.

In this case, the dosage of the compound having PAI-1 inhibitory activity can be suitably determined within the range of 0.003 to 3,000 mg/kg/day. Moreover, in this case, the administration is preferably continued for at least 1 year or more, more preferably 5 years or more, and even more preferably for the entire life.

In an embodiment in which an antitumor agent and a compound having PAI-1 inhibitory activity are separately administered, for example, an antitumor agent and a compound having PAI-1 inhibitory activity in different packaging forms are administered to a tumor patient simultaneously or at different times. In the embodiment of simultaneous administration, for example, an antitumor agent and a compound having PAI-1 inhibitory activity both in oral dosage forms are orally administered simultaneously; or when one of them is in an oral dosage form, and the other is in a parenteral dosage form, both can be administered simultaneously or in parallel. In the embodiment of administration at different times, for example, an antitumor agent and a compound having PAI-1 inhibitory activity both in oral dosage forms are orally administered at different times; or when one of them is in an oral dosage form, and the other is in a parenteral dosage form, both can be administered at different times. In the latter case, the order of administration is either of the following: the compound having PAI-1 inhibitory activity is administered before the administration of the antitumor agent, or the compound having PAI-1 inhibitory activity is administered after the administration of the antitumor agent. The compound having PAI-1 inhibitory activity and antitumor agent used in this case are provided in the form of a desired pharmaceutical composition, together with a pharmacologically acceptable carrier or additive, depending on the administration route (dosage form). The type of pharmacologically acceptable carrier or additive, and the method for producing the same will be described in the following section VI.

V. Stem-Cell Protecting Drug or Hematopoietic Disorder Improving Agent

A PAI-1 inhibitor has the effect of promoting the amplification of normal hematopoietic stem cells and can thus achieve early recovery of hematopoietic cells that decrease due to hematopoietic disorders caused by radiation, etc. This effect of the PAI-1 inhibitor also effectively acts during hematopoietic recovery in the early stage of hematopoietic stem-cell (HSC) transplantation. Accordingly, the PAI-1 inhibitor acts on normal stem cells as a stem-cell protecting drug and can be used as a hematopoietic disorder improving agent to improve hematopoietic disorders caused by radiation or administration of chemotherapy drugs, etc.

The present invention provides a stem-cell protecting drug for normal stem cells comprising a PAI-1 inhibitor as an active ingredient, and a hematopoietic disorder improving agent comprising a PAI-1 inhibitor as an active ingredient.

At present, conventionally known therapeutic agents for secondary hematopoietic disorders, such as renal anemia and neutropenia, caused by radiation or chemotherapy drug administration are erythropoietin (EPO), stem-cell factor (SCF), granulocyte colony stimulating factor (GCSF), and macrophage colony-stimulating factor (MCSF). All of these preparations act only on hematopoietic cells and exhibit their effects. Since these preparations mainly act on hematopoietic progenitor cells, the effect of amplifying hematopoietic stem cells themselves, which is necessary to maintain hematopoietic homeostasis for the entire life of the patient, cannot be obtained. Accordingly, the efficacy of the preparations is not sufficient.

In contrast, the stem-cell protecting drug or hematopoietic disorder improving agent of the present invention has the effect of improving the hematopoietic environment by acting on, for example, osteoblastic cells (normal cells), which are non-hematopoietic cells that control the differentiation and growth of hematopoietic cells, to enhance the function of hematopoietic stem cells and progenitor cells. In this respect, the stem-cell protecting drug or hematopoietic disorder improving agent of the present invention is far superior to the prior art. Therefore, a method for administering the stem-cell protecting drug or hematopoietic disorder improving agent of the present invention before or after the development of hematopoietic disorders can be a novel technique by which more effective recovery from hematopoietic disorders can be obtained, compared with the existing preparations.

The stem-cell protecting drug or hematopoietic disorder improving agent of the present invention can be provided in various forms (dosage forms) of pharmaceutical compositions depending on the administration route (administration method) thereof, and can be administered to patients with hematopoietic disorders or patients who may develop a hematopoietic disorder.

Examples of hematopoietic disorders to which the stem-cell protecting drug or hematopoietic disorder improving agent of the present invention can be applied include anemic diseases, such as hemolytic anemia, aplastic anemia, myelophthisic anemia, and secondary anemia occurring secondary to renal disease, endocrine disease, hepatic disease, chronic infection, malignant tumor, or the like; leukopenia, such as neutropenia, agranulocytosis, and lymphopenia; hematopoietic organ tumors, such as myelodysplastic syndrome, acute lymphocytic leukemia, acute myelogenous leukemia, chronic lymphocytic leukemia, chronic myelogenous leukemia, acute myelomonocytic leukemia, chronic myelomonocytic leukemia, acute monocytic leukemia, chronic monocytic leukemia, acute promyelocytic leukemia, acute megakaryocytic leukemia, erythroleukemia, eosinophilic leukemia, chronic neutrophilic leukemia, adult T-cell leukemia, hairy cell leukemia, plasma cell leukemia, multiple myeloma, and malignant lymphoma; and secondary hematopoietic disorders caused by radiation and/or chemotherapy, etc.

Patients who may develop a hematopoietic disorder refers to patients whose bone-marrow cells may be reduced due to pre-lesions of the above hematopoietic disorders, or due to radiation and/or chemotherapy.

The administration route (administration method) is not particularly limited. Examples thereof include oral administration, and parenteral administration such as intravenous administration, intramuscular administration, subcutaneous administration, transmucosal administration, transdermal administration, and intrarectal administration. Preferable are oral administration and intravenous administration, and more preferable is oral administration. The form of the pharmaceutical composition depending on each administration route (administration method) and the method for producing the same will be described in the following "VI. Pharmaceutical composition" section.

The dosage of the stem-cell protecting drug or hematopoietic disorder improving agent of the present invention can vary depending on the conditions, age, sex, and body weight of the patient to be treated, the severity of hematopoietic disorder, etc., and can be suitably determined depending on these factors.

When the stem-cell protecting drug or hematopoietic disorder improving agent of the present invention is orally administered to a human, the dosage thereof in terms of the amount of the compound having PAI-1 inhibitory activity, which is an active ingredient, can be suitably determined within the range of 0.03 to 300 mg/kg/day. When the stem-cell protecting drug or hematopoietic disorder improving agent is an intravenously administered agent, it can be administered in an amount of 0.03 to 300 mg/kg per day so that the effective blood level of the compound having PAI-1 inhibitory activity is 0.2 to 50 µg/mL, and preferably 0.5 to 20 µg/mL.

The stem-cell protecting drug or hematopoietic disorder improving agent of the present invention may be administered to a patient with a hematopoietic disorder or a patient who may develop a hematopoietic disorder, during the administration (transplantation) of hematopoietic stem cells or hematopoietic progenitor cells, or tissue (myeloid tissue) containing at least one of these cells. Further, the administration can also be performed before and after, or in parallel with, the transplantation of the above cells or tissue containing the cells. In this case, for example, when the day in which donor's hematopoietic stem cells or hematopoietic progenitor cells, or tissue containing these cells, are transplanted to a recipient is regarded as day 0, the administration of the stem-cell protecting drug or hematopoietic disorder improving agent of the present invention is started within 0 to 3 days, preferably 0 to 1 day, from the transplantation. Moreover, the frequency of administration is not limited. For example, the stem-cell protecting drug or hematopoietic disorder improving agent of the present invention can be administered daily, every other day, or every third day, for 60 days, preferably about 30 days, from the date of first administration.

Examples of the recipient include human patients whose bone-marrow cells have been killed by radiation and/or chemotherapy.

VI. Pharmaceutical Composition

The "agent for activating a stem cell," "agent for enhancing the antitumor effect of an antitumor agent," "tumor chemotherapy agent," and "stem-cell protecting drug or hematopoietic disorder improving agent" of the present invention, all described above, are prepared as pharmaceutical compositions in predetermined forms (dosage forms), and administered to target patients. Therefore, the above preparations are collectively referred to as the "pharmaceutical composition of the present invention."

The pharmaceutical composition of the present invention may comprise 100 wt. % of a compound having PAI-1 inhibitory activity, which is an active ingredient; however, the pharmaceutical composition of the present invention generally comprises a pharmacologically acceptable carrier or additive, in addition to the compound having PAI-1 inhibitory activity. In the latter case, the ratio of the compound having PAI-1 inhibitory activity in the pharmaceutical composition is not limited; however, the ratio can be generally selected from the range of 5 to 95 wt. %, and preferably 30 to 80 wt. %.

The pharmaceutical composition of the present invention can be administered orally or parenterally, such as intravenously, intramuscularly, subcutaneously, transmucosally, transdermally, intrarectally, etc. Among these, preferable are oral administration and intravenous administration, and more preferable is oral administration. The pharmaceutical composition of the present invention can be provided in various forms of preparations (dosage forms) depending on the above-mentioned administration manners.

Each dosage form is described below; however, the dosage forms employed in the present invention are not limited thereto. Any dosage forms that are usually used in the field of pharmaceutical preparations can be employed.

In the case of oral administration, the dosage form of the pharmaceutical composition of the present invention is suitably selected from powders, granules, capsules, pills, tablets, elixirs, suspensions, emulsions, and syrups. Such preparations can be imparted with sustained-release properties, stabilization, easy-degradation, difficult-degradation, enteric properties, easy adsorption properties, etc.

In the case of intravenous administration, intramuscular administration, or subcutaneous administration, the dosage form can be suitably selected from injections or drops (including dried products that are prepared upon use), and the like.

In the case of transmucosal administration, transdermal administration, or intrarectal administration, the dosage form can be suitably selected from masticatories, sublingual agents, buccal tablets, trochisci, ointments, patch agents, liquid agents, etc., according to the applied portion. Such preparations can be imparted with sustained-release properties, stabilization, easy-degradation, difficult-degradation, easy adsorption properties, etc.

The pharmaceutical composition of the present invention can contain a pharmaceutically acceptable carrier and additive according to the dosage form (oral administration or various parenteral administrations). Examples of pharmaceutically acceptable carriers and additives include solvents, excipients, coating agents, bases, binders, lubricants, disintegrators, solubilizers, suspending agents, thickening agents, emulsifiers, stabilizers, buffers, isotonizing agents, soothing agents, preservatives, corrigents, flavors, and coloring agents. Specific examples of pharmaceutically acceptable carriers and additives are mentioned below; however, the present invention is not limited thereto.

Examples of solvents include purified water, sterile purified water, water for injection, physiologic saline, peanut oil, ethanol, glycerol, etc. Examples of excipients include starches (e.g., potato starch, wheat starch, and corn starch), lactose, dextrose, saccharose, crystalline cellulose, calcium sulfate, calcium carbonate, sodium hydrogencarbonate, sodium chloride, talc, titanium oxide, trehalose, xylitol, etc.

Examples of binders include starch and starch derivatives, cellulose and cellulose derivatives (e.g., methylcellulose, ethylcellulose, hydroxypropylcellulose, and carboxymethylcellulose), natural high molecular weight compounds, such as gelatin, sodium arginine, tragacanth, gum arabic, etc., synthetic high molecular weight compounds, such as polyvinyl pyrrolidone, polyvinyl alcohol, etc., dextrin, hydroxypropyl starch, and the like.

Examples of lubricants include light anhydrous silicic acid, stearin acid and salts thereof (e.g., magnesium stearate), talc, waxes, wheat starch, macrogol, hydrogenated vegetable oil, sucrose fatty acid ester, polyethylene glycol, silicone oil, etc.

Examples of disintegrators include starch and starch derivatives, agar, gelatin powder, sodium hydrogencarbonate, calcium carbonate, cellulose and cellulose derivatives, hydroxypropyl starch, carboxymethylcellulose, salts thereof, and bridging materials thereof, low-substituted hydroxypropylcellulose, etc.

Examples of solubilizers include cyclodextrin, ethanol, propylene glycol, polyethylene glycol, etc. Examples of suspending agents include sodium carboxymethylcellulose, polyvinylpyrrolidone, gum arabic, tragacanth, sodium arginine, aluminum monostearate, citric acid, various surfactants, etc.

Examples of thickening agents include sodium carboxymethylcellulose, polyvinylpyrrolidone, methylcellulose, hydroxypropyl methylcellulose, polyvinyl alcohol, tragacanth, gum arabic, sodium arginine, etc.

Examples of emulsifiers include gum arabic, cholesterol, tragacanth, methylcellulose, lecithin, various surfactants (e.g., polyoxyl 40 stearate, sorbitan sesquioleate, polysorbate 80, and sodium lauryl sulfate), etc.

Examples of stabilizers include tocopherol, chelating agents (e.g., EDTA and thioglycolic acid), inert gases (e.g., nitrogen and carbon dioxide), reducing substances (e.g., sodium hydrogen sulfite, sodium thiosulfate, ascorbic acid, and rongalite), etc.

Examples of buffers include sodium hydrogenphosphate, sodium acetate, sodium citrate, boric acid, etc.

Examples of isotonizing agents include sodium chloride, glucose, etc. Examples of soothing agents include local anesthetics (e.g., procaine hydrochloride and lidocaine), benzyl alcohol, glucose, sorbitol, amino acid, etc.

Examples of corrigents include saccharose, saccharin, Glycyrrhiza extract, sorbitol, xylitol, glycerol, etc. Examples of flavoring agents include orange peel tincture, rose oil, etc. Examples of coloring agents include water-soluble food colors, lake pigment, etc.

Examples of preservatives include benzoic acid and salts thereof, p-hydroxybenzoate esters, chlorobutanol, invert soap, benzyl alcohol, phenol, thimerosal, dehydroacetic acid, boric acid, etc.

Examples of coating agents include saccharose, hydroxypropylcellulose (HPC), shellac, gelatin, glycerol, sorbitol, hydroxypropyl methylcellulose (HPMC), ethylcellulose, polyvinyl pyrrolidone (PVP), hydroxypropylmethylcellulose phthalate (HPMCP), cellulose acetate phthalate (CAP), methyl methacrylate-methacrylic acid copolymer, polymers described above, etc.

Examples of bases include Vaseline, liquid paraffin, carnauba wax, beef tallow, hardened oil, paraffin, yellow beeswax, vegetable oil, macrogol, macrogol fatty acid ester, stearic acid, sodium carboxymethylcellulose, bentonite, cacao butter, Witepsol, gelatin, stearyl-alcohol, hydrous lanolin, cetanol, light liquid paraffin, hydrophilic petrolatum, simple ointment, white ointment, hydrophilic ointment, macrogol ointment, hard fat, oil-in-water emulsion bases, water-in-oil emulsion bases, etc.

Known drug delivery systems (DDS) can be applied for the dosage forms given above. The term DDS preparation as used in the present specification refers to slow-release preparations, locally applied preparations (troches, buccal tablets, sublingual tablets, etc.), drug control-release preparations, enteric coated preparations, gastric soluble preparations, etc., that are all prepared in the best form considering the administration route, bioavailability, side effects, etc.

EXAMPLES

Below, the present invention is described in more detail with reference to Examples and Reference Experimental Examples. However, the present invention is not limited to these examples.

Reference Experimental Examples

Reference Experimental Example 1: Measurement of PAI-1 Inhibitory Activity of Compound Group 1

The compounds (compound examples 1 to 7 and 9 to 14) shown in Table 1 that fall within the scope of compound group 1 represented by Formula (I) and existing compounds (1) and (2) known as a PAI-inhibitor (see Table 1) were measured and evaluated for inhibitory activity against human PAI-1 (manufactured by Molecular Innovations, Inc. (USA); the same applies hereinafter).

Specifically, human-derived PAI-1 was added to a 0.1% Tween 80-containing 100 mM Tris-HCl (pH 8) solution containing each of the above compounds in a given concentration (0.29 mM or 0.12 mM), and the mixture was incubated at 37° C. for 15 minutes. Subsequently, human-derived tissue plasminogen activator (t-PA) (manufactured by American Diagnostica, Inc. (USA); the same applies hereinafter) adjusted to 0.35 pmol/µL was added thereto, and the mixture was further incubated at 37° C. for 15 minutes. Then, 1.25 mM of S-2288 synthetic substrate (manufactured by Chromogenix, (Italy); the same applies hereinafter), which was a chromogenic substrate, was added. The final mixture contained 100 mM Tris-HCl (pH 8), 30 mM NaCl, 1% DMSO, 0.1% Tween 80, 67 nM PAI-1, 9.8 nMt-PA, 1 mM S-2288 synthetic substrate, and each compound (50 µM or 20 µM).

Free radical p-nitroaniline removed from the chromogenic substrate (S-2288) by t-PA action was measured using a spectrophotometer at an absorbance of 405 nm at 5-minute intervals for 30 minutes. A systems that did not contain each of compound examples 1 to 7 and 9 to 14 was similarly evaluated, and the PAI-1 activity of the system after 30 minutes was taken as 100% to evaluate the PAI-1 activity of a system to which a test compound was added. The results are shown in Table 1.

Reference Experimental Example 2: Measurement of PAI-1 Inhibitory Activity of Compound Group 1

The compounds (compound examples 2, 4, 5, 7, 8, and 13 to 107) shown in Table 2 that fall within the scope of compound group 1 represented by Formula (I), the existing compounds (1) to (6) known as a PAI-1 inhibitor, and hydrochloride salt of the known compound (7) (see Table 2) were used as a test compound and evaluated for inhibitory activity against human PAI-1 (manufactured by Molecular Innovations, Inc. (USA); the same applies hereinafter).

Specifically, human PAI-1 was added to a 0.1% PEG-6000- and 0.2 mM CHAPS-containing 50 mM tris-HCL (pH 8) solution containing each of the above compounds in a given concentration (62.5 µM or 15.6 µM), and the mixture was incubated at 37° C. for 15 minutes. Subsequently, human-derived tissue plasminogen activator (t-PA) (manufactured by American Diagnostica, Inc. (USA); the same applies hereinafter) adjusted to 0.05 pmol/µL was added thereto, and the mixture was further incubated at 37° C. for 60 minutes. Then, 0.25 mM of Spectrozyme t-PA synthetic substrate (manufactured by American Diagnostica, Inc. (USA); the same applies hereinafter), which is a chromogenic substrate, was added. The final mixture contained 50 mM Tris-HCl (pH 8), 150 mM NaCl, 1% DMSO, 0.1% PEG-6000, 0.2 mM CHAPS, 5 nM PAI-1, 2 nM t-PA, 0.2 mM Spectrozyme t-PA synthetic substrate, and each compound (10 µM or 2.5 µM).

Free radical p-nitroaniline removed from the chromogenic substrate (Spectrozyme t-PA) by t-PA action was measured using a spectrophotometer at an absorbance of 405 nm at 20-minute intervals, for 120 minutes. A system that did not contain the test compounds was similarly evaluated, and the PAI-1 activity of the system after 120 minutes was taken as 100% to evaluate the PAI-1 activity of a system to which a test compound was added. Table 2 shows the results.

Reference Experimental Example 3: Measurement of PAI-1 Inhibitory Activity of Compound Group 2

The compounds (compound examples 1 to 95) shown in Table 3 that fall within the scope of compound group 2 represented by Formula (II) were measured and evaluated for inhibitory activity against human PAI-1 (manufactured by Molecular Innovation Inc. (USA); the same applies hereinafter).

Specifically, human-derived PAI-1 was added to a 0.1% Tween 80-containing 100 mM Tris-HCl (pH 8) solution containing the above compounds in each of given concentration (20 μM, 50 μM, or 100 μM), and the mixture was incubated at 37° C. for 15 minutes. Subsequently, human-derived tissue plasminogen activator (t-PA) (manufactured by American Diagnostica, Inc. (USA); the same applies hereinafter) adjusted to 0.3 pmol/μL was added thereto, and the mixture was further incubated at 37° C. for 15 minutes. Then, 1.25 mM of S-2288 synthetic substrate (manufactured by Chromogenix, (Italy); the same applies hereinafter), which was a chromogenic substrate, was added. The final mixture contained 100 mM Tris-HCl (pH 8), 30 mM NaCl, 1% DMSO, 0.1% Tween 80, 67 nM PAI-1, 9.8 nMt-PA, 1 mM S-2288 synthetic substrate, and each compound (100 μM, 50 μM, or 20 μM).

p-Nitroanilide, which was digested and was released from the chromogenic substrate (S-2288) by t-PA action, was measured using a spectrophotometer at an absorbance of 405 nm at 5-minute intervals for 30 minutes. A system that did not contain each of compound examples 1 to 95 was similarly evaluated, and the PAI-1 activity of the system 30 minutes after was taken as 100% to evaluate the PAI-1 activity of a system to which a test compound was added. Table 3 shows the results.

Reference Experimental Example 4: Measurement of PAI-1 Inhibitory Activity of Compound Group 3

The compounds (compound examples 1 to 77) shown in Table 4 that fall within the scope of compound group 3 represented by Formula (III) were measured and evaluated for inhibitory activity against human PAI-1 (manufactured by Molecular Innovation Inc. (USA); the same applies hereinafter).

Specifically, human-derived PAI-1 was added to a 0.1% Tween 80-containing 100 mM Tris-HCl (pH 8) solution containing the above compounds in each of given concentration (20 μM or 50 μM), and incubated at 37° C. for 15 minutes. Subsequently, tissue plasminogen activator (t-PA) (manufactured by American Diagnostica, Inc. (USA); the same applies hereinafter) adjusted to 0.3 pmol/μL was added thereto, and further incubated at 37° C. for 15 minutes. Then, 1.25 mM of S-2288 synthetic substrate (manufactured by Chromogenix) (Italy); the same applies hereinafter), which was a chromogenic substrate, was added thereto. Each of the final mixtures contained 100 mM Tris-HCl (pH 8), 30 mM NaCl, 1% DMSO, 0.1% Tween 80, 67 nM PAI-1, 9.8 nMt-PA, 1 mM S-2288 synthetic substrate, and each of the compounds (50 μM or 20 μM).

p-Nitranilide, which is digested and is released from the chromogenic substrate (S-2288) by t-PA action, was measured using a spectrophotometer at an absorbance of 405 nm at 5-minute intervals for 30 minutes. A system that did not contain the compounds (1) to (14) was similarly evaluated, and the PAI-1 activity of this system 30 minutes after was taken as 100% to evaluate the PAI-1 activity of the systems to which each of the test compounds was added. Table 4 shows the results.

EXPERIMENTAL EXAMPLES

As described below, experiments were conducted using the following compounds a to e as a test compound. However, these compounds are merely examples of the PAI-1 inhibitor targeted by the present invention, and the experimental results of the present invention are also obtained in the same manner with other compounds having PAI-1 inhibitory activity (PAI-1 inhibitors).

Test Compound

Compound a: 2-(2-(2-(4-benzhydrylpiperazine 1-yl)-2-oxethoxy)acetamide)-5-chlorosodium-benzoate salt Compound b: 5-chloro-2-{[{[3-(furan-3-yl)phenyl]amino}(oxo)acetyl]amino}benzoic acid Compound c: 2-[(biphenyl-3-ylcarbonyl)amino]-5-chlorobenzoic acid Compound d: sodium 5-chloro-2-({[3-(quinolin-8-yl)phenyl]carbonyl}amino)benzoate Compound e: 5-chloro-2-{[(2-{[3-(furan-2-yl)phenyl]amino}-2-oxoethoxy)acetyl]amino}benzoic acid Compound a falls within the scope of compound group 2 represented by Formula (II) (see compound example 30 of Table 3 for compound a), and compound a was produced in accordance with the procedure described in WO2009/013915. The bioisostere of compound a can be produced in accordance with (or in view of) the procedure described in WO2009/013915.

Compound b falls within the scope of compound group 3 represented by Formula (III) (see compound example 45 of Table 4), and compound b was produced in accordance with the procedure described in WO2009/123241. The bioisostere of compound b can be produced in accordance with (or in view of) the procedure described in WO2009/123241.

Compound c falls within the scope of compound group 1 represented by Formula (I) (see compound example 4 of Tables 1 and 2), and compound c was produced in accordance with the procedure described in WO2010/113022. The bioisostere of compound c can be produced in accordance with (or in view of) the procedure described in WO2010/113022.

Compound d falls within the scope of compound group 1 represented by Formula (I) (see compound example 68 of Table 2-2 for compound d), and compound d was produced in accordance with the procedure described in WO2010/113022. The bioisostere of compound d can be produced in accordance with (or in view of) the procedure described in WO2010/113022.

Compound e falls within the scope of compound group 3 represented by Formula (III) (see compound example 61 of Table 4-6 for compound e), and compound e was produced in accordance with the procedure described in WO2009/123241. The bioisostere of compound e can be produced in accordance with (or in view of) the procedure described in WO2009/123241.

Laboratory animals were raised at the animal facility of Tokai University School of Medicine. All the protocols for animal experiments were approved by the Animal Care Committee of Tokai University, and animals were treated in accordance with the institutional guidelines.

The symbol "E(number)" used in the specification and drawings indicates a logarithm. For example, "10E8" indicates "$10^8$."

Experimental Example 1

To demonstrate that PAI-1 has an inhibitory effect on hematopoietic regeneration, hematopoietic stem cells were experimentally transplanted into PAI-1-deficient mice (PAI-1-KO mice) (B6.129S2-Serpine1$^{thlMlg}$/J: Jackson Laboratory (Bar Harbor, Me.)) and wild-type mice (i.e., controls) as recipients. For the experiment, 9 PAI-1-KO mice and 9 wild-type mice were used (n=9).

Before transplanting hematopoietic stem cells, the recipient mice were exposed to a lethal dose of radiation (9Gy)

with an X-ray irradiator (MBR-1520R-3, Hitachi Medico, Tokyo, Japan). Thereafter, $1.0 \times 10^6$ or $2.5 \times 10^6$ bone-marrow mononucleic cells (BM MNC) were inoculated intravenously into the retro-orbital plexus. The BM MNC contained about 10 to 30 hematopoietic stem cells.

The blood of post-transplant PAI-1-KO mice and wild-type mice was collected, and (A) active PAI-1 level (ng/ml), (B) active tPA level (ng/ml), (C) plasmin level (ng/ml), (D) total MMP9 level (ng/ml), (E) cKitL (pg/ml), (F) absolute number of bone-marrow mononucleic cells (BM MNC) (×10E8 cell), (G) frequency of donor-derived Lin-SLAM positive cells (%), (H) absolute number of donor-derived Lin-SLAM positive cells (×10E4 cell), (I) frequency of LSK-CD34 negative cells (%), and (J) absolute number of LSK-CD34 negative cells (×10E5 cell) in the plasma were determined in accordance with an ordinary procedure. The LSK-CD34 negative cell is a cell surface marker, specifically, lineage-negative, c-Kit-positive, and Sca-1-positive (hereinafter, this cell surface marker is referred to as LSK), and also referred to as cell surface marker CD34 negative cell. The Lin-SLAM cell refers to the cell that expresses CD150 (CD150(+)), and does not express Lin and CD48 (lineage-negative, CD48 negative). LSK-CD34 negative or Lin-SLAM is a hematopoietic stem cell marker, and a high frequency or high level thereof indicates an increase in hematopoietic stem cells.

For cell surface marker analysis, mice were euthanized, and their bone marrow was collected from the femurs and tibiae. The following labeling antibodies were used: APC-conjugated anti mouse ckit (CD117) antibody (eBioscience, San Diego, Calif.), PE-conjugated anti mouse Sca-1 (Ly6A/E) antibody (eBioscience), FITC-conjugated anti mouse CD34 antibody, APC-conjugated anti mouse CD48 antibody (eBioscience), and PE-conjugated anti mouse CD150 antibody (eBioscience). PI stain-positive cells were removed from the fraction as dead cells. A flow cytometric analysis was performed with the FACS Calibur (BD Bioscience). Each analysis was performed on 1,000,000 cells, and the CellQuest software program (BD Bioscience) was used for analysis.

FIGS. 1A to 1J show the results. The results were statistically analyzed using Student's t-test. The symbol "*" indicates $p<0.05$, the symbol "**" indicates $p<0.001$.

As shown in FIG. 1A, whereas active PAI-1 was induced in the wild-type mice along with the transplantation of hematopoietic stem cells, active PAI-1 was not induced in the PAI-1-KO mice despite the transplantation of hematopoietic stem cells. The expressions of active tPA, plasmin, MMP9, and cKitL in plasma were more prominently observed in the PAI-1-KO mice, as compared with the wild-type mice (FIGS. 1B to 1E). The absolute number of BM MNC was more likely to be higher in the PAI-1-KO mice than in the wild-type mice (FIG. 1F). In addition, the frequency of donor-derived SLAM (CD150 marker) positive cells was higher in the PAI-1-KO mice, and this tendency was observed before transplantation (0W), 1 week after transplantation (1W), and 3 weeks after transplantation (3W) (FIGS. 1G and 1H). The frequency and total number of LSK-CD34 negative cells, which were to serve as a hematopoietic stem cell marker, were likely to be higher in the PAI-1-KO mice than in the wild-type mice (FIGS. 1I and 1J).

The results demonstrate that PAI-1-KO mice, in which PAI-1 was not induced, and hematopoietic regeneration was not inhibited by the control of fibrinolytic pathway, despite the hematopoietic stem cell transplantation, have a higher hematopoietic regeneration capacity after hematopoietic stem cell transplantation than the wild-type mice in which PAI-1 was normally expressed and generated. More specifically, the results indicate that PAI-1 can control hematopoietic regeneration.

Experimental Example 2

Severely immunocompromised mice (recipient) were exposed to radiation (2Gy), and two days later, human $CD34^+$ cells isolated from human umbilical cord blood were transplanted into the mice. Concurrently with the transplantation, compound a was orally administered into the mice as a test compound (dosage: 100 mg/kg), and the compound was further administered for 5 consecutive days; i.e., 6 doses in total (see FIG. 2A). 2 days after the last administration (7 days after the cell transplantation), the bone-marrow cells were collected, and the abundance ratio of human hematopoietic cells was measured with a flow cytometric analyzer, whereas the cKitL concentration (μg/mL) and VEGF concentration (μg/mL) in the plasma were also measured. As a control test, instead of compound a, PBS used for dissolving compound a was orally administered to NOG mice, and the same experiment was conducted (control group).

Figure 2:
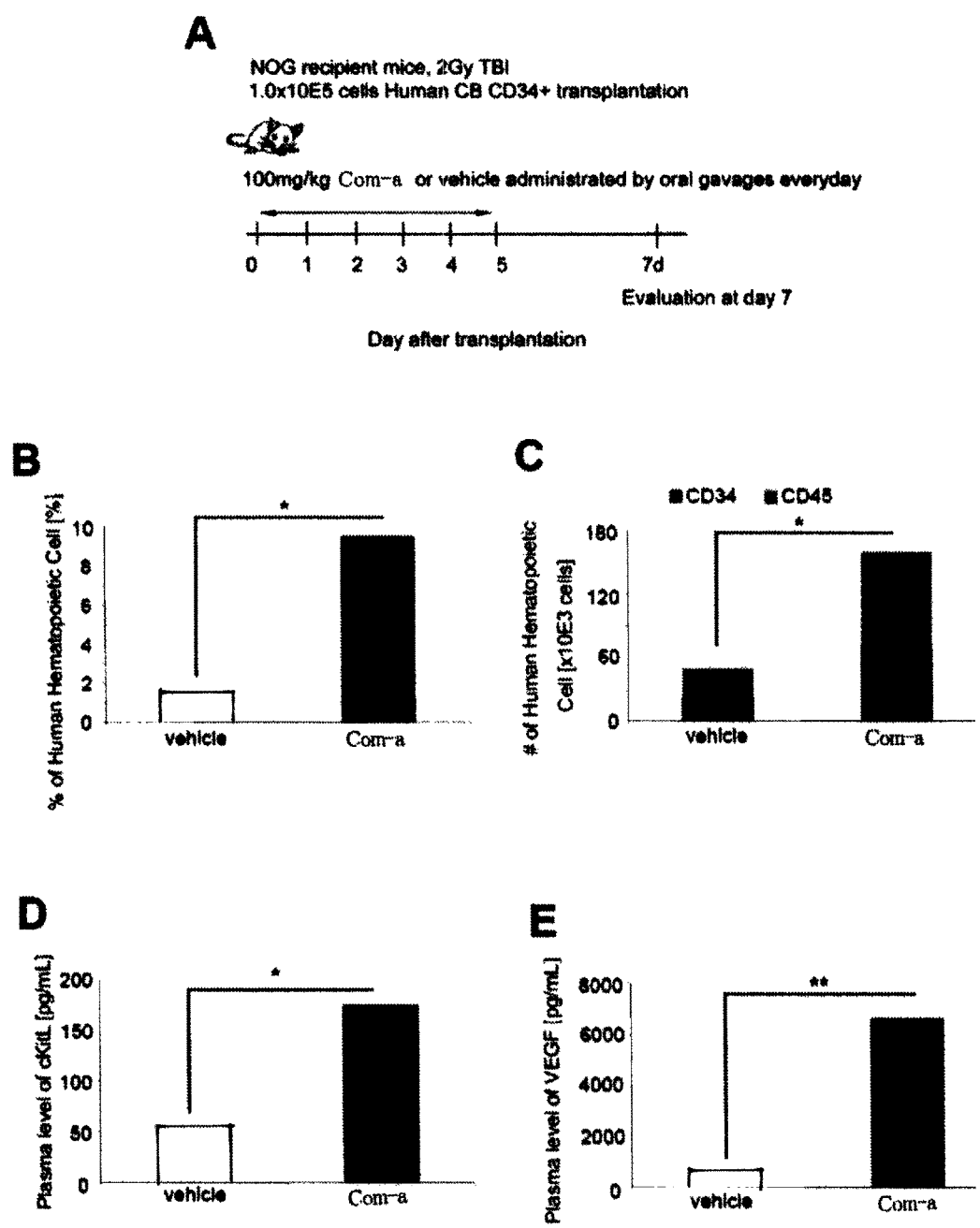
FIG. 2A shows a schematic diagram of the experiment procedure in Experimental Example 2 (A).
FIGS. 2B to 2E show the comparison between the compound a (Com-a)-administered group and the control group in chimerism of human hematopoietic cells in the bone marrow obtained in Experimental Example 1 (B), absolute number of human hematopoietic cells (CD34%, CD45%) in the bone marrow (C), concentration (μg/mL) of cKit ligand (cKitL) in the plasma, and concentration (μg/mL) of VEGF in the plasma.

FIG. 2B shows the chimerism of human hematopoietic cells in the bone marrow, and FIG. 2C shows the absolute number of the human hematopoietic cells ($CD34^+$, $CD45^+$). FIG. 2B shows the average value of the results from two independent experiments, and FIG. 2C shows the average value of the results of three independent experiments. FIG. 2D shows the results of comparison of the cKitL concentration (μg/mL) in the plasma between the administered group and the control group, and FIG. 2E shows the results of comparison of the VEGF concentration (μg/mL) in the plasma between the administered group and the control group.

As is clear from the results, the group to which the test compound (compound a) was administered (administered group) exhibited a chimerism of human hematopoietic cells ($CD45^+$) 2 to 9 times higher than the control group to which PBS, instead of the test compound, was administered (control group) (FIG. 2B), and the administered group also exhibited an absolute number 3 to 10 or more times higher (FIG. 2C). In addition, the proportion of $CD34^+$ cell, which is human HSC contained in human hematopoietic cells, was increased in the administered group. Both cKitL and VEGF in the plasma were also increased in that group (administered group) to which the test compound (compound a) was administered. As described above, the results reveal that compound a of the present invention activates the fibrinolytic pathway, and promotes the amplification of human hematopoietic stem cells and hematopoietic regeneration. More specifically, the results suggest that because compound a is effective in the early stage of hematopoietic recovery after human HSC transplantation, compound a is an effective compound to improve a hematopoietic disorder of a patient.

Experimental Example 3

Figure 3:
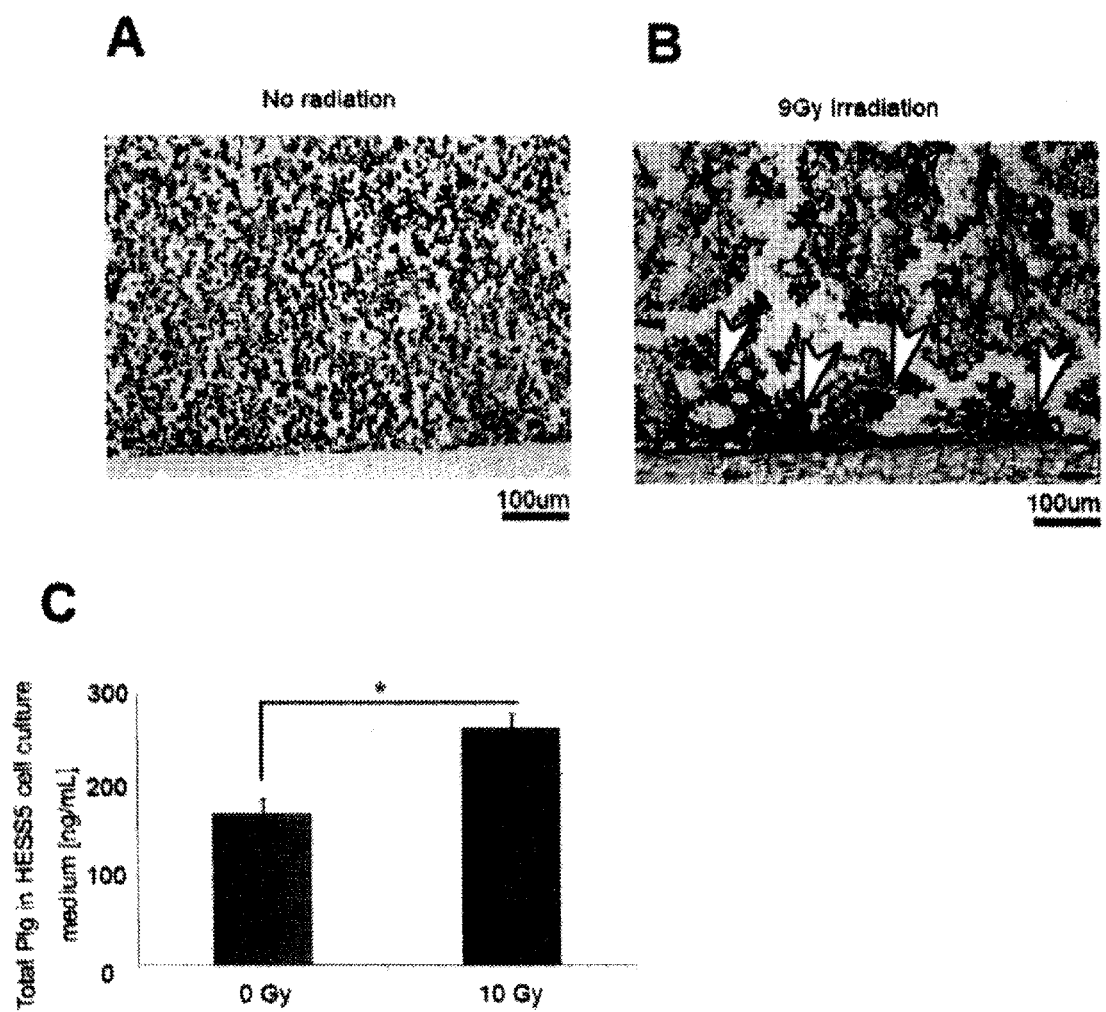
FIGS. 3A and 3B show non-irradiated bone-marrow cells stained for plasminogen/plasmin in Experimental Example 3 (A) and bone-marrow cells stained for plasminogen/plasmin 2 days after irradiation (9 Gy) (B). The white arrows in FIG. 3B indicate that plasminogen/plasmin was highly expressed in the bone-marrow microenvironment.
FIG. 3C shows the comparison of the total plasminogen (ng/mL) between HESS5 bone-marrow stromal cell culture medium 2 days after irradiation (10Gy) and non-irradiated HESS5 bone-marrow stromal cell culture medium ($*p<0.05$).

FIG. 3A shows non-irradiated bone-marrow tissue stained for plasminogen/plasmin, and FIG. 3B shows bone-marrow tissue stained for plasminogen/plasmin 2 days after irradiation (9Gy). The white arrows in FIG. 3B indicate that plasminogen/plasmin were expressed in the bone-marrow microenvironment at higher levels. The total level (ng/mL) of plasminogen in a culture medium containing HESS5 bone marrow stromal cells 2 days after irradiation (10Gy) was measured, and compared with the total level (ng/mL) of plasminogen in a culture medium containing HESS5 bone marrow stromal cells that were not exposed to radiation (0Gy) (*p<0.05); FIG. 3C shows the results.

The results reveal that irradiation increases the expression levels of plasminogen/plasmin in bone-marrow cells or bone marrow stromal cells. Thus, the results suggest that because the expression levels of fibrinolytic molecules are increased in the hematopoietic microenvironment in hematopoietic disorders induced by irradiation or the like, the molecular groups play a key role in hematopoietic recovery. In the below-described Experimental Example 4, compound a having a fibrinolytic pathway controlling effect was administered using a bone marrow transplant experimental system, and the effect was examined.

Experimental Example 4

In accordance with the procedure described in FIG. 4A, compound a was evaluated for its hematopoietic recovery effect.

Specifically, C57Bl6/J mice (recipient), which were wild-type inbred strain mice, were treated with total-body radiation (9Gy), and four hours later, bone-marrow cells were transplanted into the mice. Concurrently with the transplantation, compound a was administered to the mice as a test compound via oral gavage (dosage 100 mg/kg), and compound a was daily administered orally for 5 consecutive days (administered group). As a control test, instead of compound a, physiological saline (vehicle) used for dissolving compound a was orally administered to mice (control group).

(1) Survival Rate

Blood was collected 2, 7, and 21 days after the bone-marrow transplantation, and the plasminogen level (ng/mL), active tissue-type plasminogen activator (tPA), cKit ligand, and total MMP-9 (matrix metalloprotein-9) in the plasma and white blood cell count (×10E3 cell/μL) in the peripheral blood were measured (each group: n=6). The survival rate of the mice after bone-marrow transplantation was tracked over time (each group: n=15).

FIGS. 4B to 4G show the results. FIGS. 4B, 4C, 4D, 4E, and 4G, respectively, show the plasminogen (plg) level (ng/mL) in plasma, active tissue-type plasminogen activator (tPA) level (ng/mL) in plasma, cKit ligand (cKitL) level (ng/mL) in plasma, total MMP-9 level (ng/mL) in plasma, and white blood cell count (WBC) (×10E3 cell/μL) in peripheral blood. In these figures, the black bars "■" indicate the results of the oral administration of compound a (the results of the administered group), and the white bars "□" indicate the results of the oral administration of physiological saline, instead of compound a (the results of the control group). In these figures, the horizontal lines indicate the levels of the above-listed components in untreated mice. FIG. 4F shows the survival rate of the administered group (-■-) to which compound a was orally administered, and the control group (-○-) to which physiological saline, instead of compound a, was orally administered.

Figure 4:
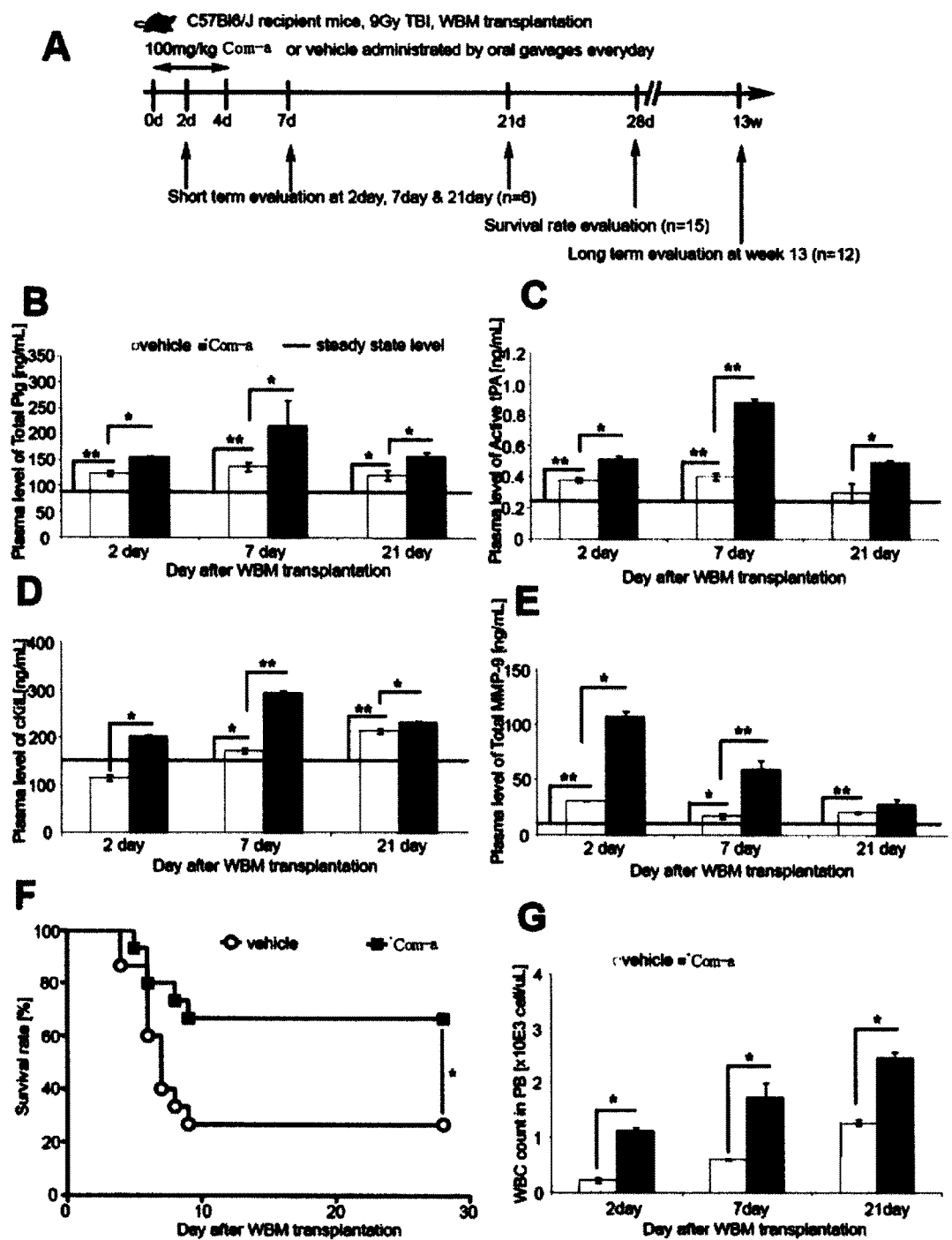

As shown in FIG. 4, the group to which compound a was administered (administered group) exhibited significantly higher levels in all of the plg level, tPA level, cKitL level, total MMP-9 level in plasma, and white blood cell count in the peripheral blood than the control group to which physiological saline (vehicle), instead of compound a, was orally administered.

In addition, the survival rate of the mice to which compound a was orally administered (administered group), concurrently with bone-marrow transplantation was significantly higher than that of the mice to which compound a was not orally administered (control group) (FIG. 4F).

The results reveal that in bone-marrow transplantation after radiation exposure, compound a activates the fibrinolytic pathway during hematopoietic regeneration, and increases the expression of hematopoietic cell proliferation-promoting factors, thereby inducing rapid recovery of white blood cells. Consequently, the results indicate that the administration of compound a prevents individual death caused by a hematopoietic disorder and increases the survival rate.

(2) Frequency of Hematopoietic Stem Cell

Figure 5:
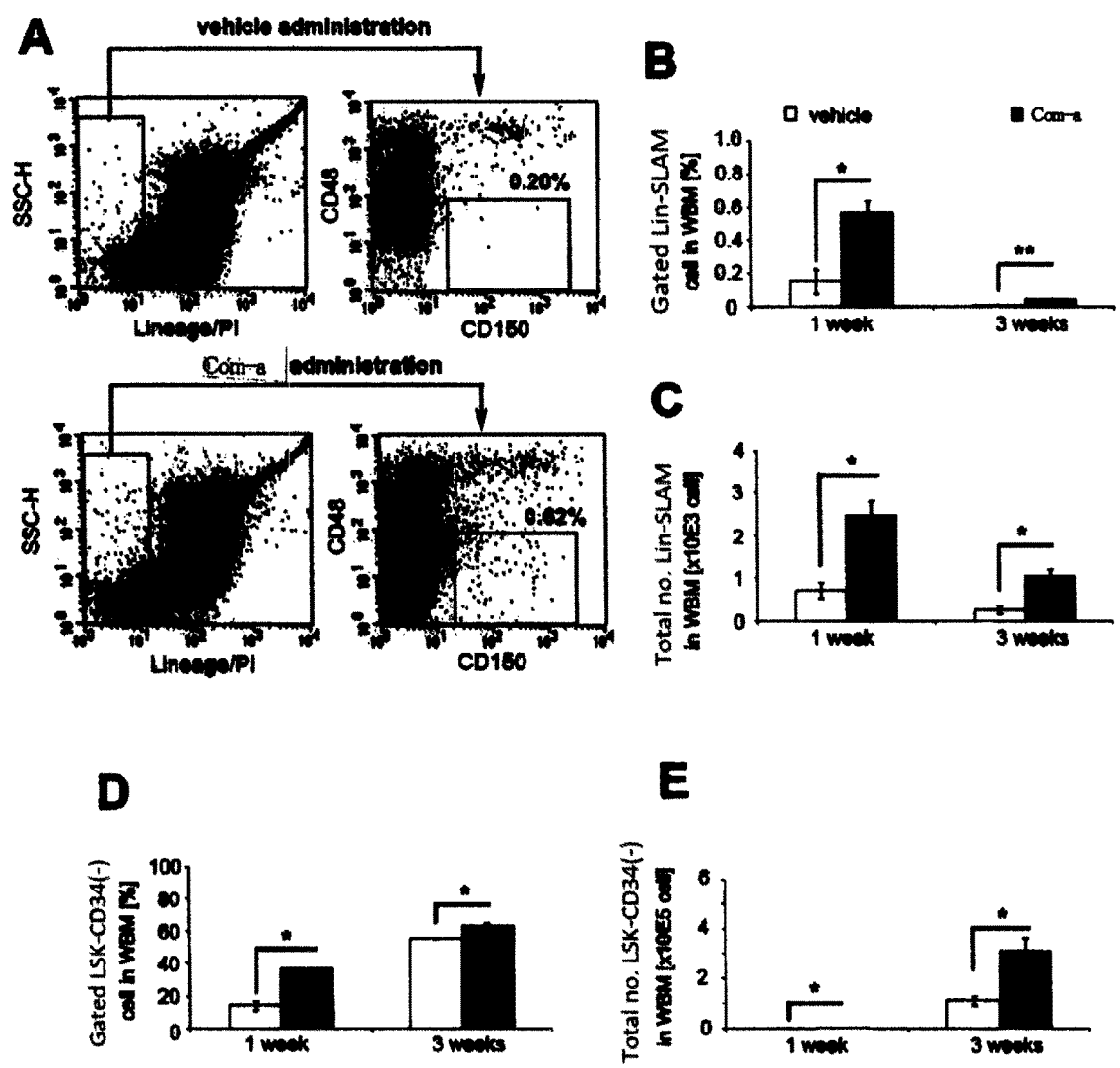
FIGS. 5A to 5E show the results of Experimental Example 4 (2) for the administered group and the control group: the measurement results of Lin-SLAM cells in bone-marrow cells collected from mice (compound a (Com-a)-administered group and control group) on day 7 from bone-marrow transplantation by a flow cytometric analyzer (A), proportion (%) of Lin-SLAM cells in the whole bone marrow (B), total number of Lin-SLAM cells in the whole bone marrow (C), proportion (%) of LSK-CD34 negative (LSK-CD34(−)) cells in the whole bone marrow (D), and total number of LSK-CD34 negative (LSK-CD34(−)) cells in the whole bone marrow (E).

Bone-marrow cells collected from the mice (administered group and control group) 7 days after bone-marrow transplantation were measured for the presence of Lin-SLAM cells with a flow cytometric analyzer (see FIG. 5A). Each test was independently conducted (each group: n=6).

The proportion (%) of Lin-SLAM cells in the whole bone marrow, the total number of Lin-SLAM cells in the bone marrow, the proportion (%) of LSK-CD34 negative cells in the bone marrow, and the total number of LSK-CD34 negative cells in the bone marrow were measured.

FIGS. 5B to 5E show the results (B: the proportion (%) of Lin-SLAM cells in the whole bone marrow, C: the total number of Lin-SLAM cells in the whole bone marrow, D: the proportion (%) of CD34(-) KSL cells in the whole bone marrow, and E: the total number of CD34(-)KSL cells in the whole bone marrow). As in FIGS. 4B to 4E, in FIGS. 5B to 5E, the black bars "■" indicate the results of the administered group, and the white bars "□" indicate the results of the control group.

The results indicate that compound a increases the frequency of hematopoietic stem cells. In other words, compound a not only simply achieves hematopoietic system recovery, but also proliferates the hematopoietic stem cells, i.e., the source of all of the hematopoietic cells, and protects the hematopoietic stem cells in a stressful environment.

(3) Plasminogen mRNA Expression Level, tPA mRNA Expression Level, and PAI-1 mRNA Expression Level The bone-marrow cells collected from the mice (administered group, control group) 7 days after bone-marrow transplantation were measured for the plasminogen (Plg) mRNA expression level, tPA mRNA expression level, and PAI-1 mRNA expression level.

Figure 6:
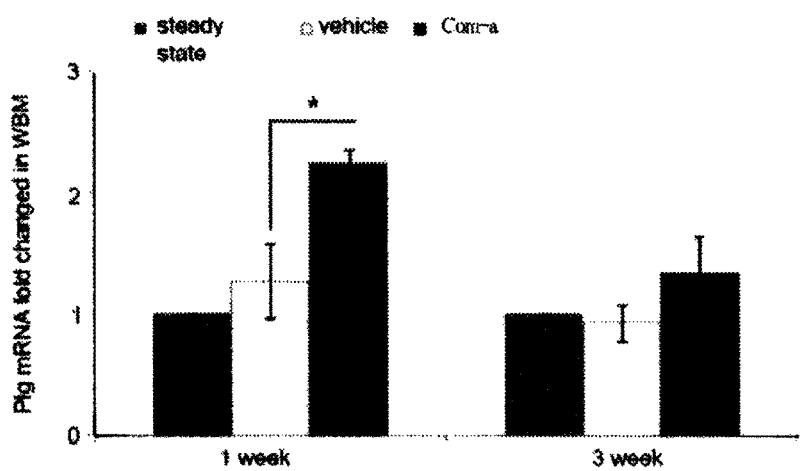
FIGS. 6A to 6C show the results of Experimental Example 4 (3): the plasminogen (Plg) mRNA expression level (A), tPA mRNA expression level (B), and PAI-1 mRNA expression level (C), all in the bone marrow collected from of mice (compound a (Com-a)-administered group and control group) on day 7 from bone-marrow transplantation.
Figure 6:
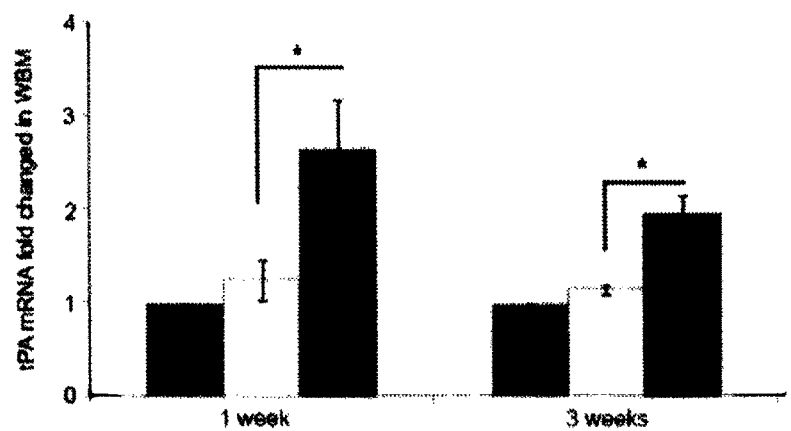
Figure 6:
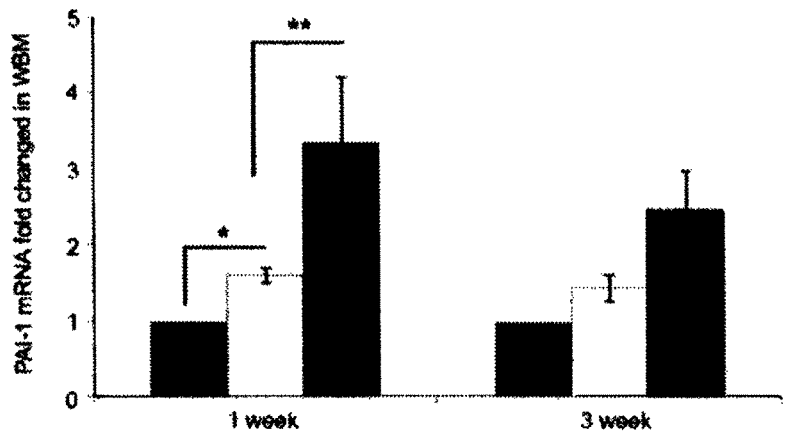

FIG. 6 shows the results.

FIGS. 6A, 6B, and 6C, respectively, show the plasminogen (Plg) mRNA expression level in the whole bone marrow, the tPA mRNA expression level in the whole bone marrow, and the PAI-1 mRNA expression level in the whole bone marrow. The results of each group (administered group and control group) are indicated as a ratio relative to each of the mRNA expression levels of Plg, tPA and PAI-1 in the whole bone marrow of untreated mice taken as 1.

The results indicate that compound a induces the mRNA expression of plasminogen, tissue-type plasminogen activator, and plasminogen activator inhibitor 1.

(4) Evaluation of Hematopoietic Stem Cell Count

Figure 7:
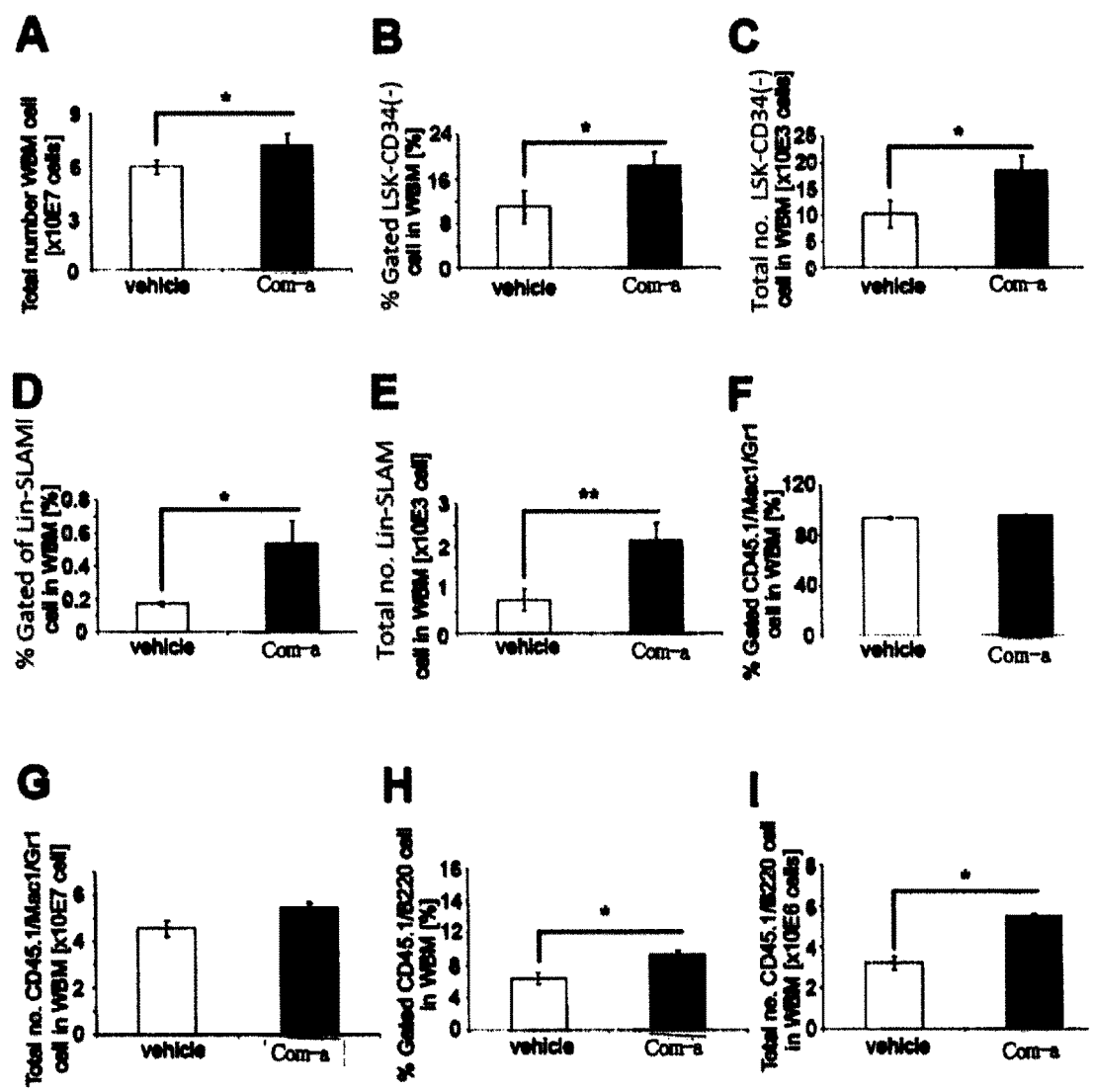
FIGS. 7A to 7I show the results of Experimental Example 4 (4): total number of whole bone marrow cells (A), proportion (%) of LSK-CD34 negative (LSK-CD34(−)) cells in the whole bone marrow (B), total number of LSK-CD34 negative (LSK-CD34(−)) cells in the whole bone marrow (C), proportion (%) of Lin-SLAM cells in the whole bone marrow (D), total number of Lin-SLAM cells in the whole bone marrow (E), proportion (%) of bone marrow differentiated cells in the whole bone marrow (F), total number of bone marrow differentiated cells in the whole bone marrow (G), proportion (%) of B-cell lymphoid differentiated cells in the whole bone marrow (H), and total number of B-cell lymphoid differentiated cells in the whole bone marrow (I), all of which were measured using the bone marrow collected from mice (compound a (Com-a)-administered group and control group) 13 weeks after bone-marrow transplantation.
Figure 8:
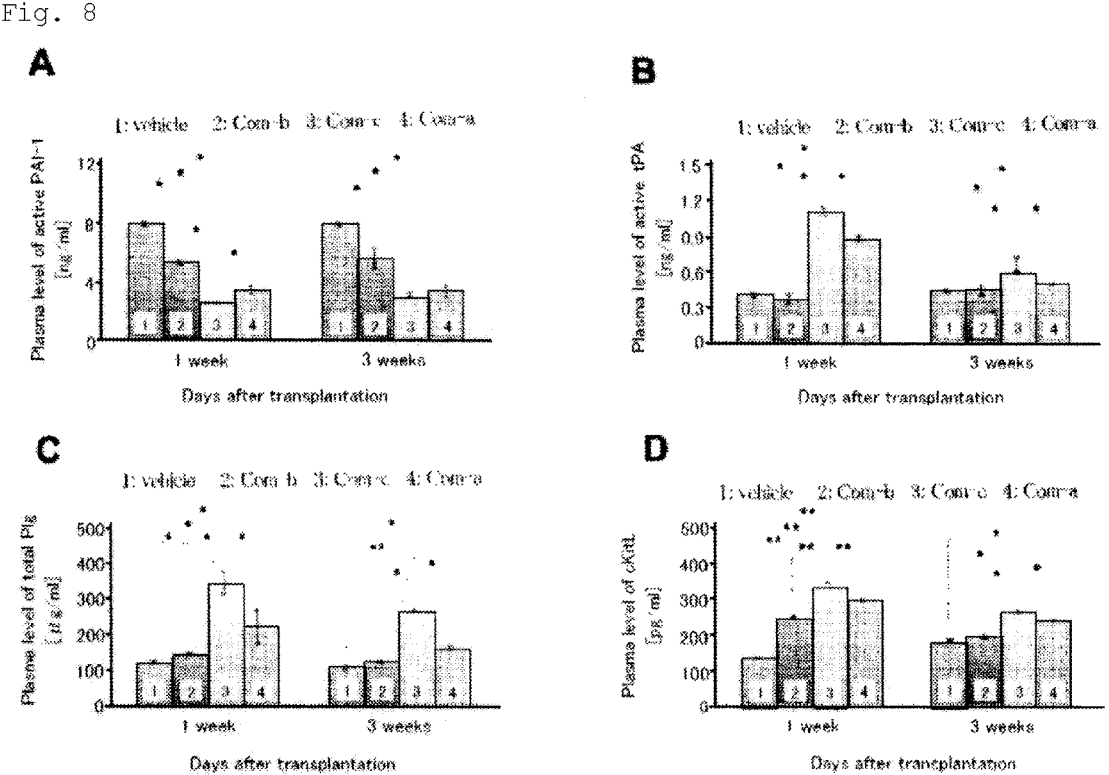
FIGS. 8A to 8D show the results of Experimental Example 5: active PAI-1 level (ng/mL) (A), active tissue-type plasminogen activator (tPA) level (ng/mL) (B), plasminogen level (μg/mL) (C), and cKit ligand level (μg/mL) (D), all of which were in plasma and measured using mouse groups (control group, compound a (Com-a)-administered group, compound b (Com-b)-administered group, and compound c (Com-c)-administered group) by collecting their blood 1 and 3 weeks after bone-marrow transplantation.

Bone marrow was collected from the mice (administered group and control group) 13 weeks after bone-marrow transplantation, and the following was measured: the total number of whole bone marrow (FIG. 7A), the proportion (%) of LSK-CD34 negative cells in the whole bone marrow (FIG. 7B), the total number of CD34(-)KSL cells in the whole bone marrow (FIG. 7C), the proportion (%) of Lin-SLAM cells in the whole bone marrow (FIG. 7D), the total number of Lin-SLAM cells in the whole bone marrow (FIG. 7E), the proportion (%) of bone marrow differentiated cells (CD45.1/Mac1/Gr1 cell) in the whole bone marrow (FIG. 7F), the total number of bone marrow differentiated cells (CD45.1/Mac1/Gr1 cell) in the whole bone marrow (FIG. 7G), the proportion (%) of B-cell lymphoid differentiated cells (CD45.1/B 220 cell) in the whole bone marrow (FIG. 7H), and the total number of B cell lymphoid differentiated cells (CD45.1/B 220 cell) in the whole bone marrow (FIG. 7I). The results are shown in the above-stated figures.

As shown in the results, all of the values were significantly higher in the administered group to which compound a was orally administered than in the control group to which a vehicle was administered (FIGS. 7A to 7I).

The results show that compound a increases the frequency of the hematopoietic stem cells, and enhances the self-renewal capacity of hematopoietic stem cells in long-term evaluation. This also indicates that because compound a achieves not only a rapid hematopoietic recovery, but also enhances a long-term hematopoietic maintenance capacity, compound a can improve hematopoietic disorders more effectively.

Experimental Example 5

The procedures of Experimental Examples 4 (1) and 4 (4) were repeated using compounds b and c, instead of compound a, as a test compound.

Compound a was orally administered in an amount of 100 mg/kg for 4 consecutive days after bone-marrow transplantation. Compounds b and c were orally administered in an amount of 10 mg/kg for 6 consecutive days after bone-marrow transplantation.

1 and 3 weeks after bone-marrow transplantation, blood was collected, and the active PAI-1 level (ng/mL), tissue-type plasminogen activator (tPA) level (ng/mL), plasminogen level (µg/mL), and cKit ligand level (µg/mL) in the plasma were measured.

FIGS. 8A to 8D show the results. FIGS. 8A, 8B, 8C, and 8D, respectively, show the active PAI-1 level (ng/mL) in plasma, active tPA level (ng/mL) in plasma, plg level (µg/mL) in plasma, and cKitL level (µg/mL) in plasma. As shown in FIG. 8, the plg level, tPA level, cKitL level, and total MMP-9 level, all in the plasma, and the white blood cell count in the peripheral blood were all significantly higher in the group (administered group) to which compound a was administered, than in the control group to which vehicle, instead of compound a, was orally administered.

Figure 9:
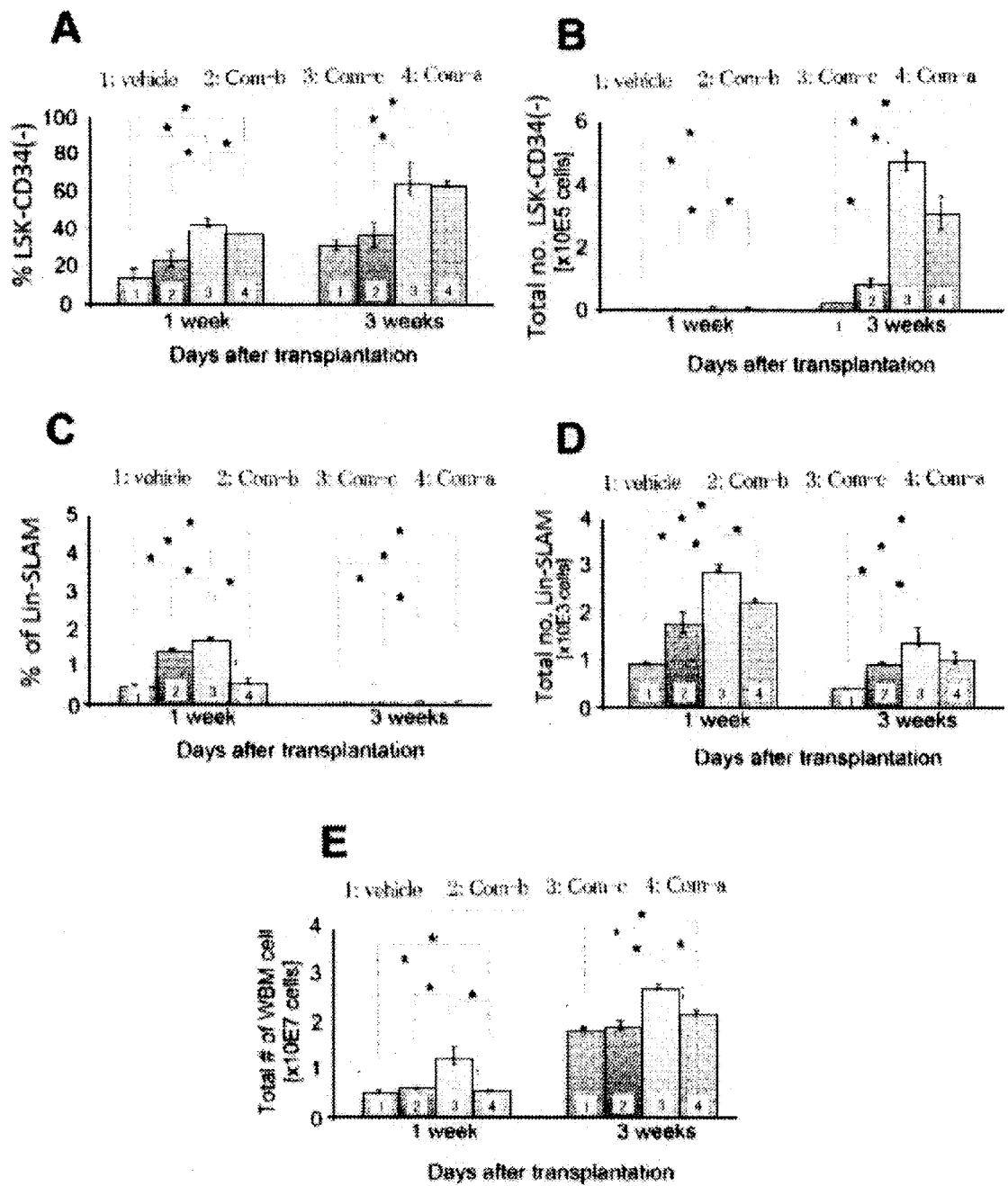
FIGS. 9A to 9E show the results of Experimental Example 5: total number of whole bone marrow cells (E), proportion (%) of LSK-CD34 negative (LSK-CD34(−)) cells in the whole bone marrow (A), total number of LSK-CD34 negative (LSK-CD34(−)) cells in the whole bone marrow (B), proportion (%) of Lin-SLAM cells in the whole bone marrow (C), and total number of Lin-SLAM cells in the whole bone marrow (D), all of which were measured using mouse groups (control (vehicle) group, compound a (Com-a)-administered group, compound b (Com-b)-administered group, and compound c (Com-c)-administered group) by collecting their bone marrow 1 and 3 weeks after bone-marrow transplantation.

Bone marrow was collected 1 and 3 weeks after bone-marrow transplantation. The total number of the whole bone-marrow cells (FIG. 9E), the proportion (%) of LSK-CD34 negative cells in the whole bone marrow (FIG. 9A), the total number of LSK-CD34 negative cells in the whole bone marrow (FIG. 9B), the proportion (%) of Lin-SLAM cells in the whole bone marrow (FIG. 9C), and the total number of Lin-SLAM cells in the whole bone marrow (FIG. 9D) were measured. The results are shown in the above-stated figures.

As shown in the results, all of the values were significantly higher in the administered group to which compound a was orally administered than in the control group to which a vehicle was administered (FIGS. 9A to 9D).

The results show that compounds b and c, as with compound a, increase the frequency of hematopoietic stem cells, and enhance the self-renewal capacity of hematopoietic stem cells (stem cell protecting effect and hematopoietic disorder improving effect). In addition, the enhancement of self-renewal capacity of hematopoietic stem cells suggests that hematopoietic stem cells supposed to be in the resting phase ($G_0$ phase) in the stem-cell niche entered into the cell cycle for cell division ($G_1$ phase).

Experimental Example 6: Toxicity (1) Single-Dose Toxicity Test and 2-Week Repeated-Dose Toxicity Test of Compound a Using In Vivo Rat
(i) Single-Dose Toxicity Test of Compound A Using Rat Male Sprague-Dawley rats (Crl:CD(SD)) with a weight of 162 to 177 g and female Sprague-Dawley rats with a weight of 120 to 136 g were purchased from Charles River Laboratories Japan, Inc. Using the rats, the single-dose toxicity of compound a was evaluated. These rats were administered compound a in amounts of 500, 1,000, and 2,000 mg/kg via oral gavage. After administration, the kinetics of these rats was monitored for 2 weeks, and the toxicity of compound a was evaluated. None of the male and female rats showed abnormality. None of the male and female rats showed obvious weight change caused by compound a, and showed a healthy increase in weight. Further, autopsy was performed and it revealed no particular abnormality in the mice. The overall results suggest that the toxicity of compound a given in a single dose is low.

(ii) 2-Week Repeated-Dose Toxicity Test of Compound a Using Rat

Male Sprague-Dawley rats (Crl:CD(SD)) with a weight of 210 to 238 g and female Sprague-Dawley rats with a weight of 145 to 166 g were purchased from Charles River Laboratories Japan, Inc. Using the rats, the repeated-dose toxicity of compound a was evaluated. Compound a was orally administered in 0 (0.5 w/v % carmellose sodium solution), 200, 600 and 2,000 mg/kg/day dosages to a male rat group and a female rat group each containing 5 Sprague-Dawley rats (Crl:CD(SD), 6-week old at the onset of administration) repeatedly for 2 weeks, and a toxicity test was conducted.

The results reveal no obvious change assumedly caused by compound a in any of general state, weight, food intake, urine test (test item: pH, protein, ketone body, glucose, occult blood, bilirubin, urobilinogen, urine volume, etc.), hematological test (test item: red blood cell count, hemoglobin level, hematocrit value, mean red blood cell volume, mean red blood cell pigment level, mean red blood cell pigment concentration, reticulocyte proportion, platelet count, white blood cell count, differential leukocyte count, etc.), blood chemical test (test item: ALP, total cholesterol, triglyceride, phospholipid, total bilirubin, glucose, urea nitrogen, creatinine, sodium, potassium, chlorine calcium, inorganic phosphorus, total protein, albumin, etc.), and pathological test (detailed morbid anatomy of organs and tissues by visualization, as well as speculum of paraffin-embedded sections of organs/tissues such as cerebellum, cerebrum, pituitary gland, thyroid, parathyroid gland, suprarenal gland, thymus gland, spleen, lung, esophagus, stomach and duodenum, jejunum, ileum, typhlon, colon, rectum, liver, pancreas, kidney, testis, and ovary, stained with hematoxylin-eosin).

(2) Pharmacokinetics

Compound a (50 mg/kg) was administered to male Wister rats (180-200 g) via oral gavage. Before administration (0 h), and 1, 2, 6 and 24 hours after the administration, blood was collected, and the concentration of compound a in plasma of each mouse was analyzed by reversed-phase HPLC. The time at which the maximum drug concentration in blood is observed ($T_{max}$), the maximum drug concentration ($C_{max}$), and half-life (T½) were determined. Table 5 shows the results.

TABLE 5

|  | $T_{max}$ | $C_{max}$ | T½ |
|---|---|---|---|
| Compound a | 2.0 hr | 35.7 µg/ml | 2.5 h |

Experimental Example 7

To demonstrate that compound a can activate the fibrinolytic pathway, and promote the self-renewal capacity of hematopoietic stem cells, the procedure of Experimental Example 4 was repeated.

(1) Experimental Procedure

Figure 10:
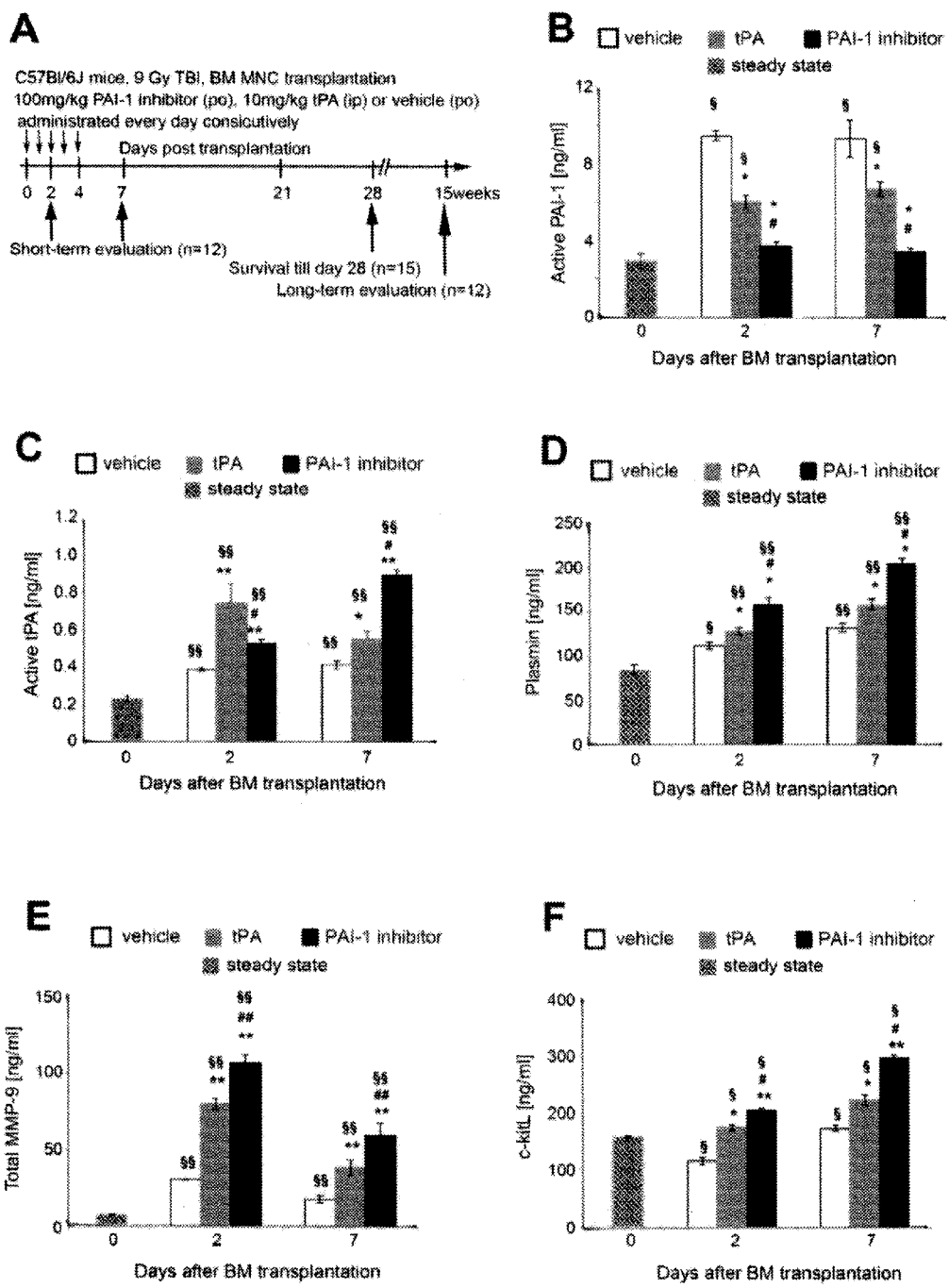
FIGS. 10A to 10F show the results of Experimental Example 7 (2): active PAI-1 (active PAI-1) level (B), active tissue-type plasminogen activator (active tPA) level (ng/mL) (C), plasmin level (ng/mL) (D), total MMP-9 level (ng/mL) (E), and cKit ligand (cKitL) level (ng/mL) (F), all of which were in plasma collected from the control (vehicle) group (white bars), the recombinant tPA-administered group (gray bars), and the PAI-1 inhibitor (compound a)-administered group (black bars) 2 and 7 weeks after bone-marrow transplantation. The hatched bars indicate the values before transplantation. The symbols in the graphs indicate significant differences: *$p<0.05$, **$p<0.001$ indicate the significant difference versus the control group; #$p<0.05$, ##$p<0.001$ indicate the significant difference versus the tPA-administered group; and § $<0.05$, §§ $p<0.001$ indicate the significant difference versus the values observed before transplantation.

In accordance with the procedure described in FIG. 10A, the effect of compound a on hematopoietic recovery was evaluated.

Specifically, before the transplantation of hematopoietic stem cells, recipient mice were exposed to a lethal dose of radiation (9Gy) with an X-ray irradiator (MBR-1520R-3, Hitachi Medico, Tokyo, Japan). Within 4 hours, $1.0 \times 10^6$ bone-marrow mononucleic cells (BM MNC) were intravenously inoculated into retro-orbital plexus. Concurrently with transplantation, compound a (dosage 100 mg/kg) or recombinant tPA (dosage 100 mg/kg, Eisai Co., Ltd) were administered as a test compound via oral gavage, and the test compound was orally administered for 5 consecutive days (administered group). As a control test, instead of the test compound, physiological saline (vehicle) used for dissolving compound a was orally administered in the same manner (control group).

(2) Evaluation of Active PAI-1 Level, Tissue-Type Plasminogen Activator, Plasmin Level, and cKit Ligand in Plasma and Total Thereof Blood was collected 2 and 7 days after bone-marrow transplantation, and the active PAI-1 level (ng/mL), active tissue-type plasminogen activator (active tPA), plasmin level (ng/mL), cKit ligand, and total MMP-9 (Matrix metalloprotein-9) in the plasma were measured. The number of mice used for evaluation was 12 for each group (n=12).

FIGS. 10B to 10F show the results. FIGS. 10B, 10C, 10D, 10E, and 10F, respectively, show the active PAI-1 level (active PAI-1) in the plasma, active tissue-type plasminogen activator (active tPA) level (ng/mL) in the plasma, plasmin level (ng/mL) in the plasma, total MMP-9 level (ng/mL) in the plasma, and cKit ligand (cKitL) level (ng/mL) in the plasma. In these figures, the black bars "■" indicate the results of the oral administration of compound a (the results of the administered group), the gray bars indicate the results of the oral administration of tPA (the results of the administered group), and the white bars "□" indicate the results of the oral administration of physiological saline, instead of compound a (the results of the control group). The hatched bars indicate the data obtained before transplantation.

As shown in FIG. 10B, the control group exhibited higher expressions of active PAI-1 2 and 7 days after bone-marrow transplantation than before transplantation (hatched bars and white bars). The tPA-administered group also exhibited an expression of active PAI-1, although the expression was lower than that of the control group (gray bars). In contrast, the compound a-administered group did not exhibit an expression of active PAI-1, and even after transplantation, the expression level of active PAI-1 was substantially the same as the level before transplantation (black bars).

The results indicate that compound a completely inhibits the activation of PAI-1 in vivo.

The tPA-administered group exhibited the highest level of active tPA in plasma 2 days after bone-marrow transplantation, but 7 days after transplantation, the compound a-administered group exhibited the highest level (FIG. 10C). The results indicate that administration of compound a can maintain the expression level of tPA for a longer time period than administration of tPA.

In addition, the compound a-administered group also exhibited the highest level of plasmin, total MMP-9, and cKitL in plasm 2 and 7 days after transplantation (FIGS. 10D to 10F).

The results indicate that compound a inhibits PAI-1 to thereby activate the fibrinolytic pathway, thus promoting the proliferation of hematopoietic cells.

(3) Evaluation of Bone-Marrow Regeneration Promoting Effect

Subsequently, to demonstrate that compound a promotes bone marrow regeneration, the effect of compound a on the survival rate after myeloablation was evaluated. As an example of myeloablation by irradiation, the survival rate of 15 mice on day 28 from transplantation, and the white blood cell (WBC) count and platelet (PLT) count in the peripheral blood of 6 mice were observed in the experimental example shown in Experimental Example 7 (1).

Figure 11:
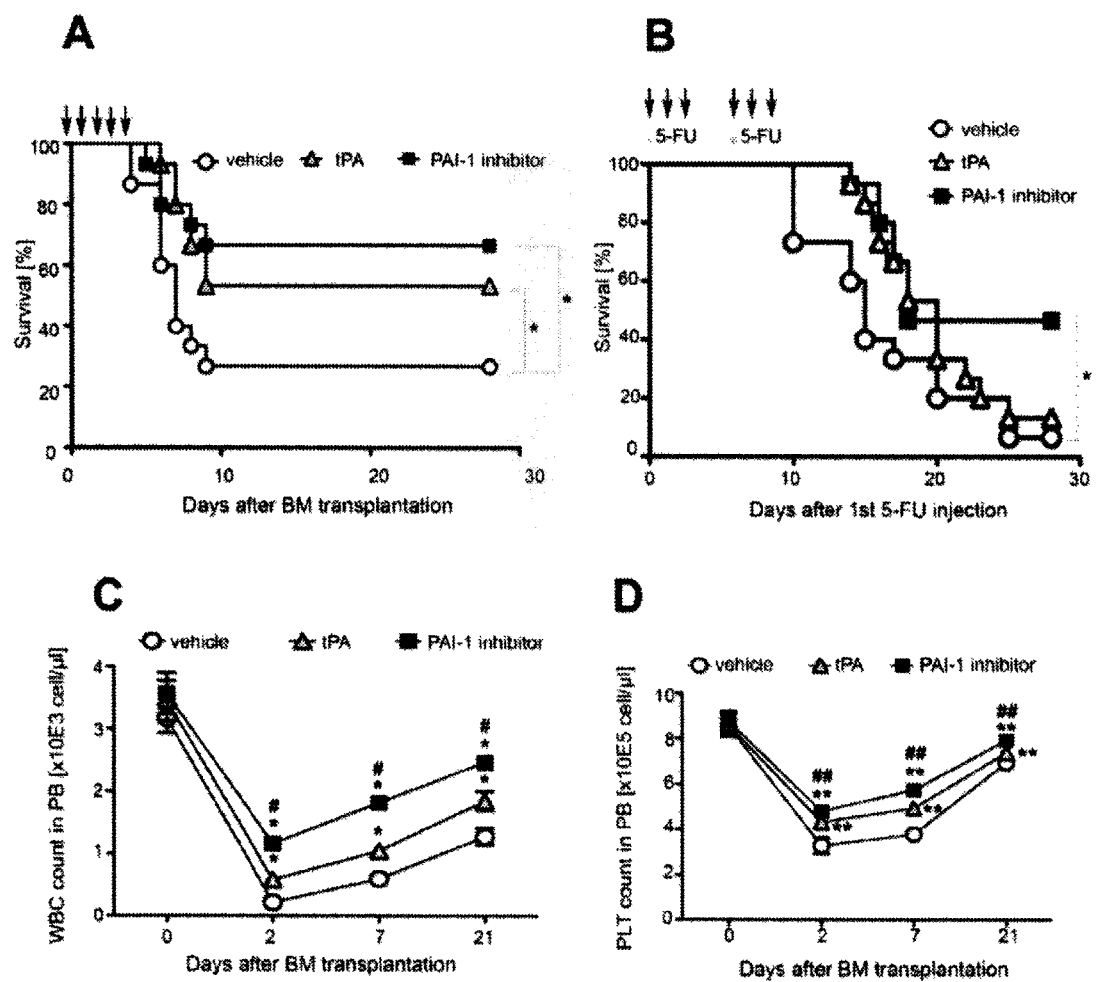
FIGS. 11A to 11D show the results of Experimental Example 7 (3): survival curve (A), white blood cell count in the peripheral blood (C), and platelet count in the peripheral blood (D), all of which were of mice of the control (vehicle) group, tPA-administered group, and PAI-1 inhibitor (compound a)-administered group during a period of 28 days after bone-marrow transplantation conducted in accordance with Experimental Example 7 (1).

As shown in FIG. 11A, the survival rate of the control group (-○-) on day 28 from bone-marrow transplantation was 20%. The survival rate of the tPA-administered group (-▲-) was 50%. In contrast, the survival rate of the compound a-administered group (-■-) was 70%. The comparison of the control group with the compound a-administered group gave a p value of 0.0278 in the log-rank test. The significant difference of the tPA-administered group or compound a-administered group versus the control group was $p<0.05$.

In addition, the white blood cell count and platelet count in the peripheral blood were significantly increased in the tPA-administered group, as compared with the control group, and the white blood cell count and platelet count in the peripheral blood were significantly increased in the compound a-administered group, as compared with the tPA-administered group. The results suggest that the administration of tPA or compound a also rapidly recovers the mature blood cell count. The results also indicate that the effect of compound a is significantly higher.

Subsequently, after administration of a lethal dose of chemotherapeutic agent, the effect produced by tPA administration or compound a administration on bone marrow regeneration was evaluated.

A lethal dose of 5-FU (225 mg/kg) was administered to each group (15 mice for each group) once a week for 2 weeks (i.e., 2 doses), and the survival rate on day 28 was observed.

In this experiment, the survival rate of the control group and tPA-administered group on day 28 was a small percent, and there was no difference in their survival rate. The survival rate of the compound a-administered group on day 28 was about 40%, and the p value of the log-rank test was 0.0190. The survival rate of the compound a-administered group versus the control group was $p<0.05$ in the significant difference test, showing a significant increase.

The results reveal that compound a can promote bone marrow regeneration after myeloablation and bone-marrow transplantation.

Experimental Example 8

The frequency and absolute number of hematopoietic stem cells after bone-marrow transplantation were measured to demonstrate that the activation of fibrinolytic pathways by compound a induces tPA-mediated hematopoietic stem-cell proliferation in bone marrow after bone-marrow transplantation.

(1) Hematopoietic Stem-Cell Proliferation-Promoting Effect of Compound a

In accordance with the procedure of Experimental Example 7 (1), bone marrow was transplanted, and tPA or compound a was administered in the same manner as in Experimental Example 7. Physiological saline was administered to a control group. 1 and 3 weeks after bone-marrow transplantation, 12 mice of each group were measured for the number of bone-marrow mononucleic cells (BM MNC), the frequency and absolute number of Lin-SLAM cells, and the frequency and absolute number of LSK-CD34 negative cells.

Figure 12:
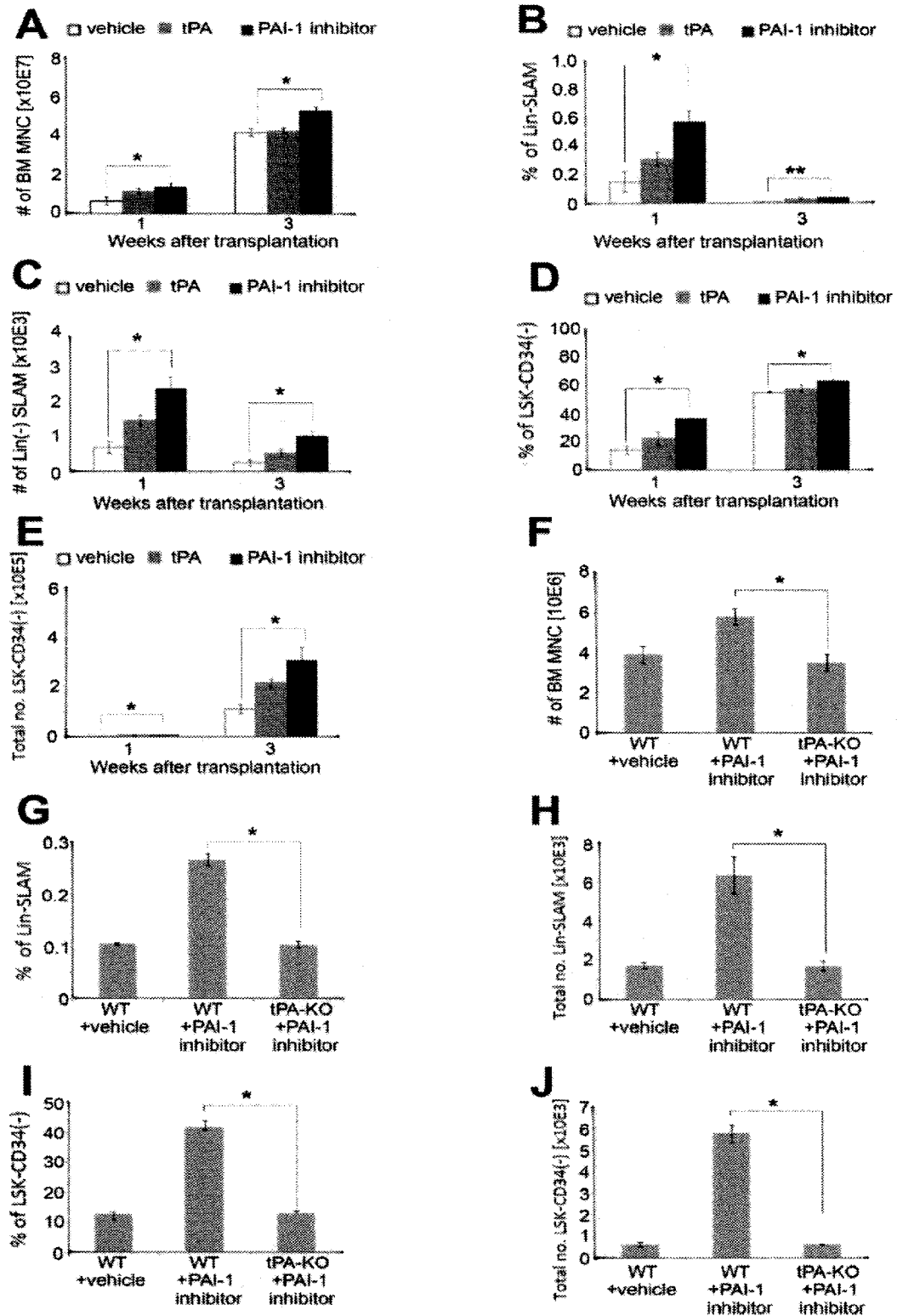
FIGS. 12A to 12E show the results of Experimental Example 8: the number of bone-marrow mononucleic cells (BM MNC) (A), frequency of Lin-SLAM cells (B) and absolute number of Lin-SLAM cells (C), frequency of LSK-CD34 negative (D) and absolute number of LSK-CD34 negative (E), all of which are of mice of the control (vehicle) group, tPA-administered group, and PAI-1 inhibitor (compound a)-administered group to which bone marrow was transplanted in accordance with Experimental Example 7 (1).
FIGS. 12F to 12J also show the number of bone-marrow mononucleic cells (BM MNC) (F), frequency of Lin-SLAM cells (G), absolute number of Lin-SLAM cells (H), frequency of LSK-CD34 negative (LSK-CD34(−)) cells (I) and absolute number LSK-CD34 negative (LSK-CD34(−)) cells (J), all of which were of wild-type mice and tPA-KO-mice that were transplanted with bone marrow and then administered compound a. In the figures, * indicates $p<0.05$, and ** indicates $p<0.001$.

As shown in the results of FIG. 12A, the number of bone-marrow mononucleic cells was increased about three-fold in 1 to 3 weeks after the transplantation. Compared with the control group, the tPA-administered group had a slightly larger number of bone-marrow mononucleic cells. In contrast, the compound a-administered group exhibited a significantly increased number of bone-marrow mononucleic cells as compared with the control group.

In addition, the frequency and absolute number of Lin-SLAM cells 1 and 3 weeks after bone-marrow transplantation were markedly increased in the compound a-administered group (FIGS. 12B and 12C). The frequency of Lin-SLAM cells was higher at 1 week than at 3 weeks after bone-marrow transplantation in every group.

LSK-CD34 negative cells were also markedly increased in the compound a-administered group (FIGS. 12D and 12E). However, the frequency and number of LSK-CD34 negative cells were higher at 3 weeks than at 1 week after bone-marrow transplantation in every group.

This indicates that compound a has a proliferation-inducing effect on both Lin-SLAM cells and LSK-CD34 negative cells. In other words, the results indicate that compound a can promote the proliferation of hematopoietic stem cells.

(2) Correlation Between Hematopoietic Stem-Cell Proliferation-Promoting Effect and PAI-1 Inhibition Subsequently, to demonstrate that the hematopoietic stem-cell proliferation-promoting effect of compound a shown in Experimental Example 8 (1) is mediated by the activation of tPA caused by PAI-1 inhibition, the same bone-marrow transplant experiment as in Experimental Example 7 was conducted on tPA gene-deficient mice (tPA-KO-mice) used as recipients, and it was examined whether the hematopoietic stem-cell proliferation-promoting effect of compound a was observed.

Because tPA-KO-mice do not produce tPA, inhibition of PAI-1 does not activate the fibrinolytic pathway through activation of tPA.

Compound a was administered to wild-type mice and tPA-KO-mice (6 mice for each) that underwent bone-marrow transplantation, and 3 weeks after, the mice were measured for the number of bone-marrow mononucleic cells (BM MNC), the frequency and absolute number of Lin-SLAM cells, and the frequency and absolute number of LSK-CD34 negative cells. Physiological saline was administered to a control group, and the same measurement was conducted.

As shown in FIG. 12F, after bone-marrow transplantation, whereas the wild-type mice exhibited an increase in bone-marrow mononucleic cells because of the administration of compound a, the tPA-KO-mice did not exhibit an increase in bone-marrow mononucleic cells despite the administration of compound a, showing almost the same number as the control group.

Although compound a was administered to tPA-KO-mice, an increase was also not observed in the frequency or absolute number of Lin-SLAM cells, or in the frequency or absolute number of LSK-CD34 negative cells, and there was no difference between the tPA-KO-mice and the control group (FIGS. 12G to 12J).

The results reveal that the promotion of increase in the number of hematopoietic stem cells by compound a after bone-marrow transplantation was mediated by tPA. The results also demonstrate that the promotion of increase in the number of hematopoietic stem cells by compound a after bone-marrow transplantation is a phenomenon caused by inhibition of PAI-1.

Experimental Example 9

Subsequently, to confirm that the promotion of increase in the number of hematopoietic stem cells caused by compound a shown in Experimental Example 8 was an effect for increasing hematopoietic stem cells themselves, the proportion of dividing cells in bone-marrow mononucleic cells and LSK cells of mice administered physiological saline or a test compound after bone-marrow transplantation was measured using a cell proliferation marker.

(1) Proliferation Effect on Hematopoietic Stem Cells (Evaluation Using Ki-67)

In accordance with Experimental Example 7 (1), bone-marrow transplantation was conducted, and after the transplantation, physiological saline (control group), tPA (tPA-administered group), or compound a (compound a-administered group) was administered.

1 week after bone-marrow transplantation, the bone marrow was collected, and Ki-67 protein, which is a cell division marker, was immunostained with anti-Ki-67-FITC antibody (BD Bioscience) to analyze the cells in the cell-division cycle by FACSCalibur.

Figure 13:
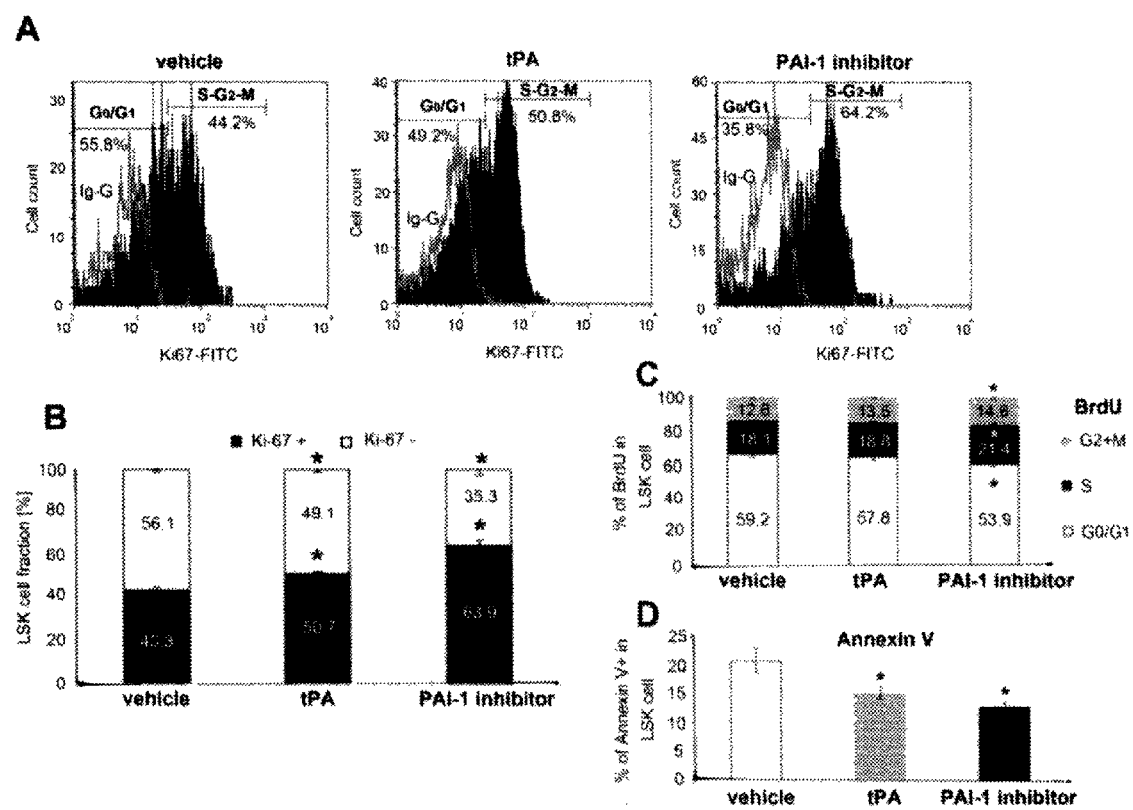
FIGS. 13A to 13D show the results of Experimental Example 9: the fluorescence intensity and positive rate of Ki-67 protein positive cells in bone-marrow mononucleic cells (A) and Ki-67 protein positive rate based on the cells classified into the LSK fraction taken as 100% (B) of the mice of the control (vehicle) group, tPA-administered group, and PAI-1 inhibitor (compound a)-administered group after bone-marrow transplantation.

As shown in FIG. 13A, cells at the $G_0/G_1$ phase are not reactive with the anti-Ki-67-FITC antibody, thus showing weak fluorescence intensity, whereas cells at the $S$-$G_2$-M phase reacted with the anti-Ki-67-FITC antibody and labeled with FITC, thus exhibiting an increased fluorescence intensity, with a shift to the right in the graph. In the control group, the cell count of cells at the $G_0/G_1$ phase was 55.8%, and the cell count of cells at the $S$-$G_2$-M phase was 44.2%, with the cells at $G_0/G_1$ phase being significant. In contrast, in the tPA-administered group, the cell count of cells at the $G_0/G_1$ phase was 49.2%, and the cell count of cells at the $S$-$G_2$-M phase was 50.8%, with the cells at the $S$-$G_2$-M phase being significant. This trend was more prominent in the compound a-administered group, with the cells at the $G_0/G_1$ phase and the cells at the $S$-$G_2$-M phase being 35.8% and 64.2%, respectively.

The results indicate that administration of tPA or compound a increases the number of dividing cells in the post-transplantation bone marrow. The results also indicate that the cell-division-promoting effect on the bone-marrow cells was more effectively produced when compound a was administered than when tPA was administered.

(2) Ki-67 Positive Rate in LSK Fraction

Subsequently, the number of Ki-67 positive cells in the cells of LSK fraction was examined to confirm that the proliferation of hematopoietic stem cells is promoted by compound a.

As shown in FIG. 13B, when the cells classified into the LSK fraction are taken as 100%, Ki-67 positive accounted for 43.3% in the control group, compared with 50.7% in the tPA group, and 63.9% in the compound a-administered group.

The results indicate that administration of tPA or compound a promotes the proliferation of hematopoietic stem-cell marker positive cells. The results also indicate that the effect was more effectively produced when compound a was administered than when tPA was administered.

(3) Proliferation Effect on Hematopoietic Stem Cell (Evaluation Using BrdU)

In addition, to more accurately detect the cells that moved to the S phase, 5-bromo-2-deoxyuridine (BrdU)-FITC (BD Pharmingen) was administered to the control group, tPA group, and compound a-administered group 1 week after bone-marrow transplantation, 3 hours before the collection of bone marrow. 6 mice were used for each group.

Because BrdU is a thymine derivative, BrdU, substituting for thymine, is incorporated into genomic DNA or the like during DNA replication. BrdU more specifically reflects the S phase than Ki-67 protein.

The BrdU incorporated into LSK cells was detected. As shown in FIG. 13C, the cells in the S phase accounted for 18.1% in the control group and 18.8% in the tPA group, compared with 21.4% in the compound a-administered group.

The results indicate that administration of compound a remarkably increases hematopoietic stem cells that move into the cell cycle and self-renew.

(4) Effect of Compound a on Hematopoietic Stem-Cell Apoptosis

After exposure to radiation, the bone-marrow environment is severe, and hematopoietic stem cells must self-renew and regenerate bone marrow in that environment. Because such conditions place substantial stress on hematopoietic stem cells, even hematopoietic stem cells, which have self-renewal capacity, are decreased in activity, and many hematopoietic stem cells undergo apoptosis.

Thus, it was examined whether tPA or compound a affects the hematopoietic stem-cell apoptosis that occurs after bone-marrow transplantation.

1 week after bone-marrow transplantation, bone marrow was collected from the control group, tPA group, and compound a-administered group (6 mice for each group), and Annexin V, which appears specifically in apoptosis, was detected with anti-Annexin V antibody immunostaining.

As shown in the results of FIG. 13D, compared with the control group, the tPA group and the compound a-administered group exhibited a decrease in the proportion of cells that were induced apoptosis. This trend was more prominent in the compound a-administered group.

The results reveal that tPA and compound a protect hematopoietic stem cells from stress under severe bone-marrow environments at the early phase of bone-marrow transplantation, and inhibit hematopoietic stem cells from undergoing apoptosis. This indicates that inhibition of PAI-1 can protect hematopoietic stem cells at the early phase of transplantation from stress.

Experimental Example 10

It is known that as in post-bone-marrow transplantation, when the proliferation of hematopoietic stem cells is promoted, bone marrow stem cells are rapidly depleted, and long-term homeostasis of the hematopoietic system cannot be maintained.

Thus, it was examined how a PAI-1 inhibitor affects the long-term maintenance of hematopoietic tissues.

(1) Frequency of LSK-CD34 Negative Cell 15 Weeks after Bone-Marrow Transplantation 15 weeks after bone-marrow transplantation, the control group, tPA group, and compound a-administered group (12 mice for each group) were measured for the number of bone-marrow mononucleic cells (BM MNC), frequency and absolute number of Lin-SLAM cells, and frequency of and absolute number LSK-CD34 negative cells.

As shown in the results of FIGS. 14A to 14E, the compound a-administered group exhibited the highest values in the number of bone-marrow mononucleic cells, frequency of and absolute number LSK-CD34 negative cells, and frequency and absolute number of Lin-SLAM cells.

(2) Evaluation in Retransplantation

Subsequently, it was examined how a PAI-1 inhibitor affects long-term hematopoietic stem cells that maintain a self-renewal capacity for a long time.

15 weeks after the initial bone-marrow transplantation, bone marrow was collected from mice of the control group, tPA group, and compound a-administered group, and the collected bone marrow was transplanted into other mice (successive transplantation). In the successive transplantation, none of physiological saline, tPA, or compound a was administered.

12 weeks after successive transplantation, the chimerism of donor-derived bone marrow hematopoietic cells was measured.

Figure 14:
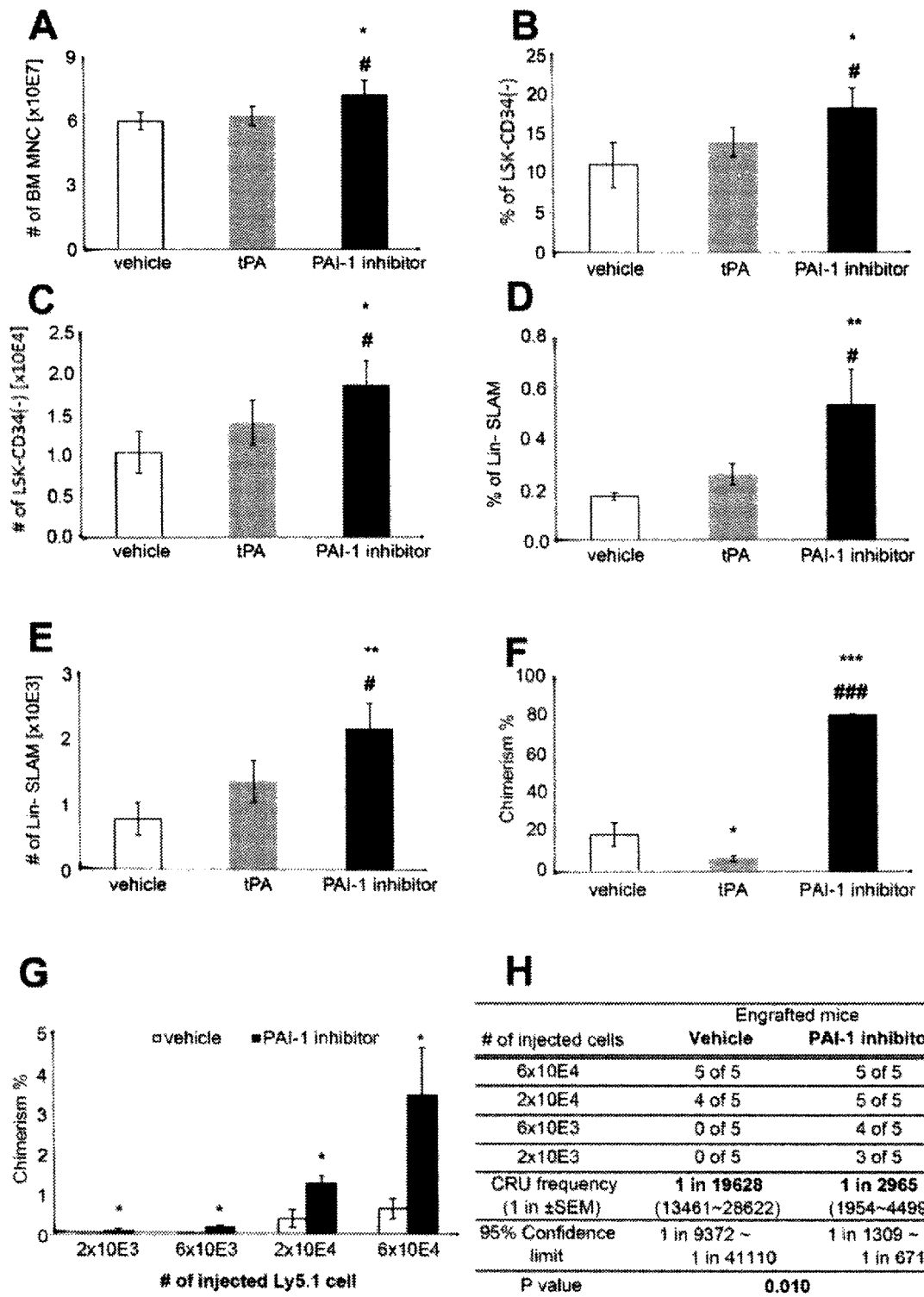
FIGS. 14A to 14H show the results of Experimental Example 10: the number of bone-marrow mononucleic cells (BM MNC) (A), frequency of LSK-CD34 negative cells (LSK-CD34(−)) (B), absolute number of LSK-CD34 negative cells (LSK-CD34(−)) (C), frequency of Lin-SLAM cells (D), and absolute number of Lin-SLAM cells (E), all of which were of the mice of the control (vehicle) group, tPA-administered group, and PAI-1 inhibitor (compound a)-administered group 15 weeks after bone-marrow transplantation. In the figures, * and ** indicate the significant difference versus the control group, * is $p<0.05$, and ** is $p<0.001$. In the figures, # indicates the significant difference versus the tPA-administered group, and # indicates $p<0.05$.

As shown in the results of FIG. 14F, the compound a-administered group exhibited a marked increase in the chimerism.

The results indicate that compound a administered at the time the first transplantation was conducted can maintain the self-renewal capacity of long-term hematopoietic stem cells.

The results also indicate that inhibition of PAI-1 activity not only promotes rapid bone marrow regeneration at the early phase of transplantation, but also enhances the self-renewal capacity of long-term hematopoietic stem cells.

(3) Graft Survival Rate of Transplanted Hematopoietic Stem Cell

To compare the frequency of long-term hematopoietic stem cell, donor-derived bone marrow to be transplanted first was diluted and transplanted, and the effect of PAI-1 inhibition was evaluated by a limiting dilution technique.

The collected bone-marrow mononucleic cells were diluted such that Ly5.1 positive bone-marrow mononucleic cell count gave 2×10E3, 6×10E3, 2×10E4, and 6×10E4, and then Ly5.1 positive bone-marrow mononucleic cells of each count were transplanted, together with 5×10E5 Ly5.2 positive competitor cells, into 20 mice. For transplantation, mice were divided into 2 groups, i.e., a compound a-administered group to which compound a was to be administered and a control group to which physiological saline was to be administered (8 groups in total), and the chimerism (the positive rate of Ly5.1 positive bone-marrow mononucleic cells) was measured 12 weeks after the transplantation.

As shown in the results of FIG. 14G, the groups to which compound a were administered exhibited significant increases in the chimerism regardless of the number of transplanted Ly5.1 positive bone-marrow mononucleic cells.

This indicates that administration of compound a increases the graft survival rate of transplanted hematopoietic stem cells.

Further, bone marrow was collected from the control groups and the compound a-administered groups to both of which Ly5.1 positive bone-marrow mononucleic cells of the above-described numbers were transplanted, and the collected bone marrow was successively transplanted into other mice. At the time successive transplantation was conducted, neither physiological saline nor the compound was administered. 12 weeks after the successive transplantation, bone marrow was collected from the mice, and Ly5.1 positive cells in the bone-marrow mononucleic cells were measured. The number of mice that exhibited more than 0.05% of the frequency of Ly5.1 positive cells was counted.

As shown in FIG. 14H, in the control group, when 2×10E4 or more Ly5.1 positive bone-marrow mononucleic cells were not transplanted, mice exhibiting 0.05% or more of the frequency of Ly5.1 positive cells were not obtained, whereas in the compound d-administered group, even mice transplanted with bone marrow derived from mice transplanted with 2×10E3 Ly5.1 positive cells exhibited more than 0.05% of the frequency of Ly5.1 positive cells at a rate of 3 out of 5 mice.

After successive transplantation, the frequency (CRU frequency) of hematopoietic stem cells having the hematopoietic regeneration capacity was calculated. The hematopoietic stem cell was observed at a rate of 1 out of 19,628 in the control group, whereas hematopoietic stem cell was observed at a rate of 1 out of 2,965 in the compound a-administered group, showing an increase in the frequency. In other words, this indicates that administration of compound a can maintain 6 or more time higher frequency of hematopoietic stem cells having the hematopoietic regeneration capacity, even after successive transplantation.

The results indicate that inhibition of PAI-1 increases the graft survival rate of hematopoietic stem cells, and an increase in the proportion of hematopoietic stem cells further enhances the self-renewal capacity of long-term stem cells.

Experimental Example 11

As shown in Experimental Examples 4 and 5, PAI-1 inhibitors such as compound a, compound b, and compound c act to increase the frequency of hematopoietic stem cells and to enhance the self-renewal capacity of hematopoietic stem cells; i.e., the inhibitors act to transit the cell cycle from the $G_0$ phase to the $G_1$ phase.

The results indicate that the PAI-1 inhibitors also have an effect on leukemia stem cells in the similar manner as on hematopoietic stem cells, and stimulation of leukemia stem cells at the $G_0$ phase may transit the leukemia stem cells to the division phase.

Typically, antitumor agents target actively dividing cells, and thus, the effect of the antitumor agents on leukemia stem cells at the resting phase is considered to be low. If a PAI-1 inhibitor can transit leukemia stem cells from the $G_0$ phase to the $G_1$ phase, leukemia stem cells will undergo active cell division, and even leukemia stem cells, which are resistant to antitumor agents, are expected to exhibit sensitivity to antitumor agents.

Thus, the combinational effect produced by compound a (PAI-1 inhibitor) and a molecular-targeted drug, imatinib, (antitumor agent) was examined using chronic myelogenous leukemia model mice.

(1) Preparation of Chronic Myelogenous Leukemia Model Mice p210(BCR-ABL) gene was inserted into a MIGR1 vector, and GFP cDNA was further incorporated as a reporter gene downstream of the gene (hereinafter, the vector is referred to as "p210-GFP"). p210-GFP was infected with 32D cells (C3H/HeJ mice cell line), and chronic myelogenous leukemia (hereinafter, referred to as "CML") cells were prepared. $2.5 \times 10^5$ of the thus-obtained CML cells (32Dp210(BCR-ABL)-GFP cells, hereinafter, referred to as "32Dp210-GFP cells") were intravenously administered into the retro-orbital plexus of C3H/HeJ mice. 7 to 10 days after the transplantation, the abundance ratio of GFP cells in the peripheral blood was analyzed, and mice with more than 3% of abundance ratio were used as chronic myelogenous leukemia model mice in the following experiments.

Figure 15:
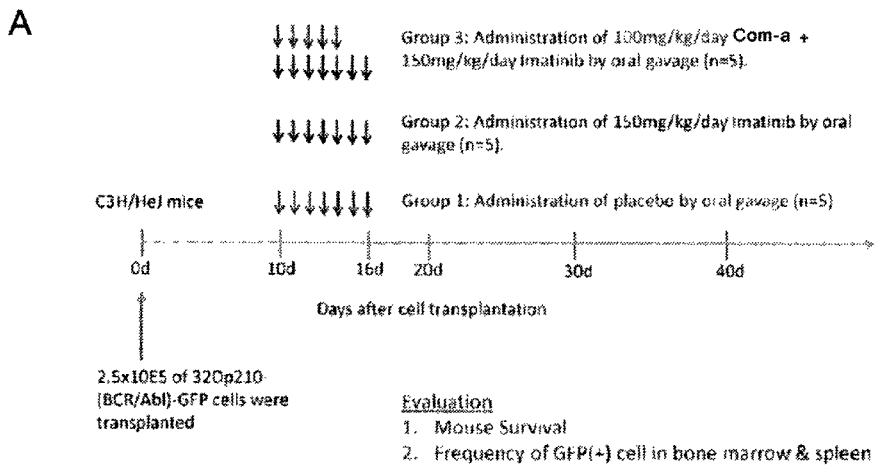
FIGS. 15A to 15D show the results of Experimental Example 11. In chronic myelogenous leukemia model mice, the effect of combinational administration of imatinib and compound a was observed.
Figure 15:
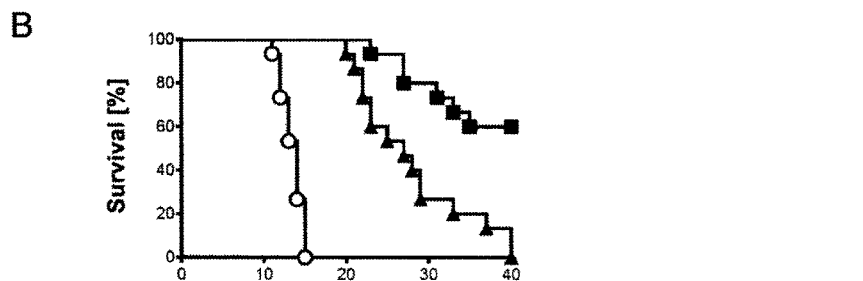
Figure 15:
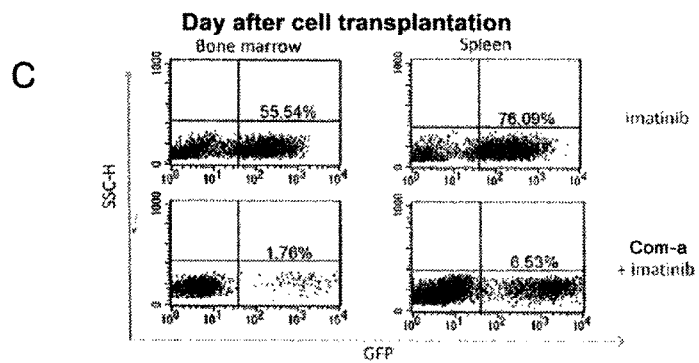
Figure 15:
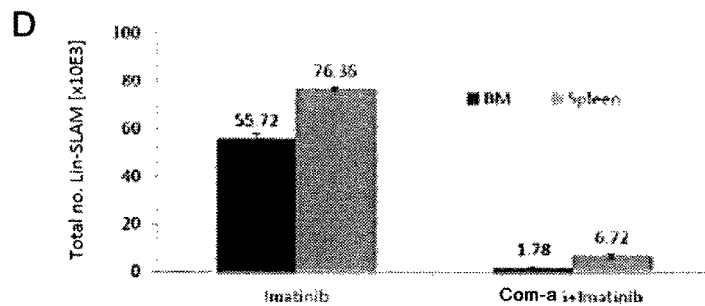

(2) Drug Administration Procedure 15 chronic myelogenous leukemia model mice prepared by using the procedure described above were divided into the following 3 groups (each group: n=15), and a test drug was administered to the mice in accordance with the protocol shown in FIG. 15A.

Group 1: placebo group (physiological saline was administered via gavage)

Group 2: imatinib group (imatinib [150 mg/kg/day] was administered via gavage)

Group 3: imatinib+compound a group (imatinib [150 mg/kg/day] and compound a [100 mg/kg/day] were administered via gavage)

10 days (day 10) after the day on which CML cells were intravenously inoculated (day 0), administration of test drugs to the groups was started. The placebo group and the imatinib group were administered the respective test drugs once a day from day 10 to day 16 (7 doses in total). The imatinib+compound a group was administered imatinib once a day from day 10 to day 16 (7 doses in total), and also administered compound a once a day from day 10 to day 14 (5 doses in total).

(3) Results (3-1) Survival Rate

FIG. 15B shows the survival rate of mice of each group. As shown in FIG. 15B, all of the 5 subject mice of the placebo group (○) died during the period from day 10 to day 17. The mice of imatinib group (▲) survived longer than the mice of the placebo group, but all of the mice died by day 40. In contrast, although 6 mice of the imatinib+compound a group (■) died during the period from day 30 to day 50, the survival rate on day 50 was 60%. The median survival period was 14 days for the placebo group, 27 days for the imatinib group, and 40 days for the imatinib+compound a group. The significant difference in survival rate of the imatinib+compound a group versus the imatinib group was p<0.0001, indicating that the use of imatinib (antitumor agent) and compound a (PAI-1 inhibitor) in combination can significantly prolong the survival rate (good prognosis).

(3-2) Number of CML Cells in Bone Marrow and Spleen

As described above, 32Dp210-GFP includes GFP as a reporter gene, and thus, the CML cells having 32Dp210-GFP inserted (32Dp210-GFP cells) are GFP-positive. Therefore, using FACS (FACS (BD Biosciences: FACSCalibur), the frequency of CML cells (32Dp210-GFP cells) in mononucleic cells of the bone marrow and spleen was measured and compared between the imatinib group and the imatinib+compound a group.

FIGS. 15C and 15D show the results. As shown in FIGS. 15C and 15D, the frequency of 32Dp210-GFP cells in bone-marrow mononucleic cells was about 55% in the imatinib group, which is compared with about 1.7% in the imatinib+compound a group. In the imatinib+compound a group, the number of CML cells (32Dp210-GFP cells) was also markedly decreased. In the spleen also, the frequency of CML cells (32Dp210-GFP cells) was about 76% in the imatinib group, compared with about 6.6% in the imatinib+compound a group, and the number of CML cells (32Dp210-GFP cells) was markedly decreased in the imatinib+compound a group.

The results indicate that the use of imatinib (antitumor agent) and compound a (PAI-1 inhibitor) in combination provides a more potent tumor-cell killing effect than the use of the antitumor agent (imatinib) alone.

The results also strongly suggest that the use of an antitumor agent in combination with compound a (PAI-1 inhibitor) inhibits the PAI-1 activity to thereby transit leukemia stem cells into the $G_1$ phase, thus enhancing the sensitivity of leukemia stem cells to the antitumor agent.

Experimental Example 12

The same experiment as in Experimental Example 11 was conducted using compound c as a PAI-1 inhibitor.
(1) Experimental Method
Chronic myelogenous leukemia model mice prepared in the same manner as in Experimental Example 11 were divided into the following 3 groups (each group: n=10), and the groups were administered respective test drugs in accordance with the protocol shown in FIG. 15A.
Group 1: placebo group (physiological saline was administered via gavage)
Group 2: imatinib group (imatinib [150 mg/kg/day] was administered via gavage)
Group 3: imatinib+compound c group (imatinib [150 mg/kg/day] and compound c [10 mg/kg/day] were administered via gavage)

Figure 16:
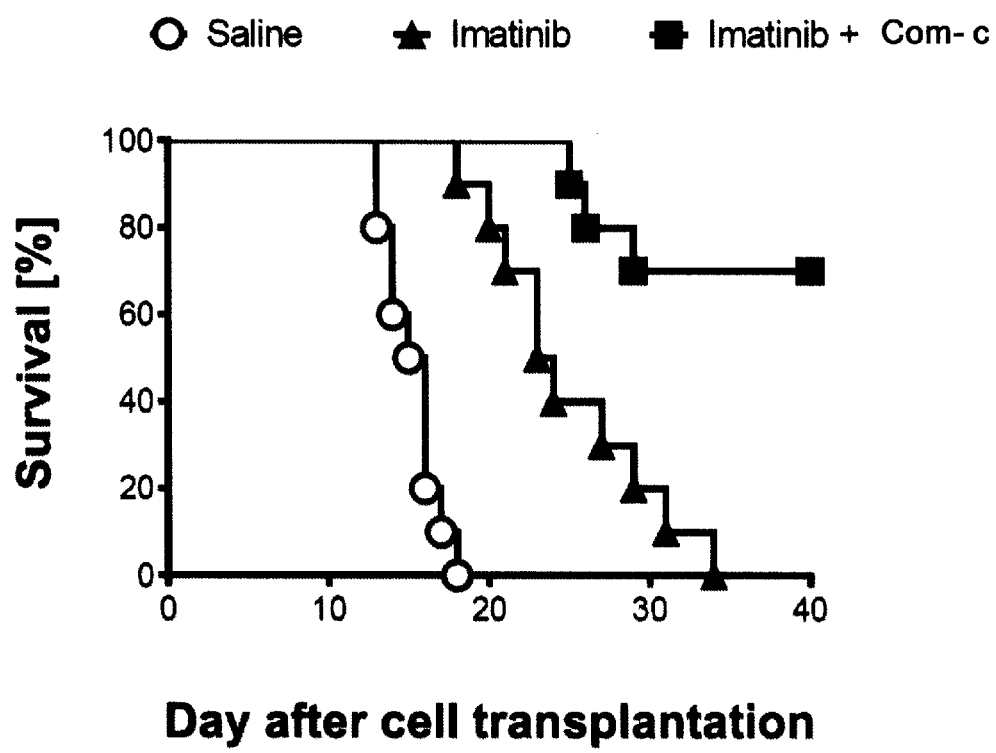
FIG. 16 shows the results of Experimental Example 12. The effect of combinational administration of imatinib and compound c was observed in chronic myelogenous leukemia model mice.

8 days (day 8) after the day on which CML cells (32Dp210-GFP cells) were intravenously inoculated (day 0), administration of the test drugs to the groups was started. The placebo group and the imatinib group were administered the respective test drugs once a day from day 8 to day 14 (7 doses in total). The imatinib+compound c group was administered imatinib once a day from day 8 to day 14 (7 doses in total), and also administered compound c once a day from day 8 to day 14 (7 doses in total).
(2) Results
FIG. 16 shows the results. As shown in FIG. 16, all of the 10 subject mice in the placebo group (○) died during the period from day 10 to day 20. The mice of the imatinib group (▲) survived longer than the mice of the placebo group, but all of the mice died by day 35. In contrast, although 3 mice in the imatinib+compound c group (■) died during the period from day 25 to day 40, the survival rate was 70% on day 40. The median survival period was 15.5 days for the placebo group, 23.5 days for the imatinib group, and 40 days for the imatinib+compound c group. The results reveal that the use of imatinib (antitumor agent) in combination with compound c (PAI-1 inhibitor) significantly prolongs the survival period (good prognosis). This indicates that as with compound a in Experimental Example 11, the use of the antitumor agent (imatinib) in combination with compound c (PAI-1 inhibitor) can provide a more potent tumor-cell killing effect than the use of imatinib alone.

The results of Experimental Examples 11 and 12 strongly suggest that the use of an antitumor agent in combination with a PAI-1 inhibitor inhibits the PAI-1 activity to thereby transit leukemia stem cells into the $G_1$ phase, enhancing the sensitivity of leukemia stem cells to the antitumor agent.

Experimental Example 13

To confirm whether the effect of PAI-1 inhibitor compound c shown in Experimental Example 12 described above is G-CSF-mediated, it was evaluated whether a neutralizing antibody of G-CSF affects the hematopoietic regeneration-promoting effect and the tumor-cell killing effect of compound c using bone-marrow transplanted animals.
(1) Experimental Method
Bone-marrow transplanted mice were prepared in the same manner as in Experimental Example 4, and compound c, G-CSF, and G-CSF neutralizing antibody were examined for the effects. Specifically, the bone-marrow transplanted mice were divided into 5 groups as shown below (each group: n=5) and orally administered respective test drugs.
Group 1: vehicle group (physiological saline was administered via gavage) ("v group")
Group 2: compound c group (compound c [10 mg/kg/day] was administered via gavage) ("TM group")
Group 3: G-CSF group (G-CSF [150 µg/kg/day] was administered via gavage) ("G group")
Group 4: vehicle+anti-G-CSF group (physiological saline+G-CSF neutralizing antibody [500 µg/kg/day] was administered via gavage) ("v+Ab group")
Group 5: compound c+anti-G-CSF group (compound c [500 µg/kg/day]+G-CSF neutralizing antibody [500 µg/kg/day] was administered via gavage) ("TM+Ab group")

Concurrently with bone-marrow transplantation, administration of physiological saline (vehicle) to the vehicle group via gavage was started, and the administration continued for 5 consecutive days. Concurrently with bone-marrow transplantation, administration of compound c (10 mg/kg/day) to the compound c group via gavage was started, and the administration continued for 5 consecutive days. Concurrently with bone-marrow transplantation, subcutaneous administration of G-CSF (150 µg/kg/day) to the G-CSF group was started, and the administration continued for 5 consecutive days. Concurrently with bone-marrow transplantation, gavage administration of physiological saline and subcutaneous administration of G-CSF neutralizing antibody (R&D) (500 µg/kg/day) to the vehicle+anti-G-CSF group were started, and the administration continued for 5 consecutive days. Concurrently with bone-marrow transplantation, gavage administration of compound c (10 mg/kg/day) and intraperitoneal administration of G-CSF neutralizing antibody (R&D) (500 µg/kg/day) to the compound c+anti-G-CSF group were started, and the administration continued for 5 consecutive days.

Figure 17:
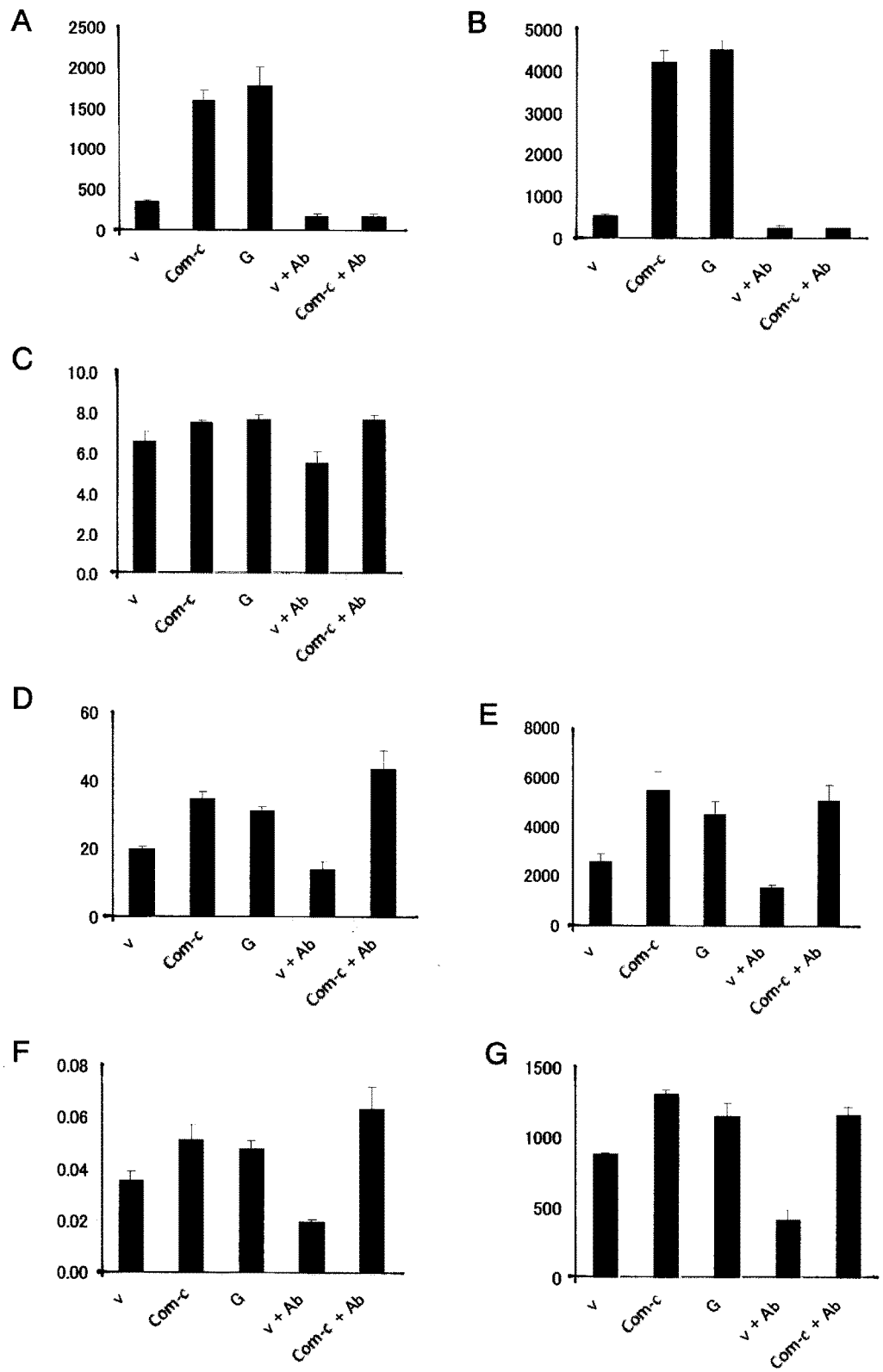
FIGS. 17A to 17G show the results of Experimental Example 13. The effect of the combinational administration of compound c on G-CSF was observed: G-CSF concentration in the plasma (pg/ml) (A), G-CSF concentration in the bone-marrow fluid (pg/ml) (B), absolute number of bone-marrow mononucleic cells (×10E7) (C), frequency of LSK-CD34 negative (LSK-CD34(−)) cells (D), number of LSK-CD34 negative (LSK-CD34(−)) cells (E), frequency of Lin-SLAM cells (F), and number of Lin-SLAM cells (G) in the vehicle (v) group, compound c (Com-c) group, G-CSF (G) group, vehicle+anti-GCF(V+Ab) group, and compound c+anti-GCF (Com-c+Ab) group.

1 week after bone-marrow transplantation, plasma and bone-marrow fluids were collected from mice of each group (v group, TM group, G group, v+Ab group, and TM+Ab group), and the G-CSF concentration (pg/ml) was measured by ELISA. The following were determined in accordance with an ordinary procedure: (B) G-CSF concentration (pg/ml) in bone-marrow fluids, (C) total number of mononucleic cells (×10E7 cell) in the bone marrow, (D) proportion (%) of LSK CD34 negative cells in the bone marrow, (E) total number of LSK CD34 negative cells in the bone marrow, (F) proportion (%) of Lin-SLAM cells in the bone marrow, and (G) total number of Lin-SLAM cells in the bone marrow.
(2) Results
FIG. 17 shows the results.
As shown in the results of FIGS. 17A and 17B, the compound c group (TM group) and G-CSF group (G group)

exhibited significant increases in G-CSF concentration in the plasma and bone-marrow fluids, as compared with the vehicle group (v group). In contrast, the vehicle+anti-G-CSF group (v+Ab group) and compound c+anti-G-CSF group (TM+Ab) administered G-CSF neutralizing antibody in combination exhibited an increase in G-CSF in neither plasma nor bone-marrow fluids.

In addition, as shown in FIG. 17C, the number of BM MNC was more increased in the TM group and G group than in the v group. Whereas the v+Ab group exhibited a decrease in the absolute number of cells, the TM+Ab group did not exhibit a decrease in the number of the cells. This indicates that the increase in the number of cells caused by compound c is mediated by a pathway totally different from the control by G-CSF.

The proportion and the number of LSK CD34 negative cells were also increased in the compound c group and G group, as compared with the v group. In contrast, the proportion and the number of LSK CD34 negative cells were markedly decreased in the v+Ab group, which had been administered G-CSF neutralizing antibody. However, the proportion and the number of LSK-CD34 negative cells were not decreased in the TM+Ab group (FIGS. 17D and 17E).

Likewise, the proportion and the number of Lin-SLAM cells were increased in the TM group and G group, as compared with the v group. In contrast, the proportion and the number of Lin-SLAM cells were markedly decreased in the v+Ab group, which had been administered G-CSF neutralizing antibody. However, the proportion and the number of Lin-SLAM cells were not decreased in the TM+Ab group (FIGS. 17F and 17G).

The results indicate that the transition of hematopoietic stem cells from the $G_0$ phase to the $G_1$ phase and the enhancement in the self-renewal capacity of hematopoietic stem cells, both caused by a PAI-1 inhibitor, are not affected by G-CSF neutralizing antibody. In other words, the results reveal that the transfer of hematopoietic stem cells from the $G_0$ to $G_1$ phase, and the enhancement in the self-renewal capacity of hematopoietic stem cells caused by a PAI-1 inhibitor are evoked by a pathway totally different from that of G-CSF.

Experimental Example 14

As shown in Experimental Examples 11 and 12, the tumor-cell killing effect of an antitumor agent is enhanced when the antitumor agent is used in combination with a PAI-1 inhibitor. In this experiment, whether G-CSF is involved in the effect was examined. Compound a was used as a PAI-1 inhibitor.

The following groups (n=5) of chronic myelogenous leukemia model mice were examined in the same manner as in Experimental Example 11.

Group 1: placebo group (physiological saline was administered via gavage)

Group 2: IM group (imatinib [150 mg/kg/day] was administered via gavage)

Group 3: IM+anti-G-CSF group (imatinib [150 mg/kg/day] was administered via gavage, G-CSF neutralizing antibody [500 µg/kg/day] was subcutaneously administered)

Group 4: IM+TM group (imatinib [150 mg/kg/day] and compound a [100 mg/kg/day] were administered via gavage)

Group 5: IM+TM+anti-G-CSF group (imatinib [150 mg/kg/day] and compound a [100 mg/kg/day] were administered via gavage, and G-CSF neutralizing antibody [500 µg/kg/day] was subcutaneously administered)

Figure 18:
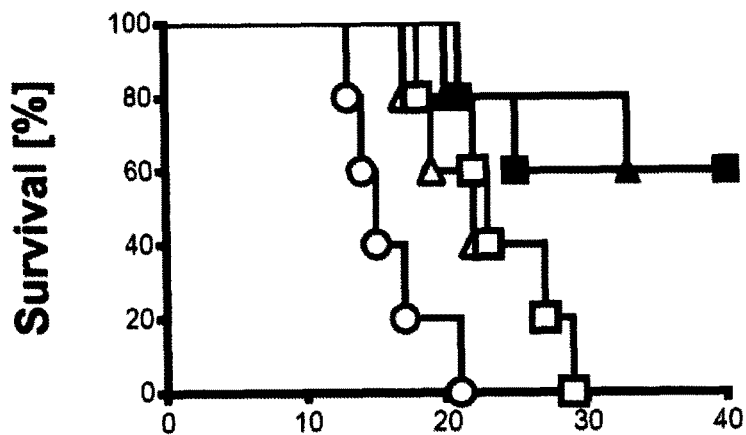
FIG. 18 shows the results of Experimental Example 14. The effect of combinational administration of imatinib and compound c on G-CSF was observed in chronic myelogenous leukemia model mice.

The day on which CML cells were inoculated was set as day 0, and each test drug was administered from day 8 to day 14 (7 doses in total). FIG. 18 shows the results.

As shown in FIG. 18, all of the 5 subject mice in the placebo group (○) died during the period from day 12 to day 21. The mice of the IM group (Δ) and the mice of the IM+anti-G-CSF group (□) survived longer than the mice of the placebo group, but all of the mice died by day 30. In contrast, although 2 mice of the IM+TM group (▲) died during the period from day 20 to day 50, the survival rate on day 40 was 60%. 2 mice of the IM+TM+anti-G-CSF group (■) administered G-CSF neutralizing antibody died during the period from day 20 to day 50, but the survival rate on day 40 was 60%. The median survival period was 15 days for the placebo group, 22 days for the IM group, 23 days for the IM+anti-G-CSF group, 40 days for the IM+TM group, and 40 days for the IM+TM+anti-G-CSF group. There was no difference in survival rate or survival period between the IM+TM group and the IM+TM+anti-G-CSF group.

The results indicate that a PAI-1 inhibitor enhances the tumor-cell-killing effect of an antitumor agent independently from G-CSF Experimental Example 15

In the same manner as in Experimental Example 11, an experiment was conducted using chronic myelogenous leukemia model mice to confirm the combinational effect of compound c and a molecular targeted drug imatinib (antitumor agent).

(1) Drug Administration Procedure

Chronic myelogenous leukemia model mice prepared in accordance with the procedure of Experimental Example 11 (1) were divided into 3 groups (each group: n=15) and administered respective test drugs.

Group 1: placebo group (physiological saline was administered via gavage)

Group 2: imatinib group (imatinib [150 mg/kg/day] was administered via gavage)

Group 3: imatinib+compound c group (imatinib [150 mg/kg/day] and compound c [10 mg/kg/day] were administered via gavage)

8 days (day 8) after the day on which CML cells were intravenously inoculated (day 0), administration of test drugs to the groups was started. The placebo group and the imatinib group were administered the respective test drugs once a day from day 8 to day 14 (7 doses in total). The imatinib+compound c group was administered imatinib once a day from day 8 to day 14 (7 doses in total), and also administered compound c once a day from day 8 to day 14 (7 doses in total).

(2) Results

Figure 19:
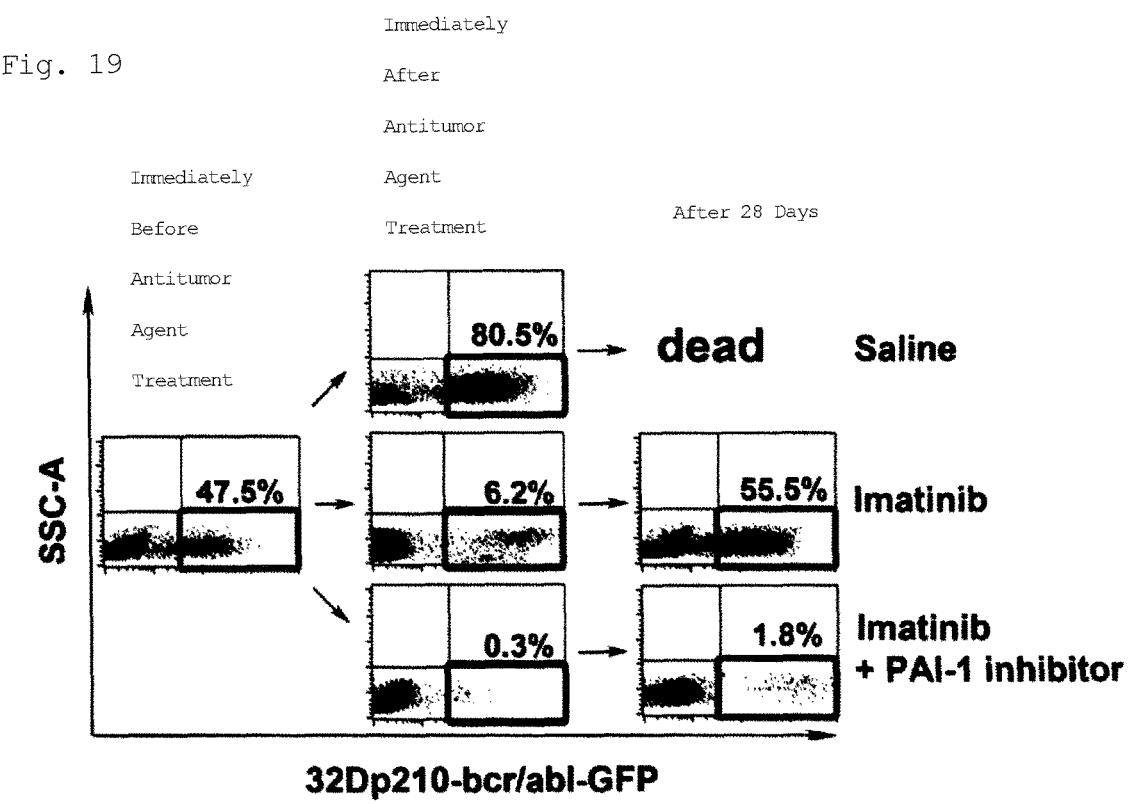
FIG. 19 shows the results of Experimental Example 15: CML cells engrafted on the bone marrow were analyzed by FACS immediately before the administration of a test drug (day 8.

CML cells engrafted onto bone marrow were analyzed by FACS immediately before the administration of a test drug (day 8; "immediately before antitumor agent treatment" in FIG. 19), immediately after the completion of administration of a test drug (day 14; "immediately after antitumor agent treatment" in FIG. 19), and day 28 from the start of administration of a test drug (day 36; "after 28 days" in FIG. 19). FIG. 19 shows the results. About 50% leukemia cells were grafted on the bone marrow immediately before administration of a test drug (day 8; "immediately before antitumor agent treatment" in FIG. 19). After the tumor-bearing mice were administered a test drug 7 times (day 14), the proportion of CML cells was analyzed. The analysis confirmed a marked decrease in CML cells in the imatinib group as well as in the imatinib+compound c group. After a course of observation, mice surviving on day 36 were analyzed again, and the analysis confirmed that the group administered imatinib alone relapsed and exhibited an increase in leukemia cells in the bone marrow (55.5%). In contrast, the imatinib+compound c group did not exhibit an increase in CML cells (1.8%), demonstrating a higher therapeutic effect. All of the mice in the group administered physiological saline died.

The results indicate that chemotherapy using an antitumor agent in combination with a PAI-1 inhibitor produces a higher therapeutic effect than chemotherapy using the antitumor agent alone.

Experimental Example 16

In the same manner as in Experimental Example 11 described above, an experiment was conducted using chronic myelogenous leukemia model mice to examine the combinational effect of compound a and a molecular targeted drug imatinib (antitumor agent).
(1) Drug Administration Procedure Chronic myelogenous leukemia model mice prepared in accordance with the procedure of Experimental Example 11 (1) were divided into the following 4 groups (each group: n=15) and administered respective test drugs.

Group 1: placebo group (physiological saline was administered via gavage)

Group 2: compound a group (compound a [100 mg/kg/day] was administered via gavage)

Group 3: imatinib group (imatinib [150 mg/kg/day] was administered via gavage)

Group 4: imatinib+compound a group (imatinib [150 mg/kg/day] and compound a [100 mg/kg/day] were administered via gavage)

Figure 20:
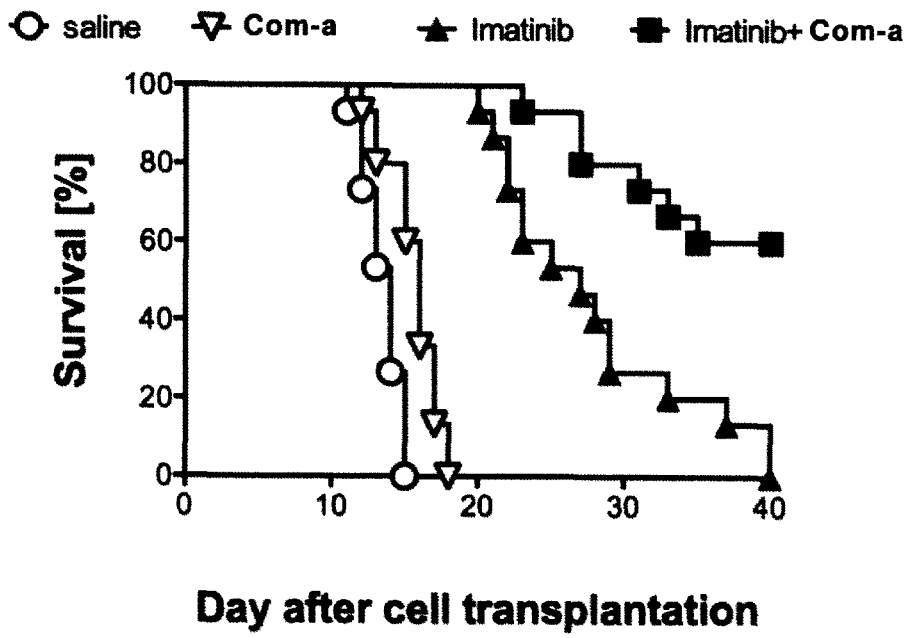
FIG. 20 shows the results of Experimental Example 16. The effect of combinational administration of imatinib and compound a (Com-a) was observed in chronic myelogenous leukemia model mice.

10 days after (day 10) the day on which CML cells were intravenously inoculated (day 0), administration of test drugs to the groups was started. The placebo group, the compound a group, and the imatinib group were administered the respective test drugs once a day from day 10 to day 16 (7 doses in total). The imatinib+compound a group was administered imatinib once a day from day 10 to day 16 (7 doses in total), and also administered compound a once a day from day 10 to day 16 (7 doses in total).
(2) Results FIG. 20 shows the survival rate of mice of each group. As shown in FIG. 20, all of the subject mice in the placebo group (○) and the compound a group (▽) died during the period from day 10 to day 20. The mice in the imatinib group (▲) survived longer than the mice in the placebo group, but all of the mice died by day 40. In contrast, although 6 mice in the imatinib+compound a group (■) died during the period from day 30 to day 50, the survival rate on day 50 was 60%.

The results indicate that chemotherapy using an antitumor agent in combination with a PAI-1 inhibitor can improve the prognosis (survival rate) more than chemotherapy using the antitumor agent alone.

Experimental Example 17

In the same manner as in Experimental Example 11 described above, an experiment was conducted using chronic myelogenous leukemia model mice to confirm the combinational effect of compound d or compound e, with a molecular targeted drug imatinib (antitumor agent).

(1) Drug Administration Procedure 20 chronic myelogenous leukemia model mice prepared in accordance with the procedure of Experimental Example 11 (1) were divided into the following 4 groups (each group: n=5) and administered respective test drugs.

Group 1: placebo group (physiological saline was administered via gavage)

Group 2: imatinib group (imatinib [150 mg/kg/day] was administered via gavage)

Group 3: imatinib+compound d group (imatinib [150 mg/kg/day] and compound d [10 mg/kg/day] were administered via gavage)

Group 4: imatinib+compound e group (imatinib [150 mg/kg/day] and compound e [10 mg/kg/day] were administered via gavage)

Figure 21:
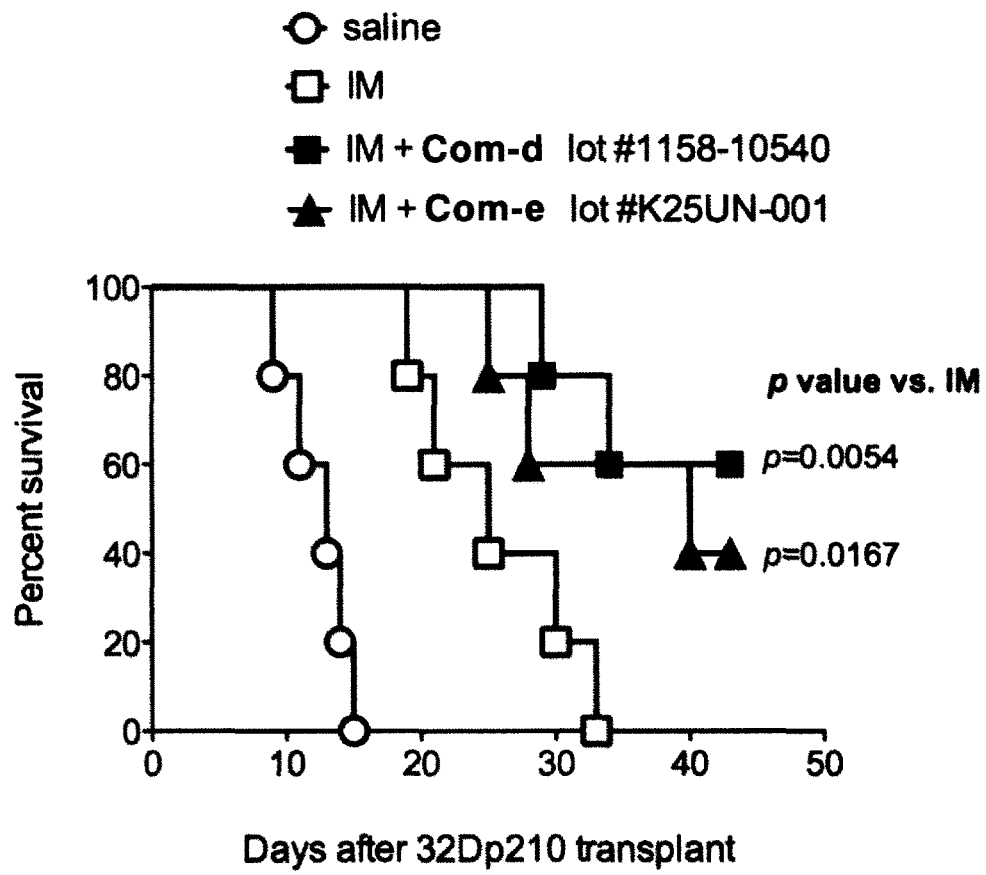
FIG. 21 shows the results of Experimental Example 17. The effect of combinational administration of imatinib and compound d or compound e was observed in chronic myelogenous leukemia model mice.

8 days after (day 8) the day (day 0) on which CML cells were intravenously inoculated, administration of test drugs to the groups was started. The placebo group and the imatinib group were administered the respective test drugs once a day from day 8 to day 14 (7 doses in total). The imatinib+compound d group and imatinib+compound e group were administered imatinib once a day from day 8 to day 14 (7 doses in total), and also administered compound d or e once a day from day 8 to day 14 (7 doses in total).
(2) Results FIG. 21 shows the survival rate of the mice of each group. As shown in FIG. 21, all of the subject mice of the placebo group (○) died during the period from day 10 to day 20. The mice of the imatinib group (□) survived longer than the mice of the placebo group, but all of the mice died by day 40. In contrast, although some of the mice of the imatinib+compound d group (■) and imatinib+compound e group (▲) died during the period from day 25 to day 50, some mice survived even after day 40. The significant difference in survival rate was p=0.0054 for the imatinib+compound d group versus the imatinib group, and p=0.0167 for the imatinib+compound e group versus the imatinib group, demonstrating good prognosis.

The results indicate that chemotherapy using an antitumor agent in combination with a PAI-1 inhibitor can improve prognosis (survival rate) more than chemotherapy using the antitumor agent alone.

Experimental Example 18

Subsequently, an experiment was conducted using ovarian cancer cells to evaluate whether chemotherapy using an antitumor agent in combination with a PAI-1 inhibitor is also effective for a solid tumor.
(1) Procedure HER2-positive human ovarian cancer cell lines SKOV3 ($5\times10^6$) were subcutaneously inoculated into BALB/c-nude mice. For better cell engraftment, the mice were intraperitoneally administered 25 μl of anti-Asialo GM1 antibody (Wako Pure Chemical Industries, Ltd., Code No. 014-09801) 2 days and 1 day before the cancer cell inoculation. When the tumor size became 50 mm$^3$ or more (day 0), Herceptin, a human anti-HER2 antibody, (5 mg/kg/day) was intraperitoneally administered once, and oral administration of compound c (10 mg/kg/day) or physiological saline was also started at the same time. Compound c or physiological saline was administered once a day, 5 doses in total (day 0 to day 4). The following week, without administration of Herceptin, only compound c or physiological saline was administered once a day, 5 doses in total in the same manner as the first week (day 7 to day 11). The group to which Herceptin and compound c were administered in combination is referred to as "compound c-combined group", and the group to which Herceptin and physiological saline were administered in combination is referred to as "compound c-non-combined group." The group to which only physiological saline was administered without Herceptin is referred to as "placebo group."

(2) Results

Figure 22:
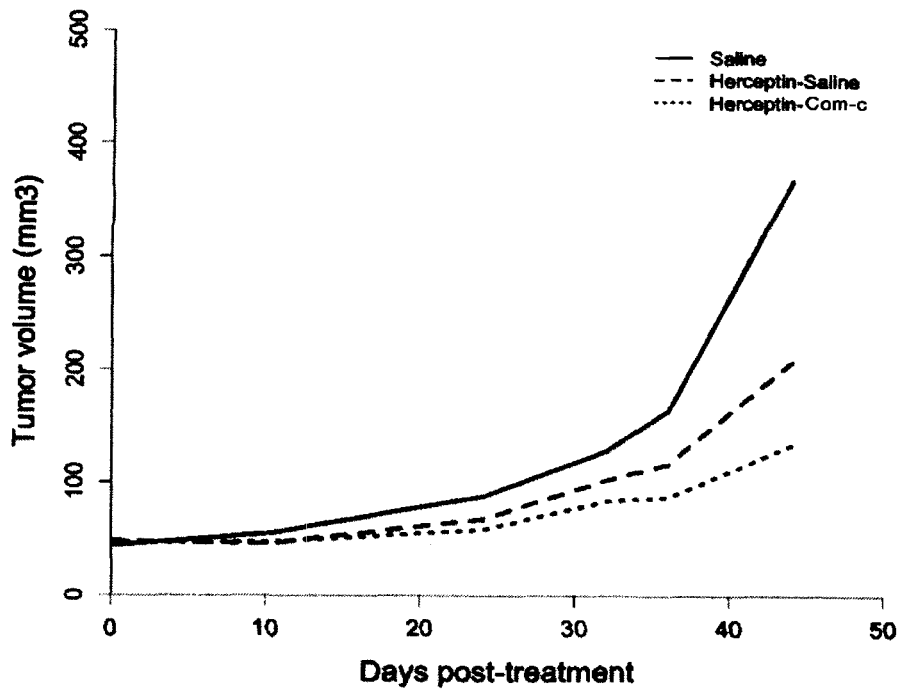
FIG. 22 shows the results of Experimental Example 18. The effect of chemotherapy using an antitumor agent in combination with a PAI-1 inhibitor on a solid tumor was observed.

FIG. 22 shows the change in tumor volume after test drug administration. The compound c-combined group (dotted line) and the compound c-non-combined group (dashed line) showed a tumor volume smaller than the placebo group (solid line). About 20 days after the test drug administration, the compound c-non-combined group started to show a tumor volume larger than the compound c-combined group. Even 45 days after the test drug administration, the compound c-combined group showed a tumor volume significantly smaller than other groups. The results indicate that chemotherapy using an antitumor agent in combination with a PAI-1 inhibitor is more effective in suppressing the tumor tissue proliferation than chemotherapy using the antitumor agent alone.

Experimental Example 19

Subsequently, to demonstrate the efficacy of the use of an antitumor agent in combination with a PAI-1 inhibitor in the treatment of a HER2 positive tumor, an in vivo experiment was conducted using cells enforced to express HER2 gene.

(1) Procedure

At first, A20 cell line (mouse B lymphoma) was transfected with human Her2 cDNA using MIGR1 vector to prepare transformed cells (hereinafter, "Her2-A20 cell"). The Her2-A20 cells ($5\times10^6$) were subcutaneously inoculated into BALB/c-nude mice. When the tumor size became 30 mm$^3$ or more (day 0), Herceptin, a human anti-HER2 antibody, (20 mg/kg/day) was intraperitoneally administered once, and oral administration of compound c (10 mg/kg/day) or physiological saline was started at the same time. Compound c or physiological saline was administered once a day, 5 doses in total (day 0 to day 4). In the following week, Herceptin (20 mg/kg/day) was intraperitoneally administered once, and oral administration of compound c or physiological saline was started at the same time. Compound c or physiological saline was administered once a day, 7 doses in total (day 7 to day 13). The group to which Herceptin and compound c were administered in combination is referred to as "compound c-combined group," and the group to which Herceptin and physiological saline were administered in combination is referred to as "compound c-non-combined group." The group to which physiological saline alone was administered without Herceptin is referred to as "placebo group." The number n is 3 for the compound c-combined group, 4 for the compound c-non-combined group, and 3 for the placebo group.

(2) Results

Figure 23:
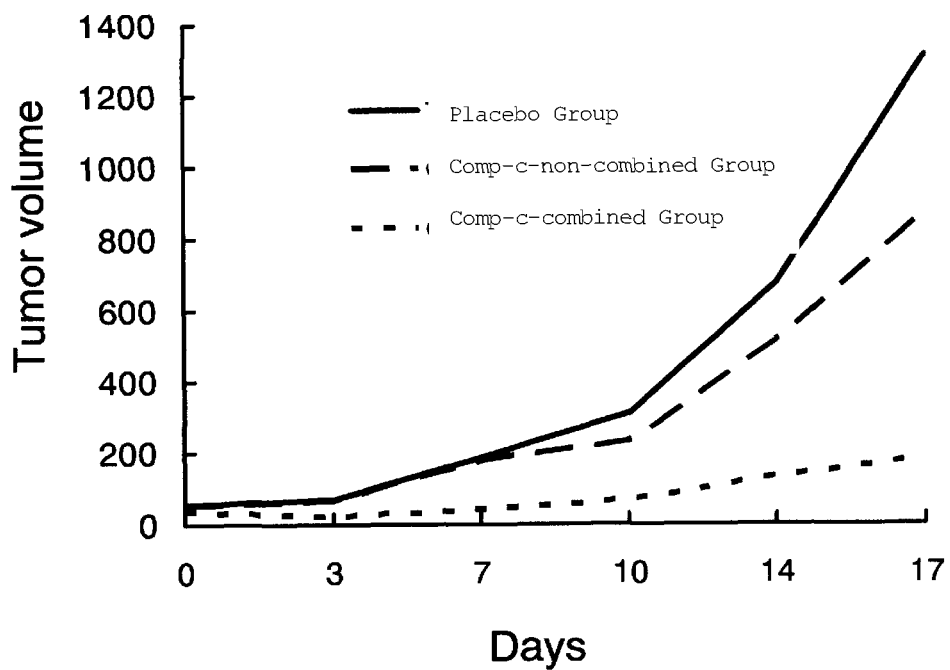
FIG. 23 shows the results of Experimental Example 19. The effect of chemotherapy using an antitumor agent in combination with a PAI-1 inhibitor on a HER2 positive tumor was observed.

FIG. 23 shows the change in tumor volume after the test drug administration. The compound c-combined group (dotted line) showed a tumor volume smaller than the placebo group (solid line) and the compound c-non-combined group (dashed line). Even 15 days after the test drug administration, the compound c-combined group showed a tumor volume significantly smaller than other groups. The results indicate that chemotherapy using an antitumor agent in combination with a PAI-1 inhibitor is more effective in suppressing HER2 positive tumor tissue proliferation than chemotherapy using the antitumor agent alone.

Experimental Example 20

The procedure of Experimental Example 19 was repeated except that the PAI-1 inhibitor (compound c) was replaced with compound d.

(1) Procedure

Her2-A20 cells ($1.8\times10^6$) were subcutaneously inoculated into BALB/c-nude mice. When the tumor size became 10 mm$^3$ or more (day 0), Herceptin (20 mg/kg/day) was intraperitoneally administered once, and the administration of compound d (10 mg/kg/day) or physiological saline was started at the same time. Compound d or physiological saline was administered once a day, 9 doses in total, (day 0 to day 4, and day 7 to day 10). Subsequently, on day 11, Herceptin (20 mg/kg/day) was intraperitoneally administered again. compound d or physiological saline was continuously administered once a day, 5 doses in total (day 11 to day 15). The group to which Herceptin and compound d were administered in combination is referred to as "compound d-combined group," and the group to which Herceptin and physiological saline were administered in combination is referred to as "compound d-non-combined group." The group to which physiological saline alone was administered, without Herceptin, is referred to as "placebo group." The number n is 3 for the compound d-combined group, 4 for the compound d-non-combined group, and 3 for the placebo group.

(2) Results

Figure 24:
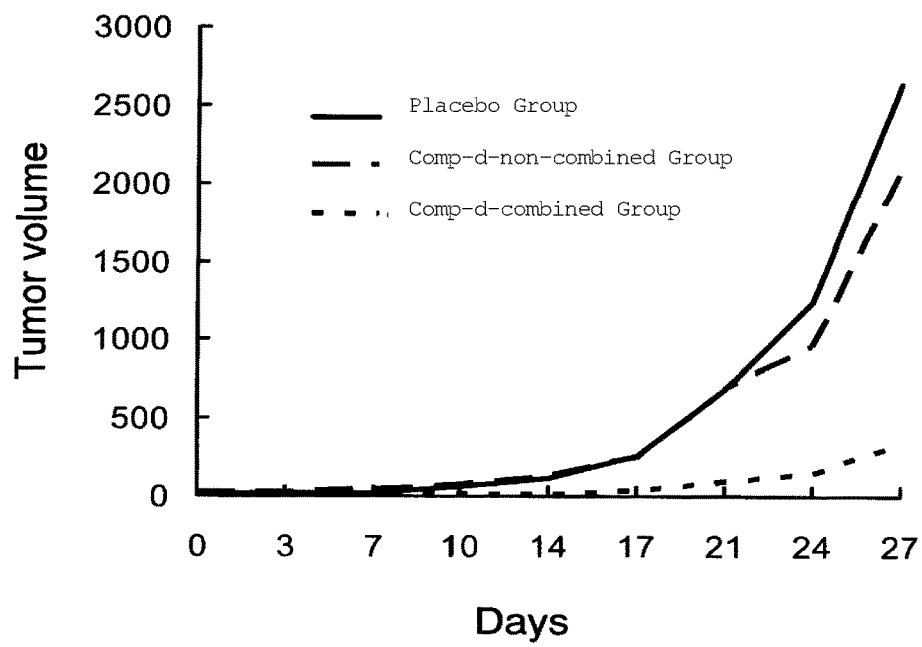
FIG. 24 shows the results of Experimental Example 20. The effect of chemotherapy using an antitumor agent in combination with a PAI-1 inhibitor on a HER2 positive tumor was observed.

FIG. 24 shows the change in tumor volume after the test drug administration. The compound d-combined group (dotted line) showed a tumor volume smaller than the placebo group (solid line) and the compound d-non-combined group (dashed line). Even 25 days after the test drug administration, the compound d-combined group showed a tumor volume significantly smaller than other groups. The results indicate that the use of an antitumor agent in combination with a different PAI-1 inhibitor is also effective in suppressing HER2-positive tumor tissue proliferation.

Experimental Example 21

The procedure of Experimental Example 18 was repeated using a different PAI-1 inhibitor.

(1) Procedure

HER2-positive human ovarian cancer cell lines SKOV3 ($1\times10^7$) were suspended in matrigel and subcutaneously inoculated into BALB/c-nude mice. For better cell engraftment, the mice were intraperitoneally administered 25 µl of anti-Asialo GM1 antibody 2 days and 1 day before the cancer cell inoculation. When the tumor size became 50 mm$^3$ or more (day 0), Herceptin (5 mg/kg/day) or physiological saline was intraperitoneally administered once, and oral administration of compound d (10 mg/kg/day) was started at the same time. In this experiment, a group to which compound d (10 mg/kg/day) alone was administered, without Herceptin, was also examined. Compound d was administered once a day, 5 doses in total (day 0 to day 4). In the following week, Herceptin was not administered, but compound d or physiological saline was administered once a day, 5 doses in total (day 7, day 9 to day 11, and day 14). The group to which Herceptin and compound d were administered in combination is referred to as "compound d-combined group," and the group to which compound d alone was administered is referred to as "group administered compound d alone." The group to which physiological saline alone was administered, without Herceptin, is referred to as "placebo group."

(2) Results

Figure 25:
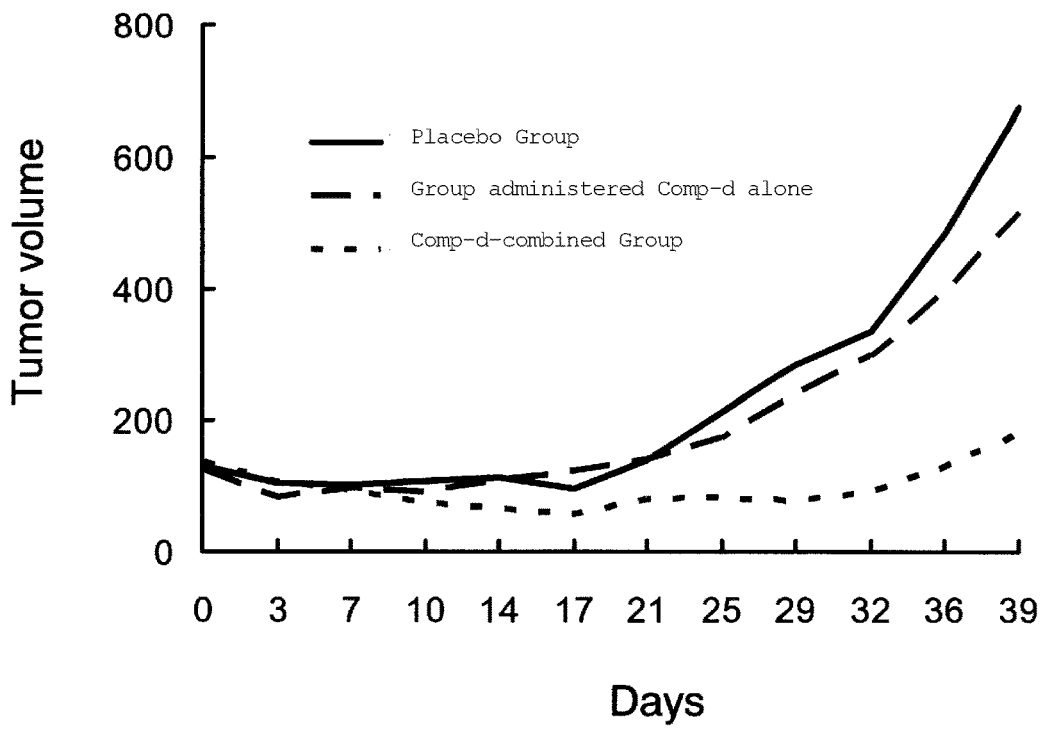
FIG. 25 shows the results of Experimental Example 21. The effect of chemotherapy using an antitumor agent in combination with a PAI-1 inhibitor on a HER2 positive tumor was observed.

FIG. 25 shows the change in tumor volume after the test drug administration. Because of the administration of Herceptin, the compound d-combined group (dotted line) showed a tumor volume smaller than the placebo group (solid line) and the group administered compound d alone (dashed line). Even 30 days after the test drug administration, the compound d-combined group showed a tumor volume significantly smaller than other groups. The results reveal that even the combination of an antitumor agent with a different PAI-1 inhibitor can produce a therapeutic effect on a tumor. When administered alone, compound d did not show a marked difference from the placebo group.

The results of Experimental Examples 18 to 20 indicate that even though administration of Herceptin alone does not produce a therapeutic effect, the use of an antitumor agent in combination with a PAI-1 inhibitor can produce a prominent therapeutic effect on a tumor.

From the results of Experimental Examples 19 to 22, the administration of a PAI-1 inhibitor and Herceptin is considered to be effective for HER2-positive tumors, such as breast cancer, ovarian cancer, and stomach cancer.

Experimental Example 22

The expression of PAI-1 in tumor stem cells was confirmed by the following method.
(1) Collection of CML Cells From the bone marrow of mice, lineage marker (CD5, CD11b, CD45R, Gr-1, 7-4, and Ter119; Miltenyi Biotec, Germany) positive cells were removed using a biotin-labeled antibody cocktail, and the remaining cells were stained with an APC-conjugated anti-mouse c-kit (CD117) antibody (eBioscience) and a PE-conjugated anti-mouse SCA-1 (Ly6A/E) antibody (eBioscience). Lineage (Lin)-negative, c-Kit-positive, and Sca-1-positive cells (LSK cell) were then separated by a cell sorter. The p210-GFP used in Experimental Example 11 was introduced into the separated LSK cells. The p210-GFP-introduced cells were transplanted into mice that had been exposed to radiation to kill their own bone-marrow cells. The mice transplanted with p210-GFP-introduced cells exhibited chronic myelogenous leukemia (CML)-like pathology.

2 weeks after the transplantation of p210-GFP-introduced cells, the mice were euthanized, and bone-marrow cells (CML cells) of femurs and tibiae were collected. The number of bone-marrow cells was counted, and the cells were immunostained with the following antibodies.

Figure 26:
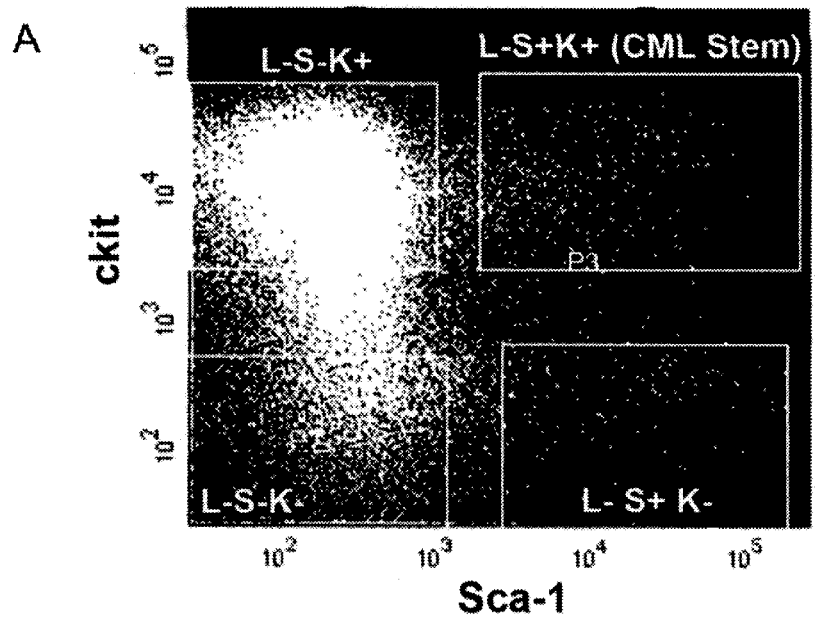
FIGS. 26A to 26C show the results of Experimental Example 22. The upper-right area of FIG. 26A shows lineage-negative, Sca-1-positive, and c-kit-positive (L−S+K+) cells, and the cells fractioned in this area are CML stem cells. The upper-left area of FIG. 26A shows lineage-negative, Sca-1 negative, and c-kit-positive cells (L−S−K+); the lower-right area shows lineage-negative, Sca-1 positive, and c-kit-negative cells (L−S+K−); and the lower-left area shows lineage-negative, Sca-1-negative, and c-kit-negative cells (L−S−K−). The cells in these three areas are progenitor cells that are more differentiated than the stem cells.
Figure 26:
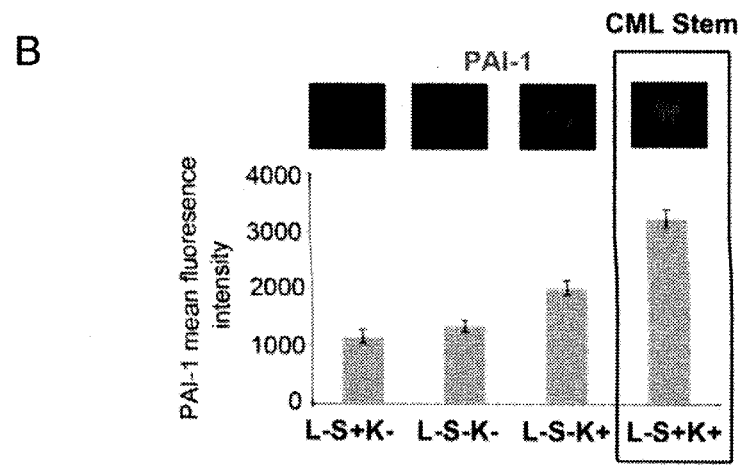
Figure 26:
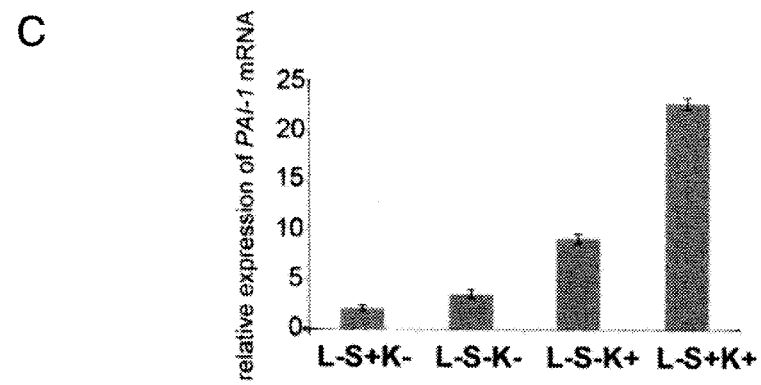

In the manner described above, lineage marker positive cells were removed from the collected CML cells using a biotin-labeled antibody cocktail, and the remaining cells were stained with PerCPCy 5.5-conjugated streptavidin (BD Biosciences), APC-conjugated anti-mouse c-kit (CD117) antibody, and PE-conjugated anti-mouse SCA-1 (Ly6A/E) antibody, followed by analysis with a flow cytometric analyzer. The analysis was conducted with a FACSAria device (BD Biosciences) using the FACSDiva software program (BD Biosciences). Dead cells were gated out by staining with propidium iodide. The upper-right area of FIG. 26A shows lineage-negative, Sca-1-positive, and c-kit-positive (L−S+K+) cells, and the cells fractioned in this area are CML stem cells. The upper-left area of FIG. 26A shows lineage-negative, Sca-1 negative, and c-kit-positive cells (L−S−K+), and the lower-right area shows lineage-negative, Sca-1 positive, and c-kit-negative cells (L−S+K−). The lower-left area of FIG. 26A shows lineage-negative, Sca-1-negative, and c-kit-negative cells (L−S−K−). The cells in these three areas are progenitor cells, which were more differentiated than the stem cells.

(2) Comparison of PAI-1 Expression Level Between Fractions

The PAI-1 expression levels in the cells fractioned in the areas (L−S+K−), (L−S−K−), (L−S−K+), and (L−S+K+) were compared in the protein level and mRNA level. FIG. 26B shows the fractions of the collected cells. FIG. 26C shows the results of comparing protein-level expressions. The upper part of FIG. 26B shows a picture of PAI-1 immunostained with the fluorescence-conjugated antibody observed with a fluorescence microscope. The lower part of FIG. 26B shows a graph of quantified fluorescence intensity. The results reveal that the PAI-1 protein expression was increased in the order of (L−S+K−), (L−S−K−), (L−S−K+), and (L−S+K+). The results indicate that CML stem cells expressed PAI-1 at a higher level than progenitor cells that stated to differentiate.

FIG. 26C shows the expression of PAI-1 mRNA in each fraction. As observed with PAI-1 protein, CML stem cells also exhibited PAI-1 mRNA expression at a higher level than the progenitor cells that started to differentiate. This reveals that the expression of PAI-1 is more highly induced in CML stem cells.

The results indicate that tumor stem cells express PAI-1 at a higher level than differentiated cells. In other words, PAI-1 expression in tumor stem cells declines as cell differentiation proceeds. The difference in PAI-1 expression level between the tumor stem cells and the differentiated cells indicates that tumor stem cells have a higher sensitivity to a PAI-1 inhibitor than non-stem tumor cells.

Tumor stem cells affected by a PAI-1 inhibitor appear to transit into the active phase of its cell cycle, for example, because of separation from the niche environment, or by other action. The tumor stem cells transit into the active phase then appear to be subjected to the action of an antitumor agent, and destroyed.

Moreover, it is assumed that when the PAI-1 expression level is high, cells exhibit sensitivity despite a low concentration of an administered PAI-1 inhibitor, and when the PAI-1 expression level is low, cells are not affected unless the PAI-1 inhibitor is administered in a large amount. In other words, tumor stem cells, which express PAI-1 at a high level, are affected by a PAI-1 inhibitor in a smaller dosage, as compared with other cells that express PAI-1 at a low level.

Thus, when the PAI-1 expression level is higher in tumor stem cells than in other cells, a relatively smaller dosage of a PAI-1 inhibitor (preferable from a standpoint of side effects) can control the tumor stem cells to lead them into the active phase, thereby enabling an antitumor agent to act on the cells.

The observation described above further suggests that a PAI-1 inhibitor can effectively act on other kinds of tumors when the PAI-1 expression level is higher in tumor stem cells than in tumor cells other than the tumor stem cells.

The invention claimed is:
1. A method for treating a tumor in a patient, the method comprising:
(i) administering a compound having PAI-1 inhibitory activity to a patient having a tumor, wherein said tumor is selected from the group consisting of chronic myelogenous leukemia, lymphoma, and ovarian cancer, and wherein the compound is represented by Formula (I) or a pharmacologically acceptable salt thereof:

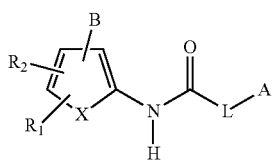

wherein
either $R_1$ or $R_2$ is hydrogen, and the other is halogen;
X is vinylene (—CH=CH—);
A is a group represented by Formula (I-1):

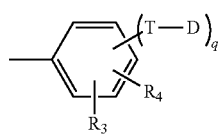

in Formula (I-1), q is an integer of 1;
both of $R_3$ and $R_4$ are hydrogen;
T is a single bond;
D is phenyl, quinolyl, isoquinolyl, or furyl;
L is a single bond, —CONH—, or alkyleneoxyalkylene-CONH—; and
B is $COOR_9$, wherein $R_9$ is hydrogen or a group converted to hydrogen in vivo, wherein the compound does not show an antitumor effect in vivo when the compound is administered alone, and
(ii) administering an antitumor agent, wherein the antitumor agent has anti-tumor activity against one or more of chronic myelogenous leukemia, lymphoma, and ovarian cancer.

2. The method according to claim 1, wherein
B is located at the ortho position of the benzene ring to which imino is bound, and $R_9$ is hydrogen in Formula (I).

3. The method according to claim 1, wherein the compound having PAI-1 inhibitory activity is at least one member selected from the group consisting of
2-[(biphenyl-3-ylcarbonyl)amino]-5-chlorobenzoic acid,
sodium 5-chloro-2-({[3-(quinolin-8-yl)phenyl]carbonyl}amino)benzoate,
5-chloro-2-{[{[3-(furan-3-yl)phenyl]amino}(oxo)acetyl]amino}benzoic acid, and
5-chloro-2-{[(2-{[3-(furan-2-yl)phenyl]amino}-2-oxoethoxy)acetyl]amino}benzoic acid.

4. The method according to claim 1, wherein the antitumor agent is at least one member selected from the group consisting of antimetabolites, microtubule inhibitors, antitumor antibiotics, topoisomerase inhibitors, platinum-based drugs, alkylating agents, hormone-like drugs, molecular targeted drugs, antibody drugs, cytokines, and non-specific immunostimulants.

5. The method according to claim 1, wherein D is quinolyl.

* * * * *